United States Patent
Adams et al.

(10) Patent No.: US 9,765,067 B2
(45) Date of Patent: Sep. 19, 2017

(54) THIOPHEN-2-YL-PYRIDIN-2-YL-1H-PYRAZOLE-4-CARBOXYLIC ACID DERIVATIVES AND THE USE THEREOF AS SOLUBLE GUANYLATE CYCLASE ACTIVATORS

(71) Applicants: Christopher M. Adams, Arlington, MA (US); David B. Belanger, Lexington, MA (US); Doug Bevan, Chelmsford, MA (US); Takeru Ehara, Arlington, MA (US); Luciana Ferrara, Stoughton, MA (US); Nan Ji, Arlington, MA (US); Donglei Liu, Dover, MA (US); Erik Meredith, Hudson, MA (US); Muneto Mogi, Waltham, MA (US); James Powers, Waltham, MA (US); Ganesh Prasanna, Acton, MA (US); Mitsunori Kato, Cambridge, MA (US)

(72) Inventors: Christopher M. Adams, Arlington, MA (US); David B. Belanger, Lexington, MA (US); Doug Bevan, Chelmsford, MA (US); Takeru Ehara, Arlington, MA (US); Luciana Ferrara, Stoughton, MA (US); Nan Ji, Arlington, MA (US); Donglei Liu, Dover, MA (US); Erik Meredith, Hudson, MA (US); Muneto Mogi, Waltham, MA (US); James Powers, Waltham, MA (US); Ganesh Prasanna, Acton, MA (US); Mitsunori Kato, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/320,813

(22) PCT Filed: Jul. 2, 2015

(86) PCT No.: PCT/IB2015/055007
§ 371 (c)(1),
(2) Date: Dec. 21, 2016

(87) PCT Pub. No.: WO2016/001876
PCT Pub. Date: Jan. 7, 2016

(65) Prior Publication Data
US 2017/0197950 A1    Jul. 13, 2017

Related U.S. Application Data

(60) Provisional application No. 62/020,182, filed on Jul. 2, 2014, provisional application No. 62/168,640, filed on May 29, 2015.

(51) Int. Cl.
*A61K 31/4545* (2006.01)
*A61K 31/4725* (2006.01)
*A61K 31/4439* (2006.01)
*C07D 409/14* (2006.01)
*A61K 9/00* (2006.01)

(52) U.S. Cl.
CPC .......... *C07D 409/14* (2013.01); *A61K 9/0048* (2013.01); *A61K 31/4439* (2013.01); *A61K 31/4545* (2013.01); *A61K 31/4725* (2013.01)

(58) Field of Classification Search
None
See application file for complete search history.

(56) References Cited

U.S. PATENT DOCUMENTS

| 6,335,334 B1 | 1/2002 | Schindler et al. |
| 2009/0209556 A1 | 8/2009 | Bittner et al. |
| 2010/0216764 A1 | 8/2010 | Kim et al. |
| 2011/0028493 A1 | 2/2011 | Matsunaga et al. |

FOREIGN PATENT DOCUMENTS

| EP | 1420023 A1 | 5/2004 |
| WO | 02070462 A1 | 9/2002 |
| WO | 02070510 A2 | 9/2002 |
| WO | 03086407 A1 | 10/2003 |
| WO | 2008073452 A1 | 6/2008 |
| WO | 2008119458 A1 | 10/2008 |
| WO | 2009032249 A1 | 3/2009 |
| WO | 2009068652 A1 | 6/2009 |
| WO | 2009071504 A1 | 6/2009 |
| WO | 2009127338 A1 | 10/2009 |
| WO | 2010099054 A2 | 9/2010 |
| WO | 2010102717 A1 | 9/2010 |
| WO | 2011051165 A1 | 5/2011 |
| WO | 2012058132 A1 | 5/2012 |
| WO | 2012076466 A2 | 6/2012 |
| WO | 2012122340 A1 | 9/2012 |
| WO | 2012139888 A1 | 10/2012 |
| WO | 2013025425 A1 | 2/2013 |
| WO | 2014057740 A1 | 10/2014 |
| WO | 2015011086 A1 | 1/2015 |
| WO | 2015033307 A1 | 3/2015 |

OTHER PUBLICATIONS

Shie, et al., "Puring derivatives as potent Bruton's tyrosine kinase (BTK) inhibitors for autoimmune diseases", Bioorganic & Medicinal Cemistry Letters, 24(9):2212-2221 (2014).
Abdel-Rahman, et al., "Synthesis of Novel Fluorine Substituted isolated and Fused Heterobicyckic Nitrogen Systems Bearing 6-(2'-Phosphorylanilido)-1,2,4-Triazin-5-One Moiety as Potential Inhibitor towards HIV-1 Activity", International Journal of Organic Chemistry, 4(4):247-268 (2014).
Stasch, et al., "Renal effects of soluble guanylate cyclase stimunlators and activators: A review of the preclinical evidence", Current Opinion in Pharmacology, 21:95-104 (2015).

*Primary Examiner* — Samantha Shterengarts
(74) *Attorney, Agent, or Firm* — Shawn D. Britt

(57) ABSTRACT

The present invention provides a compound of formula (I) or a pharmaceutically acceptable salt thereof; a method for manufacturing the compounds of the invention, and its therapeutic uses. The present invention further provides a combination of pharmacologically active agents and a pharmaceutical composition.

19 Claims, No Drawings

THIOPHEN-2-YL-PYRIDIN-2-YL-1H-PYRAZOLE-4-CARBOXYLIC ACID DERIVATIVES AND THE USE THEREOF AS SOLUBLE GUANYLATE CYCLASE ACTIVATORS

This application is a U.S. National Phase filing of International Application No. PCT/IB2015/055007 filed 2 Jul. 2015, which claims priority to U.S. Application No. 62/020,182, filed 2 Jul. 2014, and also claims priority to U.S. Application No. 62/168,640, filed May 29, 2015, the contents of which are incorporated herein by reference in their entireties.

FIELD OF THE INVENTION

The present invention is related generally to compounds which activate soluble guanylate cyclase (sGC). The invention further relates to the use of said sGC activators in the treatment of glaucoma and in the lowering of intraocular pressure (IOP) such as that associated with glaucoma and ocular hypertension.

BACKGROUND OF THE INVENTION

The eye disease glaucoma is characterized by a permanent loss of visual function due to irreversible damage to the optic nerve. The several morphologically or functionally distinct types of glaucoma are typically characterized by an undesirable elevation of IOP, which is considered to be causally related to the pathological course of the disease. Continuously elevated IOP has been associated with the progressive loss of retinal ganglion cells and optic nerve damage ultimately resulting in the loss of visual function. In some cases, ocular hypertension, a condition in which IOP is elevated, can present without apparent loss of visual function. However, patients with ocular hypertension are considered to be at a high risk for eventually developing the visual loss associated with glaucoma. Therefore, lowering IOP is the current treatment objective for the of glaucoma patients and for patients with ocular hypertension in order to decrease the potential for, or severity of, glaucomatous retinopathy. Unfortunately, many individuals do not achieve or maintain desired level of IOP reduction when treated with existing glaucoma therapies.

Patients known as normotensive or low-tension glaucoma patients have relatively low IOP, yet present with glaucomatous visual field loss. These patients may benefit from agents that lower and control IOP, because glaucoma that is detected early and treated promptly may have reduced or delayed loss of visual function. Conventional therapeutic agents that have proven to be effective for the reduction of IOP include both agents that decrease aqueous humor production and agents that increase the outflow facility. Such agents are in general administered by one of two routes; topically by direct application to the eye, or orally. However, many of these agents have associated side effects which may render them undesirable as ocular therapeutic agents.

Soluble guanylate cyclase (sGC) is a receptor enzyme for the second messenger, nitric oxide (NO) in several cell types including muscle, epithelial, neuronal, and endothelial cells. In humans, functional sGC is a heterodimer composed of either an alpha 1 or alpha 2 subunit combined with the beta 1 subunit which has a heme prosthetic group. Under physiological conditions, NO binds to the prosthetic heme of sGC which activates the enzyme to catalyze the conversion of guanosine-5'-triphosphate (GTP) to cyclic guanosine monophosphate (cGMP). cGMP is a second messenger which in turn exerts its effects by activating cGMP dependent protein kinase (PKG) isoforms, phosphodiesterases, and cGMP gated ion channels. In doing so, sGC can thus modulate numerous pathways associated with diseases including hypertension (arterial and pulmonary), heart failure, atherosclerosis, erectile dysfunction, liver cirrhosis, and renal fibrosis. Under aforementioned pathologic conditions, prolonged oxidative stress can cause the oxidation of the heme group of sGC (from ferrous to ferric state) which is incapable of being activated by NO and can contribute to exacerbation of disease processes. As a consequence of sGC oxidation and unresponsiveness to NO, endothelial dysfunction, atherosclerosis, hypertension, stable or unstable angina pectoris, thromboses, myocardial infarction, strokes or erectile dysfunction are worsened. Therefore, pharmacological stimulation or activation of sGC offers a possibility to normalize cGMP production and therefore makes possible the treatment and/or prevention of such disorders.

To this effort, there are two classes of compounds have been identified, including NO-independent/reduced heme-dependent sGC stimulators and NO-independent/heme-independent sGC activators. sGC stimulators are dependent on heme, but they are not active once sGC become oxidized. sGC activators on the other hand can still activate the enzyme to generate cGMP even in the absence of nitric oxide (NO) and/or under oxidative stress induced oxidation of sGC in disease tissue. Thus, the activity of sGC in these situations will be corrected by sGC activators, but not by sGC stimulators, and will have the potential to provide benefit in many diseases caused by defective signaling in the NO pathway especially following oxidative stress.

SUMMARY OF THE INVENTION

The present invention in part relates to new activators of sGC and the use thereof in the treatment of disease. In one aspect the sGC activators provided herein are suitable for use in methods of treating glaucoma in human patients or other mammals. The present invention also relates to methods of lowering or controlling normal or elevated IOP in a human patient or other mammals. In particular, the invention provides methods of treating and/or preventing glaucoma by administration of an sGC activator compound described infra.

In the eye, the trabecular outflow pathway accounts for 70-80% of aqueous humor outflow from the anterior chamber and thus is a major component of maintaining normal intraocular pressure (IOP). This outflow pathway is pathologically compromised in primary open angle glaucoma (POAG). Oxidative stress is thought to be an underlying factor that can adversely affect trabecular meshwork function, resulting from/in IOP elevation in POAG. Reactive oxygen species (ROS) not only decrease the bioavailability of nitric oxide (NO) but also shift the sGC redox equilibrium to its oxidized form, which as mentioned before is unresponsive to NO. Selective activation of the oxidized form of sGC should target only the diseased state of the enzyme in the putative target tissue (trabecular meshwork/Schlemm's canal), thus offering a highly innovative therapy for glaucoma that should work adjunctively with current therapies.

In one aspect of the invention, sGC activators, and salts thereof, are provided which have the structure of formula (I):

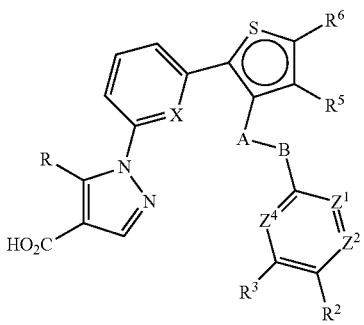

(I)

Wherein the variables are defined infra.

Certain embodiments of the present invention comprise compositions or methods which include or use compounds capable of activating sGC thereby modulating intraocular pressure in the eye. By activating sGC enzymatic activity, subject compounds according to certain embodiments of the present invention are accordingly useful for lowering and/or controlling IOP associated with normal-tension glaucoma, ocular hypertension, and glaucoma, including primary open-angle glaucoma in humans and other warm-blooded animals. When used in such applications, the compounds may be formulated in pharmaceutical compositions suitable for topical delivery to the eye.

The foregoing brief summary broadly describes the features and technical advantages of certain embodiments of the present invention. Additional features and technical advantages will be described in the detailed description of the invention that follows.

DESCRIPTION OF THE INVENTION

As the term is used herein, a "sGC activator" is a compound capable of modulating sGC activity to generate cGMP signaling which would otherwise be unresponsive to nitric oxide. In contrast, "sGC stimulators" refers to compounds that are capable of synergizing with nitric oxide and can directly stimulate cGMP production so long as the reduced heme domain is present in the enzyme.

In a first embodiment, the invention provides a compound according to Formula (I)

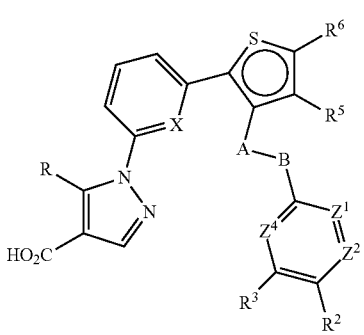

(I)

Or a pharmaceutically acceptable salt thereof, wherein
X is N or CH;
$Z^1$ is N or $CR^1$;
$Z^2$ is N or CH;
$Z^4$ is N or $CR^4$;

A is $CHR^A$ or O, wherein $R^A$ is hydrogen or $C_1$-$C_4$alkyl;
B is $CHR^A$, O or N(H); wherein one or both of A and B is $CHR^A$;
R is hydrogen, $C_1$-$C_4$alkyl, monofluoromethyl, difluoromethyl or trifluoromethyl;
$R^1$ is hydrogen, halogen or $C_1$-$C_4$alkyl;
$R^4$ is hydrogen, halogen, $C_1$-$C_4$alkyl, hydroxylmethyl, halo$C_1$-$C_4$alkyl or $C_1$-$C_4$alkoxy;
$R^2$ is piperidinyl which is N-substituted with $C_1$-$C_4$alkyl, $C_3$-$C_6$cycloalkyl, halo$C_1$-$C_4$alkyl, C(O)$C_1$-$C_4$alkyl, C(O)NH($C_1$-$C_4$alkyl), C(O)N($C_1$-$C_4$alkyl)$_2$, S(O)$_2$$C_1$-$C_4$alkyl, C(O)$C_3$-$C_6$cycloalkyl, heterocycle, C(O)heterocycle, C(O)halo$C_1$-$C_4$alkyl, C(O)$C_1$-$C_4$alkoxy, C(O)$C_1$-$C_4$alkenoxy, heteroaryl or CO(O)$_2$benzyl, wherein each cycloalkyl is optionally substituted by hydroxy and each alkyl or alkoxy is optionally substituted by hydroxyl, $C_1$-$C_4$alkoxy, $C_3$-$C_6$cycloalkyl or heterocycle, wherein each heterocycle has 4, 5 or 6 ring atoms and 1 or 2 ring oxygen atoms independently selected from N, O or S, and is optionally substituted with 1 or 2 $C_1$-$C_4$alkyl or hydroxy substituents and wherein each heteroaryl has 5 or 6 ring atoms, 1, 2 or 3 ring heteroatoms independently selected from N, O and S and is optionally substituted with 1 or 2 $C_1$-$C_4$alkyl substituents, and wherein the piperidinyl is optionally further substituted by hydroxy or by 1-4 independently selected $C_1$-$C_4$alkyl groups;
$R^3$ is hydrogen, halogen, $C_1$-$C_4$alkyl, $C_3$-$C_6$cycloalkyl, hydroxymethyl or $C_1$-$C_4$alkoxy;
$R^2$ and $R^3$, taken in combination, form a 5 or 6 member fused saturated azacyclic ring optionally substituted with benzyl or 5 or 6 member heteroarylmethyl, which heteroaryl has 1 or 2 ring heteroatoms independently selected from N, O and S;
$R^5$ is hydrogen, $C_1$-$C_4$alkyl, trifluoromethyl, halogen or $C_3$-$C_6$cycloalkyl; and
$R^6$ is hydrogen, $C_1$-$C_4$alkyl, halogen or $C_3$-$C_6$cycloalkyl.

In one aspect of the first embodiment, compounds of Formula (I) are provided in which $Z^1$ is N, $Z^2$ is CH and $Z^4$ is $CR^4$. Certain other compounds of the first embodiment are provided in which $Z^1$ is $CR^1$, $Z^2$ is CH and $Z^4$ is N. In still another aspect of the first embodiment, compounds of Formula (I) are provided in which Z' is $CR^1$, $Z^2$ is N and $Z^4$ is $CR^4$.

In a second embodiment, the invention provides compounds of Formula (Ia)

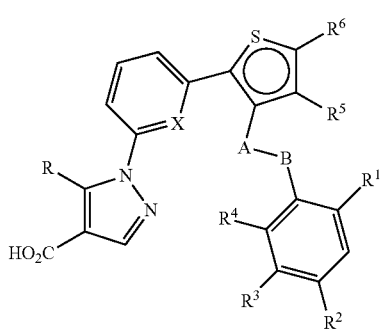

(Ia)

Or a pharmaceutically acceptable salt thereof, wherein
X is N or CH;
A is $CHR^A$ or O, wherein $R^A$ is hydrogen or $C_1$-$C_4$alkyl;

B is CHR$^4$, O or N(H); wherein one or both of A and B is CHR$^4$; or

R is C$_1$-C$_4$alkyl or trifluoromethyl;

R$^1$ and R$^4$ are each independently selected from hydrogen, halogen or C$_1$-C$_4$alkyl; or R$^4$ is haloC$_1$-C$_4$alkyl or C$_1$-C$_4$alkoxy;

R$^2$ is piperidinyl which is N-substituted with C$_1$-C$_4$alkyl, C$_3$-C$_5$cycloalkyl-haloC$_1$-C$_4$alkyl, C(O)C$_1$-C$_4$alkyl, which alkyl is optionally substituted with hydroxyl or amino, C(O)C$_1$-C$_4$alkyl, C(O)C$_3$-C$_6$cycloalkyl, which cycloalkyl is optionally substituted by hydroxy, C(O)CH$_2$—C$_3$-C$_6$cycloalkyl C(O)haloC$_1$-C$_4$alkyl, C(O)heterocycle, C(O)NH(C$_1$-C$_4$alkyl), C(O)N(C$_1$-C$_4$alkyl)$_2$, C(O)C$_1$-C$_4$alkoxy, wherein the piperidinyl is optionally further substituted by hydroxy or by 1-4 independently selected C$_1$-C$_4$alkyl groups and wherein the heterocycle is a 4 to 6 member saturated ring having 1 or 2 ring oxygen atoms and substituted with 0, 1, or 2 C$_1$-C$_4$alkyl groups;

R$^3$ is hydrogen, halogen, C$_1$-C$_4$alkyl, hydroxymethyl or C$_1$-C$_4$alkoxy; or R$^2$ and R$^3$, taken in combination form a 6 member fused saturated azacyclic ring optionally substituted with benzyl or 5, 6, 9 or 10 member heteroarylmethyl, which heteroaryl has 1 or 2 rings and 1 or 2 ring heteroatoms independently selected from N, O and S;

R$^5$ is hydrogen, C$_1$-C$_4$alkyl, halogen or C$_3$-C$_6$cycloalkyl; and

R$^6$ is hydrogen, C$_1$-C$_4$alkyl, halogen or C$_3$-C$_6$cycloalkyl.

In a third embodiment, compounds of embodiment one or embodiment two are provided in which R$^2$ is N-substituted piperidin-4-yl wherein the N-substituent is C(O)cyclopropyl, C(O)C$_1$-C$_4$alkyl, haloC$_1$-C$_4$alkyl, or C(O)C$_1$-C$_4$alkoxy.

In a fourth embodiment, compounds of any one of embodiments one to three are provided in which R$^2$ is N-substituted piperidin-4-yl wherein the N-substituent is 2,2,2-trifluoroethyl, C(O)cyclopropyl or C(O)C$_1$-C$_4$alkyl.

In a fifth embodiment, compounds of any one of embodiments one to four are provided in which R$^1$ is methyl and R$^3$ and R$^4$ are hydrogen.

In a sixth embodiment, compounds of any one of embodiments one to four are provided in which R$^1$ and R$^4$ are hydrogen and R$^3$ is ethyl.

In a seventh embodiment, compounds of any one of embodiments one to four are provided in which R$^1$ and R$^4$ are hydrogen and R$^3$ is methoxy.

In an eighth embodiment, compounds of any one of embodiments one to four are provided in which R$^1$ and R$^3$ are hydrogen and R$^4$ is methoxy.

In a ninth embodiment, compounds of any one of embodiments one to eight are provided in which R is trifluoromethyl, methyl or ethyl.

In a tenth embodiment, compounds of any one of embodiments one to nine are provided in which R is methyl or ethyl.

In an eleventh embodiment, compounds of any one of embodiments one to nine are provided in which R is trifluoromethyl.

In a twelfth embodiment, compounds of any one of embodiments one to eleven are provided in which R$^5$ is hydrogen, C$_1$-C$_4$alkyl, cyclopropyl or trifluoromethyl and R$^6$ is hydrogen, C$_1$-C$_4$alkyl, cyclopropyl or chloro.

In a thirteenth embodiment, compounds of any one of embodiments one to twelve are provided in which R$^5$ is hydrogen, methyl, ethyl or trifluoromethyl; and R$^6$ is hydrogen, methyl, cyclopropyl or chloro.

In a fourteenth embodiment, compounds of any one of embodiments one to thirteen are provided in which R$^5$ is hydrogen or methyl; and R$^6$ is hydrogen or methyl, wherein at least one of R$^5$ or R$^6$ is methyl.

In a fifteenth embodiment, compounds of any one of embodiments one to fourteen are provided in which A is CH$_2$ or CH(CH$_3$) and B is CH$_2$, O or N(H).

In a sixteenth embodiment, compounds of any one of embodiments one to ten or twelve to fifteen, wherein A is CH$_2$;

B is O or N(H);

R is methyl or ethyl;

R$^1$ is methyl;

R$^2$ is N-substituted piperidin-4-yl wherein the N-substituent is C(O)cyclopropyl, 2,2,2-trifluoroethyl or C(O)C$_1$-C$_4$alkyl;

R$^3$ is hydrogen, methyl, ethyl or methoxy;

R$^4$ is hydrogen;

R$^5$ is hydrogen, methyl, ethyl or trifluoromethyl; and R$^6$ is hydrogen, methyl, cyclopropyl or chloro, wherein at least one of R$^5$ or R$^6$ is not hydrogen.

Certain compounds of the sixteenth embodiment are provided in which B is O. In other compounds of the sixteenth embodiment B is N(H).

In a seventeenth embodiment of the invention, compounds of embodiment one are provided which are selected from the group consisting of:

1-(6-(3-((4-(1-propionylpiperidin-4-yl)phenoxy)methyl)thiophen-2-yl)pyridin-2-yl)-5-(trifluoromethyl)-1H-pyrazole-4-carboxylic acid;

1-(6-(3-((4-(1-propionylpiperidin-4-yl)phenoxy)methyl)-4-(trifluoromethyl)thiophen-2-yl)pyridin-2-yl)-5-(trifluoromethyl)-1H-pyrazole-4-carboxylic acid;

1-(6-(3-((4-(1-(methoxycarbonyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)phenoxy)methyl)thiophen-2-yl)pyridin-2-yl)-5-(trifluoromethyl)-1H-pyrazole-4-carboxylic acid;

1-(6-(3-((2-methyl-4-(1-propionylpiperidin-4-yl)phenoxy)methyl)-4-(trifluoromethyl)thiophen-2-yl)pyridin-2-yl)-5-(trifluoromethyl)-1H-pyrazole-4-carboxylic acid;

1-(6-(3-((2-methyl-4-(1-propionylpiperidin-4-yl)phenoxy)methyl)thiophen-2-yl)pyridin-2-yl)-5-(trifluoromethyl)-1H-pyrazole-4-carboxylic acid;

1-(6-(3-((4-(1-(methoxycarbonyl)piperidin-4-yl)-2-methylphenoxy)methyl)-5-methylthiophen-2-yl)pyridin-2-yl)-5-(trifluoromethyl)-1H-pyrazole-4-carboxylic acid;

1-(6-(3-((2,6-dimethyl-4-(1-propionylpiperidin-4-yl)phenoxy)methyl)thiophen-2-yl)pyridin-2-yl)-5-(trifluoromethyl)-1H-pyrazole-4-carboxylic acid;

1-(6-(5-methyl-3-((4-(1-propionylpiperidin-4-yl)phenoxy)methyl)thiophen-2-yl)pyridin-2-yl)-5-(trifluoromethyl)-1H-pyrazole-4-carboxylic acid;

1-(6-(5-ethyl-3-((4-(1-(methoxycarbonyl)piperidin-4-yl)-2-methylphenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-4-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-5-methylthiophen-2-yl)pyridin-2-yl)-5-(trifluoromethyl)-1H-pyrazole-4-carboxylic acid;

1-(3-(3-((4-(1-(cyclopropanecarbonyl)piperidin-4-yl)-2-methylphenoxy)methyl)thiophen-2-yl)phenyl)-5-(trifluoromethyl)-1H-pyrazole-4-carboxylic acid;

1-(6-(3-((4-(1-(cyclopropanecarbonyl)piperidin-4-yl)-2,3-dimethylphenoxy)methyl)thiophen-2-yl)pyridin-2-yl)-5-(trifluoromethyl)-1H-pyrazole-4-carboxylic acid;

1-(6-(5-chloro-3-((4-(1-(cyclopropanecarbonyl)piperidin-4-yl)-2-methylphenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methoxyphenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-methoxyphenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-ethylphenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-5-cyclopropylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-4,5-dimethylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)thiophen-2-yl)pyridin-2-yl)-5-ethyl-1H-pyrazole-4-carboxylic acid;

1-(6-(3-((4-(1-(cyclopropanecarbonyl)-2,2,6,6-tetramethylpiperidin-4-yl)-2-methylphenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-ethylphenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-isopropylphenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-fluorophenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-fluorophenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-ethylphenoxy)methyl)-5-methylthiophen-2-yl)pyridin-2-yl)-5-(trifluoromethyl)-1H-pyrazole-4-carboxylic acid;

1-(6-(5-methyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(5-ethyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(4-ethyl-5-methyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(3-((2-chloro-4-(1-propionylpiperidin-4-yl)phenoxy)methyl)thiophen-2-yl)pyridin-2-yl)-5-(trifluoromethyl)-1H-pyrazole-4-carboxylic acid;

1-(6-(3-((2-chloro-4-(1-(cyclopropanecarbonyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)thiophen-2-yl)pyridin-2-yl)-5-methyl-1H-pyrazole-4-carboxylic acid;

1-(6-(3-((4-(1-(cyclopropanecarbonyl)piperidin-4-yl)-3-ethylphenoxy)methyl)thiophen-2-yl)pyridin-2-yl)-5-methyl-1H-pyrazole-4-carboxylic acid;

1-(6-(3-((4-(1-(cyclopropanecarbonyl)piperidin-4-yl)-3-ethylphenoxy)methyl)thiophen-2-yl)pyridin-2-yl)-5-ethyl-1H-pyrazole-4-carboxylic acid;

1-(6-(3-((4-(1-(cyclopropanecarbonyl)piperidin-4-yl)-2-methylphenoxy)methyl)-5-methylthiophen-2-yl)pyridin-2-yl)-5-methyl-1H-pyrazole-4-carboxylic acid;

1-(6-(3-((4-(1-(cyclopropanecarbonyl)piperidin-4-yl)-3-ethylphenoxy)methyl)-5-methylthiophen-2-yl)pyridin-2-yl)-5-methyl-1H-pyrazole-4-carboxylic acid;

1-(6-(3-((4-(1-(cyclopropanecarbonyl)piperidin-4-yl)-3-ethylphenoxy)methyl)-4-methylthiophen-2-yl)pyridin-2-yl)-5-(trifluoromethyl)-1H-pyrazole-4-carboxylic acid 1-(6-(3-((4-(1-(cyclopropanecarbonyl)piperidin-4-yl)-2-methylphenoxy)methyl)-4,5-dimethylthiophen-2-yl)pyridin-2-yl)-5-ethyl-1H-pyrazole-4-carboxylic acid;

1-(6-(3-(((5-methyl-2-(pyridin-2-ylmethyl)-1,2,3,4-tetrahydroisoquinolin-6-yl)oxy)methyl)thiophen-2-yl)pyridin-2-yl)-5-(trifluoromethyl)-1H-pyrazole-4-carboxylic acid;

1-(3-(3-(1-(4-(1-(cyclopropanecarbonyl)piperidin-4-yl)-2-methylphenoxy)ethyl)thiophen-2-yl)phenyl)-5-(trifluoromethyl)-1H-pyrazole-4-carboxylic acid;

1-(6-(3-((4-(1-(2-cyclopropylacetyl)piperidin-4-yl)-2-methylphenoxy)methyl)thiophen-2-yl)pyridin-2-yl)-5-(trifluoromethyl)-1H-pyrazole-4-carboxylic acid;

1-(6-(3-((4-(1-(cyclobutanecarbonyl)piperidin-4-yl)-2-methylphenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)thiophen-2-yl)pyridin-2-yl)-5-(trifluoromethyl)-1H-pyrazole-4-carboxylic acid;

(±)-1-(6-(3-((2-methyl-4-(1-(tetrahydrofuran-3-carbonyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(2-cyclopropylacetyl)piperidin-4-yl)-3-ethylphenoxy)methyl)-5-methylthiophen-2-yl)pyridin-2-yl)-5-(trifluoromethyl)-1H-pyrazole-4-carboxylic acid;

1-(6-(3-((4-(1-(3-hydroxycyclobutanecarbonyl)piperidin-4-yl)-2-methylphenoxy)methyl)thiophen-2-yl)pyridin-2-yl)-5-(trifluoromethyl)-1H-pyrazole-4-carboxylic acid;

(±)-1-(6-(3-((4-(1-(2,2-dimethyl-1,3-dioxolane-4-carbonyl)piperidin-4-yl)-2-methylphenoxy)methyl)thiophen-2-yl)pyridin-2-yl)-5-(trifluoromethyl)-1H-pyrazole-4-carboxylic acid;

1-(6-(3-((2-methyl-4-(1-(oxetane-3-carbonyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(2-cyclopropylacetyl)piperidin-4-yl)-3-ethylphenoxy)methyl)-5-methylthiophen-2-yl)pyridin-2-yl)-5-methyl-1H-pyrazole-4-carboxylic acid;

(S)-1-(6-(3-((3-ethyl-4-(1-(2-hydroxypropanoyl)piperidin-4-yl)phenoxy)methyl)-5-methylthiophen-2-yl)pyridin-2-yl)-5-(trifluoromethyl)-1H-pyrazole-4-carboxylic acid;

1-(6-(3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(2,2,2-Trifluoroethyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(cyclopropylmethyl)piperidin-4-yl)-2-methylphenoxy)methyl)thiophen-2-yl)pyridin-2-yl)-5-(trifluoromethyl)-1H-pyrazole-4-carboxylic acid;

1-(6-(3-(((4-(1-(cyclopropanecarbonyl)piperidin-4-yl)-2-methylphenyl)amino)methyl)thiophen-2-yl)pyridin-2-yl)-5-methyl-1H-pyrazole-4-carboxylic acid;

1-(6-(3-(((4-(1-(cyclopropanecarbonyl)piperidin-4-yl)-2-methylphenyl)amino)methyl)thiophen-2-yl)pyridin-2-yl)-5-(trifluoromethyl)-1H-pyrazole-4-carboxylic acid;

1-(6-(3-(((4-(1-(cyclopropanecarbonyl)piperidin-4-yl)-2-methylphenyl)amino)methyl)-5-methylthiophen-2-yl)pyridin-2-yl)-5-methyl-1H-pyrazole-4-carboxylic acid;

1-(6-(3-(((4-(1-(cyclopropanecarbonyl)piperidin-4-yl)phenyl)amino)methyl)-5-methylthiophen-2-yl)pyridin-2-yl)-5-methyl-1H-pyrazole-4-carboxylic acid;

1-(6-(3-((4-(1-(cyclopropanecarbonyl)piperidin-4-yl)-2-methylphenoxy)methyl)-4-ethyl-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-4-isopropyl-5-methylthiophen-2-yl)pyridin-2-yl)-5-(trifluoromethyl)-1H-pyrazole-4-carboxylic acid;

5-ethyl-1-(6-(5-methyl-3-((2-methyl-4-(1-(2,2,2-trifluoroethyl)piperidin-4-yl)phenoxy)methyl)thiophen-2-yl)pyridin-2-yl)-1H-pyrazole-4-carboxylic acid;

1-(6-(4,5-dimethyl-3-((2-methyl-4-(1-(2,2,2-trifluoroethyl)piperidin-4-yl)phenoxy)methyl)thiophen-2-yl)pyridin-2-yl)-5-ethyl-1H-pyrazole-4-carboxylic acid;

1-(6-(3-(((4-(1-(cyclopropanecarbonyl)piperidin-4-yl)-2-methylphenyl)amino)methyl)-4-methylthiophen-2-yl)pyridin-2-yl)-5-(trifluoromethyl)-1H-pyrazole-4-carboxylic acid;

1-(6-(3-(((4-(1-(cyclopropanecarbonyl)piperidin-4-yl)phenyl)amino)methyl)-4-methylthiophen-2-yl)pyridin-2-yl)-5-(trifluoromethyl)-1H-pyrazole-4-carboxylic acid;

1-(6-(3-(((4-(1-(cyclopropanecarbonyl)piperidin-4-yl)-2-methylphenyl)amino)methyl)-4,5-dimethylthiophen-2-yl)pyridin-2-yl)-5-ethyl-1H-pyrazole-4-carboxylic acid;

1-(6-(5-methyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-5-ethylthiophen-2-yl)pyridin-2-yl)-5-(trifluoromethyl)-1H-pyrazole-4-carboxylic acid;

1-(6-(3-(((2-(pyridin-2-ylmethyl)-1,2,3,4-tetrahydroisoquinolin-6-yl)oxy)methyl)thiophen-2-yl)pyridin-2-yl)-5-(trifluoromethyl)-1H-pyrazole-4-carboxylic acid;

1-(6-(3-(((4-(1-(cyclopropanecarbonyl)piperidin-4-yl)-3-ethylphenyl)amino)methyl)-5-methylthiophen-2-yl)pyridin-2-yl)-5-(trifluoromethyl)-1H-pyrazole-4-carboxylic acid;

1-(6-(3-(4-(1-(cyclopropanecarbonyl)piperidin-4-yl)-2-methylphenethyl)-5-methylthiophen-2-yl)pyridin-2-yl)-5-(trifluoromethyl)-1H-pyrazole-4-carboxylic acid;

1-(6-(3-(4-(1-(cyclopropanecarbonyl)piperidin-4-yl)-2-methylphenethyl)thiophen-2-yl)pyridin-2-yl)-5-(trifluoromethyl)-1H-pyrazole-4-carboxylic acid;

1-(6-(3-(4-(1-(cyclopropanecarbonyl) piperidin-4-yl)phenethyl)thiophen-2-yl)pyridin-2-yl)-5-(trifluoromethyl)-1H-pyrazole-4-carboxylic acid;

1-(6-(3-(((4-(1-(cyclopropanecarbonyl)piperidin-4-yl)phenyl)amino)methyl)thiophen-2-yl)pyridin-2-yl)-5-(trifluoromethyl)-1H-pyrazole-4-carboxylic acid;

1-(6-(3-((2-methyl-4-(1-(oxetan-3-yl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-(hydroxymethyl)phenoxy)methyl)-5-methylthiophen-2-yl)pyridin-2-yl)-5-(trifluoromethyl)-1H-pyrazole-4-carboxylic acid;

1-(6-(3-((4-(1-propionylpiperidin-4-yl)benzyl)oxy)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-(trifluoromethyl)phenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-(trifluoromethyl)phenoxy)methyl)thiophen-2-yl)pyridin-2-yl)-5-(trifluoromethyl)-1H-pyrazole-4-carboxylic acid;

1-(6-(3-((4-(1-propionylpiperidin-4-yl)-2-(trifluoromethyl)phenoxy)methyl)thiophen-2-yl)pyridin-2-yl)-5-(trifluoromethyl)-1H-pyrazole-4-carboxylic acid;

1-(6-(4-cyclopropyl-5-methyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-2-methylphenoxy)methyl)-5-isopropylthiophen-2-yl)pyridin-2-yl)-5-(trifluoromethyl)-1H-pyrazole-4-carboxylic acid;

1-(6-(5-isopropyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylic acid;

1-(6-(3-((2-methyl-4-(1-propionylpiperidin-4-yl)phenoxy)methyl)-5-propylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-methylphenoxy)methyl)-5-methylthiophen-2-yl)pyridin-2-yl)-5-(trifluoromethyl)-1H-pyrazole-4-carboxylic acid;

1-(6-(3-((4-(1-(cyclopropanecarbonyl)piperidin-4-yl)-3-methylphenoxy)methyl)thiophen-2-yl)pyridin-2-yl)-5-(trifluoromethyl)-1H-pyrazole-4-carboxylic acid;

(+)-trans-1-(6-(3-((4-((3,4)-1-(cyclopropanecarbonyl)-3-hydroxypiperidin-4-yl)phenoxy)methyl)-5-methylthiophen-2-yl)pyridin-2-yl)-5-(trifluoromethyl)-1H-pyrazole-4-carboxylic acid;

1-(6-(3-((4-(1-(dimethylcarbamoyl)piperidin-4-yl)-3-ethylphenoxy)methyl)-5-methylthiophen-2-yl)pyridin-2-yl)-5-(trifluoromethyl)-1H-pyrazole-4-carboxylic acid;

1-(6-(3-((4-(1-(dimethylcarbamoyl)piperidin-4-yl)-3-ethylphenoxy)methyl)-5-methylthiophen-2-yl)pyridin-2-yl)-5-methyl-1H-pyrazole-4-carboxylic acid;

1-(3-(3-(1-((4-(1-(cyclopropanecarbonyl)piperidin-4-yl)-2-methylphenyl)amino)ethyl)thiophen-2-yl)phenyl)-5-(trifluoromethyl)-1H-pyrazole-4-carboxylic acid;

1-(6-(3-(((5-(1-(Cyclopropanecarbonyl)piperidin-4-yl)pyridin-2-yl)oxy)methyl)thiophen-2-yl)pyridin-2-yl)-5-(trifluoromethyl)-1H-pyrazole-4-carboxylic acid;

1-(6-(4-methyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(3-((3-Ethyl-4-(1-(3-hydroxy-2,2-dimethylpropanoyl)piperidin-4-yl)phenoxy)methyl)-5-methylthiophen-2-yl)pyridin-2-yl)-5-(trifluoromethyl)-1H-pyrazole-4-carboxylic acid;

1-(6-(3-((3-Ethyl-4-(1-(2-hydroxyacetyl)piperidin-4-yl)phenoxy)methyl)-5-methylthiophen-2-yl)pyridin-2-yl)-5-(trifluoromethyl)-1H-pyrazole-4-carboxylic acid;

1-(6-(3-((4-(1-(Cyclopropanecarbonyl)piperidin-4-yl)-2-methylphenoxy)methyl)-4-ethylthiophen-2-yl)pyridin-2-yl)-5-(trifluoromethyl)-1H-pyrazole-4-carboxylic acid;

1-(6-(4,5-Dimethyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(4-Ethyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(4-Methyl-3-(((2-methyl-4-(1-(2,2,2-trifluoroethyl)piperidin-4-yl)phenyl)amino)methyl)thiophen-2-yl)pyridin-2-yl)-5-(trifluoromethyl)-1H-pyrazole-4-carboxylic acid;

1-(6-(3-((4-(1-(Cyclopropanecarbonyl)piperidin-4-yl)-3-ethylphenoxy)methyl)-5-methylthiophen-2-yl)pyridin-2-yl)-5-ethyl-1H-pyrazole-4-carboxylic acid;

1-(6-(3-((4-(1-(Cyclopropanecarbonyl)piperidin-4-yl)-2-methylphenoxy)methyl)-5-methylthiophen-2-yl)pyridin-2-yl)-5-ethyl-1H-pyrazole-4-carboxylic acid;

(±)-trans-1-(6-(3-((4-(1-(Cyclopropanecarbonyl)-3-hydroxypiperidin-4-yl)phenoxy)methyl)-5-methylthiophen-2-yl)pyridin-2-yl)-5-(trifluoromethyl)-1H-pyrazole-4-carboxylic acid;

1-(6-(3-((4-(1-(Cyclopropanecarbonyl)piperidin-4-yl)-3-cyclopropylphenoxy)methyl)-5-methylthiophen-2-yl)pyridin-2-yl)-5-(trifluoromethyl)-1H-pyrazole-4-carboxylic acid;

1-(6-(3-((4-(1-(Cyclopropanecarbonyl)piperidin-4-yl)-3-ethyl-2-fluorophenoxy)methyl)-5-methylthiophen-2-yl)pyridin-2-yl)-5-(trifluoromethyl)-1H-pyrazole-4-carboxylic acid;

1-(6-(3-(((6-(1-(Cyclopropanecarbonyl)piperidin-4-yl)-5-ethylpyridin-3-yl)oxy)methyl)-5-methylthiophen-2-yl)pyridin-2-yl)-5-(trifluoromethyl)-1H-pyrazole-4-carboxylic acid;

1-(6-(3-((4-(1-(Cyclopropanecarbonyl)piperidin-4-yl)-3-propylphenoxy)methyl)-5-methylthiophen-2-yl)pyridin-2-yl)-5-(trifluoromethyl)-1H-pyrazole-4-carboxylic acid;

1-(6-(3-(((4-(1-(Cyclopropanecarbonyl)piperidin-4-yl)-3-ethylphenyl)amino)methyl)-5-methylthiophen-2-yl)pyridin-2-yl)-5-ethyl-1H-pyrazole-4-carboxylic acid;

1-(6-(3-(((4-(1-(Cyclopropanecarbonyl)piperidin-4-yl)-3-ethylphenyl)amino)methyl)-4-(trifluoromethyl)thiophen-2-yl)pyridin-2-yl)-5-ethyl-1H-pyrazole-4-carboxylic acid;

tert-Butyl 4-(6-((2-(6-(4-(ethoxycarbonyl)-5-(trifluoromethyl)-1H-pyrazol-1-yl)pyridin-2-yl)-5-methylthiophen-3-yl)methoxy)-2-ethylpyridin-3-yl)piperidine-1-carboxylate;

1-(6-(5-Isopropyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid;

1-(6-(3-((2-Methyl-4-(1-(2,2,2-trifluoroethyl)piperidin-4-yl)phenoxy)methyl)-5-propylthiophen-2-yl)pyridin-2-yl)-5-(trifluoromethyl)-1H-pyrazole-4-carboxylic acid;

(±)-1-(6-(3-((2-Methyl-4-(1-(pyrrolidine-3-carbonyl)piperidin-4-yl)phenoxy)methyl)thiophen-2-yl)pyridin-2-yl)-5-(trifluoromethyl)-1H-pyrazole-4-carboxylic acid;

1-(6-(3-((4-(1-(Azetidine-3-carbonyl)piperidin-4-yl)-2-methylphenoxy)methyl)thiophen-2-yl)pyridin-2-yl)-5-(trifluoromethyl)-1H-pyrazole-4-carboxylic acid;

(±)-1-(6-(3-((4-(1-(2,3-Ddihydroxypropanoyl)piperidin-4-yl)-3-ethylphenoxy)methyl)-5-methylthiophen-2-yl)pyridin-2-yl)-5-(trifluoromethyl)-1H-pyrazole-4-carboxylic acid;

1-(6-(3-(4-(1-(Cyclopropanecarbonyl)piperidin-4-yl)-2-methylphenethyl)-5-methylthiophen-2-yl)pyridin-2-yl)-5-ethyl-1H-pyrazole-4-carboxylic acid;

1-(6-(3-(4-(1-(tert-Butoxycarbonyl)piperidin-4-yl)-2-methylphenethyl)-5-methylthiophen-2-yl)pyridin-2-yl)-5-(trifluoromethyl)-1H-pyrazole-4-carboxylic acid;

and pharmaceutically acceptable salts thereof.

In an eighteenth embodiment, the present invention relates to a method of treating or preventing glaucoma or reducing intraocular pressure comprising administering to a subject in need thereof a sGC activator selected from the compounds of any one of embodiments one to seventeen. The invention has surprisingly shown that administration of sGC activators to a patient in need of therapy has desirable sustained efficacy in reducing IOP and in the treatment of glaucoma.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Depending on the choice of the starting materials and procedures, the compounds can be present in the form of one of the possible isomers or as mixtures thereof, for example as pure optical isomers, or as isomer mixtures, such as racemates and diastereomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, $^{2}H$, $^{3}H$, $^{11}C$, $^{13}C$, $^{14}C$, $^{15}N$, $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, activation of soluble guanylate cyclase activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by activation of sGC, or (ii) associated with decreased sGC activity, or (iii) characterized by activity (normal or abnormal) of sGC. In another non-limiting embodiment, the term "a therapeutically effective amount" refers to the amount of the compound of the present invention that, when administered to a cell, or a tissue, or a non-cellular biological material, or a medium, is effective to at least partially increasing the activity of sGC.

As used herein, the term "subject" refers to an animal. Typically the animal is a mammal. A subject also refers to for example, primates (e.g., humans, male or female), cows, sheep, goats, horses, dogs, cats, rabbits, rats, mice, and the like. In certain embodiments, the subject is a primate. In yet other embodiments, the subject is a human. In certain other embodiments, the compounds of the invention may be suitable for use in the treatment of glaucoma or reduction of IOP in dogs.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "activate", "activation" or "activating" refers to the significant increase in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra General Synthetic Aspects The following Examples serve to illustrate the invention without limiting the scope thereof.

Typically, the compounds of formula (I) can be prepared according to the Schemes provided below.

Compounds such as 1-3; wherein $R^a$ is $C_1$-$C_4$ alkyl (preferably methyl or ethyl), $R^b$ is $R^a$ or trifluoromethyl, $W^a$ is CH or N, and $X^a$ is Cl or Br; can be prepared according to Scheme 1.

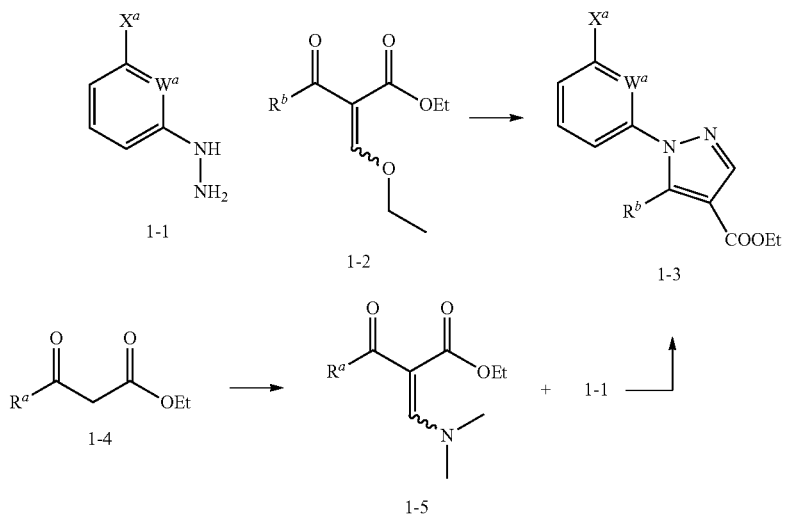

Scheme 1

Aryl hydrazines 1-1 and beta-ketoester derivatives 1-2 can be reacted in an alcoholic solvent such as EtOH at temperatures between room temperature and at reflux to provide the pyrazole derivatives 1-3. Alternatively, the beta-ketoester derivatives 1-5 can be prepared by a reaction of the corresponding beta-ketoesters 1-4 with dimethylformamide dimethyl acetal at room temperature. Reaction with 1-5 and 1-1 to afford 1-3 can be achieved by applying the similar condition described above for the reaction with 1-2.

Compounds such as 2-5; wherein $R^{c-1}$ is H, F, $R^a$, $C_1$-$C_4$ alkoxy, or hydroxymethyl; $R^{c-2}$ is $R^b$, hydrogen, $C_1$-$C_4$ alkoxy, or fluorine; and $R^d$ is hydrogen or methyl; $R^w$ is C(O)-Et, —C(O)-cPr; and $R^e$ is —CO-Et, —CO-cPr, or Boc; can be synthesized according to Scheme 2

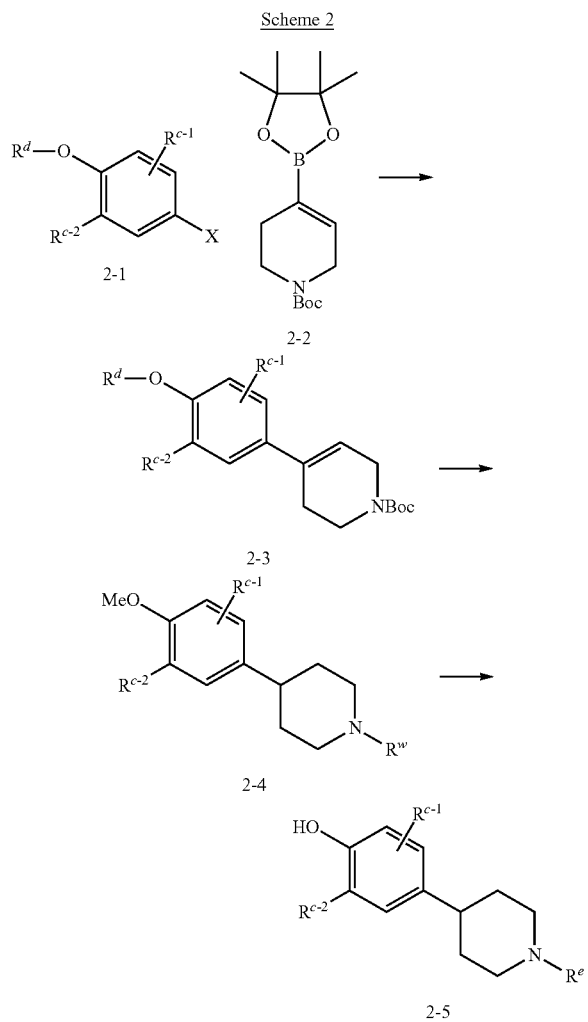

2-1 can be transformed to 2-3 utilizing a Suzuki-type coupling with boronate 2-2. 2-3, when $R^d$=Me, can be transformed into 2-4 via hydrogenation over catalysts such as Pd/C or platinum oxide, followed by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine). 2-4 can be transformed into 2-5 via treatment with boron tribromide in the appropriate solvent such as dichloromethane at low temperatures. Alternatively 2-3 when $R^d$=H can be directly converted to 2-5 ($R^e$=Boc) by hydrogenation over catalysts such as Pd/C or platinum oxide, or 2-3 when $R^d$=H can be directly converted to 2-5 ($R^e$=$R^w$) by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine) followed by treatment with MeOH in the presence of $K_2CO_3$.

Compounds such as 3-3 can be prepared according to Scheme 3.

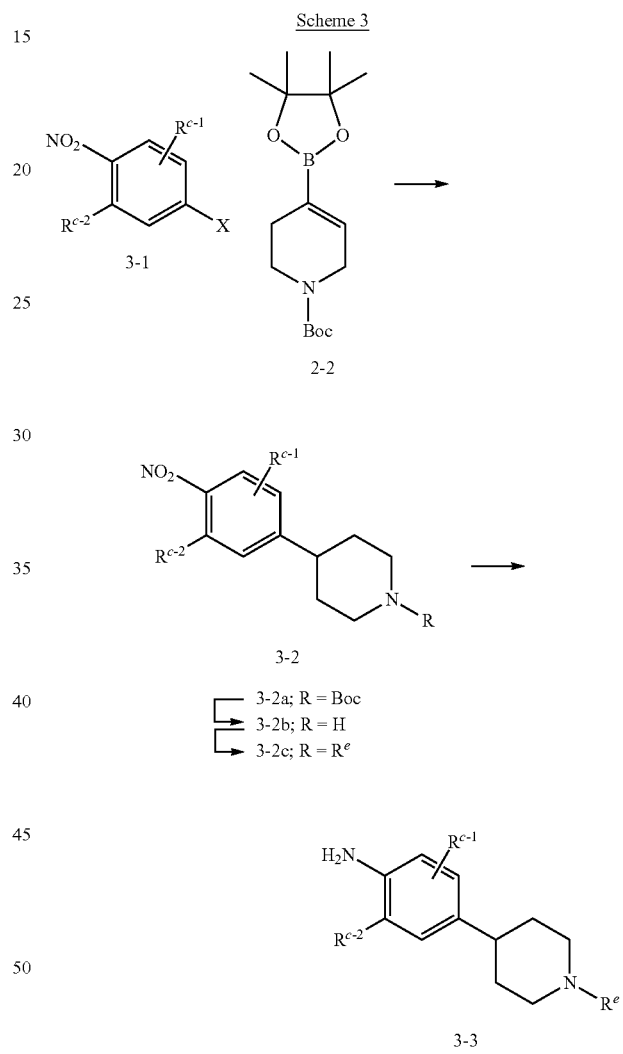

Transformation of 3-1 to 3-2 can be accomplished via Suzuki-type coupling with boronates of type 2-2. When R=Boc (i.e., 3-2a) can be converted to 3-2c, when necessary, by treatment with acids such as TFA in an appropriate solvent such as $CH_2Cl_2$, followed by reaction with acid anhydrides such as propionic anhydride or acid chlorides such as cyclopropylcarbonyl chloride. Catalytic hydrogenation of compounds such type 3-2 over Pd/C in appropriate solvents such as EtOH can furnish compounds of type 3-3.

Compounds such as 4-4 and 4-6 wherein $R^f$ is H, Me or Et; and $R^g$ is H or Me or $CF_3$; can be prepared according to Scheme 4.

Scheme 4

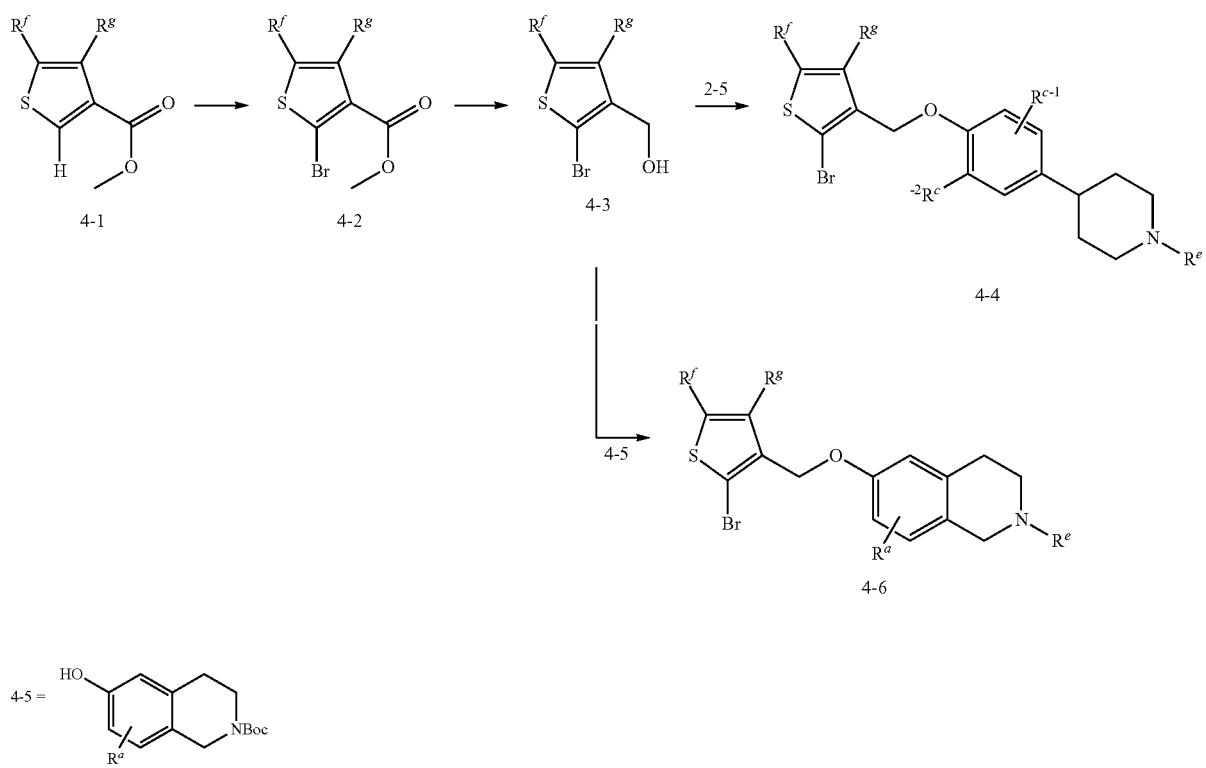

Bromination of 4-1 with NBS in appropriate solvents such as DMF can afford 4-2. The ester 4-2 can then be reduced by reducing reagents such as LiAlH$_4$ in THF at temperatures between 0° C. to room temperature, or LiBH$_4$ in suitable solvents such as THF in temperatures between room temperature to 70° C. The generated alcohol of 4-3 can then be reacted with a wide variety of phenol derivatives such as 2-5, or 6-hydroxytetrahydroisoquinoline derivatives 4-5 by employing PPh$_3$ and DIAD in suitable solvents such as THF at temperatures between 0° C. to room temperature to afford 4-4 or 4-6 respectively. In some instances, treatment of 4-3 with MsCl in the presence of base preferably DIPEA in CH$_2$Cl$_2$, followed by the reaction with 2-5, or 4-5 can also afford 4-4 or 4-6 respectively.

In certain compounds of the invention, such as 5-6, R$^a$ is preferably selected from the group consisting of methyl, ethyl, n-propyl, cyclopropyl, or 2-propyl; and R$^a$ can be selected independently at each occurrence in 5-6 from the list provided supra and said compound can be prepared according to Scheme 5.

Scheme 5

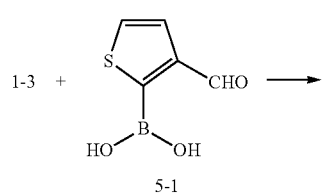

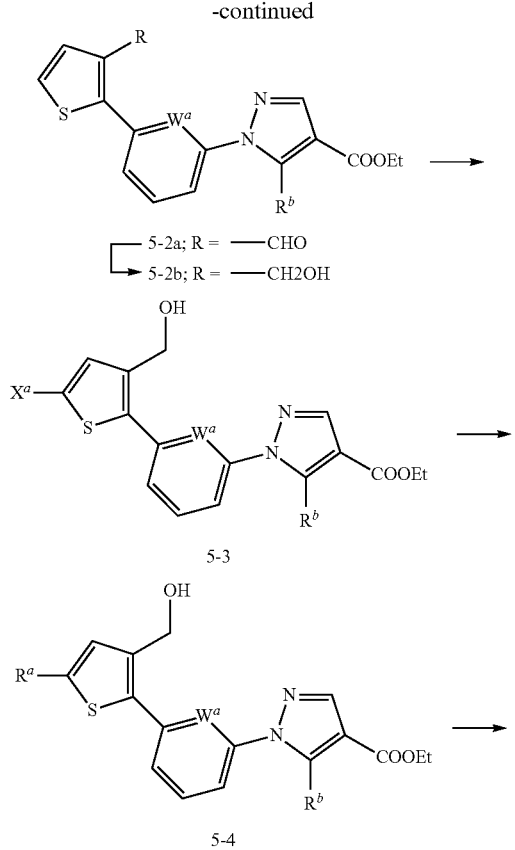

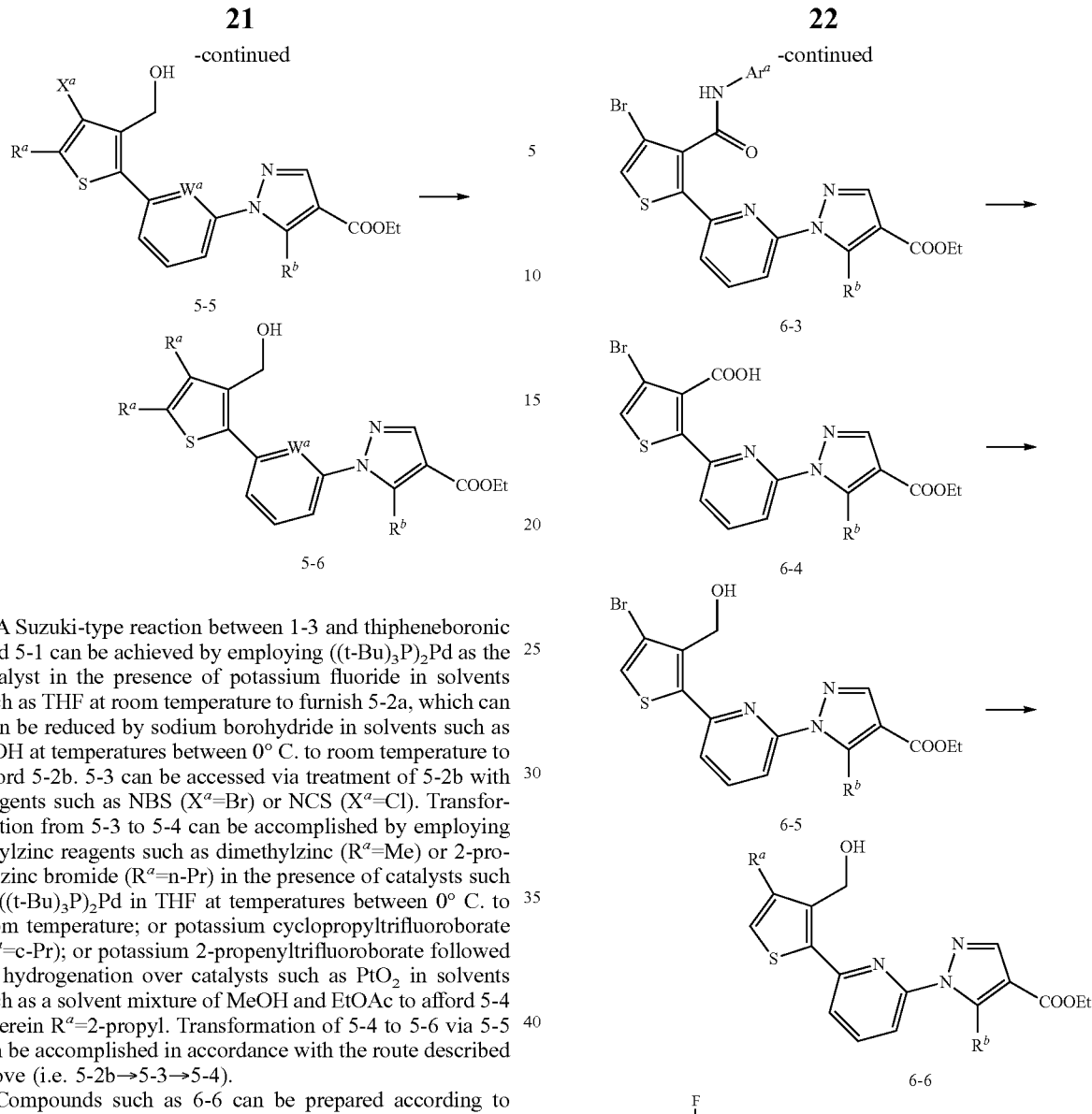

A Suzuki-type reaction between 1-3 and thipheneboronic acid 5-1 can be achieved by employing ((t-Bu)$_3$P)$_2$Pd as the catalyst in the presence of potassium fluoride in solvents such as THF at room temperature to furnish 5-2a, which can then be reduced by sodium borohydride in solvents such as EtOH at temperatures between 0° C. to room temperature to afford 5-2b. 5-3 can be accessed via treatment of 5-2b with reagents such as NBS (X$^a$=Br) or NCS (X$^a$=Cl). Transformation from 5-3 to 5-4 can be accomplished by employing alkylzinc reagents such as dimethylzinc (R$^a$=Me) or 2-propylzinc bromide (R$^a$=n-Pr) in the presence of catalysts such as ((t-Bu)$_3$P)$_2$Pd in THF at temperatures between 0° C. to room temperature; or potassium cyclopropyltrifluoroborate (R$^a$=c-Pr); or potassium 2-propenyltrifluoroborate followed by hydrogenation over catalysts such as PtO$_2$ in solvents such as a solvent mixture of MeOH and EtOAc to afford 5-4 wherein R$^a$=2-propyl. Transformation of 5-4 to 5-6 via 5-5 can be accomplished in accordance with the route described above (i.e. 5-2b→5-3→5-4).

Compounds such as 6-6 can be prepared according to Scheme 6.

Scheme 6

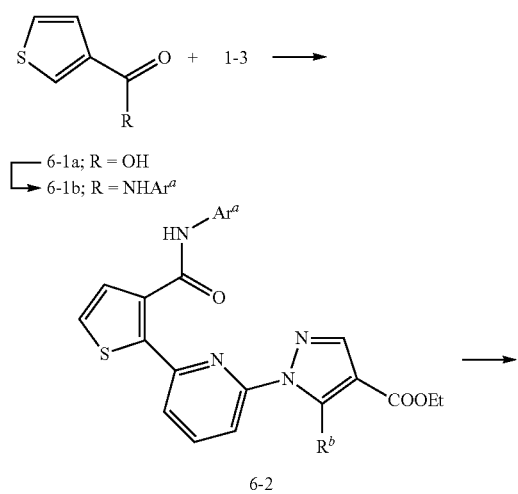

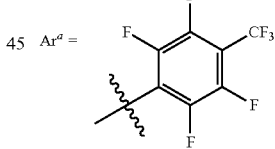

3-Thiophenecarboxylic acid 6-1a can be condensed with 2,3,5,6-tetrafluoro-4-(trifluoromethyl)aniline in the presence of T3P and bases such as DIPEA in solvents such as DMF at elevated temperature preferably 100° C. to afford the corresponding amide 6-1b. Reaction between 6-1b and 1-3 (wherein W$^a$=N) can be accomplished by employing Pd(OAc)$_2$, Cs$_2$CO$_3$, and triphenylphosphine in solvents preferably toluene at elevated temperature preferably 100° C. to afford 6-2. Bromination of 6-2 can be achieved by NBS in the presence of base such as potassium acetate and catalysts preferably bis[(pentamethylcyclopentadienyl)dichloro-rhodium] in solvents such as DCE at elevated temperatures such as 80° C. to furnish 6-3. Hydrolysis of the amide in 6-3 can occur at 70° C. in MsOH to afford 6-4. The carboxylic acid of 6-4 can then be reduced by employing BH$_3$ in THF to furnish 6-5. Transformation of the bromide of 6-5 to furnish compounds of type 6-6 can be achieved by a similar manner as described in Scheme 5 (i.e., 5-3→5-4).

Compounds such as 7a-2, 7b-3, 7b-5, and 7b-7 wherein $R^h$=H, $C_1$-$C_4$alkyl, or Cl; and $R^j$=H, $C_1$-$C_4$alkyl, or $CF_3$; can be prepared in accordance with Scheme 7a and Scheme 7b.

phosphorane in suitable solvents such as toluene at temperatures between 70° C. to 110° C. Alternatively, 7a-1 can be accessed by treatment of the hydroxymethylthiophene derivatives 5-2b, 5-3, 5-4, 5-6, or 6-6 with $CBr_4$ in the presence of $PPh_3$ in $CH_2Cl_2$ at temperatures between 0° C.

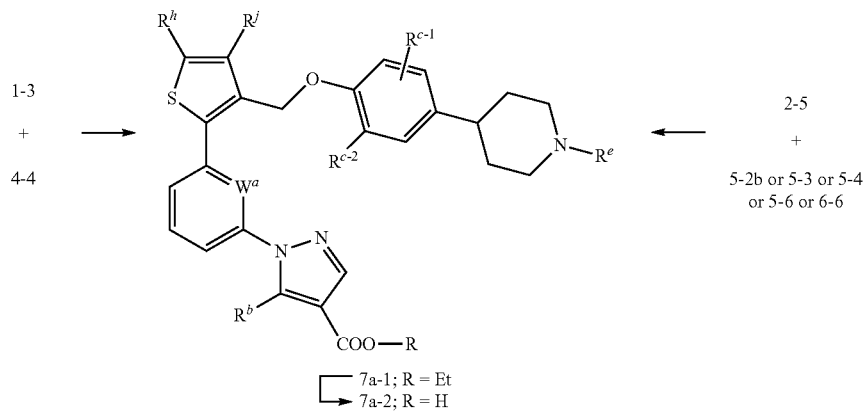

Scheme 7a

A Miyaura-type borylation of 1-3 with bis(pinacolato)diboron employing conditions such as Pd(OAc)$_2$, 2,2-dicyclohexylphosphino-2',4',6'-triisopropylbiphenyl and potassium acetate in dioxane at temperatures between 60° C. and 100° C. can provide corresponding boronic ester, which can then be reacted with one of 4-4 by a Suzuki-type reaction utilizing conditions such as Pd(dppf)Cl$_2$ in the presence of aqueous sodium carbonate in 1,4-dioxane at temperatures between 80° C. to 100° C. to afford 7a-1.

Alternatively, a reaction between phenols such as 2-5 and hydroxymethylthiophene derivatives such as 5-2b, 5-3, 5-4, 5-6, or 6-6 can furnish 7a-1 with conditions such as PPh$_3$ and DIAD in THF at temperatures between 0° C. and room temperature, or by employing tri-n-butyl cyanomethyleneand room temperature followed by treatment with phenol derivatives of type 2-5 and potassium carbonate in DMF; or treating the 5-2b, 5-3, 5-4, 5-6, or 6-6 with MsCl in the presence of suitable base such as DIPEA in $CH_2Cl_2$, followed by treatment with phenol derivatives of type 2-5 and potassium carbonate in DMF as the solvent.

Ester 7a-1 can then be saponified by employing a base, preferably LiOH, in a suitable solvent system, preferably a mixture THF, MeOH, and water, at temperatures ranging from room temperature to 60° C. to afford 7a-2.

7a-1, when $R^e$=Boc, can be further functionalized according to Scheme 7b.

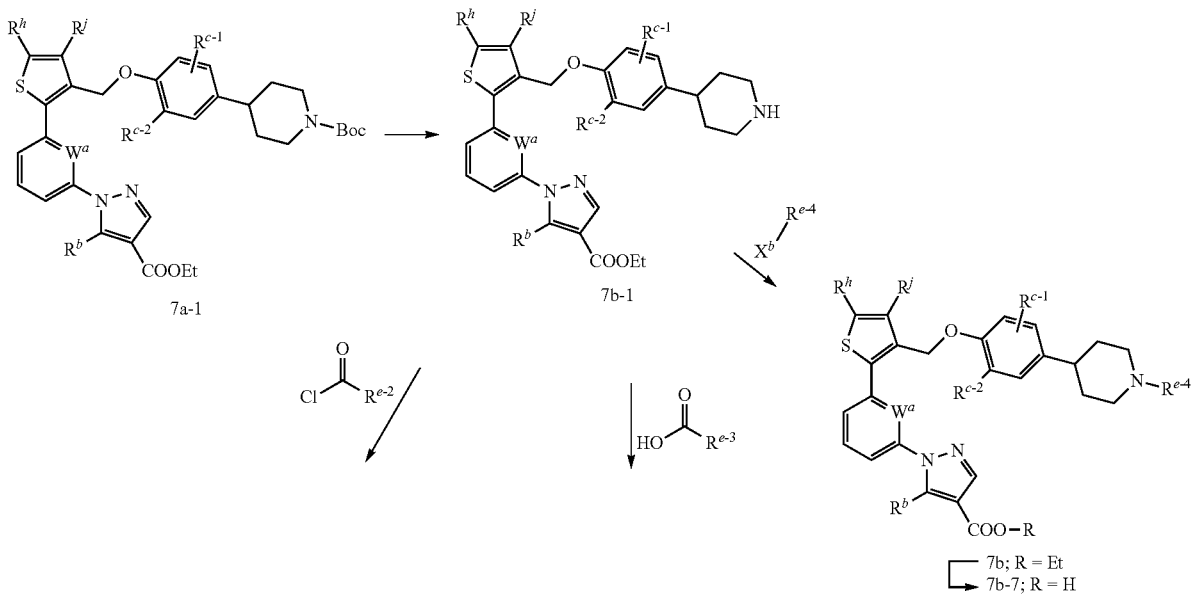

Scheme 7b

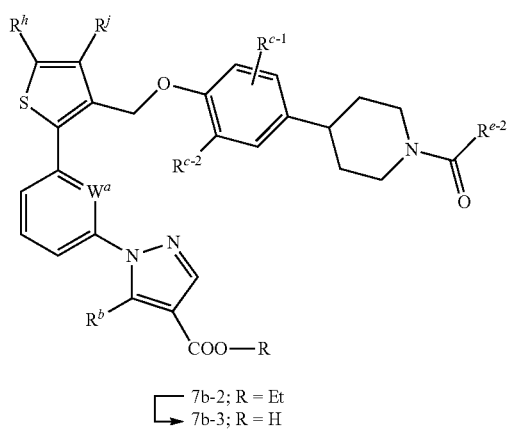
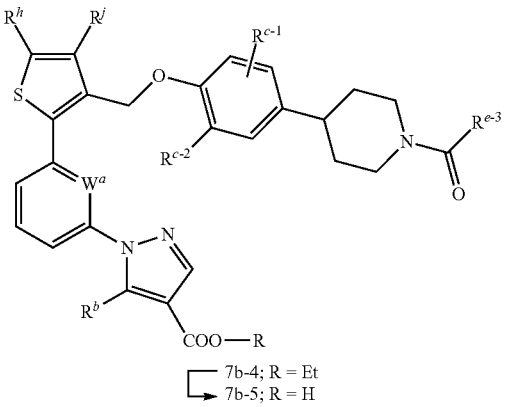

7b-2; R = Et
7b-3; R = H 7b-4; R = Et
7b-5; R = H

Treatment of 7a-1 with suitable acids such as TFA in solvents such as $CH_2Cl_2$ at temperatures between 0° C. to room temperature can provide 7b-1, which can then be transformed to 7b-2 by reactions with chloroformates such as methyl chloroformate ($R^{e-2}$=—OMe), or carbamic chlorides such as dimethylcarbamic chloride ($R^{e-2}$=—NMe$_2$) in the presence of a trialkylamine base. 7b-1 can be converted to 7b-4 by reaction with wide variety of carboxylic acids such as 2-cyclopropylacetic acid ($R^{e-3}$=—$CH_2$-cPr) or 2-hydroxypropanoic acid ($R^{e-3}$=—CH(OH)—$CH_3$) by employing peptide coupling methods of those are well known to those skilled in the art (e.g., HATU and DIPEA). Also, 7b-1 can be converted to 7b-6 by alkylation with electrophiles such as 2,2,2-trifluoroethyl trifluoromethanesulfonate ($R^{e-4}$=—$CH_2CF_3$ and $X^b$=OTf) or cyclopropylmethyl bromide ($R^{e-4}$=—$CH_2$-cPr and $X^b$=Br) in the presence of bases such as $K_2CO_3$ in solvents such as DMF at temperatures between room temperature to 100° C.

Lastly, saponification of 7b-2, 7b-4, or 7b-6 can be accomplished employing conditions such as aqueous LiOH in a solvent such as $CH_3CN$ or in a solvent mixture of MeOH and THF at temperatures between room temperature to 70° C. to afford 7b-3, 7b-5, or 7b-7 respectively.

Compounds such as 8-3 can be prepared according to Scheme 8.

Scheme 8

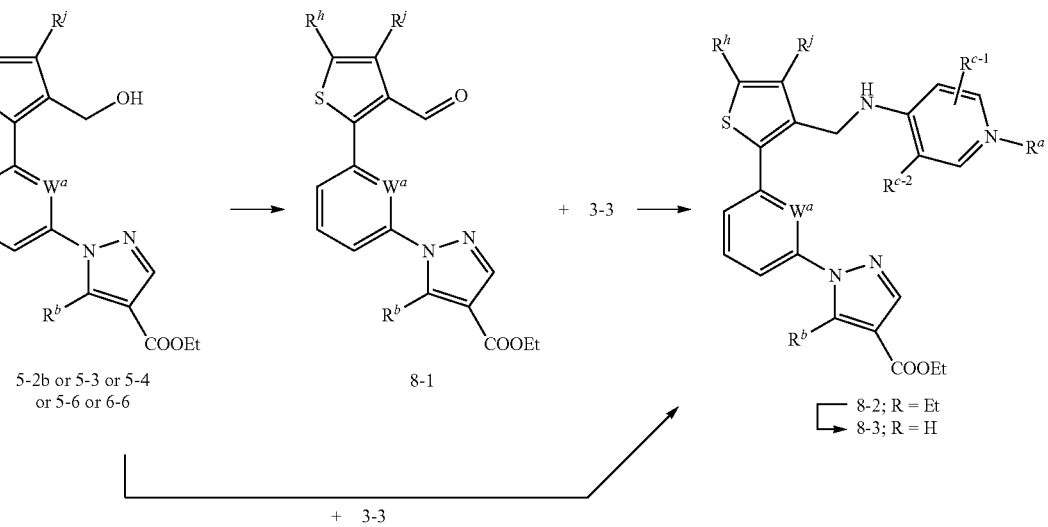

5-2b or 5-3 or 5-4
or 5-6 or 6-6

8-1

8-2; R = Et
8-3; R = H

The hydroxymethyl thiophene derivatives such as 5-2b, 5-3, 5-4, 5-6, or 6-6 can be transformed to corresponding aldehyde 8-1 by employing suitable oxidation reagents such as Dess-Martin periodinane in solvents such as $CH_2Cl_2$ at temperatures between 0° C. to room temperature. Aldehydes 8-1 can then be reacted with anilines 3-3 utilizing reductive amination conditions such as $NaB(OAc)_3H$ in AcOH at room temperature to afford 8-2. Alternatively, 8-2 can be accessible from the hydroxymethyl thiophene derivatives 5-2b, 5-3, 5-4, 5-6, or 6-6 employing $CBr_4$ in the presence of $PPh_3$, followed by addition of 3-3 and $K_2CO_3$ to afford 8-2. When the aniline, 3-3, employed possesses $R^e$=Boc the described sequences can afford 8-2 ($R^e$=Boc), which can then be further functionalized by treatment with an acid, preferably TFA, in solvents such as $CH_2Cl_2$ at temperatures between 0° C. to room temperature and the resulting piperidine amine can undergo reaction with a wide variety of carboxylic acids, such as cyclopropanecarboxylic acid, by employing peptide coupling methods of those that are well known to those skilled in the art (e.g., HATU and DIPEA) to afford 8-2 wherein $R^e = C_1\text{-}C_4$ alkyl or cycloalkyl. Lastly, hydrolysis of 8-2 can afford 8-3 by employing conditions such as aqueous LiOH in a solvent such as $CH_3CN$ or in a solvent mixture of MeOH and THF at temperatures between room temperature to 70° C.

Compounds such as 9-5 can be prepared according to Scheme 9.

are well known to those skilled in the art (e.g., HATU and DIPEA), the piperidine amine can undergo reaction with an acid chloride in the presence of a trialkylamine base, to afford 9-4 wherein $R^e = C_1\text{-}C_4$ alkyl or cycloalkyl. Lastly, hydrolysis of 9-4 can afford 9-5 by employing conditions such as aqueous LiOH in a solvent such as $CH_3CN$ or in a solvent mixture of MeOH and THF at temperatures between room temperature to 70° C.

Compounds such as 10-5 can be prepared according to Scheme 10.

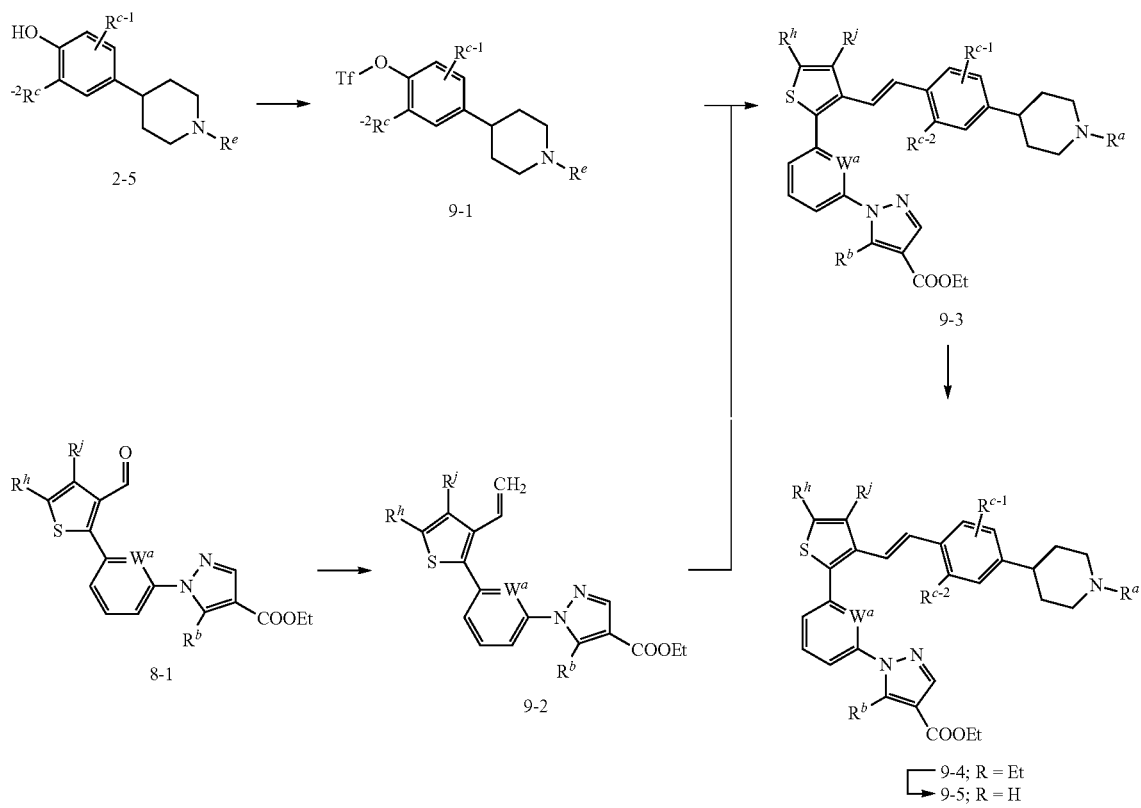

Phenol derivatives 2-5 can be converted to corresponding triflates employing triflic anhydride in the presence of a base such as pyridine in suitable solvents such as $CH_2Cl_2$ preferably at about 0° C. to afford 9-1. Compounds of type 9-2 can be synthesized by adding 8-1 to methyl triphenylphosphonium salt in the presence of a suitable base, such as LiHMDS, in an appropriate solvent, such as THF, at temperatures between 0° C. to room temperature. A Heck-type reaction between 9-1 and 9-2 can then be accomplished utilizing conditions such as $Pd(dppf)Cl_2$, tri(2-furyl)phosphine, and DIPEA in DMF at elevated temperature preferably 110° C. under microwave irradiation to afford 9-3. Subsequently, hydrogenation of 9-3 over catalysts such as Pd/C in suitable solvents such as MeOH can furnish 9-4. 9-4, when $R^e = $ Boc, can be further functionalized by treatment with an acid, preferably TFA, in solvents such as $CH_2Cl_2$ at temperatures between 0° C. to room temperature and the resulting piperidine amine can undergo reaction with a wide variety of carboxylic acids, such as cyclopropanecarboxylic acid, by employing peptide coupling methods of those that

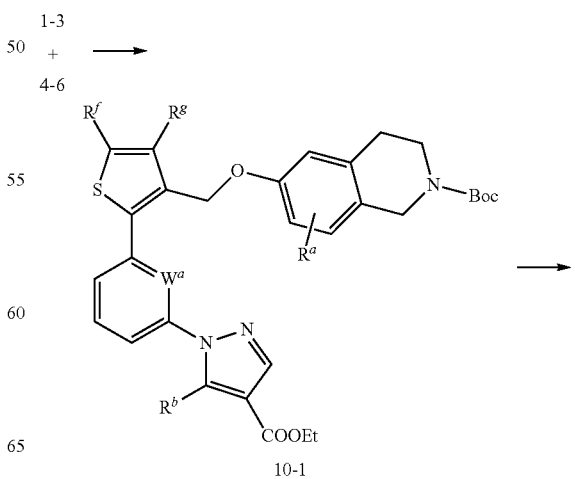

10-2

10-4; R = Et
10-5; R = H

A reaction between 1-3 and thiophene bromides such as 4-6 can be accomplished in a similar manner as described in Scheme 7a (1-3→7a-1) to afford 10-1. 10-1 can undergo treatment with suitable acids such as TFA in solvents such as $CH_2Cl_2$ at temperatures between 0° C. to room temperature to furnish 10-2. Reductive amination of 10-2 with 2-picolylaldehyde (10-3) can be achieved by employing conditions such as $NaB(OAc)_3H$ in a mixture of AcOH and MeOH to furnish compounds of type 10-4. Finally, hydrolysis of 10-4 can then provide 10-5 by employing conditions such as aqueous LiOH in a solvent such as $CH_3CN$ or in a solvent mixture of MeOH and THF at temperatures between room temperature to 70° C.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, topical administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
   a) diluents, e.g., lactose, dextrose, sucrose, mannitol, sorbitol, cellulose and/or glycine;
   b) lubricants, e.g., silica, talcum, stearic acid, its magnesium or calcium salt and/or polyethyleneglycol; for tablets also
   c) binders, e.g., magnesium aluminum silicate, starch paste, gelatin, tragacanth, methylcellulose, sodium carboxymethylcellulose and/or polyvinylpyrrolidone; if desired
   d) disintegrants, e.g., starches, agar, alginic acid or its sodium salt, or effervescent mixtures; and
   e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Compositions of the present invention may be utilized in various dosage regimens known to those of skill in the art. Such dosing frequency is maintained for a varying duration of time depending on the therapeutic regimen. The duration of a particular therapeutic regimen may vary from one-time dosing to a maintenance regimen that extends for a month, year or more. One of ordinary skill in the art would be familiar with determining a therapeutic regimen for a specific indication. Preferred dosage regimens of the present invention include, but are not limited to, once a day dosing and twice a day dosing.

In the methods for the treatment of ocular disease and particularly for the treatment of glaucoma, set forth herein, administration to a subject of a composition of the present invention may be by various methods known to those of skill in the art, including, but not limited to, topical, subconjunctival, periocular, retrobulbar, subtenon, intraocular, subretinal, posterior juxtascleral, or suprachoroidal administration. In preferred embodiments, administration of a composition of the present invention is by topical administration to the ocular surface.

It is contemplated that the concentration of the sGC activator in the compositions of the present invention can vary, but is preferably 0.01 to 3.0 w/v % and more preferably 0.05-2.0 w/v %. The most preferred concentration range is from 0.1-1 w/v % and the most preferred concentration is about 0.3 w/v %. The sGC activators of the present invention comprise the pharmaceutically useful hydrates and salts of such compounds and stereoisomers (where applicable), and may be formulated with a pharmaceutically acceptable vehicle.

The methods of treating glaucoma may include administering the sGC activator compound by a technique selected from the group consisting of: periocular injection, subconjunctival injection, sub-tenon injection, intracameral injection, intravitreal injection, intracanalicular injection, implanting delivery device in the cul-de-sac, implanting delivery device adjacent to the sclera, implanting delivery device within the eye, oral administration, intravenous administration, subcutaneous administration, intramuscular administration, parenteral administration, dermal administration, and nasal administration.

In certain aspects of the invention, compounds of the invention may be formulated in either fixed and unfixed combinations of two therapeutic agents effective in the treatment of glaucoma wherein one therapeutic agent is sGC activator disclosed supra and the second therapeutic agent is an efficacious glaucoma drug. In other embodiments, a pharmaceutical composition of the invention comprising a sGC activator can be administered to a patient alone or in combination with other IOP-lowering agents to increase the potency, efficacy and/or duration of the IOP reduction. In certain preferred combinations, the second IOP-lowering agent is selected from carbonic anhydrase inhibitors, beta-blockers, prostaglandins, alpha-2 agonists, serotonin-2 agonists, alpha-1 antagonists, dopamine agonists, Rho kinase inhibitors, myosin-II Ca2 +ATPase, inhibitors, matrix metalloproteinase activators, activator protein-1 (AP-1) activators, natriuretic peptide receptor-B agonists, phosphodiesterase inhibitors, K+-channel blockers and maxi-K-channel activators. The combination therapy of the invention provides the benefit of lowering IOP by two mechanisms, including inducing uveoscleral outflow of aqueous humor and inhibiting aqueous humor inflow, which can allow for reduced dosages of the compounds thereby lowering the risk of side effects.

Pharmaceutical compositions of the invention can also be advantageously combined with suitable neuroprotective agents such as memantine, eliprodil, Ca2+-channel blockers, and betaxolol.

In a further aspect of the invention, the sGC activator may be administered alone or in combination with a second therapeutic agent which is suitable for the treatment of glaucoma. Certain preferred second therapeutic agents include beta-blockers, prostaglandin analogs, carbonic anhydrase inhibitors, α2 agonists, miotics, PDE-V inhibitors, Rho kinase inhibitors and neuroprotectants. In one preferred combination, a prostaglandin F2α analogue selected from the group consisting of Latanaprost and Travoprost is administered in combination with sGC activator of Formula (I) or subformulae thereof. In another preferred combination, a PDE-V inhibitor selected from the group consisting of Sildenafil, Tadalafil, Vardenafil, Udenafil, Avanafil, Lodenafil and Mirodenafil is administered in combination with a sGC activator of Formula (I) or subformulae thereof. In yet another preferred combination, a sGC activator of Formula (I) or subformulae thereof is administered in combination with a sGC stimulator (such as Riociguat) or a NO precursor (such as sodium nitroprusside or nitroglycerine). In another preferred combination, a sGC activator of Formula (I) or subformulae thereof is administered in combination with a Rho-kinase inhibitor (such as AR-13324 alone or combination of AR-13324 and Latanaprost).

In a further embodiment of the invention, a sGC activator of Formula (I) is administered in combination with a carbonic anhydrase inhibitor (such as Brinzolamide) for the treatment of glaucoma or to reduce IOP. In another embodiment, a sGC activator of Formula (I) is administered in combination with a α2 adrenergic agonist (such as Brimonidine) for the treatment of glaucoma or to reduce IOP. In a particularly preferred combination therapy, a sGC activator of Formula (I) is administered in combination with a fixed combination of Brimonidine and Brinzolamide (such as SIMBRINZA™ from by Alcon, Fort Worth, Tex.) for the treatment of glaucoma or to reduce IOP.

In certain embodiments, a sGC activator and the second pharmaceutical agent are administered concurrently in separate pharmaceutical compositions. In other embodiments, a sGC activator and the second pharmaceutical agent are administered formulated together in a pharmaceutical composition. In yet other embodiments, the sGC activator and the second pharmaceutical agent are administered sequentially in separate pharmaceutical compositions.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

In addition to a sGC activator, the compositions of the present invention optionally comprise one or more excipients. Excipients commonly used in pharmaceutical compositions include, but are not limited to, tonicity agents, preservatives, chelating agents, buffering agents, surfactants and antioxidants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl cellulose or starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the sGC activator. In preferred embodiments, excipients are selected on the basis of their inertness towards the sGC activator.

Relative to ophthalmic formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68. Suitable antioxidants include, but are not limited to, sulfites, ascorbates, butylated hydroxyanisole (BHA) and butylated hydroxytoluene (BHT).

The compositions set forth herein may comprise one or more preservatives. Examples of such preservatives include p-hydroxybenzoic acid ester, sodium chlorite, benzalkonium chloride, parabens such as methylparaben or propylparaben, alcohols such as chlorobutanol, benzyl alcohol or phenyl ethanol, guanidine derivatives such as polyhexamethylene biguanide, polymeric quaternary ammonium compounds such as Onamer M and Polyquaterium-1 (POLYQUAD® from Alcon), sodium perborate, or sorbic acid. In certain embodiments, the composition may be self-preserved that no preservation agent is required.

In preferred compositions a sGC activator of the present invention will be formulated for topical application to the eye in aqueous solution in the form of drops. The term "aqueous" typically denotes an aqueous composition wherein the composition is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

In other aspects, components of the invention may be delivered to the eye as a concentrated gel or a similar vehicle, or as dissolvable inserts that are placed beneath the eyelids. In yet other aspects, components of the invention may be delivered to the eye as ointments, water-in-oil and oil-in-water emulsions, solutions, or suspensions.

The compositions of the present invention, and particularly the topical compositions, are preferably isotonic or slightly hypotonic in order to combat any hypertonicity of tears caused by evaporation and/or disease. This may require a tonicity agent to bring the osmolality of the composition to a level at or near 210-320 milliosmoles per kilogram (mOsm/kg). The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

In certain embodiments, a sGC activator of the present invention is formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; guars, such as HP-guar and other guar derivatives, and carbomers, such as carbomer 934P, carbomer 941, carbomer 940 and carbomer 974P. Certain compositions of the present invention may be used with contact lenses or other ophthalmic products.

In certain embodiments, the compositions set forth herein have a viscosity of 0.5-100 cps, preferably 0.5-50 cps, and most preferably 1-20 cps. These viscosities insure that the product is comfortable, does not cause blurring, and is easily processed during manufacturing, transfer and filling operations.

Preferred compositions are prepared using a buffering system that maintains the composition at a pH of about 3 to a pH of about 8.0, preferably 5.5-7.5, and most preferably 6.0-7.4. Topical compositions (particularly topical ophthalmic compositions) are preferred which have a physiological pH matching the tissue to which the composition will be applied or dispensed.

The following examples are presented to further illustrate selected embodiments of the present invention.

TOPICAL OCULAR FORMULATION EXAMPLE

| Ingredient | Concentration (w/v %) |
|---|---|
| sGC activator | 1.0% |
| Dibasic Sodium Phosphate | 0.2% |
| Sodium Chloride | 0.75% |
| Disodium EDTA | 0.01% |
| Polysorbate 80 | 0.05% |
| Benzalkonium Chloride Solution | 0.01% |
| Hydroxypropyl Methylcellu lose | 0.5% |

The compounds of formula I in free form or in pharmaceutically acceptable salt form, exhibit valuable pharmacological properties, e.g. sGC modulating properties, e.g. as indicated in vitro and in vivo tests as provided in the next sections, and are therefore indicated for therapy or for use as research chemicals, e.g. as tool compounds. More particularly, the compounds of formula I, in free form or in pharmaceutically acceptable salt form, activate sGC which is suitable for use in treatment of disease.

In one preferred use, the compounds of Formula I are suitable for use in lowering intraocular pressure (IOP) and in the treatment of glaucoma. The compounds of the invention may be used alone or in combination with a second therapeutic agent for the treatment of glaucoma. The embodiment further provides methods of treating glaucoma or reducing intraocular pressure in a subject, the method comprising administering a compound of Formula I alone or in combination with a second therapeutic agent. In certain aspects, the method contemplates to topical ocular administration of the compound of Formula I to the subject in need of such therapy. In preferred aspects, the method comprises administration of the compound of Formula I as a mono-therapy. In certain other aspects, the method comprises the co-administration (either concomitantly or sequentially) of a compound of Formula I and a PDE-V inhibitor.

Compounds of the invention may also be useful in the treatment of an indication selected from: kidney disease, urologic disorders hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. In addition, the compounds of the invention have the potential to treat renal disease, diabetes, fibrotic disorders (including those of the liver, kidney and lungs), urologic disorders (including overactive bladder), benign prostatic hyperplasia, erectile dysfunction, neuropathic pain and neurological disorders (Including Alzheimer's disease and Parkinson's disease). Treatment with an sGC activator of the invention may further provide benefit in the treatment of inflammatory disorder such as psoriasis, multiple sclerosis, arthritis, asthma and chronic obstructive pulmonary disease.

Thus, as a further embodiment, the present invention provides the use of a compound of formula (I) in therapy. In a further embodiment, the therapy is selected from a disease which may be treated by activation of sGC. In a preferred application, the disease is selected from the afore-mentioned list, suitably glaucoma.

In another embodiment, the invention provides a method of treating a disease which is treated by activation of sGC comprising administration of a therapeutically acceptable amount of a compound of formula (I) or a salt thereof. In a further embodiment, the disease is selected from the afore-mentioned list, suitably glaucoma.

Thus, as a further embodiment, the present invention provides the use of a compound of formula (I) or subformulae thereof for the manufacture of a medicament. In a further embodiment, the medicament is for treatment of a disease which may be treated by activation of sGC. In another embodiment, the disease is selected from the afore-mentioned list, suitably glaucoma.

For systemic administration, the administered pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

ABBREVIATIONS

Ac acetyl
AcOH acetic acid
App apparent
aq. aqueous
atm atmosphere
Bis(pinacolato) diboron 4,4,4',4',5,5,5',5'-Octamethyl-2,2'-bi-1,3,2-dioxaborolane (CAS#73183-34-3)
Boc tertiary butyl carboxy Boc-anhydride di-tert-butyl dicarbonate
(Boc)₂O di-tert-butyl dicarbonate
br. broad
BSA bovine serum albumin
BuOH butanol
calcd. calculated
CHAPS 3-[(3-cholamidopropyl)dimethylammonio]-1-propanesulfonate
CH₃CN acetonitrile
Cs₂CO₃ cesium carbonate
d doublet
dd doublet of doublets
DCE 1,2-dichloroethane
DCM dichloromethane
DEA diethylamine
DIAD diisopropyl azodicarboxylate
DIPEA N,N-diisopropylethylamine
DIBAL-H diisobutylaluminium hydride
DIPEA N,N-diisopropylethylamine
DMAP 4,4-dimethylaminopyridine
DME 1,4-dimethoxyethane
DMF N,N-dimethylformamide
Dess-Martin Periodinane Dess-Martin reagent; 1,1,1-Triacetoxy-1,1-dihydro-1,2-benziodoxol-3(1H)-one (CAS#87413-09-0)
DMSO dimethylsulfoxide
ESI electrospray ionization
EtOAc or AcOEt ethyl acetate
Et ethyl
EtOH ethanol
g grams
h hour(s)
HATU 2-(1H-7-azabenzotriazol-1-yl)-1,1,3,3-tetramethyl uronium hexafluorophosphate methanaminium
HBSS Hank's Balanced Salt Solution
HC HPLC condition
HEPES 4-(2-hydroxyethyl)-1-piperazineethanesulfonic acid
HFIP 1,1,1,3,3,3-hexafluoro-2-propanol
HPLC high performance liquid chromatography
IBMX 1-methyl-3-(2-methylpropyl)-7H-purine-2,6-dione
IPA 2-propanol
IR infrared spectroscopy
L liter(s)
LDA lithium diisopropyl amide
LHMDS lithium bis(trimethylsilyl)amide (CAS#4039-32-1)
M molar
MHz mega Hertz
m multiplet
Me methyl
MeCN acetonitrile
MeI iodomethane
MeOH methanol
mg milligram(s)
mm millimeter(s)
min minutes
ml or mL milliliter(s)
mmol millimoles
MP melting point
MS mass spectrometry
MsCl methanesulfonyl chloride
MsOH methanesulfonic acid
MTBE methyl tert-butylether
m/z mass to charge ratio
N normal
NaBH₄ sodium borohydride
Na(AcO)₃BH sodium triacetoxyborohydride
NBS N-bromosuccinimide
NCS N-chlorosuccinimide
NH₄Cl ammonium chloride
NMR nuclear magnetic resonance
ODQ 1H-[1,2,4]Oxadiazolo[4,3-a]quinoxalin-1-one (CAS#41443-28-1)
PBS phosphate buffered saline
Pd/C palladium on carbon
Pd(dppf)₂Cl₂CH₂Cl₂ adduct 1,1'-bis(diphenylphosphino) ferrocene-palladium(II)dichloride complex
Pd(PPh₃)₄ tetrakis(triphenylphosphine)palladium(0)
Ph phenyl
ppm parts per million
PyBOP benzotriazol-1-yloxytripyrrolidinophosphonium hexafluorophosphate
rac racemic
RP—reverse phase
rt room temperature
s singlet
sat., satd. saturated
SFC Supercritical Fluid Chromatography
t triplet
$t_r$ retention time
T3P propylphosphonic anhydride
TBAF tetra-n-butylammonium fluoride
TBSCl tert-butyldimethylsilyl chloride
TEA, Et₃N triethylamine
tert—tertiary
TFA trifluoroacetic acid
THF tetrahydrofuran
TLC Thin Layer Chromatography
TMS trimethylsilyl
Ts p-toluenesulfonyl
TsOH p-toluenesulfonic acid
UPLC ultra performance liquid chromatography
v/v volume per volume
w/v weight per volume
w/w weight per weight The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH, using D line of a sodium lamp.

Proton NMR (¹H NMR) is conducted in deuterated solvent. In certain compounds disclosed herein, one or more ¹H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu. The smaller mass is reported in the Experimental infra.

Following preparation methods were used for RP-HPLC.
HC-A:
Stationary phase: Waters SunFire™ Prep C18 OBD™ 5 µm, 30×100 mm
Mobile phase: gradient, water with 0.1% TFA/acetonitrile
HC-B
Stationary phase: Gemini® NX 5µ C18 110A 100×30 mm
Mobile phase: gradient, water with 0.1% (28% ammonium hydroxide)/acetonitrile
HC-C
Stationary phase: X-bridge® BEH C18 OBD Prep 5 µm, 30 mm 50 mm
Mobile phase: gradient, water with 0.1% (28% ammonium hydroxide)/acetonitrile Absolute stereochemistry, retention times on chiral HPLC, and/or optical rotations are provided for the embodiments of the invention where applicable. The invention contemplates all stereochemical forms of the compounds provided herein. Where absolute stereochemistry is provided the assessment was made via X-ray diffraction, and/or chemical correlation, and/or at least one chiral center was from a purchased commercial enantiopure (>15:1 er) starting material In the case of a racemic samples, including intermediates, enantiomers are separated by chromatography using a chiral stationary phase and are identified/differentiated either by HPLC retention time employing a chiral stationary phase and the monikers "enantiomer-1" or "enantiomer-2", and/or by a specific "+" or "−" sign referring to the rotation of polarized light when this data is available.

In some instances examples possess an acidic functional group as such during final purification procedures samples may contain an undetermined mixture of the free acid along with potassium and/or lithium salts of the titled compound. Small changes in the amount of salt present may change the observed chemical shift or intensity for some peaks in the $^1$H NMR spectra.

Intermediate 1-1. Ethyl 1-(6-bromopyridin-2-yl)-5-(trifluoromethyl)-1H-pyrazole-4-carboxylate

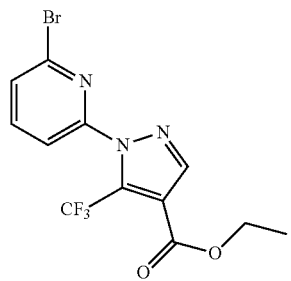 [SMILES: CCOC(=O)c1cnn(-c2cccc(Br)n2)c1C(F)(F)F]

A solution of 2-bromo-6-hydrazinylpyridine (CAS#26944-71-8; 12.63 g, 67 mmol) in THF (350 mL) was cooled in an acetone/CO$_2$ bath, and then ethyl 2-(ethoxymethylene)-4,4,4-trifluoro-3-oxobutyrate (CAS#571-55-1, 13.72 mL, 71 mmol) was added dropwise. Once the addition was complete, the reaction mixture was gradually allowed to warm to room temperature over 2 h. The reaction mixture was then concentrated, and dissolved in EtOAc. The organic layer was then washed successively with sat. aq. NaHCO$_3$ and brine, dried over MgSO$_4$, filtered, and then concentrated. The resulting residue was purified by silica gel flash column chromatography (10% EtOAc in hexane) to afford the title compound. $^1$H NMR (400 MHz, CD$_3$OD) δ 8.19 (s, 1H), 7.96 (t, J=7.82 Hz, 1H), 7.74-7.80 (m, 2H), 4.37 (q, J=7.13 Hz, 2H), 1.38 (t, J=7.15 Hz, 3H).

Intermediate 1-2

The following compounds were prepared by a similar method as described above using the appropriate hydrazines as starting materials.

| intermediate | Structure/Chemical Name | Starting materials | Analytical data |
|---|---|---|---|
| 1-2-1 | Ethyl 1-(6-chloropyridin-2-yl)-5-(trifluoromethyl)-1H-pyrazole-4-carboxylate | 2-chloro-6-hydrazinylpyridine (CAS# 5193-03-3) | $^1$H NMR (400 MHz, DMSO-d$_6$) δ 8.38 (s, 1H), 8.22 (dd, J = 7.8, 7.9 Hz, 1H), 7.86 (dd, J = 0.63, 8.0 Hz, 1H), 7.81 (dd, J = 0.63, 8.0 Hz, 1H), 4.33 (q, J = 7.15 Hz, 2H), 1.31 (t, J = 7.15 Hz, 3H) |

| inter-mediate | Structure/Chemical Name | Starting materials | Analytical data |
|---|---|---|---|
| 1-2-2 | Ethyl 1-(3-bromophenyl)-5-(trifluoromethyl)-1H-pyrazole-4-carboxylate | (3-bromophenyl) hydrazine hydrochloride (CAS# 27246-81-7) the reaction was carried in the presence of Et₃N | MS (ESI+) m/z 362.9 (M + H) |

Intermediate 1-3. Ethyl 1-(6-bromopyridin-2-yl)-5-ethyl-1H-pyrazole-4-carboxylate

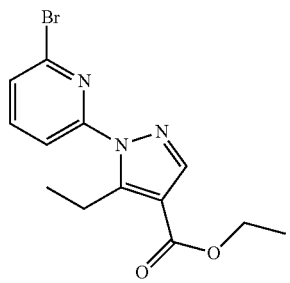 [SMILES: CCOC(=O)c1cnn(-c2cccc(Br)n2)c1CC]

A solution of 2-bromo-6-hydrazinylpyridine (2 g, 10.64 mmol) and ethyl 2-((dimethylamino)methylene)-3-oxopentanoate (CAS#89193-23-7, 2.33 g, 11.7 mmol) in EtOH (32 mL) was stirred at 70° C. for 1.5 h, and then cooled to room temperature. The reaction mixture was then poured into $H_2O$. The resulting precipitate was collected by filtration and washed with $H_2O$ to furnish the title compound. MS (ESI+) m/z 324.1 (M+H)

Intermediate 1-4

The following compounds were prepared with similar methods as described above for Intermediate 1-3, using the appropriate starting materials delineated in the table below.

| inter-mediate | Structure/Chemical Name | Starting materials | Analytical data |
|---|---|---|---|
| 1-4-1 | Ethyl 1-(6-chloropyridin-2-yl)-5-methyl-1H-pyrazole-4-carboxylate | 2-chloro-6-hydrazinylpyridine (CAS# 5193-03-3) and ethyl 2-((dimethylamino)methylene)-3-oxobutanoate (CAS#; 51145-57-4) | ¹H NMR (400 MHz, CDCl₃) δ 8.02 (s, 1H), 7.86-7.76 (m, 2H), 7.30 (dd, J = 6.4, 2.1 Hz, 1H), 4.33 (q, J = 7.1 Hz, 2H), 2.97 (s, 3H), 1.38 (t, J = 7.1 Hz, 3H). |
| 1-4-2 | Ethyl 1-(6-bromopyridin-2-yl)-5-methyl-1H-pyrazole-4-carboxylate | 2-Bromo-6-hydrazinylpyridine and ethyl 2-acetyl-3-(dimethylamino)acrylate (CAS# 51145-57-4) | MS (ESI+) m/z 310.1 (M + H) |

Intermediate 2-1

Intermediate 2-1-A. tert-Butyl 4-(4-hydroxy-3-methylphenyl)-5,6-dihydropyridine-1(2H)-carboxylate

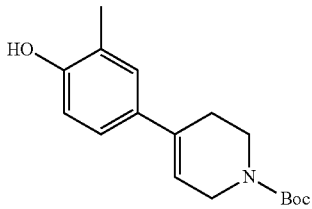 [SMILES: Cc1cc(C2=CCN(C(=O)OC(C)(C)C)CC2)ccc1O]

To a suspension of 4-bromo-2-methyl phenol (CAS#2362-12-1, 5 g, 26.7 mmol), tert-butyl 4-(4,4,5,5-tetramethyl-1,3,2-dioxaborolan-2-yl)-5,6-dihydropyridine-1(2H)-carboxylate (CAS#286961-14-6, 8.27 g, 26.7 mmol), and $K_3PO_4$ (2M in $H_2O$, 26.7 mL, 53.5 mmol) in acetonitrile (54 ml) was added $PdCl_2$(dppf) dichloromethane adduct (1.09 g, 1.33 mmol). The mixture was then stirred at 80° C. for 3 h, and then cooled to room temperature. To the reaction mixture was added Celite®, and then concentrated. The resulting residue was purified by silica gel flash column chromatography (heptane/EtOAc=1/0 to 1/1) to afford the title compound. MS (ESI+) m/z 290.1 (M+H).

Intermediate 2-1. tert-Butyl 4-(4-hydroxy-3-methylphenyl)piperidine-1-carboxylate

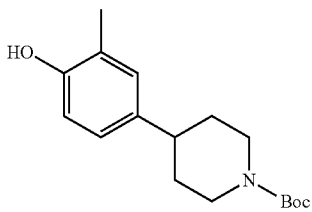 [SMILES: Cc1cc(C2CCN(C(=O)OC(C)(C)C)CC2)ccc1O]

A mixture of Intermediate 2-1-A (4.4 g, 15.21 mmol) and Pd/C (5%, 0.8 g) in MeOH (50 mL) was stirred under an $H_2$ atmosphere at room temperature for 2 h. The reaction mixture was then filtered through a plug of Celite®. The filtrate was then concentrated to furnish the title compound directly. MS (ESI−) m/z 290.2 (M−H).

Intermediate 2-2

Intermediate 2-2-A. tert-Butyl 4-(2-ethyl-4-hydroxyphenyl)-5,6-dihydropyridine-1(2H)-carboxylate

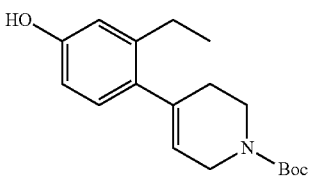 [SMILES: CCc1cc(O)ccc1C1=CCN(C(=O)OC(C)(C)C)CC1]

To a mixture of 4-chloro-3-ethylphenol (CAS#14143-32-9, 3 g, 19.16 mmol), tert-butyl 4-(4,4,5,5-tetramethyl-1,3,2-dioxaborolan-2-yl)-5,6-dihydropyridine-1(2H)-carboxylate (7.70 g, 24.90 mmol), chloro(2-dicyclohexylphosphino-2',6'-dimethoxy-1,1'-biphenyl)[2-(2-aminoethylphenyl)]palladium(II) methyl-tert-butylether adduct (CAS#1028206-58-7, 0.644 g, 0.958 mmol) in DMF (96 mL) was added 2 M aq. potassium phosphate (28.7 mL, 57.5 mmol). The mixture was stirred at 110° C. for 1 h, and then cooled to room temperature. The reaction mixture was diluted with EtOAc and $H_2O$. The organic layer was then separated, and dried over $Na_2SO_4$, filtered, and then concentrated. The resulting residue was purified by silica gel flash column chromatography (heptane/EtOAc=1/0 to 6/4) to afford the title compounds. MS (ESI+) m/z 248.2 (M-tBu+2H).

Intermediate 2-2. tert-Butyl 4-(2-ethyl-4-hydroxyphenyl)piperidine-1-carboxylate

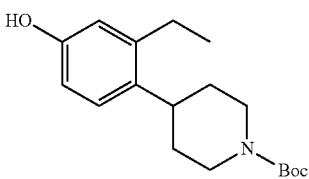

A mixture of Intermediate 2-2-A (5.4 g, 17.80 mmol) and 10% Pd/C (1.89 g) in MeOH (250 mL) was stirred under an $H_2$ atmosphere at room temperature for 1 h. The reaction mixture was then filtered through a plug of Celite® which was then washed with MeOH. The filtrate was then concentrated to furnish the title compound directly. MS (ESI+) m/z 250.2 (M-tBu+2H).

Intermediate 2-3

The following compounds were prepared by a similar method as described above for Intermediate 2-2 using the appropriate phenol starting material delineated in the table below.

| Intermediate | Structure/Chemical Name | Starting material(s) | MS or NMR data |
|---|---|---|---|
| 2-3-1 | ![structure] tert-Butyl 4-(4-hydroxy-3-(trifluoromethyl)phenyl)-piperidine-1-carboxylate | 4-bromo-2-(trifluoromethyl)phenol (CAS# 50824-04-9) | MS (ESI−) m/z 344.5 (M − H) |
| 2-3-2 | ![structure] tert-Butyl 4-(4-hydroxy-2-methylphenyl)piperidine-1-carboxylate | 4-bromo-3-methylphenol (CAS# 14472-14-1) | MS (ESI+) m/z 236.1 (M − tBu + 2H) |

Intermediate 2-4

Intermediate 2-4-A.
2-Methyl-4-(piperidin-4-yl)phenol

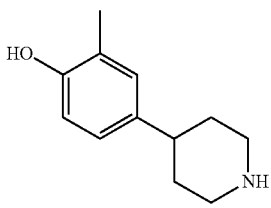

To a solution of Intermediate 2-1 (3.98 g, 13.66 mmol) in CH$_2$Cl$_2$ (137 mL) at 0° C. was added TFA (12.6 mL, 164 mmol). The mixture was then stirred for 1.5 h, and then concentrated to dryness to furnish the title compound. MS (ESI+) m/z 192.1 (M+H).

Intermediate 2-4. Cyclopropyl(4-(4-hydroxy-3-methylphenyl)piperidin-1-yl)methanone

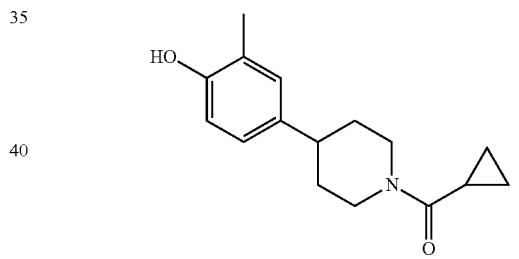

To a solution of Intermediate 2-4-A (2.6 g, 13.59 mmol) in CH$_2$Cl$_2$ (68 mL) at 0° C. was added DIPEA (9.5 mL, 54.4 mmol), followed by cyclopropanecarbonyl chloride (2.47 mL, 27.2 mmol). The mixture was then stirred at 0° C. for 1 h, and then quenched with H$_2$O. The mixture was then extracted with CH$_2$Cl$_2$. The organic layer was then concentrated. A mixture of the resulting residue and K$_2$CO$_3$ (9.39 g, 68 mmol) in MeOH (68 mL) at room temperature was stirred for 2 h, and then diluted with CH$_2$Cl$_2$ and H$_2$O. The mixture was then passed through an ISOLUTE® Phase Separator. The resulting organic layer was then concentrated to furnish the title compound. MS (ESI+) m/z 260.1 (M+H).

Intermediate 2-5

The following compounds were prepared by a similar method as described above for Intermediate 2-2 and Intermediate 2-4 using the appropriate starting materials as delineated in the table below.

| Intermediate | Structure/Chemical Name | Starting material(s) | MS or NMR data |
|---|---|---|---|
| 2-5-1 | 1-(4-(4-Hydroxyphenyl)piperidin-1-yl)propan-1-one | tert-butyl 4-(4-hydroxyphenyl)piperidine-1-carboxylate (CAS# 149377-19-5) and propyonyl chloride | MS (ESI+) m/z 234.0 |
| 2-5-2 | Methyl 4-(4-hydroxy-3-methylphenyl)piperidine-1-carboxylate | Intermediate 2-1, and methyl chloroformate (CAS# 79-22-1) | MS (ESI+) m/z (M + H) 250.3 |
| 2-5-3 | Cyclopropyl(4-(4-hydroxy-3-methoxyphenyl)piperidin-1-yl)methanone | 4-bromo-2-methoxphenol (CAS# 7368-78-7) and cyclopropanecarbonyl chloride | MS (ESI+) m/z 276.3 (M + H) |
| 2-5-4 | Cyclopropyl(4-(4-hydroxy-2-methoxyphenyl)piperidin-1-yl)methanone | 4-bromo-3-methoxphenol (CAS# 102127-34-4) and cyclopropanecarbonyl chloride | MS (ESI+) m/z 276.3 (M + H) |
| 2-5-5 | Cyclopropyl(4-(2-ethyl-4-hydroxyphenyl)piperidin-1-yl)methanone | Intermediate 2-2 and cyclopropanecarbonyl chloride | MS (ESI+) m/z 274.3 (M + H) |

| Intermediate | Structure/Chemical Name | Starting material(s) | MS or NMR data |
|---|---|---|---|
| 2-5-6 | 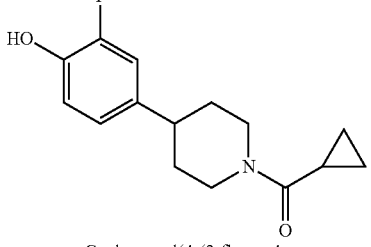<br>Cyclopropyl(4-(3-fluoro-4-hydroxyphenyl)piperidin-1-yl)methanone | 4-bromo-2-fluorophenol (CAS# 2105-94-4) and cyclopropanecarbonyl chloride | MS (ESI+) m/z 264.2 (M + H) |
| 2-5-7 | 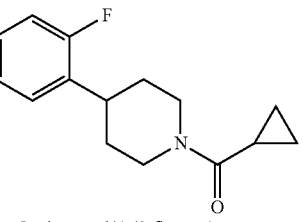<br>Cyclopropyl(4-(2-fluoro-4-hydroxyphenyl)piperidin-1-yl)methanone | 4-bromo-3-fluorophenol (CAS# 121219-03-2) and cyclopropanecarbonyl chloride | MS (ESI+) m/z 264.2 (M + H) |
| 2-5-8 | 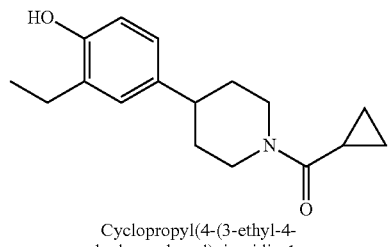<br>Cyclopropyl(4-(3-ethyl-4-hydroxyphenyl)piperidin-1-yl)methanone | 4-bromo-2-ethylphenol (CAS# 18980-21-7) and cyclopropanecarbonyl chloride | MS (ESI+) m/z 274.3 (M + H) |
| 2-5-9 | 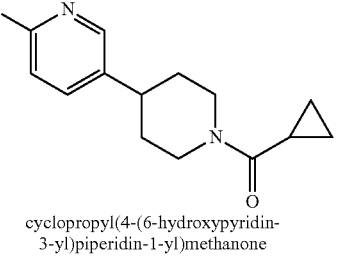<br>cyclopropyl(4-(6-hydroxypyridin-3-yl)piperidin-1-yl)methanone | 5-bromopyridin-2-ol (CAS# 13466-38-1) and cyclopropanecarbonyl chloride | MS (ESI+) m/z 247.1 (M + H) |

Intermediate 2-6

Intermediate 2-6-A. 1-Benzyl-4-(4-methoxy-3-methylphenyl)piperidin-4-ol

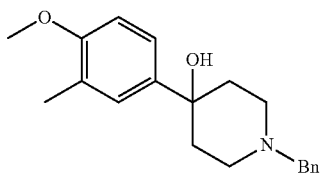 [SMILES: COc1ccc(C2(O)CCN(Cc3ccccc3)CC2)cc1C]

Magnesium turnings (3.63 g, 149.2 mmol) and a catalytic amount of iodine were suspended in THF (20 mL), 4-bromo-1-methoxy-2-methylbenzene (CAS#14804-31-0, 30.0 g, 149.2 mmole) in THF (140 mL) was added dropwise over 60 min. The mixture was refluxed for 1 h. After cooling to room temperature a solution of N-benzyl-4-piperidone (CAS#3612-20-2, 31.06 g, 164 mmol) in THF (100 mL) was then added dropwise over 50 min and then the mixture was stirred at reflux for 20 min. The mixture was cooled to room temperature and quenched with sat. aq. NH$_4$Cl and diluted with EtOAc. The organic layer was then separated. The aqueous phase was extracted twice with EtOAc. The combined organic layers were dried over MgSO$_4$, filtered and concentrated. The resulting residue was purified by silica gel flash column chromatography (hexane/EtOAc=5/1 to 3/1) to afford the title compound. MS (ESI+) m/z 312.3 (M+H).

Intermediate 2-6-B. 1-Benzyl-4-(4-methoxy-3-methylphenyl)-1,2,3,6-tetrahydropyridine

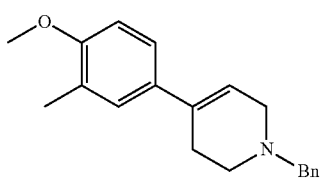 [SMILES: COc1ccc(C2=CCN(Cc3ccccc3)CC2)cc1C]

A mixture of Intermediate 2-6-A (29.3 g, 94.1 mmol) and 6M aq. HCl (100 mL) in 1,4-dioxane (50 mL) was stirred under the reflux conditions for 3.5 h, and then concentrated. The resulting residue was triturated with diethyl ether. The resulting solid was collected by filtration to afford the title compound as an HCl salt. MS (ESI+) m/z 294.3 (M+H).

Intermediate 2-6-C. 4-(4-Methoxy-3-methylphenyl)piperidine

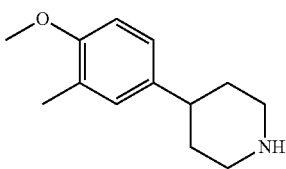

To a degassed solution of Intermediate 2-6-B (32.0 g, 97.1 mmol) in MeOH/$H_2O$ (80 mL/40 mL) was added Pd/C (10%, 30 mg), and the mixture was then stirred under $H_2$ atmosphere at 50° C. for 16 h. The $H_2$ atmosphere was then replaced to $N_2$, and then the additional Pd/C (10%, 30 mg) was added to the mixture. The mixture was then placed back under a $H_2$ atmosphere and stirred at 50° C. for 16 h. The reaction mixture was then filtered through a plug of Celite®, which was rinsed with MeOH. The filtrate was then concentrated and the resulting residue was suspended in diethyl ether, and then the resulting precipitate was collected by filtration to afford the title compound. MS (ESI+) m/z 206.0 (M+H).

Intermediate 2-6-D. 1-(4-(4-Methoxy-3-methylphenyl)piperidin-1-yl)propan-1-one

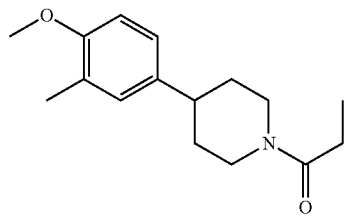 [SMILES: CCC(=O)N1CCC(c2ccc(OC)c(C)c2)CC1]

To a solution of Intermediate 2-6-C (6.3 g, 26 mmol) and triethylamine (9.09 mL, 65 mmol) in $CH_2Cl_2$ (63 mL) at 0° C. was added propionic anhydride (3.67 mL, 29 mmol) dropwise. The mixture was stirred at room temperature for 2 h and then quenched with $H_2O$. The mixture was then washed with $H_2O$, dried over $MgSO_4$, filtered and concentrated to furnish the title compound. MS (ESI+) m/z 261.9 (M+H).

Intermediate 2-6. 1-(4-(4-Hydroxy-3-methylphenyl)piperidin-1-yl)propan-1-one

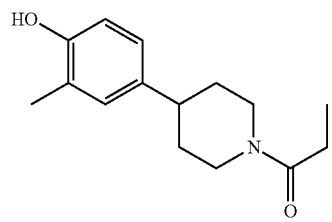 [SMILES: CCC(=O)N1CCC(c2ccc(O)c(C)c2)CC1]

To a solution of Intermediate 2-6-D (6.4 g, 25 mmol) in $CH_2Cl_2$ (32 mL) at −78° C. was added a solution of boron tribromide (1M in $CH_2Cl_2$, 61 mL, 61 mmol). The mixture was stirred at −78° C. for 1.5 h, and then stirred at room temperature for 16 h. The reaction was then quenched with 1M solution of $NaHCO_3$ until the pH=~9. Then the mixture was then washed with $H_2O$, dried over $Na_2SO_4$, filtered, and concentrated. The resulting solid was triturated with i-PrOH to afford the title compound. MS (ESI+) m/z 248.1 (M+H).

Intermediate 2-7. 1-(4-(4-Hydroxy-3,5-dimethylphenyl)piperidin-1-yl)propan-1-one

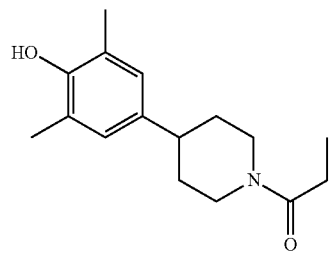 [SMILES: CCC(=O)N1CCC(c2cc(C)c(O)c(C)c2)CC1]

The title compound was synthesized starting from 5-bromo-2-methoxy-1,3-dimethylbenzene (CAS#14804-38-7). Reaction of 5-bromo-2-methoxy-1,3-dimethylbenzene with tert-butyl 4-(4,4,5,5-tetramethyl-1,3,2-dioxaborolan-2-yl)-5,6-dihydropyridine-1(2H)-carboxylate and subsequent hydrogenation, in a manner analogous to Intermediate 2-1, afforded a Boc protected amine which was deprotected analogous to the transformation outlined in Intermediate 2-4-A, the subsequent amine was then reacted with propionyl chloride in a similar manner to the procedure as described in Intermediate 2-6-D. The resulting product was demethylated in a similar manner as described in Intermediate 2-6 to furnish 1-(4-(4-hydroxy-3,5-dimethylphenyl)piperidin-1-yl)propan-1-one. MS (ESI+) m/z 303.1 $(M+CH_3CN)^+$.

Intermediate 2-8

Cyclopropyl(4-(4-hydroxy-2,3-dimethylphenyl)piperidin-1-yl)methanone.

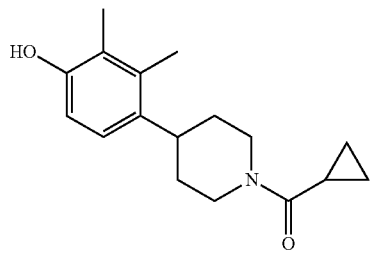 [SMILES: Cc1c(O)ccc(C2CCN(C(=O)C3CC3)CC2)c1C]

The title compound was synthesized in a similar manner to the preparation of Intermediate 2-7 using 1-bromo-4-methoxy-2,3-dimethylbenzene (CAS#50638-48-7), tert-butyl 4-(4,4,5,5-tetramethyl-1,3,2-dioxaborolan-2-yl)-5,6-dihydropyridine-1(2H)-carboxylate, and cyclopropylcarbonyl chloride. MS (ESI+) m/z 274.1 (M+H).

Intermediate 2-9. Cyclopropyl(4-(4-hydroxy-3-methylphenyl)-2,2,6,6-tetramethylpiperidin-1-yl)methanone

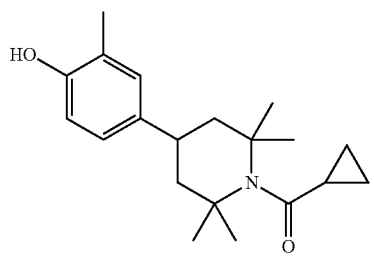 [SMILES: Cc1cc(C2CC(C)(C)N(C(=O)C3CC3)C(C)(C)C2)ccc1O]

The title compound was synthesized starting from 4-bromo-2-methylphenol. Reaction of 4-bromo-2-methylphenol with 2,2,6,6-tetramethyl-4-(4,4,5,5-tetramethyl-1,3,2-dioxaborolan-2-yl)-1,2,3,6-tetrahydropyridine (CAS#1257651-11-8) followed by the hydrogenation, in a fashion analogous to Intermediate 2-1, afforded an amine which was then reacted with cyclopropylcarbonyl chloride as outlined in the procedure for Intermediate 2-4 to afford the title compound, cyclopropyl(4-(4-hydroxy-3-methylphenyl)-2,2,6,6-tetramethylpiperidin-1-yl)methanone. MS (ESI+) m/z 316.3 (M+H).

Intermediate 2-10

Intermediate 2-10-A. tert-Butyl 4-(2-isopropyl-4-methoxyphenyl)piperidine-1-carboxylate

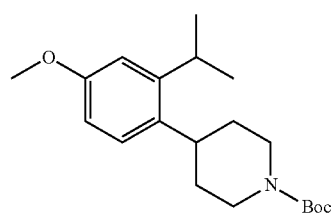 [SMILES: COc1ccc(C2CCN(C(=O)OC(C)(C)C)CC2)c(C(C)C)c1]

The title compound was synthesized in a fashion analogous to the protocol for Intermediate 2-1 but using 1-bromo-2-isopropyl-4-methoxybenzene (CAS#34881-45-3) in the place of 4-bromo-2-methyl phenol. MS (ESI+) m/z 278.2 (M-tBu+2H).

Intermediate 2-10-B. 3-Isopropyl-4-(piperidin-4-yl)phenol

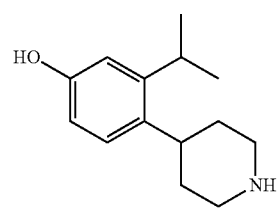 [SMILES: CC(C)c1cc(O)ccc1C1CCNCC1]

To a solution of tert-butyl 4-(2-isopropyl-4-methoxyphenyl)piperidine-1-carboxylate (0.79 g, 2.369 mmol) in CH$_2$Cl$_2$ (11.9 mL) at 0° C. was added boron tribromide (1M in CH$_2$Cl$_2$, 2.61 mL, 2.61 mmol) dropwise. The mixture was then stirred for 4 h, and then poured into ice. The mixture was then neutralized with satd. aq. NaHCO$_3$, and then the CH$_2$Cl$_2$ layer was separated. The aqueous layer was then extracted twice with a mixture of EtOAc/TFE (ca. 8/2). The combined organic layers were dried over Na$_2$SO$_4$, filtered, and then concentrated to furnish the title compound directly. MS (ESI+) m/z 220.3 (M+H).

Intermediate 2-10. Cyclopropyl(4-(4-hydroxy-2-isopropylphenyl)piperidin-1-yl)methanone

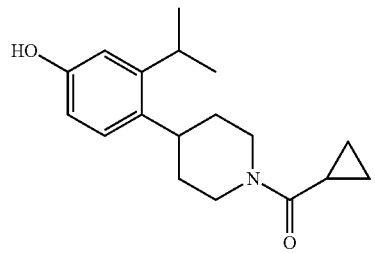 [SMILES: CC(C)c1cc(O)ccc1C1CCN(C(=O)C2CC2)CC1]

The title compound was synthesized starting from 3-isopropyl-4-(piperidin-4-yl)phenol by the method as described for the synthesis for Intermediate 2-4. MS (ESI+) m/z 288.3 (M+H).

Intermediate 2-11. tert-Butyl 4-(3-chloro-4-hydroxyphenyl)piperidine-1-carboxylate

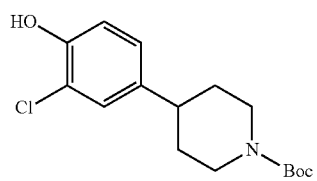 [SMILES: CC(C)(C)OC(=O)N1CCC(c2ccc(O)c(Cl)c2)CC1]

To a solution of tert-Butyl 4-(4-hydroxyphenyl)piperidine-1-carboxylate (CAS#149377-19-5, 270 mg, 0.973 mmol) in CH₃CN (5 mL) was added NCS (143 mg, 1.071 mmol). The mixture was then stirred at 130° C. under the microwave irradiation for 1.5 h, and then concentrated. The resulting residue was purified by silica gel flash column chromatography (hexane/EtOAc=1/0 to 85/15) to afford the title compound. MS (ESI+) m/z 312.1 (M+H).

Intermediate 2-12

Intermediate 2-12-A.
5-Methyl-1,2,3,4-tetrahydroisoquinolin-6-ol

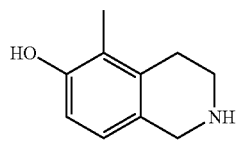

A mixture of tert-butyl 6-hydroxy-5-methyl-3,4-dihydroisoquinoline-2(1H)-carboxylate, prepared as described in J. Med. Chem., 2011, 54 (19), pp 6724-6733, (2.6 g, 9.87 mmol) and TFA (7.6 mL) in CH₂Cl₂ (20 mL) was stirred at room temperature for 2 h, and then diluted with CH₂Cl₂ and H₂O. The mixture was rendered basic (pH=~8) by addition of aq. NH₄OH. The organic layer was separated, and then concentrated to furnish the title compound directly. MS (ESI+) m/z 164.0 (M+H)

Intermediate 2-12. 5-Methyl-2-(pyridin-2-ylmethyl)-1,2,3,4-tetrahydroisoquinolin-6-ol

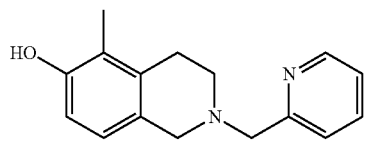 [SMILES: Cc1c(O)ccc2c1CCN(Cc1ccccn1)C2]

To a solution of Intermediate 2-12-A (420 mg, 2.57 mmol) in CH₂Cl₂ (12 mL) and triethylamine (1.18 mL, 8.49 mmol) at 0° C. was added 2-(bromomethyl)pyridine hydrobromide (781 mg, 3.09 mmol). The mixture was stirred at room temperature for 16 h, and then diluted with CH₂Cl₂ and H₂O. The organic layer was separated. The aqueous layer was then extracted with CH₂Cl₂. The organic layers were then combined and concentrated. The resulting residue was purified by silica gel flash column chromatography (heptane/EtOAc=1/0 to 0/1) to afford the title compound. MS (ESI+) m/z 255.2 (M+H).

Intermediate 2-13

Intermediate 2-13-A. tert-Butyl 4-(4-(benzyloxy)-3-methylphenyl)piperidine-1-carboxylate

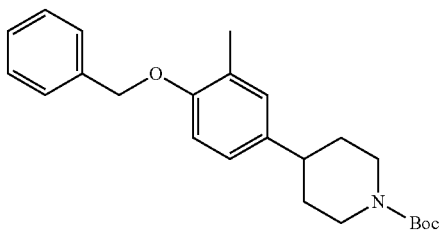 [SMILES: Cc1cc(C2CCN(C(=O)OC(C)(C)C)CC2)ccc1OCc1ccccc1]

To a suspension of Intermediate 2-1 (10 g, 34.3 mmol) and K₂CO₃ (10 g, 72.4 mmol) in DMF (100 mL) was added benzyl bromide (5 mL, 42.1 mmol). The mixture was then stirred at room temperature for 67 h. The reaction was then quenched with N,N-dimethylaminoethylenediamine. The mixture was then stirred for 3 h, and then diluted with H₂O/sat.aq. KHSO₄ (ca. 3/1). The mixture was then extracted with EtOAc. The organic layer was then washed successively with H₂O and brine, dried over Na₂SO₄, filtered, and then concentrated to furnish the title compound. MS (ESI+) m/z 326.3 (M-tBu+2H).

Intermediate 2-13-B.
4-(4-(Benzyloxy)-3-methylphenyl)piperidine

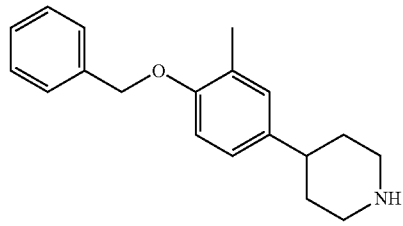 [SMILES: Cc1cc(C2CCNCC2)ccc1OCc1ccccc1]

The title compound was synthesized in a similar manner to the preparation of Intermediate 2-4-A using Intermediate 2-13-A. MS (ESI+) m/z 282.0 (M+H).

Intermediate 2-13-C. 4-(4-(Benzyloxy)-3-methylphenyl)-1-(2,2,2-trifluoroethyl)piperidine

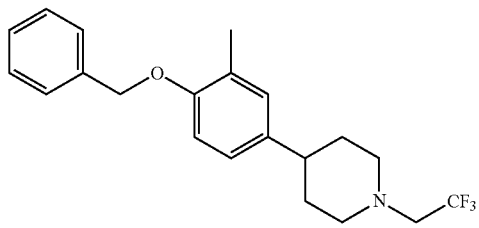 [SMILES: Cc1cc(C2CCN(CC(F)(F)F)CC2)ccc1OCc1ccccc1]

To a suspension of Intermediate 2-13-B (5 g, 17.77 mmol) and K₂CO₃ (5 g, 36.2 mmol) in DMF (40 mL) was added 2,2,2-trifluoroethyl trifluoromethanesulfonate (4 mL, 27.8 mmol). The mixture was then stirred at 40° C. for 23 h. The reaction was then quenched with H₂O. The mixture was then stirred at room temperature for 3 h. The mixture was then extracted with EtOAc. The organic layer was then washed successively with H₂O and brine, dried over Na₂SO₄, filtered, and then concentrated. The resulting residue was purified by silica gel flash column chromatography (heptane/EtOAc=1/0 to 4/1) to afford the title compound. MS (ESI+) m/z 364.0 (M+H).

Intermediate 2-13. 2-Methyl-4-(1-(2,2,2-trifluoro-ethyl)piperidin-4-yl)phenol

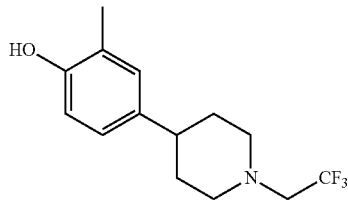 [SMILES: Cc1cc(C2CCN(CC(F)(F)F)CC2)ccc1O]

A mixture of Intermediate 2-13-C (4.9 g, 13.48 mmol) and Pd/C (10%) (500 mg, 13.5 mmol) in MeOH (100 mL) was stirred under $H_2$ atmosphere for 12 h. The mixture was then filtered through a plug of Celite®, which was rinsed with a mixture of EtOAc/MeOH (ca. 2/1). The filtrate was then concentrated to furnish the title compound. MS (ESI+) m/z 274.3 (M+H).

Intermediate 2-14

Intermediate 2-14-A. tert-Butyl 4-(3-methyl-4-nitrophenyl)-5,6-dihydropyridine-1(2H)-carboxylate

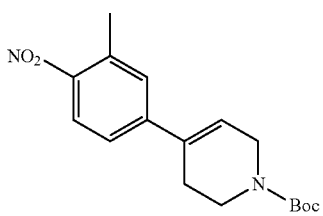 [SMILES: Cc1cc(C2=CCN(C(=O)OC(C)(C)C)CC2)ccc1[N+](=O)[O-]]

The title compound was synthesized in a similar manner to the preparation of Intermediate 2-1-A using 4-bromo-2-methyl-1-nitrobenzene (CAS#52414-98-9) and tert-butyl 4-(4,4,5,5-tetramethyl-1,3,2-dioxaborolan-2-yl)-5,6-dihydropyridine-1(2H)-carboxylate. MS (ESI−) m/z 317.2 (M−H).

Intermediate 2-14-B. Cyclopropyl(4-(3-methyl-4-nitrophenyl)-5,6-dihydropyridin-1(2H)-yl)methanone

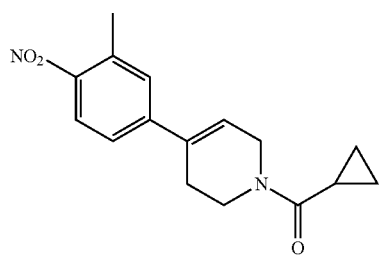 [SMILES: Cc1cc(C2=CCN(C(=O)C3CC3)CC2)ccc1[N+](=O)[O-]]

The title compound was synthesized in a similar manner as described in the synthesis of Intermediate 2-4. MS (ESI+) m/z 287.2 (M+H).

Intermediate 2-14. (4-(4-Amino-3-methylphenyl)piperidin-1-yl)(cyclopropyl)methanone

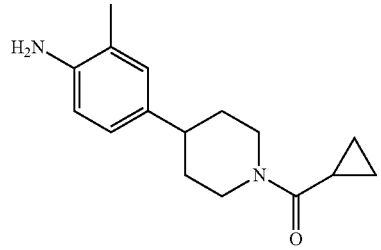 [SMILES: Cc1cc(C2CCN(C(=O)C3CC3)CC2)ccc1N]

A mixture of Intermediate 2-14-B (5.98 g, 20.89 mmol) and Pd/C (1.11 g) in EtOH (104 mL) was stirred under an $H_2$ atmosphere at room temperature for 8 h. The mixture was filtered through a plug of Celite®, which was rinsed with EtOH. The filtrate was concentrated. The resulting residue was resubjected to the same reaction conditions for 8 h, and the mixture was filtered through a plug of Celite®, which was rinsed with EtOH. The filtrate was concentrated and the resulting residue was purified by silica gel flash column chromatography (0.2% $Et_3N$ in heptane/EtOAc=1/0 to 0/1) to afford the title compound. MS (ESI+) m/z 259.3 (M+H).

Intermediate 2-15. (4-(4-Aminophenyl)piperidin-1-yl)(cyclopropyl)methanone

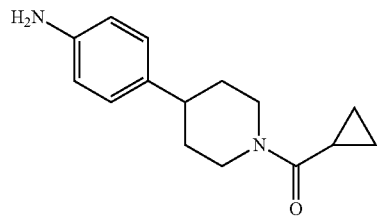 [SMILES: Nc1ccc(C2CCN(C(=O)C3CC3)CC2)cc1]

The title compound was synthesized starting from 1-bromo-4-nitrobenzene (CAS#586-78-7). Reaction of 1-bromo-4-nitrobenzene with tert-butyl 4-(4,4,5,5-tetramethyl-1,3,2-dioxaborolan-2-yl)-5,6-dihydropyridine-1(2H)-carboxylate, in a fashion analogous to Intermediate 2-1-A, afforded a Boc protected amine which was deprotected analogous to the transformation outlined in Intermediate 2-4-A, the subsequent amine was then reacted with cyclopropanecarboyl chloride in a similar manner to the procedure as described in Intermediate 2-4. The resulting product was hydrogenated in a similar manner as described in the synthesis of Intermediate 2-1 to furnish (4-(4-aminophenyl)piperidin-1-yl)(cyclopropyl)methanone. MS (ESI+) m/z 245.1 (M+H).

Intermediate 2-16

Intermediate 2-16-A. tert-Butyl 4-(4-amino-2-ethylphenyl)-5,6-dihydropyridine-1(2H)-carboxylate

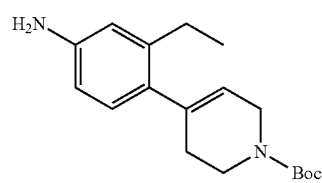 [SMILES: CCc1cc(N)ccc1C1=CCN(C(=O)OC(C)(C)C)CC1]

To a mixture of 4-bromo-3-ethylaniline (CAS#52121-42-3, 5 g, 24.99 mmol), dihydro-2H-pyran-4-yl)-4,4,5,5-tetramethyl-1,3,2-dioxaborolane (9.66 g, 31.2 mmol), and Pd(dppf)Cl$_2$CH$_2$Cl$_2$ adduct (1.02 g, 1.25 mmol) in DMF (100 mL) was added 2 M aq. potassium phosphate (37.5 mL, 75.0 mmol). The mixture was then stirred at 110° C. for 50 min, and then cooled to room temperature, and then diluted with EtOAc. The organic layer was then separated from the aqueous layer, and dried over Na$_2$SO$_4$, filtered, and then concentrated. The resulting residue was purified by silica gel flash column chromatography (heptane/EtOAc=1/0 to 4/6) to afford the title compound. MS (ESI+) m/z 303.1 (M+H).

Intermediate 2-16. tert-Butyl 4-(4-amino-2-ethylphenyl)piperidine-1-carboxylate

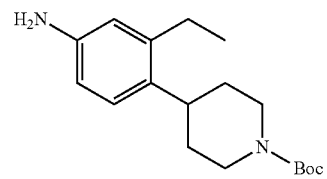

The title compound was synthesized in a similar manner as described in the synthesis of Intermediate 2-1 starting from tert-butyl 4-(4-amino-2-ethylphenyl)-5,6-dihydropyridine-1(2H)-carboxylate. MS (ESI+) m/z 249.3 (M-tBu+2H).

Intermediate 2-17. tert-Butyl 4-(3-methyl-4-(((trifluoromethyl)sulfonyl) oxy)phenyl)piperidine-1-carboxylate

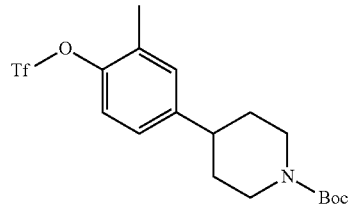

To a solution of Intermediate 2-1 (3 g, 10.30 mmol) and pyridine (8.33 mL, 103 mmol) in CH$_2$Cl$_2$ (103 mL) at 0° C. was added triflic anhydride (1.74 mL, 10.3 mmol). The mixture was then stirred at 0° C. for 1 h. The reaction mixture was purified by silica gel flash column chromatography (heptane/EtOAc=1/0 to 0/1) to afford the title compound. MS (ESI−) m/z 422.3 (M−H).

Intermediate 2-18

The following compounds were prepared by similar methods as described above for Intermediate 2-17 using the appropriate starting materials delineated in the table below.

| Intermediate | Structure/Chemical Name | Starting material(s) | MS or NMR data |
|---|---|---|---|
| 2-18-1 | tert-Butyl 4-(4-(((trifluoromethyl)sulfonyl)oxy)phenyl)piperidine-1-carboxylate | tert-butyl 4-(4-hydroxphenyl)-piperidine-1-carboxylate | $^1$H NMR (400 MHz, CD$_3$CN) δ 7.39-7.45 (m, 2H), 7.31-7.37 (m, 2H), 4.15-4.24 (m, 2H), 2.74-2.91 (m, 3H), 1.78-1.86 (m, 2H), 1.50-1.64 (m, 2H), 1.47 (s, 9H). |
| 2-18-2 | 4-(1-(Cyclopropanecarbonyl)piperidin-4-yl)-2-methylphenyl trifluoromethanesulfonate | Intermediate 2-4 | MS (ESI+) m/z 392.1 (M + H) |

Intermediate 2-20

Intermediate 2-20-A. tert-butyl 4-(2-chloro-4-hydroxyphenyl)-5,6-dihydropyridine-1(2H)-carboxylate

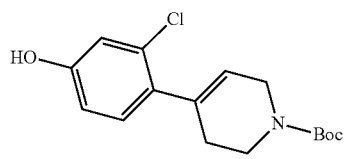 [SMILES: CC(C)(C)OC(=O)N1CC=C(c2ccc(O)cc2Cl)CC1]

To a solution of 4-bromo-3-chlorophenol (CAS #13631-21-5) (1.44 g, 6.94 mmol) in DMF (35 mL) were added tert-butyl 4-(4,4,5,5-tetramethyl-1,3,2-dioxaborolan-2-yl)-5,6-dihydropyridine-1(2H)-carboxylate (CAS #286961-14-6) (2.79 g, 9.02 mmol), $PdCl_2(dppf)$ $CH_2Cl_2$ adduct (0.28 g, 0.35 mmol) and 2 M potassium phosphate (10.41 mL, 20.82 mmol). The mixture was then degassed and placed under nitrogen atmosphere, and then the mixture was stirred at 100° C. for 1 h. The reaction mixture was cooled to room temperature, and then diluted with EtOAc. The mixture was then washed with $H_2O$, dried over $Na_2SO_4$, filtered, and then concentrated. The resulting residue was purified by silica gel flash column chromatography (0-50% EtOAc/heptane) to afford the title compound. MS (ESI+) m/z 254.1 (M-t-butyl+2H).

Intermediate 2-20-B. tert-butyl 4-(2-chloro-4-hydroxyphenyl)piperidine-1-carboxylate

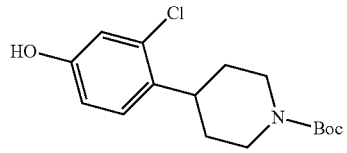 [SMILES: CC(C)(C)OC(=O)N1CCC(c2ccc(O)cc2Cl)CC1]

A mixture of Intermediate 2-20-A (0.78 g, 2.52 mmol) and $PtO_2$ (0.11 g, 0.50 mmol) in EtOAc (22 mL) was stirred under the H2 atmosphere at room temperature for 1 h. The reaction mixture was then filtered, and then concentrated to furnish the title compound. MS (ESI+) m/z 256.1, 258.1 (M-t-butyl+2H).

Intermediate 2-20. tert-butyl 4-(2-cyclopropyl-4-hydroxyphenyl)piperidine-1-carboxylate

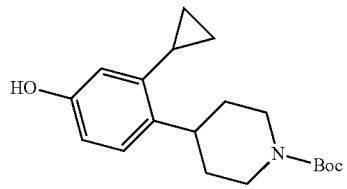 [SMILES: CC(C)(C)OC(=O)N1CCC(c2ccc(O)cc2C2CC2)CC1]

To a suspension of Intermediate 2-20-B (0.2 g, 0.64 mmol), potassium cyclopropyltrifluoroborate (0.190 g, 1.283 mmol), and $K_2CO_3$ (0.164 g, 1.283 mmol) in DME (2.4 mL) and $H_2O$ (0.8 mL) was added chloro(2-dicyclohexylphosphino-2',6'-dimethoxy-1,1'-biphenyl)[2-(2-aminoethylphenyl)]palladium(II)-methyl-t-butyl ether adduct (CAS#1028206-58-7) (0.086 g, 0.128 mmol). The mixture was then stirred at 140° C. for 1 h, and then cooled to room temperature. The reaction mixture was then diluted with EtOAc. The mixture was then washed with $H_2O$, dried over $Na_2SO_4$, filtered, and then concentrated. The resulting residue was purified by silica gel flash column chromatography (0-50% EtOAc/heptane) to afford the title compound. MS (ESI+) m/z 262.3 (M-t-butyl+2H).

Intermediate 2-21. tert-butyl 4-(4-hydroxy-2-propylphenyl)piperidine-1-carboxylate

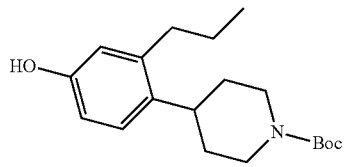 [SMILES: CCCc1cc(O)ccc1C1CCN(C(=O)OC(C)(C)C)CC1]

The title compound was synthesized starting with tert-butyl 4-(2-chloro-4-hydroxphenyl)-5,6-dihydropyridine-1(2H)-carboxylate (Intermediate 2-20-A), which underwent reaction with 4,4,5,5-tetramethyl-2-(prop-1-en-1-yl)-1,3,2-dioxaborolane (CAS #72824-04-5), in a fashion analogous to the preparation of Intermediate 2-20, followed by hydrogenation by the procedure as described in the synthesis of Intermediate 2-20-B to furnish tert-butyl 4-(4-hydroxy-2-propylphenyl)piperidine-1-carboxylate. MS (ESI+) m/z 264.3 (M-t-butyl+2H).

Intermediate 2-22

Intermediate 2-22-A. 1-(Benzyloxy)-4-bromo-2-fluoro-3-vinylbenzene

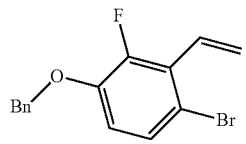

To a solution of 3-(benzyloxy)-6-bromo-2-fluorobenzaldehyde (CAS #1114809-05-0) (0.5 g, 1.617 mmol) and methyltriphenylphosphonium iodide (0.949 g, 2.022 mmol) in DMF (16 mL) at 0° C. was added NaH (60% in oil, 0.29 g, 7.3 mmol). The mixture was then stirred at room temperature for 16 h. The reaction was then quenched with satd. aq. $NH_4Cl$. The mixture was then extracted with EtOAc. The organic phase was then dried over $Na_2SO_4$, filtered, and then concentrated. The resulting residue was purified by silica gel flash column chromatography (0-40% EtOAc in heptane) to afford the title compound. MS (ESI+) m/z 307.03, 309.14 (M+H).

Intermediate 2-22-B. tert-Butyl 4-(4-(benzyloxy)-3-fluoro-2-vinylphenyl)-5,6-dihydropyridine-1(2H)-carboxylate

The title compound was synthesized starting with 1-(benzyloxy)-4-bromo-2-fluoro-3-vinylbenzene by the similar method as described for the synthesis of Intermediate 2-1. MS (ESI+) m/z 354.4 (M-t-butyl+2H).

Intermediate 2-22. tert-Butyl 4-(2-ethyl-3-fluoro-4-hydroxyphenyl)piperidine-1-carboxylate

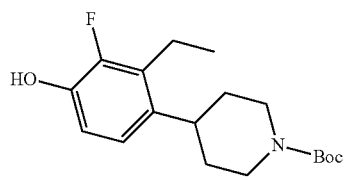 [SMILES: CCc1c(C2CCN(C(=O)OC(C)(C)C)CC2)ccc(O)c1F]

A mixture of tert-butyl 4-(4-(benzyloxy)-3-fluoro-2-vinylphenyl)-5,6-dihydropyridine-1(2H)-carboxylate (0.277 g, 0.677 mmol) and 10% Pd/C (0.07 g) in MeOH (13.5 mL) was stirred at room temperature for 4 h. The reaction mixture was filtered through a plug of Celite®, and then concentrated. The resulting residue was purified by silica gel flash column chromatography (0-100% EtOAc in heptane) to afford the title compound. MS (ESI+) m/z 268.2 (M-t-butyl+2H).

Intermediate 2-23

Intermediate 2-23-A. tert-butyl 2-chloro-6-methoxy-5',6'-dihydro-[3,4'-bipyridine]-1'(2'H)-carboxylate

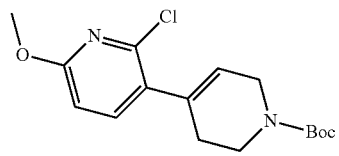 [SMILES: COc1ccc(C2=CCN(C(=O)OC(C)(C)C)CC2)c(Cl)n1]

To a solution of (2-chloro-6-methoxypyridin-3-yl)boronic acid (CAS#1072946-25-8)(0.077 g, 0.41 mmol) and tert-butyl 4-bromo-5,6-dihydropyridine-1(2H)-carboxylate (CAS#159503-91-0)(0.14 g, 0.52 mmol) in DMF (2.1 mL) were added Pd(PPh$_3$)$_4$ (0.024 g, 0.021 mmol) and cesium carbonate (0.12 g, 0.37 mmol). The mixture was then stirred at 100° C. for 1 h, and then cooled to room temperature. The reaction mixture was diluted with EtOAc. The organic layer was then washed with H$_2$O, dried over Na$_2$SO$_4$, filtered, and then concentrated. The resulting residue was purified by silica gel flash column chromatography (0-50% EtOAc in heptane) to afford the title compound. MS (ESI+) m/z 269.15, 271.1 (M-t-butyl+2H).

Intermediate 2-23-B. tert-butyl 2-ethyl-6-methoxy-5',6'-dihydro-[3,4'-bipyridine]-1'(2'H)-carboxylate

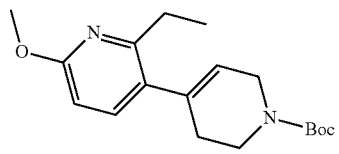 [SMILES: CCc1nc(OC)ccc1C1=CCN(C(=O)OC(C)(C)C)CC1]

To a solution of Intermediate 2-23-A (0.65 g, 2.0 mmol) in THF (10 mL) was added K$_2$CO$_3$ (0.830 g, 6.0 mmol), and PdCl$_2$(dppf) dichloromethane adduct (0.163 g, 0.20 mmol). The mixture was then degassed and placed under nitrogen. To the mixture at room temperature was added a solution of diethylzinc (ca. 15% in toluene, 2.3 mL, 2.5 mmol) dropwise. The mixture was then stirred at 64° C. for 7 h, and then diluted with EtOAc. The mixture was then washed with H$_2$O, dried over Na$_2$SO$_4$, filtered, and then concentrated. The resulting residue was purified by silica gel flash column chromatography (0-100% EtOAc in heptane) to afford the title compound. MS (ESI+) m/z 319.4 (M+H).

Intermediate 2-23-C. tert-butyl 4-(2-ethyl-6-methoxypyridin-3-yl)piperidine-1-carboxylate

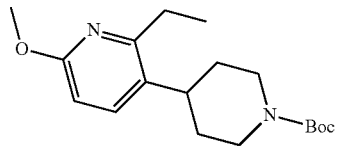 [SMILES: CCc1nc(OC)ccc1C1CCN(C(=O)OC(C)(C)C)CC1]

The title compound was synthesized via hydrogenation in the same manner as the preparation of Intermediate 2-2 starting from Intermediate 2-23-B. MS (ESI+) m/z 321.4 (M+H).

Intermediate 2-23. tert-Butyl 4-(2-ethyl-6-hydroxypyridin-3-yl)piperidine-1-carboxylate

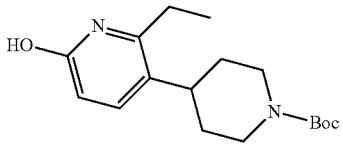 [SMILES: CCc1nc(O)ccc1C1CCN(C(=O)OC(C)(C)C)CC1]

A mixture of Intermediate 2-23-C (0.19 g, 0.58 mmol) and 48% HBr (1.5 mL, 13.3 mmol) was stirred at 110° C. for 2 h. To the mixture was then added an additional aliquot of 48% aq. HBr, and then the mixture was continued stirring at the 110° C. for 4 h. The reaction was then put at 0° C. and was made basic with portionwise addition of NaOH (pellets, 1.06 g, 26.6 mmol). To the resulting slurry was successively added 1 mL of H$_2$O, 1.5 mL of THF, and Boc$_2$O (0.32 g, 1.4 mmol). The whole mixture was stirred at 0° C. for 1 h, and then diluted with EtOAc. The mixture was washed with H₂O, dried over Na₂SO₄, filtered, and then concentrated to furnish the title compound. MS (ESI+) m/z 307.3 (M+H).

Intermediate 2-24

Intermediate 2-24-A. tert-butyl 3-chloro-5-hydroxy-5',6'-dihydro-[2,4'-bipyridine]-1'(2'H)-carboxylate

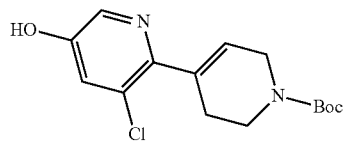 [SMILES: CC(C)(C)OC(=O)N1CC=C(c2ncc(O)cc2Cl)CC1]

The title compound was synthesized in the same manner as described in the synthesis of Intermediate 2-1-A starting from 6-bromo-5-chloropyridin-3-ol (CAS #52764-12-2). MS (ESI+) m/z 255.2, 257.1 (M-t-butyl+2H).

Intermediate 2-24. tert-butyl 4-(3-ethyl-5-hydroxy-pyridin-2-yl)piperidine-1-carboxylate

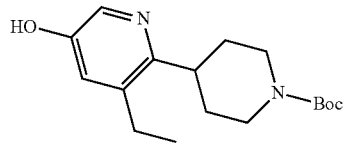 [SMILES: CCc1cc(O)cnc1C1CCN(C(=O)OC(C)(C)C)CC1]

Reaction of tert-butyl 3-chloro-5-hydroxy-5',6'-dihydro-[2,4'-bipyridine]-1'(2'H)-carboxylate (Intermediate-2-24-A) with 2,4,6-trivinylcyclotriboroxane pyridine complex (CAS#442850-89-7), in a fashion analogous to the synthesis of Intermediate 2-20, followed by hydrogenation by the method described in the preparation of Intermediate 2-1 furnished the title compound. MS (ESI+) m/z 307.3 (M+H).

Intermediate 2-25. 2-Methyl-4-(1-(2,2,2-trifluoro-ethyl)piperidin-4-yl)aniline

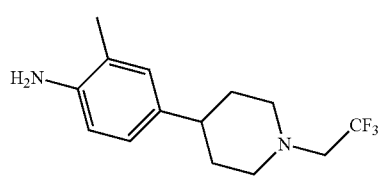 [SMILES: Cc1cc(C2CCN(CC(F)(F)F)CC2)ccc1N]

The title compound was synthesized starting from tert-butyl 4-(3-methyl-4-nitrophenyl)-5,6-dihydropyridine-1(2H)-carboxylate (Intermediate 2-14-A). Deprotection of tert-butyl 4-(3-methyl-4-nitrophenyl)-5,6-dihydropyridine-1(2H)-carboxylate with TFA, in a fashion analogous to the preparation of Intermediate 2-4-A, and subsequent alkylation of the amine as outlined in the preparation of Intermediate 2-13-C followed by hydrogenation as described for Intermediate 2-14, afforded the title compound, 2-methyl-4-(1-(2,2,2-trifluoroethyl)piperidin-4-yl)aniline. (ESI+) m/z 273.3 (M+H).

Intermediate 2-26

Intermediate 2-26-A. tert-Butyl 4-(4-(methoxycarbonyl)-3-methylphenyl)piperidine-1-carboxylate

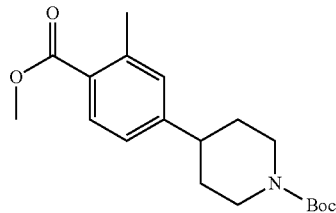 [SMILES: COC(=O)c1ccc(C2CCN(C(=O)OC(C)(C)C)CC2)cc1C]

The title compound was synthesized as outlined for the synthesis of Intermediate 2-1 starting from methyl 4-bromo-2-methylbenzoate (CAS#148547-19-7) in the place of 4-bromo-2-methyl phenol. MS (ESI+) m/z 334.3 (M+H).

Intermediate 2-26-B. tert-Butyl 4-(4-(hydroxymethyl)-3-methylphenyl)piperidine-1-carboxylate

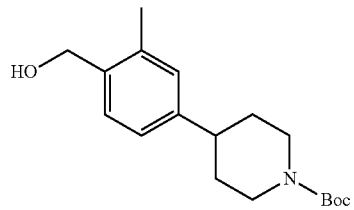

To a solution of tert-butyl 4-(4-(methoxycarbonyl)-3-methylphenyl)piperidine-1-carboxylate (1 g, 3.00 mmol) in THF (100 mL) at 0° C. was added LiAlH₄ (0.2 g, 5.27 mmol). The mixture was then stirred at 0° C. for 1.5 h. The reaction at 0° C. was then quenched with H₂O (0.2 mL), 15% aq. NaOH (0.2 mL), and H₂O (0.6 mL). The mixture was then diluted with THF, and then the mixture was stirred at room temperature for 16 h. The mixture was dried over Na₂SO₄, and then filtered through a plug of silica gel which was rinsed with EtOAc. The filtrate was concentrated to furnish the title compound. (ESI+) m/z 306.3 (M+H).

Intermediate 2-26-C. tert-Butyl 4-(4-(bromomethyl)-3-methylphenyl)piperidine-1-carboxylate

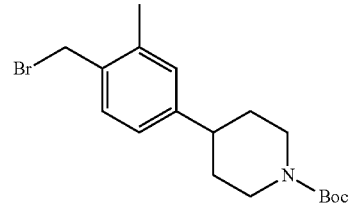 [SMILES: Cc1cc(C2CCN(C(=O)OC(C)(C)C)CC2)ccc1CBr]

To a solution of tert-butyl 4-(4-(hydroxymethyl)-3-methylphenyl)piperidine-1-carboxylate (0.916 g, 3 mmol) and PPh₃ (0.9 g, 3.43 mmol) in CH₂Cl₂ (10 mL) at 0° C. was added CBr₄ (1.2 g, 3.62 mmol). The mixture was then stirred at 0° C. for 2.5 h. The reaction mixture was then directly purified by silica gel flash column chromatography (heptane//EtOAc=1/0 to 2/1) to afford the title compound. MS (ESI+) m/z 368.2, 370.1 (M+H).

Intermediate 2-26. (4-(1-(tert-Butoxycarbonyl)piperidin-4-yl)-2-methylbenzyl)triphenylphosphonium bromide

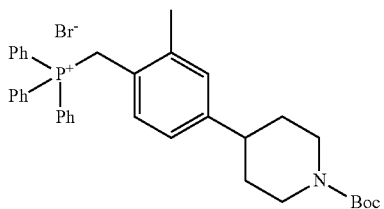 [SMILES: Cc1cc(C2CCN(C(=O)OC(C)(C)C)CC2)ccc1C[P+](c1ccccc1)(c1ccccc1)c1ccccc1 ; [Br-]]

A mixture of tert-butyl 4-(4-(bromomethyl)-3-methylphenyl)piperidine-1-carboxylate (0.62 g, 1.69 mmol) and triphenylphosphine (0.49 g, 1.86 mmol) in toluene (8 mL) was stirred at 60° C. for 4 h. The mixture was then concentrated to about 2 mL volume, which was then filtered. The collected solid was washed with toluene, and then dried under the reducing pressure to furnish the title compound. MS (ESI+) m/z 550.4 (M)$^+$.

Intermediate 3-1. tert-Butyl 4-(4-((2-bromothiophen-3-yl)methoxy)phenyl)piperidine-1-carboxylate

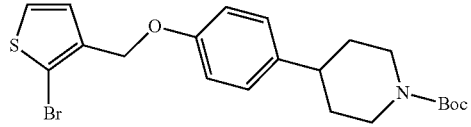 [SMILES: CC(C)(C)OC(=O)N1CCC(c2ccc(OCc3ccsc3Br)cc2)CC1]

A mixture of 2-bromo-3-(bromomethyl)-thiophene (CAS #40032-76-6, 1.50 g, 5.9 mmol), tert-butyl 4-(4-hydroxyphenyl)piperidine-1-carboxylate (0.93 g, 5.9 mmol), and K$_2$CO$_3$ (0.81 g, 5.9 mmol) in DMF (56 ml) was stirred at 70° C. for 22 h, and then cooled to room temperature, and then diluted with EtOAc. The organic phase was then washed successively with H$_2$O twice, then brine, and dried over MgSO$_4$, filtered and then concentrated. The resulting residue was purified by silica gel flash column chromatography (hexane/EtOAc=4/1) to afford the title compound. MS (ESI+) m/z 395.1 (M-tBu+2H).

Intermediate 3-2

Intermediate 3-2-A. Methyl 2-bromo-5-methylthiophene-3-carboxylate

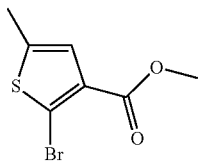

To a solution of methyl 5-methylthiophene-3-carboxylate (CAS#88770-18-7, 440 mg, 2.817 mmol) in DMF (4.8 mL) at 0° C. was added a solution of NBS (501 mg, 2.817 mmol) in DMF (4 mL). The mixture was then stirred at room temperature for 18 h. At that point additional NBS (50 mg, 0.281 mmol) was added and then the mixture was stirred at room temperature for another 18 h. The reaction mixture was then diluted with EtOAc, and then washed with H$_2$O. The aqueous layer was then extracted three times with EtOAc. The combined organics were then washed with brine, dried over MgSO$_4$, filtered, and then concentrated. The resulting residue was purified by silica gel flash column chromatography (hexane/EtOAc=1/0 to 9/1) to afford the title compound. $^1$H-NMR (400 MHz, DMSO-d$_6$) δ 7.10 (d, J=1.2 Hz, 1H), 3.79 (s, 3H), 2.40 (d, J=1.2 Hz, 3H).

Intermediate 3-2-B. (2-Bromo-5-methylthiophen-3-yl)methanol

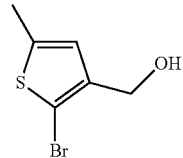

To a solution of Intermediate 3-2-A (590 mg, 2.510 mmol) in THF (15 mL) was added lithium borohydride (109 mg, 5.02 mmol). The mixture was then stirred at reflux for 18 h, and then cooled to room temperature, and then quenched with H$_2$O. The mixture was extracted three times with EtOAc. The combined organic extracts were washed with brine, dried over MgSO$_4$, filtered, and then concentrated to furnish the title compound. $^1$H-NMR (400 MHz, DMSO-d$_6$) δ 6.76 (d, J=1.1 Hz, 1H), 5.19 (t, J=5.7 Hz, 1H), 4.29 (d, J=5.7 Hz, 2H), 2.38 (d, J=1.1 Hz, 3H).

Intermediate 3-2. 1-(4-(4-((2-Bromo-5-methylthiophen-3-yl)methoxy)phenyl)piperidin-1-yl)propan-1-one

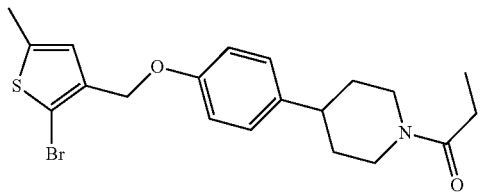 [SMILES: CCC(=O)N1CCC(c2ccc(OCc3cc(C)sc3Br)cc2)CC1]

To a solution of Intermediate 3-2-B (270 mg, 1.30 mmol) in CH$_2$Cl$_2$ (5.4 mL) at 0° C. was added triethylamine (710 μL, 5.09 mmol), followed by MsCl (131 μL, 1.70 mmol) dropwise. The mixture was then stirred at room temperature for 2 h before being diluted with CH$_2$Cl$_2$. The organic layer was washed with H$_2$O. The aqueous layer was then extracted three times with CH$_2$Cl$_2$. The combined organics were then washed with brine (10 mL), dried over MgSO$_4$, filtered, and then concentrated. The resulting residue was dissolved in DMF (3.6 mL) and Intermediate 2-5-1 (145 mg, 0.621 mmol) was added, followed by potassium carbonate (239 mg, 1.73 mmol). The mixture was stirred at room temperature for 18 h. To the mixture was then added additional potassium carbonate (120 mg, 0.87 mmol), and then the mixture was stirred at 50° C. for 18 h, and then diluted with EtOAc. The organic layer was washed with H₂O. The resulting aqueous wash was extracted three times with EtOAc. The organic layers were combined and were the washed twice with brine, dried over MgSO₄, filtered, and then concentrated to afford the title compound. MS (ESI+) m/z 421.8 (M+H).

Intermediate 3-3

The following compounds were prepared by similar methods as described above for Intermediate 3-2 using the appropriate starting materials delineated in the table below. In some instances one of the starting materials is commercially available 2-bromo-3-(bromomethyl)-thiophene, in which case there is no need to synthesize the mesylate, however, the base and solvent to affect the alkylation described for Intermediate 3-2, can be employed with the bromide as well.

| Intermediate | Structure/Chemical Name | Starting material(s) | MS or NMR data |
|---|---|---|---|
| 3-3-1 | Methyl 4-(4-((2-bromo-5-methylthiophen-3-yl)methoxy)-3-methylphenyl)piperidine-1-carboxylate | Intermediate 2-5-2 and Intermediate 3-2-B | (ESI+) m/z 437.7 (M + H) |
| 3-3-2 | 1-(4-(4-((2-Bromothiophen-3-yl)methoxy)-3,5-dimethylphenyl)piperidin-1-yl)propan-1-one | Intermediate 2-7 and 2-bromo-3-(bromomethyl)-thiophene | (ESI+) m/z 477.0 (M + H + CH₃CN) |
| 3-3-3 | Methyl 4-(4-((2-bromo-5-ethylthiophen-3-yl)methoxy)-3-methylphenyl)piperidine-1-carboxylate | Intermediate 2-5-2 and methyl 5-ethylthiophene-3-carboxylate (CAS# 938006-77-0) | (ESI+) m/z 451.9 (M + H) |
| 3-3-4 | tert-Butyl 4-(4-((2-bromothiophen-3-yl)methoxy)-3-methylphenyl)piperidine-1-carboxylate | Intermediate 2-1 and 2-bromo-3-(bromomethyl)-thiophene | (ESI+) m/z 450.9 (M-t-butyl + CH₃CN + H) |

Intermediate 3-4

Intermediate 3-4-A. Methyl 2-amino-4-hydroxy-4-(trifluoromethyl)-4,5-dihydrothiophene-3-carboxylate

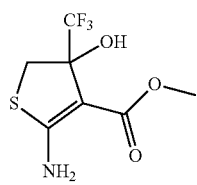

To a solution of NaSH hydrate (CAS #207683-19-0, 12.3 g, 0.22 mol) in H₂O (60 mL) at 0° C. was added 1M aq. NaOH (60 mL) dropwise, followed by a solution of 3-bromo-1,1-trifluoropropan-2-one (CAS#431-35-6, 16.4 mL, 0.157 mol) in diethyl ether (15 mL) dropwise. The mixture was then stirred at 0° C. for 1 h. To the mixture at 0° C. was then added methyl cyanoacetate (13.2 mL, 0.149 mol), followed by triethylamine (20.9 mL, 0.150 mol). The mixture was then stirred at 0° C. for 1 h, and then room temperature for 4 h. The resulting white solid was then collected by filtration, and then washed with H₂O, dried under vacuum to furnish the title compound. ¹H-NMR (400 MHz, DMSO-d₆) δ 8.02 (s, 2H), 6.20 (s, 1H), 3.60 (s, 3H), 3.49 (d, J=12.6 Hz, 1H), 3.19 (d, J=12.6 Hz, 1H).

Intermediate 3-4-B. Methyl 2-bromo-4-(trifluoromethyl)thiophene-3-carboxylate

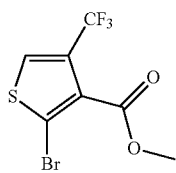

To a suspension of Intermediate 3-4-A (10.0 g, 41.12 mmol) in CH₃CN (200 mL) at 0° C. was added CuBr₂ (CAS#7789-45-9, 11.39 g, 51 mmol), followed by t-butyl nitrite (CAS#540-80-7, 8.15 mL, 61.68 mmol) dropwise. The mixture was stirred at 0° C. for 2 h, and then at room temperature for 16 h. The reaction mixture was then diluted with H₂O and EtOAc. The resulting layers were separated. The organic layer was then washed three times with brine, dried over MgSO₄, filtered, and then concentrated. The resulting residue was purified by silica gel flash column chromatography (CH₂Cl₂/MeOH=100/0 to 100/1) to afford the title compound. ¹H-NMR (400 MHz, DMSO-d₆) δ 8.42 (s, 1H), 4.09 (s, 3H).

Intermediate 3-4-C. (2-Bromo-4-(trifluoromethyl)thiophen-3-yl)methanol

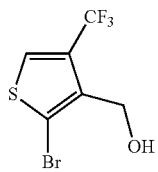 [SMILES: OCc1c(C(F)(F)F)csc1Br]

To a solution of Intermediate 3-4-B (3.5 g, 12.11 mmol) in THF (34 mL) at 0° C. was added DIBAL-H (1M in toluene, 34.14 mL, 34.14 mmol), and then the mixture was then stirred at 0° C. for 3 h. The reaction was quenched with 1N aq. HCl until reaching a pH ~3.0. The reaction mixture was partially concentrated, and then extracted three times with CH₂Cl₂. The combined organics were dried over MgSO₄, filtered and then concentrated. The resulting residue was purified by silica gel flash column chromatography (CH₂Cl₂) to afford the title compound. ¹H NMR (400 MHz, DMSO-d₆) δ 8.29 (s, 1H), 5.24 (t, J=5.2 Hz, 1H), 4.45 (d, J=5.2 Hz, 2H).

Intermediate 3-4. tert-Butyl 4-(4-((2-bromo-4-(trifluoromethyl)thiophen-3-yl)methoxy)-3-methylphenyl)piperidine-1-carboxylate

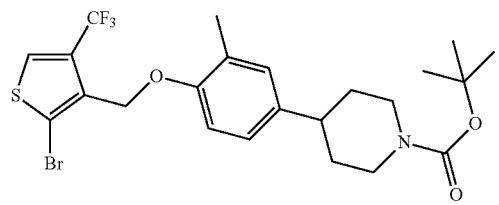 [SMILES: Cc1cc(C2CCN(C(=O)OC(C)(C)C)CC2)ccc1OCc1c(C(F)(F)F)csc1Br]

The title compound was synthesized in a similar manner to the preparation of Intermediate 3-2 using Intermediate 2-1 and Intermediate 3-4-C. MS (ESI+) m/z 518.9 (M-tBu+CH₃CN+H).

Intermediate 3-5. tert-Butyl 4-(4-((2-bromo-4-(trifluoromethyl)thiophen-3-yl)methoxy)phenyl)piperidine-1-carboxylate

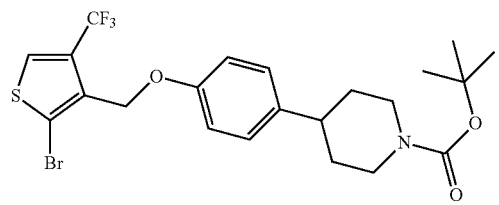 [SMILES: CC(C)(C)OC(=O)N1CCC(c2ccc(OCc3c(C(F)(F)F)csc3Br)cc2)CC1]

The title compound was synthesized in a similar manner to the preparation of Intermediate 3-2 using tert-butyl 4-(4-hydroxyphenyl)piperidine-1-carboxylate (CAS#149377-19-5) and Intermediate 3-4-C. MS (ESI+) m/z 504.9 (M-tBu+CH₃CN+H).

Intermediate 3-6

Intermediate 3-6-A. 2-Bromo-4-methylthiophene-3-carboxylic acid

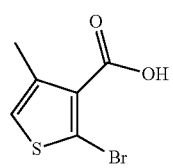

To a solution of 1M LDA in THF (14.77 ml, 14.77 mmol) at −78° C. was added a solution of 4-methylthiophene-3-carboxylic acid (CAS#78071-30-4, 1 g, 7.03 mmol) in THF (5 mL) over 0.25 h, and then the mixture was stirred at −78° C. for 0.5 h. To the solution was then added a solution of CBr₄ (2.57 g, 7.74 mmol) in THF (8 mL) dropwise over 15 min. The mixture was then stirred at −78° C. for 0.5 h, and then allowed to warm to room temperature over 1 h. The reaction was then quenched with 1N HCl until the pH reached 1. The mixture was then extracted twice with EtOAc. The combined organics were washed with brine, dried over Na₂SO₄, filtered, and then concentrated. The resulting residue was purified by silica gel flash column chromatography (hexane/EtOAc=1/0 to 0/1) to afford the title compound. ¹H-NMR (400 MHz, CDCl₃) δ 6.92 (s, 1H), 2.45 (s, 3H).

Intermediate 3-6-B.
(2-Bromo-4-methylthiophen-3-yl)methanol

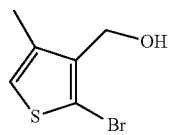

To a solution of Intermediate 3-6-A (1.22 g, 5.52 mmol) in THF (8 mL) at room temperature was added BH₃-THF in THF (CAS#14044-65-6, 16.56 mL, 16.56 mmol). The mixture was then stirred at room temperature for 2 h. The reaction was then quenched with MeOH. The mixture was then concentrated. The resulting residue was purified by silica gel flash column chromatography (hexane/EtOAc=1/0 to 7/3) to afford the title compound. ¹H-NMR (400 MHz, CD₃OD) δ 7.02 (d, J=1.0 Hz, 1H), 4.45-4.60 (m, 2H), 2.29 (d, J=1.0 Hz, 3H).

Intermediate 3-6. (4-(4-((2-Bromo-4-methylthiophen-3-yl)methoxy)-3-methylphenyl)piperidin-1-yl)(cyclopropyl)methanone

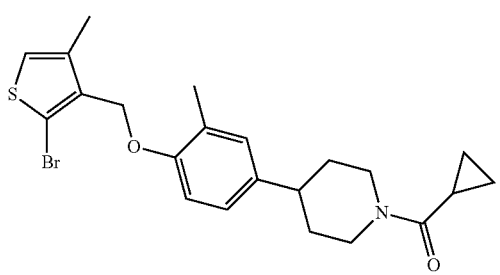 [SMILES: Cc1cc(C2CCN(C(=O)C3CC3)CC2)ccc1OCc1c(C)csc1Br]

To a solution of Intermediate 3-6-B (1.22 g, 5.52 mmol), Intermediate 2-4 (158 mg, 0.608 mmol), and triphenylphosphine (160 mg, 0.608 mmol) in THF (2.5 ml) at 0° C. was added DIAD (156 mg, 0.608 mmol). The mixture was then stirred at room temperature for 16 h, and then diluted with CH₂Cl₂ and H₂O. The organic layer was then passed through an ISOLUTE® Phase Separator. The organic layer was then concentrated with Celite®. The resulting residue was purified by silica gel flash column chromatography (hexane/EtOAc=1/0 to 0/1) to afford the title compound. MS (ESI+) m/z 448.0 (M+H).

Intermediate 3-7. ((2-Bromo-4-methylthiophen-3-yl)methoxy)(tert-butyl)dimethylsilane

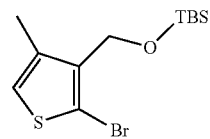

To a solution of Intermediate 3-6-B (400 mg, 1.93 mmol) and imidazole (145 mg, 2.12 mmol) in DMF (3.86 mL) at 0° C. was added TBSCl (306 mg, 2.03 mmol), and then the mixture was stirred for 1 h at room temperature. The reaction was then quenched with 1/1 water and brine. The mixture was then extracted with EtOAc. The organic layer separated and then concentrated. The resulting residue was purified by silica gel flash column chromatography (hexane/EtOAc=1/0 to 8/2) to afford the title compound. ¹H-NMR (400 MHz, CDCl₃) δ 6.77 (d, J=1.1 Hz, 1H), 4.53 (s, 2H), 2.21 (d, J=1.1 Hz, 3H), 0.82 (s, 9H), 0.00 (s, 6H).

Intermediate 3-8. tert-Butyl 6-((2-bromothiophen-3-yl)methoxy)-3,4-dihydroisoquinoline-2(1H)-carboxylate

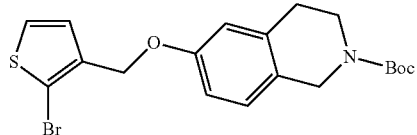 [SMILES: CC(C)(C)OC(=O)N1CCc2cc(OCc3ccsc3Br)ccc2C1]

The title compound was synthesized in a similar manner to the preparation of Intermediate 3-1 using tert-butyl 6-hydroxy-3,4-dihydroisoquinoline-2(1H)-carboxylate (CAS#158984-83-9) and 2-bromo-3-(bromomethyl)thiophene. MS (ESI+) m/z 408.9 (M-tBu+CH₃CN+H).

Intermediate 3-9. ((2-Bromo-4-(trifluoromethyl)thiophen-3-yl)methoxy)(tert-butyl)dimethylsilane

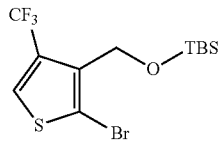

The title compound was synthesized in a similar manner to the preparation of Intermediate 3-7 starting from 2-bromo-4-(trifluoromethyl)thiophen-3-yl)methanol (Intermediate 3-4-C). ¹H NMR (400 MHz, CDCl₃) δ 7.68 (d, J=1.0 Hz, 1H), 4.69 (s, 2H), 0.90-0.95 (m, 9H), 0.11 (s, 6H).

Intermediate 4-1

Intermediate 4-1-A. Ethyl 1-(6-(3-formylthiophen-2-yl)pyridin-2-yl)-5-(trifluoromethyl)-1H-pyrazole-4-carboxylate

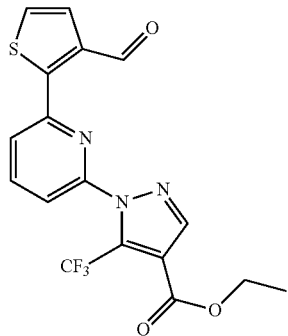 [SMILES: CCOC(=O)c1cnn(-c2cccc(-c3sccc3C=O)n2)c1C(F)(F)F]

To a suspension of Intermediate 1-1 (4.44 g, 12.19 mmol), (3-formylthiophen-2-yl)boronic acid (CAS#17303-83-2, 3.75 g, 24.04 mmol) and potassium fluoride (4.19 g, 72.1 mmol) in THF (60 mL) was added Pd(t-Bu$_3$P)$_2$ (CAS #53199-31-8, 500 mg, 0.978 mmol). The mixture was stirred at room temperature for 18 h. The reaction mixture was diluted with CH$_2$Cl$_2$, and filtered. The filtrate was concentrated. The resulting residue was purified by silica gel flash column chromatography (heptane/EtOAc=1/0 to 0/1) to afford the title compound. MS (ESI+) m/z 396.1 (M+H).

Intermediate 4-1-B. Ethyl 1-(6-(3-(hydroxymethyl)thiophen-2-yl)pyridin-2-yl)-5-(trifluoromethyl)-1H-pyrazole-4-carboxylate

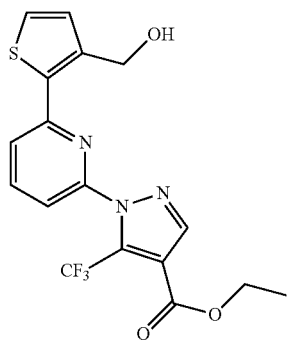 [SMILES: CCOC(=O)c1cnn(-c2cccc(-c3sccc3CO)n2)c1C(F)(F)F]

To a solution of Intermediate 4-1-A (4.42 g, 11.18 mmol) in EtOH (56 ml) at 0° C. was added sodium borohydride (0.423 g, 11.2 mmol) portionwise. The mixture was stirred at room temperature for 2 h, and then diluted with H$_2$O and CH$_2$Cl$_2$. The organic layer was then passed through an ISOLUTE® Phase Separator. The organic layer was then concentrated. The resulting residue was purified by silica gel flash column chromatography (heptane/EtOAc=1/0 to 0/1) to afford the title compound. MS (ESI+) m/z 398.1 (M+H).

Intermediate 4-1-C. Ethyl 1-(6-(5-bromo-3-(hydroxymethyl)thiophen-2-yl)pyridin-2-yl)-5-(trifluoromethyl)-1H-pyrazole-4-carboxylate

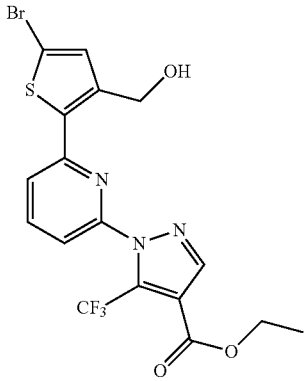

A solution of Intermediate 4-1-B (2 g, 5.03 mmol) and NBS (1.1 g, 6.18 mmol) in DMF (20 mL) was stirred at room temperature for 14 h. The reaction mixture was diluted with H$_2$O. The whole mixture was stirred at room temperature for 0.5 h. The resulting solid was collected by filtration. The collected solid was purified by silica gel flash column chromatograph (heptane/EtOAc=8/2 to 6/4) to afford the title compound. MS (ESI+) m/z 475.9 (M+H)

Intermediate 4-1-D. Ethyl 1-(6-(3-(hydroxymethyl)-5-methylthiophen-2-yl)pyridin-2-yl)-5-(trifluoromethyl)-1H-pyrazole-4-carboxylate

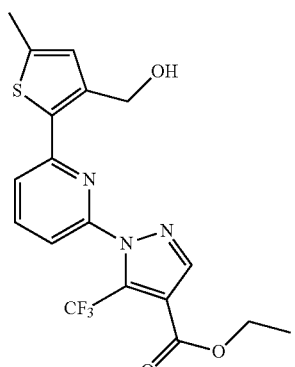

To a solution of Intermediate 4-1-C (1.5 g, 3.15 mmol) in THF (10 mL) was added dimethylzinc (2M in toluene, 6 mL, 12.00 mmol), followed by Pd(t-Bu$_3$P)$_2$ (200 mg, 0.391 mmol). The mixture was then stirred at room temperature for 16 h, and then quenched with EtOH. The mixture was diluted with EtOAc. The mixture was filtered through a plug of silica gel, which was rinsed with EtOAc. The filtrate was concentrated. The resulting residue was purified by silica gel flash column chromatography (heptane/EtOAc=67/33) to afford the title compound. MS (ESI+) m/z 412.1.

Intermediate 4-1-E. Ethyl 1-(6-(4-bromo-3-(hydroxymethyl)-5-methylthiophen-2-yl)pyridin-2-yl)-5-(trifluoromethyl)-1H-pyrazole-4-carboxylate

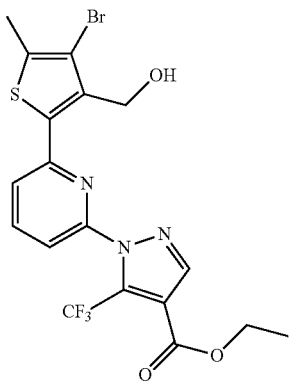 [SMILES: CCOC(=O)c1cnn(-c2cccc(-c3sc(C)c(Br)c3CO)n2)c1C(F)(F)F]

A solution of ethyl 1-(6-(3-(hydroxymethyl)-5-methylthiophen-2-yl)pyridin-2-yl)-5-(trifluoromethyl)-1H-pyrazole-4-carboxylate (450 mg, 1.094 mmol) and NBS (220 mg, 1.236 mmol) in DMF (4 mL) was stirred at room temperature for 3.5 h. The reaction mixture was diluted with H$_2$O, and then extracted with EtOAc. The organic layer was then washed successively with H$_2$O and brine, dried over Na$_2$SO$_4$, filtered, and then concentrated. The resulting residue was purified by silica gel flash column chromatograph (heptane/EtOAc=1/0 to 6/4) to afford the title compound. MS (ESI+) m/z 489.9 (M+H).

Intermediate 4-1. Ethyl 1-(6-(3-(hydroxymethyl)-4,5-dimethylthiophen-2-yl)pyridin-2-yl)-5-(trifluoromethyl)-1H-pyrazole-4-carboxylate

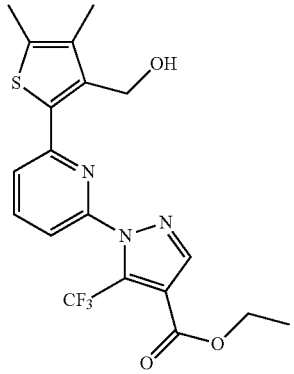 [SMILES: CCOC(=O)c1cnn(-c2cccc(-c3sc(C)c(C)c3CO)n2)c1C(F)(F)F]

To a solution of ethyl 1-(6-(4-bromo-3-(hydroxymethyl)-5-methylthiophen-2-yl)pyridin-2-yl)-5-(trifluoromethyl)-1H-pyrazole-4-carboxylate (400 mg, 0.82 mmol) and dimethylzinc (2M in toluene, 0.9 mL, 1.80 mmol) in THF (5 mL) was added Pd(t-Bu$_3$P)$_2$ (50 mg, 0.098 mmol). The mixture was then stirred at room temperature for 13.5 h. The reaction was quenched with EtOH. The mixture was diluted with EtOAc. The mixture was then filtered through a plug of silica gel, which was rinsed with EtOAc. The filtrate was concentrated. The resulting residue was purified by silica gel flash column chromatography (heptane/EtOAc=73/27) to afford the title compound. MS (ESI+) m/z 426.0 (M+H).

Intermediate 4-2

The following compounds were prepared by similar methods as described above for Intermediate 4-1 using the appropriate starting materials as delineated in the table below.

| | Structure/Chemical Name | Starting materials | MS |
|---|---|---|---|
| 4-2-1 | Ethyl 5-ethyl-1-(6-(3-(hydroxymethyl)thiophen-2-yl)pyridin-2-yl)-1H-pyrazole-4-carboxylate | Intermediate 1-3 and (3-formylthiophen-2-yl)boronic acid | MS (ESI+) m/z 358.3 |

| | Structure/Chemical Name | Starting materials | MS |
|---|---|---|---|
| 4-2-2 | 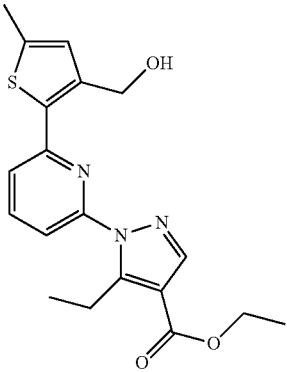 [SMILES: CCOC(=O)c1cnn(-c2cccc(-c3sc(C)cc3CO)n2)c1CC]<br>Ethyl 5-ethyl-1-(6-(3-(hydroxymethyl)-5-methylthiophen-2-yl)pyridin-2-yl)-1H-pyrazole-4-carboxylate | Intermediate 1-3 and (3-formylthiophen-2-yl)boronic acid | MS (ESI+) m/z 372.3 (M + H) |
| 4-2-3 | 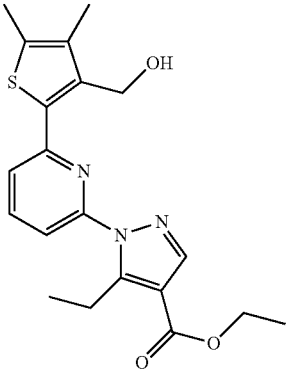 [SMILES: CCOC(=O)c1cnn(-c2cccc(-c3sc(C)c(C)c3CO)n2)c1CC]<br>Ethyl 5-ethyl-1-(6-(3-(hydroxymethyl)-4,5-dimethylthiophen-2-yl)pyridin-2-yl)-1H-pyrazole-4-carboxylate | Intermediate 1-3 and (3-formylthiophen-2-yl)boronic acid | MS (ESI+) m/z 386.3 (M + H) |
| 4-2-4 | 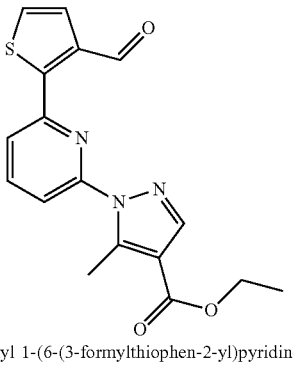<br>Ethyl 1-(6-(3-formylthiophen-2-yl)pyridin-2-yl)-5-methyl-1H-pyrazole-4-carboxylate | Intermediate 1-4-2 and (3-formylthiophen-2-yl)boronic acid | MS (ESI+) m/z 342.2 (M + H) |

-continued

| | Structure/Chemical Name | Starting materials | MS |
|---|---|---|---|
| 4-2-5 | 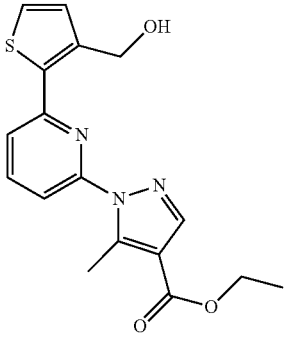 [SMILES: CCOC(=O)c1cnn(-c2cccc(-c3sccc3CO)n2)c1C]<br>Ethyl 1-(6-(3-(hydroxymethyl)thiophen-2-yl)pyridin-2-yl)-5-methyl-1H-pyrazole-4-carboxylate | Intermediate 4-2-4 | MS (ESI+) m/z 344.2 (M + H) |
| 4-2-6 | 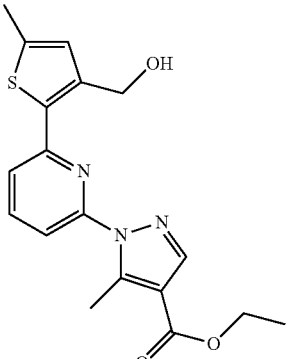<br>Ethyl 1-(6-(3-(hydroxymethyl)-5-methylthiophen-2-yl)pyridin-2-yl)-5-methyl-1H-pyrazole-4-carboxylate | Intermediate 1-4-2 and (3-formylthiophen-2-yl)boronic acid | MS (ESI+) m/z 358.3 (M + H) |
| 4-2-7 | 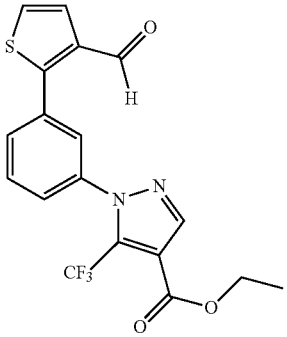 [SMILES: CCOC(=O)c1cnn(-c2cccc(-c3sccc3C=O)c2)c1C(F)(F)F]<br>Ethyl 1-(3-(3-formylthiophen-2-yl)phenyl)-5-(trifluoromethyl)-1H-pyrazole-4-carboxylate | Intermediate 1-2-2 and (3-formylthiophen-2-yl)boronic acid | MS (ESI+) m/z 395.0 (M + H) |

| | Structure/Chemical Name | Starting materials | MS |
|---|---|---|---|
| 4-2-8 | 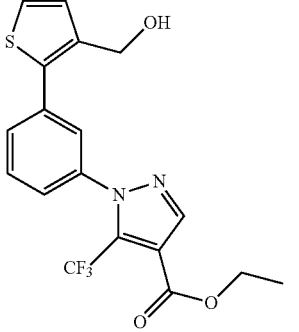 [SMILES: CCOC(=O)c1cnn(-c2cccc(-c3sccc3CO)c2)c1C(F)(F)F]<br>Ethyl 1-(3-(3-(hydroxymethyl)thiophen-2-yl)phenyl)-5-(trifluoromethyl)-1H-pyrazole-4-carboxylate | Intermediate 1-2-2 and (3-formylthiophen-2-yl)boronic acid | MS (ESI+) m/z 397.0 (M + H) |
| 4-2-9 | 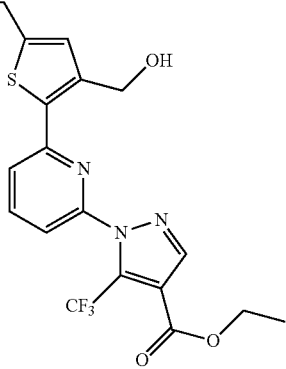<br>Ethyl 1-(6-(5-ethyl-3-(hydroxymethyl)thiophen-2-yl)pyridin-2-yl)-5-(trifluoromethyl)-1H-pyrazole-4-carboxylate | Intermediate 4-1-C and diethylzinc | MS (ESI+) m/z 425.9 (M + H) |
| 4-2-10 | 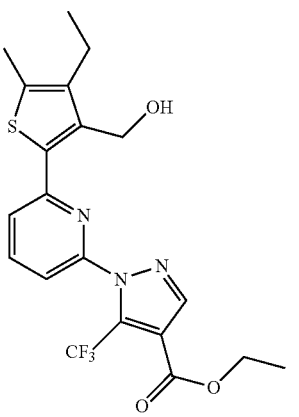 [SMILES: CCOC(=O)c1cnn(-c2cccc(-c3sc(C)c(CC)c3CO)n2)c1C(F)(F)F]<br>Ethyl 1-(6-(4-ethyl-3-(hydroxymethyl)-5-methylthiophen-2-yl)pyridin-2-yl)-5-(trifluoromethyl)-1H-pyrazole-4-carboxylate | Intermediate 4-1-E and diethylzinc | MS (ESI+) m/z 440.3 (M + H) |

85
-continued

| Structure/Chemical Name | Starting materials | MS |
|---|---|---|
| 4-2-11 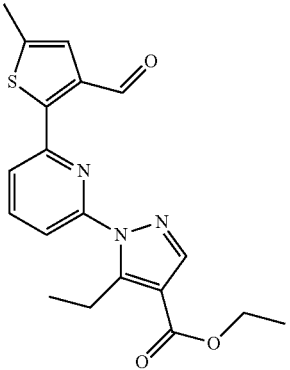 [SMILES: CCOC(=O)c1cnn(-c2cccc(-c3sc(C)cc3C=O)n2)c1CC]<br>Ethyl 5-ethyl-1-(6-(3-formyl-5-methylthiophen-2-yl)pyridin-2-yl)-1H-pyrazole-4-carboxylate | Intermediate 1-3 and (3-formylthiophen-2-yl)boronic acid (CAS # 17303-83-2) | MS (ESI+) m/z 370.3 (M + H) |

Intermediate 4-3. Ethyl 1-(6-(5-chloro-3-(hydroxymethyl)thiophen-2-yl)pyridin-2-yl)-5-(trifluoromethyl)-1H-pyrazole-4-carboxylate

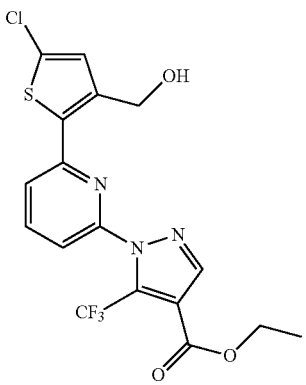 [SMILES: CCOC(=O)c1cnn(-c2cccc(-c3sc(Cl)cc3CO)n2)c1C(F)(F)F]

The title compound was synthesized in a similar manner to the preparation of Intermediate 4-1-B using NCS (CAS #128-09-6) in the place of NBS. MS (ESI+) m/z 432.2 (M+H).

Intermediate 4-4. Ethyl 1-(6-(5-cyclopropyl-3-(hydroxymethyl)thiophen-2-yl)pyridin-2-yl)-5-(trifluoromethyl)-1H-pyrazole-4-carboxylate

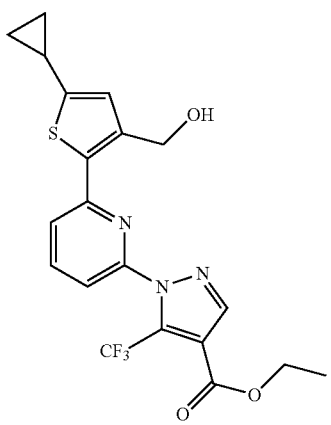 [SMILES: CCOC(=O)c1cnn(-c2cccc(-c3sc(C4CC4)cc3CO)n2)c1C(F)(F)F]

To a suspension of Intermediate 4-1-C (200 mg, 0.420 mmol), potassium cyclopropyltrifluoroborate (CAS#1065010-87-8, 120 mg, 0.811 mmol), and Cs$_2$CO$_3$ (300 mg, 0.921 mmol) in toluene/H$_2$O (2 mL/1 mL) was added chloro[di(1-adamantyl)-N-butylphosphine)-2-(2-aminobiphenyl)]palladium (CAS#1375477-29-4, 30 mg, 0.045 mmol). The mixture was then stirred at 100° C. for 15 h, and then cooled to room temperature. The reaction mixture was extracted with CH$_2$Cl$_2$. The organic extract was concentrated. The resulting residue was purified by silica gel flash column chromatography (heptane/EtOAc=69/31) to afford the title compound. MS (ESI+) m/z 438.1 (M+H).

Intermediate 4-5. Ethyl 1-(6-(4-cyclopropyl-3-(hydroxymethyl)-5-methylthiophen-2-yl)pyridin-2-yl)-5-(trifluoromethyl)-1H-pyrazole-4-carboxylate

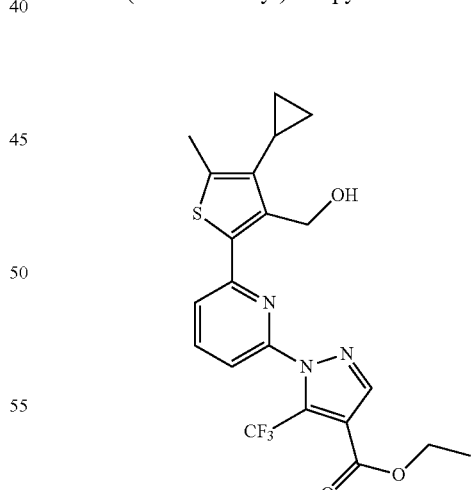

The title compound was synthesized in a similar manner to the preparation of Intermediate 4-4 using Intermediate 4-1-E and potassium cyclopropyltrifluoroborate. MS (ESI+) m/z 452.0 (M+H).

Intermediate 4-6

Intermediate 4-6-A. Ethyl 1-(6-(3-(hydroxymethyl)-5-(prop-1-en-2-yl)thiophen-2-yl)pyridin-2-yl)-5-(trifluoromethyl)-1H-pyrazole-4-carboxylate

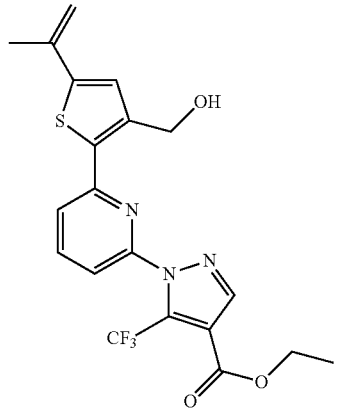 [SMILES: C=C(C)c1cc(CO)c(-c2cccc(-n3ncc(C(=O)OCC)c3C(F)(F)F)n2)s1]

The title compound was synthesized in a similar manner to the preparation of Intermediate 4-4 using Intermediate 4-1-C and potassium isopropenyltrifluoroborate (CAS#395083-14-4). MS (ESI+) m/z 438.0 (M+H).

Intermediate 4-6. Ethyl 1-(6-(3-(hydroxymethyl)-5-isopropylthiophen-2-yl)pyridin-2-yl)-5-(trifluoromethyl)-1H-pyrazole-4-carboxylate

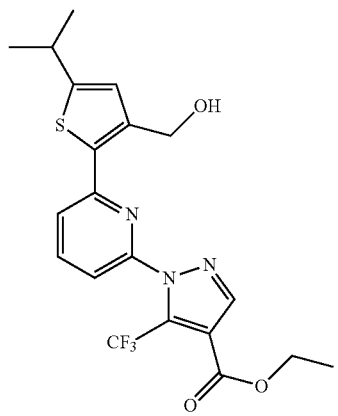 [SMILES: CCOC(=O)c1cnn(-c2cccc(-c3sc(C(C)C)cc3CO)n2)c1C(F)(F)F]

A mixture of Intermediate 4-6-A (300 mg, 0.686 mmol) and PtO$_2$ (CAS #1314-15-4, 50 mg, 0.686 mmol) in MeOH/EtOAc (20 mL/10 mL) was stirred under H$_2$ atmosphere for 13.5 h. The mixture was then filtered through a plug of Celite®, which was rinsed with EtOAc/MeOH (ca. 2/1). The filtrate was then concentrated to furnish the title compound. MS (ESI+) m/z 440.1 (M+H).

Intermediate 4-7. Ethyl 1-(6-(3-(hydroxymethyl)-5-propylthiophen-2-yl)pyridin-2-yl)-5-(trifluoromethyl)-1H-pyrazole-4-carboxylate

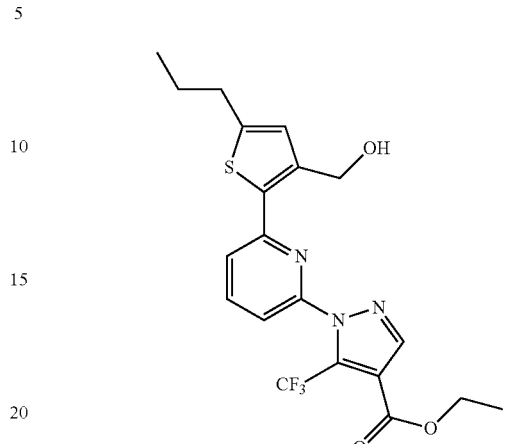

The title compound was synthesized analogously to the preparation of Intermediate 4-1-D using Intermediate 4-1-C and 2-propylzinc bromide (CAS#77047-87-1). MS (ESI+) m/z 440.0 (M+H).

Intermediate 4-8

Intermediate 4-8-A. Ethyl 1-(6-(3-(((tert-butyldimethylsilyl)oxy)methyl)-4-methylthiophen-2-yl)pyridin-2-yl)-5-(trifluoromethyl)-1H-pyrazole-4-carboxylate

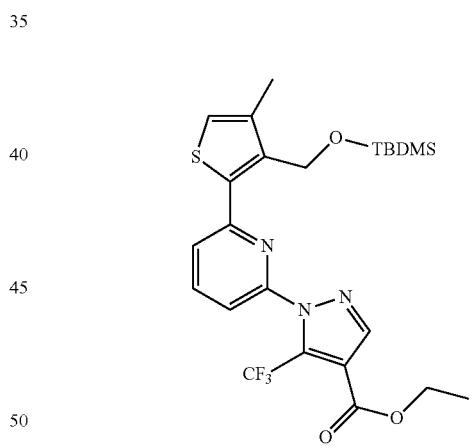

To a suspension of ethyl 1-(6-chloropyridin-2-yl)-5-(trifluoromethyl)-1H-pyrazole-4-carboxylate (Intermediate 1-1) (624 mg, 1.95 mmol), Bis(pinacolato)diboron (496 mg, 1.95 mmol), and potassium acetate (479 mg, 4.88 mmol) in dioxane (8.0 mL) was added chloro(2-dicyclohexylphosphino-2',6'-dimethoxy-1,1'-biphenyl)[2-(2-aminoethylphenyl)]palladium(II) methyl-tert-butylether adduct (CAS#1028206-58-7, 55 mg, 0.081 mmol). The mixture was then stirred at 120° C. under microwave irradiation, and then cooled to room temperature. To the mixture was then added Intermediate 3-7 (523 mg, 1.63 mmol) in 1,4-dioxane (8.0 mL), followed by 1M aq. sodium carbonate (3.25 mL, 3.26 mmol) and chloro(2-dicyclohexylphosphino-2',6'-dimethoxy-1,1'-biphenyl)[2-(2-aminoethylphenyl)]palladium(II) methyl-tert-butylether adduct (55 mg, 0.081 mmol). The mixture was then stirred at 110° C. for 40 min, and then cooled to room temperature, and then diluted with EtOAc. The organic layer was separated and then concentrated. The resulting residue was purified by silica gel flash column chromatography (hexane/EtOAc=1/0 to 1/1) to afford the title compound. MS (ESI+) m/z 526.2 (M+H).

Intermediate 4-8. Ethyl 1-(6-(3-(hydroxymethyl)-4-methylthiophen-2-yl)pyridin-2-yl)-5-(trifluoromethyl)-1H-pyrazole-4-carboxylate

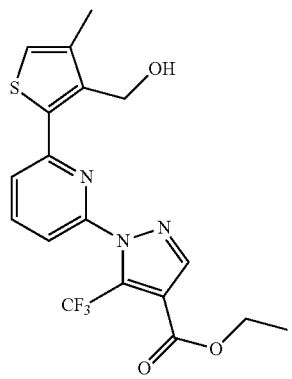 [SMILES: CCOC(=O)c1cnn(-c2cccc(-c3scc(C)c3CO)n2)c1C(F)(F)F]

To a solution of Intermediate 4-8-A (446 mg, 0.848 mmol) in THF (8.5 mL) at 0° C. was added a solution of TBAF (1M in THF, 0.89 mL 0.89 mmol). The mixture was then stirred at 0° C. for 1 h, and then diluted with EtOAc. The mixture was then washed successively with 1/1 water and sat. aq. NaHCO₃, brine. The filtrate was concentrated with Celite®, which was purified by silica gel flash column chromatography (hexane/EtOAc=1/0 to 6/4) to afford the title compound. MS (ESI+) m/z 412.2 (M+H).

Intermediate 4-9

Intermediate 4-9-A. N-(2,3,5,6-Tetrafluoro-4-(trifluoromethyl)phenyl)thiophene-3-carboxamide

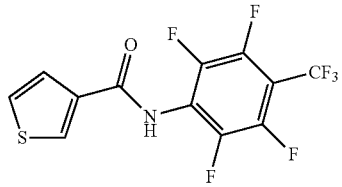 [SMILES: O=C(Nc1c(F)c(F)c(C(F)(F)F)c(F)c1F)c1ccsc1]

A mixture of thiophene-3-carboxylic acid (CAS#88-13-1, 2.24 g, 17.5 mmol), T3P (2 M in DMF, 12.5 mL, 25 mmol), DIPEA (6.2 mL, 35.5 mmol) and 2,3,5,6-tetrafluoro-4-(trifluoromethyl)aniline (4.45 g, 19.1 mmol) was stirred at 100° C. for 18 h, and then cooled to room temperature. The reaction mixture was then poured into sat. aq. NH₄Cl, and then stirred for 0.5 h. Resulting precipitate was collected by filtration. The precipitate was then triturated with CH₂Cl₂ (ca. 60 mL). The solid was collected by filtration, rinsed with CH₂Cl₂, to afford the title compound. MS (ESI+) m/z 344.0 (M+H).

Intermediate 4-9-B. Ethyl 1-(6-(3-((2,3,5,6-tetrafluoro-4-(trifluoromethyl)phenyl)carbamoyl)thiophen-2-yl)pyridin-2-yl)-5-(trifluoromethyl)-1H-pyrazole-4-carboxylate

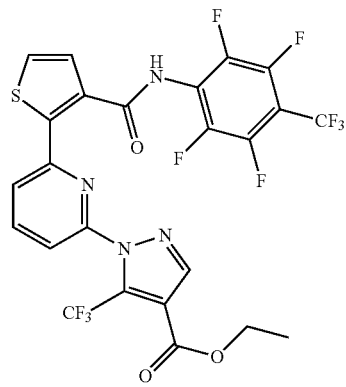 [SMILES: CCOC(=O)c1cnn(-c2cccc(-c3sccc3C(=O)Nc3c(F)c(F)c(C(F)(F)F)c(F)c3F)n2)c1C(F)(F)F]

A mixture of Intermediate 4-9-A (2.33 g, 6.8 mmol), Intermediate 1-1 (1.98 g, 5.43 mmol), Pd(OAc)₂ (121 mg, 0.54 mmol), Cs₂CO₃ (5.31 g, 16.30 mmol) and triphenylphosphine (547 mg, 2.09 mmol) in toluene (9.9 mL) was sparged with N₂, and then the mixture was stirred at 100° C. for 1.5 hr. The reaction mixture was then cooled to room temperature, and then diluted with EtOAc and satd. aq. NH₄Cl. The organic layer was then separated, and then successively washed with H₂O and brine, dried over Na₂SO₄, filtered and concentrated. The resulting residue was purified by silica gel flash column chromatography (heptane/EtOAc=85/15 to 4/6) to afford the title compound. MS (ESI+) m/z 627.0 (M+H).

Intermediate 4-9-C. Ethyl 1-(6-(4-bromo-3-((2,3,5,6-tetrafluoro-4-(trifluoromethyl)phenyl)carbamoyl)thiophen-2-yl)pyridin-2-yl)-5-(trifluoromethyl)-1H-pyrazole-4-carboxylate

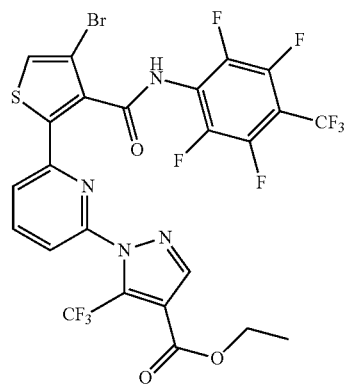 [SMILES: CCOC(=O)c1cnn(-c2cccc(-c3scc(Br)c3C(=O)Nc3c(F)c(F)c(C(F)(F)F)c(F)c3F)n2)c1C(F)(F)F]

To a mixture of Intermediate 4-9-B (503.8 mg, 0.804 mmol), potassium acetate (281.7 mg, 2.87 mmol) and NBS (217.1 mg, 1.220 mmol) in DCE (5 mL) was added bis[(pentamethylcyclopentadienyl)dichloro-rhodium] (CAS#12354-85-7, 25.4 mg, 0.041 mmol). The mixture was then stirred at 80° C. for 1 hr. To the mixture was then added additional amount of NBS (168.2 mg, 0.945 mmol) and continued stirring at 80° C. for 0.5 h. To the mixture was then added bis[(pentamethylcyclopentadienyl)dichloro-rhodium] (33.2 mg, 0.054 mmol) and stirred at 80° C. for 0.5 h. The reaction mixture was then cooled to room temperature, and filtered through a plug of Celite®, which was rinsed with EtOAc. The filtrate was then concentrated. The resulting residue was purified by silica gel flash column chromatography (heptane/EtOAc=85/15 to 70/30) to afford the title compound. MS (ESI+) m/z 704.8 (M+H).

Intermediate 4-9-D. 4-Bromo-2-(6-(4-(ethoxycarbonyl)-5-(trifluoromethyl)-1H-pyrazol-1-yl)pyridin-2-yl)thiophene-3-carboxylic acid

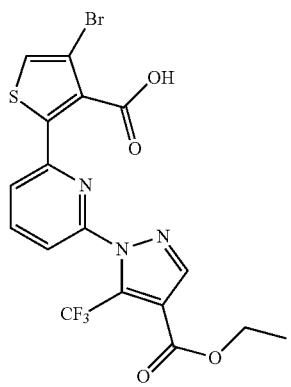 [SMILES: CCOC(=O)c1cnn(-c2cccc(-c3scc(Br)c3C(=O)O)n2)c1C(F)(F)F]

A mixture of Intermediate 4-9-C (1.47 mg, 2.08 mmol) and MsOH (7.5 mL) was stirred at 70° C. for 2.25 h, and then cooled to room temperature. The mixture was then poured into ice water, and then stirred for 0.75 h. The resulting precipitate was collected by filtration to furnish the title compound. MS (ESI+) m/z 489.9 (M+H).

Intermediate 4-9-E. Ethyl 1-(6-(4-bromo-3-(hydroxymethyl)thiophen-2-yl)pyridin-2-yl)-5-(trifluoromethyl)-1H-pyrazole-4-carboxylate

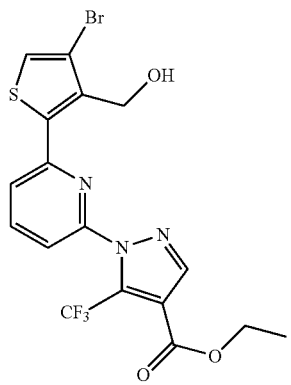 [SMILES: CCOC(=O)c1cnn(-c2cccc(-c3scc(Br)c3CO)n2)c1C(F)(F)F]

To a solution of BH$_3$-THF complex (6.6 mL, 6.60 mmol) at 4° C. was added a solution of Intermediate 4-9-D (644 mg, 1.31 mmol) in THF (5 mL). The mixture was then stirred for 3 h at room temperature. To the mixture was then added additional BH$_3$-THF complex (6.6 mL, 6.6 mmol), and then the mixture was stirred at room temperature for 3 h. The reaction was then quenched with MeOH (6.0 mL). The mixture was then concentrated. The resulting residue was purified by silica gel flash column chromatography (heptane/EtOAc=85/15 to 40/60) to afford the title compound. MS (ESI+) m/z 475.9 (M+H).

Intermediate 4-9. Ethyl 1-(6-(4-ethyl-3-(hydroxymethyl)thiophen-2-yl)pyridin-2-yl)-5-(trifluoromethyl)-1H-pyrazole-4-carboxylate

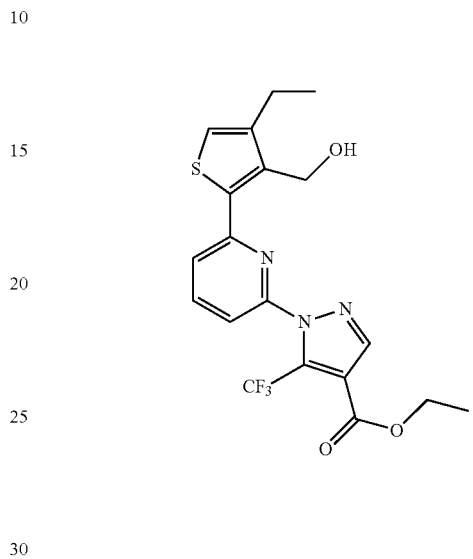

The title compound was synthesized from Intermediate 4-9-E in a similar manner to the preparation of Intermediate 4-1-D using diethylzinc. MS (ESI+) m/z 426.2 (M+H).

Intermediate 4-10. Ethyl 1-(6-(3-formyl-5-methylthiophen-2-yl)pyridin-2-yl)-5-methyl-1H-pyrazole-4-carboxylate.

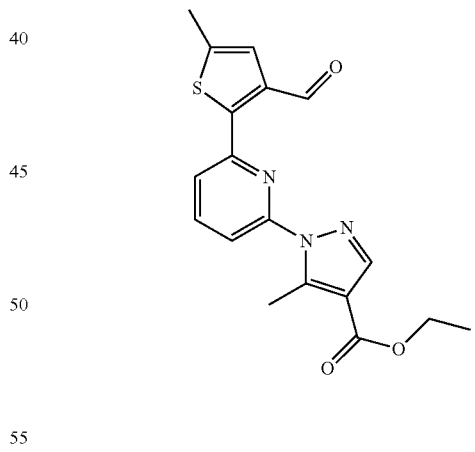

To a solution of Intermediate 4-2-6 (281 mg, 0.786 mmol) in CH$_2$Cl$_2$ (7.9 mL) was added Dess-Martin periodinane (367 mg, 0.865 mmol) and H$_2$O (20 μL). The mixture was then stirred at room temperature for 1.5 h. The reaction was then quenched with sat. aq. NaHCO$_3$. The organic layer was then separated from the aqueous layer. The organic layer was then dried over Na$_2$SO$_4$ filtered and concentrated. The resulting residue was purified by silica gel flash column chromatography (heptane/EtOAc=1/0 to 0/1) to afford the title compound. MS (ESI+) m/z 356.2.

Intermediate 4-11. Ethyl 1-(6-(3-formyl-5-methylthiophen-2-yl)pyridin-2-yl)-5-(trifluoromethyl)-1H-pyrazole-4-carboxylate

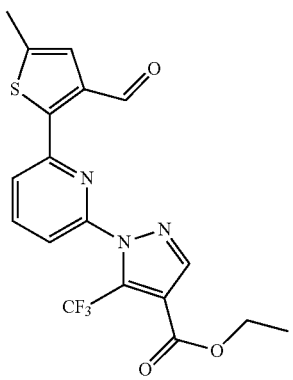 [SMILES: CCOC(=O)c1cnn(-c2cccc(-c3sc(C)cc3C=O)n2)c1C(F)(F)F]

The title compound was synthesized in a similar manner to the preparation of Intermediate 4-10 using Intermediate 4-1-D. MS (ESI+) m/z 410.2 (M+H).

Intermediate 4-12. Ethyl 1-(6-(3-(hydroxymethyl)-4-isopropyl-5-methylthiophen-2-yl)pyridin-2-yl)-5-(trifluoromethyl)-1H-pyrazole-4-carboxylate

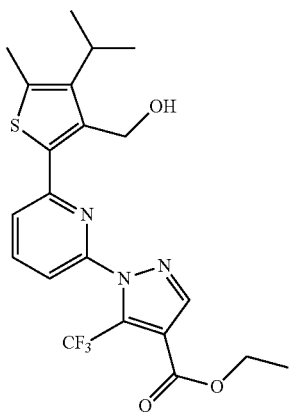 [SMILES: CCOC(=O)c1cnn(-c2cccc(-c3sc(C)c(C(C)C)c3CO)n2)c1C(F)(F)F]

The title compound was synthesized starting from Intermediate 4-1-E. Reaction of Intermediate 4-1-E with potassium isopropenyltrifluoroborate, in a fashion analogous Intermediate 4-4, afforded an alkene which was hydrogenated as outlined in the protocol for Intermediate 4-6, to furnish the title compound, ethyl 1-(6-(3-(hydroxymethyl)-4-isopropyl-5-methylthiophen-2-yl)pyridin-2-yl)-5-(trifluoromethyl)-1H-pyrazole-4-carboxylate. MS (ESI+) m/z 454.2 (M+H).

Intermediate 4-13. Ethyl 1-(6-(5-methyl-3-vinylthiophen-2-yl)pyridin-2-yl)-5-(trifluoromethyl)-1H-pyrazole-4-carboxylate

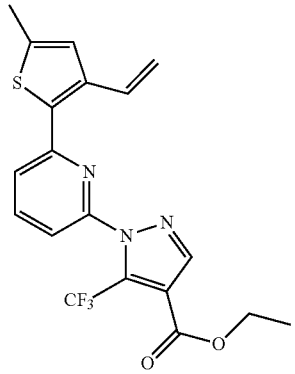 [SMILES: C=Cc1cc(C)sc1-c1cccc(-n2ncc(C(=O)OCC)c2C(F)(F)F)n1]

To a suspension of methyltriphenylphosphonium chloride (CAS#1031-15-8, 1.72 g, 5.50 mmol) in THF (5 mL) at room temperature was added LHMDS (5.13 mL, 5.13 mmol). The resulting yellow suspension was stirred at room temperature for 0.5 h. To the suspension was then added a solution of Intermediate 4-11 (1.5 g, 3.66 mmol) in THF (1 mL), and then the mixture was then stirred at room temperature for 3 h. The reaction was then quenched with sat. aq. NH₄Cl. The mixture was then extracted with CH₂Cl₂. The organic layer was then dried over Na₂SO₄, filtered and then concentrated. The resulting residue was purified by silica gel flash column chromatography (heptane/EtOAc=1/0 to 0/1) to afford the title compound. MS (ESI+) m/z 408.2 (M+H).

Intermediate 4-14. Ethyl 5-(trifluoromethyl)-1-(6-(3-vinylthiophen-2-yl)pyridin-2-yl)-1H-pyrazole-4-carboxylate

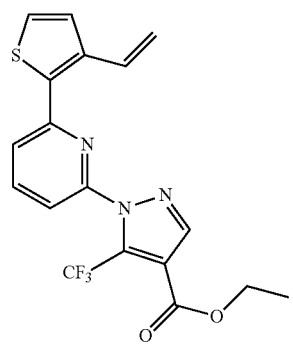 [SMILES: C=Cc1ccsc1-c1cccc(-n2ncc(C(=O)OCC)c2C(F)(F)F)n1]

The title compound was synthesized in a similar manner to the synthesis of Intermediate 4-13 starting from Intermediate 4-1-A. MS (ESI+) m/z 394.0 (M+H).

Intermediate 4-15. Ethyl 1-(3-(3-(1-hydroxyethyl)thiophen-2-yl)phenyl)-5-(trifluoromethyl)-1H-pyrazole-4-carboxylate

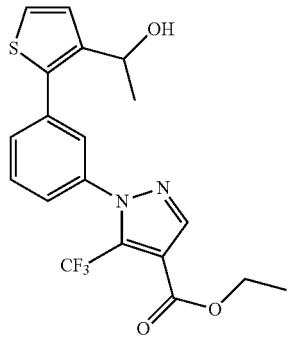 [SMILES: CCOC(=O)c1cnn(-c2cccc(-c3sccc3C(C)O)c2)c1C(F)(F)F]

To a solution of Intermediate 4-2-7 (465 mg, 1.179 mmol) in THF (5 mL) at −78° C. was added methylmagnesium chloride (CAS#676-58-4, 3 M in THF, 0.393 mL, 1.179 mmol). The mixture was then stirred at 0° C. for 1 h. The reaction was then quenched with satd. aq. NH$_4$Cl. The mixture was then extracted with EtOAc. The organic layer was then concentrated. The resulting residue was purified by silica gel flash column chromatography (heptane/EtOAc=1/0 to 0/1) to afford the title compound. MS (ESI+) m/z 393.3 (M−OH)$^+$.

Intermediate 4-16. Ethyl 1-(3-(3-acetylthiophen-2-yl)phenyl)-5-(trifluoromethyl)-1H-pyrazole-4-carboxylate

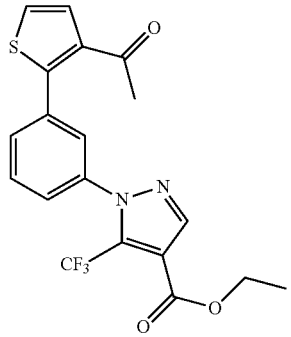 [SMILES: CCOC(=O)c1cnn(-c2cccc(-c3sccc3C(C)=O)c2)c1C(F)(F)F]

The title compound was synthesized in a similar manner as described in Intermediate 4-10 using Intermediate 4-15. MS (ESI+) m/z 409.2 (M+H).

Intermediate 4-17. Ethyl 5-ethyl-1-(6-(3-(hydroxymethyl)-4-(trifluoromethyl)thiophen-2-yl)pyridin-2-yl)-1H-pyrazole-4-carboxylate

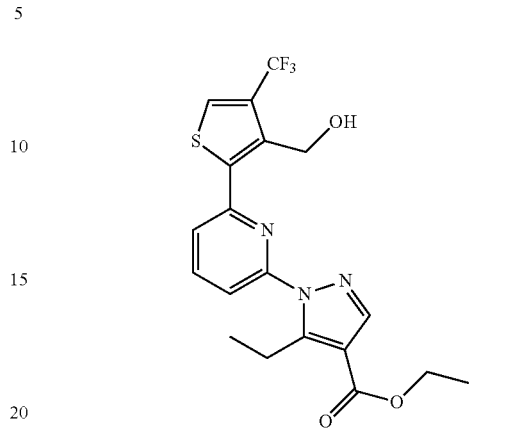

The title compound was synthesized starting from ethyl 1-(6-bromopyridin-2-yl)-5-ethyl-1H-pyrazole-4-carboxylate (Intermediate 1-3) via the protocol described for the synthesis of Intermediate 4-8, i.e., reaction with bis(pinacolato)diboron and subsequent Suzuki-type coupling with ((2-bromo-4-(trifluoromethyl)thiophen-3-yl)methoxy)(tert-butyl)dimethylsilane (Intermediate 3-9) followed by TBDMS deprotection. MS (ESI+) m/z 426.2 (M+H).

Example 1

Example 1-A. tert-Butyl 4-(4-((2-(6-(4-(ethoxycarbonyl)-5-(trifluoromethyl)-1H-pyrazol-1-yl)pyridin-2-yl)thiophen-3-yl)methoxy)phenyl)piperidine-1-carboxylate

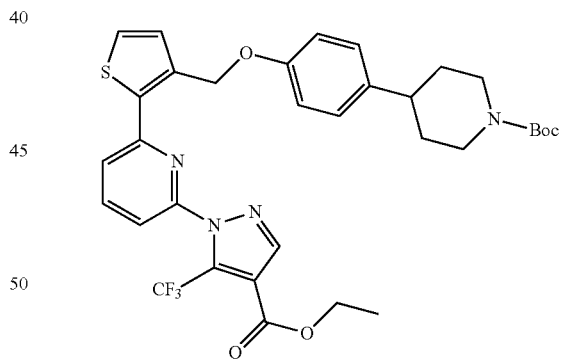

To a suspension of Intermediate 1-1 (500 mg, 1.373 mmol), bis(pinacolato)diboron (384 mg, 1.51 mmol), potassium acetate (404 mg, 4.12 mmol) and 2-dicyclohexylphosphino-2',4',6'-triisopropylbiphenyl (CAS#564483-18-7, 98 mg, 0.21 mmol) in 1,4-dioxane (13 mL) was added Pd(OAc)$_2$ (12 mg, 0.053 mmol). The mixture was then stirred at 100° C. for 3 h, and the cooled to room temperature. The mixture was then filtered through a plug of Celite®. The filtrate was then concentrated. To the resulting residue was added 1,4-dioxane (12 mL) followed by Intermediate 3-1 (500 mg, 1.1 mmol), aq. sodium carbonate (2M, 2.21 ml, 4.4 mmol), and Pd(dppf)Cl$_2$CH$_2$Cl$_2$ adduct. The mixture was then stirred at 80° C. for 30 h, and then cooled to room temperature. The mixture was diluted with EtOAc, and then washed successively with H₂O and brine, dried over MgSO₄, filtered and then concentrated. The resulting residue was purified by silica gel flash column chromatography (hexane/EtOAc=4/1) to afford the title compound. MS (ESI+) m/z 657.4 (M+H).

Example 1-B. Ethyl 1-(6-(3-((4-(piperidin-4-yl)phenoxy)methyl)thiophen-2-yl)pyridin-2-yl)-5-(trifluoromethyl)-1H-pyrazole-4-carboxylate

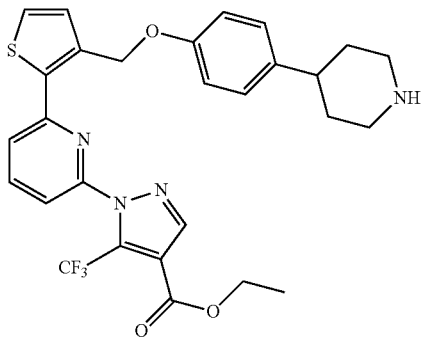 [SMILES: CCOC(=O)c1cnn(-c2cccc(-c3sccc3COc3ccc(C4CCNCC4)cc3)n2)c1C(F)(F)F]

A mixture of tert-butyl 4-(4-((2-(6-(4-(ethoxycarbonyl)-5-(trifluoromethyl)-1H-pyrazol-1-yl)pyridin-2-yl)thiophen-3-yl)methoxy)phenyl)piperidine-1-carboxylate (300 mg, 0.46 mmol) and TFA (4 mL) in CH₂Cl₂ (20 mL) was stirred at room temperature for 1 h, and then concentrated. The resulting residue was dissolved in toluene and concentrated to dryness. The resulting residue was triturated with Et₂O. The precipitate was collected by filtration, and then washed with Et₂O to afford the title compound. MS (ESI+) m/z 557.3 (M+H).

Example 1-C. Ethyl 1-(6-(3-((4-(1-propionylpiperidin-4-yl)phenoxy)methyl)thiophen-2-yl)pyridin-2-yl)-5-(trifluoromethyl)-1H-pyrazole-4-carboxylate

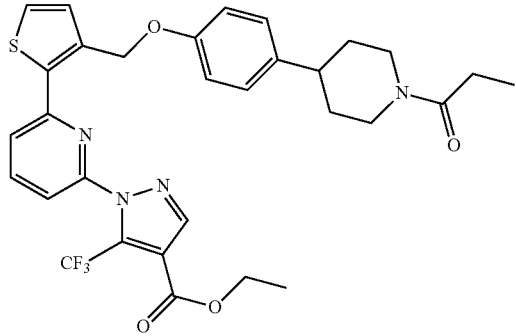 [SMILES: CCOC(=O)c1cnn(-c2cccc(-c3sccc3COc3ccc(C4CCN(C(=O)CC)CC4)cc3)n2)c1C(F)(F)F]

To a solution of ethyl 1-(6-(3-((4-(piperidin-4-yl)phenoxy)methyl)thiophen-2-yl)pyridin-2-yl)-5-(trifluoromethyl)-1H-pyrazole-4-carboxylate (0.25 g, 0.45 mmol) and Et₃N (0.15 mL, 1.12 mmol) in CH₂Cl₂ (20 mL) was added propionyl chloride (0.05 ml, 0.054 mmol). The mixture was then stirred at room temperature for ca. 80 min, and then diluted with CH₂Cl₂. The organic phase was then washed successively with H₂O (three times) and brine, and then dried over MgSO₄, filtered and then concentrated. The resulting residue was purified by silica gel flash column chromatography (hexane/EtOAc=1/1) to afford the title compound. MS (ESI+) m/z 613.4 (M+H).

Example 1. 1-(6-(3-((4-(1-Propionylpiperidin-4-yl)phenoxy)methyl)thiophen-2-yl)pyridin-2-yl)-5-(trifluoromethyl)-1H-pyrazole-4-carboxylic acid

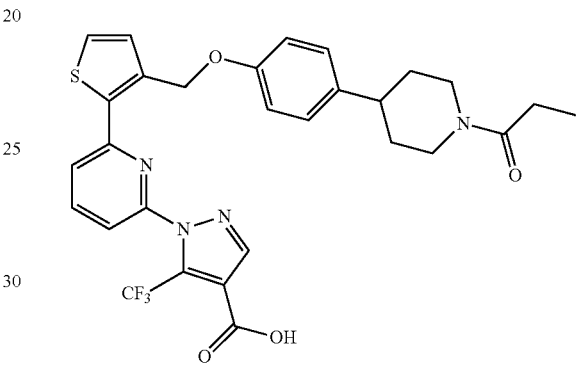

To a solution of ethyl 1-(6-(3-((4-(1-propionylpiperidin-4-yl)phenoxy)methyl)thiophen-2-yl)pyridin-2-yl)-5-(trifluoromethyl)-1H-pyrazole-4-carboxylate (0.12 g, 0.2 mmol) in THF/H₂O (2 mL/2 mL) was added lithium hydroxide hydrate (0.08 g, 2.0 mmol). The mixture was the stirred at 40° C. for 16 h, and then partially concentrated. The resulting residue was rendered pH-5 by the addition of 2N aq. HCl, and then extracted twice with EtOAc. The organic extracts were combined and were washed with brine, dried over MgSO₄, filtered and then concentrated. The resulting residue was crystallized from hexane to afford the title compound. $^1$H NMR (400 MHz, CD₃OD) δ 8.15 (s, 1H), 8.07 (dd, J=7.80, 8.00 Hz, 1H), 7.84 (dd, J=0.60, 8.00 Hz, 1H), 7.59 (dd, J=0.60, 8.00 Hz, 1H), 7.53 (d, J=5.26 Hz, 1H), 7.26 (d, J=5.13 Hz, 1H), 7.08-7.13 (m, 2H), 6.82-6.88 (m, 2H), 5.31 (s, 2H), 4.63-4.70 (m, 1H), 4.01-4.09 (m, 1H), 3.14-3.22 (m, 1H), 2.64-2.79 (m, 2H), 2.45 (q, J=7.54 Hz, 2H), 1.80-1.92 (m, 2H), 1.46-1.66 (m, 2H), 1.14 (t, J=7.46 Hz, 3H). HRMS calcd. for C₂₉H₂₈F₃N₄O₄S (M+H) 585.1783, found 585.1808.

Example 2

The following compounds were synthesized with a similar method as described above for Example 1 using the appropriate starting materials delineated in the table below and purified by the conditions detailed below in place of the crystalization described by Example 1.

| Example | Structure/Chemical Name | Starting materials | NMR and HRMS |
|---|---|---|---|
| 2-1 | 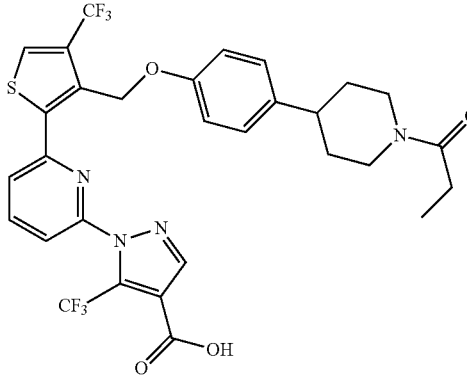<br>1-(6-(3-((4-(1-Propionylpiperidin-4-yl)phenoxy)methyl)-4-(trifluoromethyl)thiophen-2-yl)pyridin-2-yl)-5-(trifluoromethyl)-1H-pyrazole-4-carboxylic acid | Intermediate 1-1, Intermediate 3-5 and propionyl chloride Purified by trituration with hexanes | $^1$H NMR (400 MHz, CD$_3$OD) δ 8.50 (d, J = 0.73 Hz, 1H), 8.23 (dd, J = 7.80, 8.10 Hz, 1H), 8.16 (br. s., 1H), 7.77-7.85 (m, 2H), 7.18 (d, J = 8.68 Hz, 2H), 6.95 (d, J = 8.56 Hz, 2H), 5.16 (s, 2H), 4.55 (br. d, J = 12.00 Hz, 1H), 3.95 (br. d, J = 13.30 Hz, 1H), 3.07 (t, J = 11.98 Hz, 1H), 2.65-2.77 (m, 1H), 2.53-2.62 (m, 1H), 2.31-2.38 (m, 2H), 1.71-1.83 (m, 2H), 1.46-1.59 (m, 1H), 1.33-1.46 (m, 1H), 1.01 (t, J = 7.40 Hz, 3H). HRMS calcd. for C$_{30}$H$_{27}$F$_6$N$_4$O$_4$S (M + H) 653.1657, found 653.1668. |
| 2-2 | 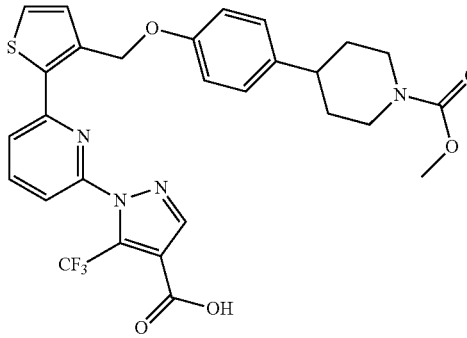<br>1-(6-(3-((4-(1-(Methoxycarbonyl)piperidin-4-yl)phenoxy)methyl)thiophen-2-yl)pyridin-2-yl)-5-(trifluoromethyl)-1H-pyrazole-4-carboxylic acid | Intermediate 1-1, Intermediate 3-1 and methyl chloroformate Product precipitates from the reaction mixture, collection of solid and trituration with water afforded the title compound with sufficient purity | $^1$H NMR (300 MHz, DMSO-d$_6$) δ 8.13 (t, J = 8.1 Hz, 1H), 8.07 (br s, 1H), 7.77 (d, J = 7.8 Hz, 1H), 7.69 (d, J = 5.1 Hz, 1H), 7.66 (d, J = 7.7 Hz, 1H), 7.25 (d, J = 5.1 Hz, 1H), 7.13 (d, J = 8.7 Hz, 2H), 6.90 (d, J = 8.7 Hz, 2H), 5.27 (s, 2H), 4.10-4.00 (m, 2H), 3.58 (s, 3H), 2.92-2.76 (m, 2H), 2.62 (m, 1H), 1.75-1.66 (m, 2H), 1.52-1.37 (m, 2H). HRMS calcd. for C$_{28}$H$_{26}$F$_3$N$_4$O$_5$S (M + H) 587.1576, found 587.1601. |
| 2-3 | 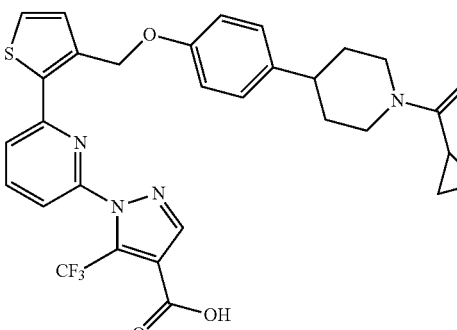<br>1-(6-(3-((4-(1-(Cyclopropanecarbonyl)piperidin-4-yl)phenoxy)methyl)thiophen-2-yl)pyridin-2-yl)-5-(trifluoromethyl)-1H-pyrazole-4-carboxylic acid | Intermediate 1-1, Intermediate 3-1 and cyclopropanecarbonyl chloride Product precipitates from the reaction mixture, collection of solid and trituration with water afforded the title compound with sufficient purity | $^1$H NMR (300 MHz, DMSO-d$_6$) δ 8.29 (s, 1H), 8.20 (t, J = 7.9 Hz, 1H), 7.85 (d, J = 7.9 Hz, 1H), 7.77-7.67 (m, 2H), 7.29 (d, J = 5.2 Hz, 1H), 7.16 (d, J = 8.7 Hz, 2H), 6.92 (d, J = 8.7 Hz, 2H), 5.30 (s, 2H), 4.45-4.33 (m, 2H), 3.21-3.04 (m, 2H), 2.73 (s, 2H), 2.01-1.98 (m, 1H), 1.77 (s, 2H), 1.59-1.36 (m, 1H), 0.76-0.67 (m, 4H). HRMS calcd. for C$_{30}$H$_{28}$F$_3$N$_4$O$_4$S (M + H) 597.1783, found 597.1794 |

| Example | Structure/Chemical Name | Starting materials | NMR and HRMS |
|---|---|---|---|
| 2-4 | 1-(6-(3-((2-Methyl-4-(1-propionylpiperidin-4-yl)phenoxy)methyl)-4-(trifluoromethyl)thiophen-2-yl)pyridin-2-yl)-5-(trifluoromethyl)-1H-pyrazole-4-carboxylic acid | Intermediate 1-1, Intermediate 3-4 and propionyl chloride No further purification was necessary after EtOAc extraction and concentration | $^1$H NMR (400 MHz, CD$_3$OD) δ 8.19 (d, J = 0.67 Hz, 1H), 8.12 (s, 1H), 8.03-8.10 (m, 1H), 7.82 (dd, J = 0.67, 7.89 Hz, 1H), 7.72 (dd, J = 0.67, 7.89 Hz, 1H), 6.95-7.01 (m, 2H), 6.86-6.91 (m, 1H), 5.22 (s, 2H), 4.63-4.71 (m, 1H), 4.02-4.11 (m, 1H), 3.14-3.25 (m, 1H), 2.64-2.78 (m, 2H), 2.45 (q, J = 7.52 Hz, 2H), 2.03 (s, 3H), 1.80-1.94 (m, 2H), 1.47-1.68 (m, 2H), 1.14 (t, J = 7.52 Hz, 3H). HRMS calcd. for C$_{31}$H$_{29}$F$_6$N$_4$OS (M + H) 667.1814, found 667.1826. |
| 2-5 | 1-(6-(3-((2-Methyl-4-(1-propionylpiperidin-4-yl)phenoxy)methyl)thiophen-2-yl)pyridin-2-yl)-5-(trifluoromethyl)-1H-pyrazole-4-carboxylic acid | Intermediate 1-1, Intermediate 3-3-4, and propionyl chloride Purified by RP-HPLC (HC-B) | $^1$H NMR (400 MHz, CD$_3$OD) δ 8.03 (dd, J = 7.8, 8.0 Hz, 1H), 8.00 (s, 1H), 7.78 (d, J = 7.8 Hz, 1H), 7.58 (d, J = 8.0 Hz, 1H), 7.52 (d, J = 5.1 Hz, 1H), 7.26 (d, J = 5.1 Hz, 1H), 6.97-7.00 (m, 1H), 6.92-6.96 (m, 1H), 6.80 (d, J = 8.4 Hz, 1H), 5.33 (s, 2H), 4.62-4.70 (m, 1H), 4.02-4.08 (m, 1H), 3.12-3.22 (m, 1H), 2.66-2.75 (m, 2H), 2.44 (q, J = 7.5 Hz, 2H), 2.14 (s, 3H), 1.79-1.91 (m, 2H), 1.46-1.65 (m, 2H), 1.14 (t, J = 7.5 Hz, 3H). HRMS calcd. for C$_{30}$H$_{30}$F$_3$N$_4$O$_4$S (M + H) 599.1940, found 599.1999. |

Example 3. 1-(6-(3-((4-(1-(Methoxycarbonyl)piperidin-4-yl)-2-methylphenoxy)methyl)-5-methylthiophen-2-yl)pyridin-2-yl)-5-(trifluoromethyl)-1H-pyrazole-4-carboxylic acid

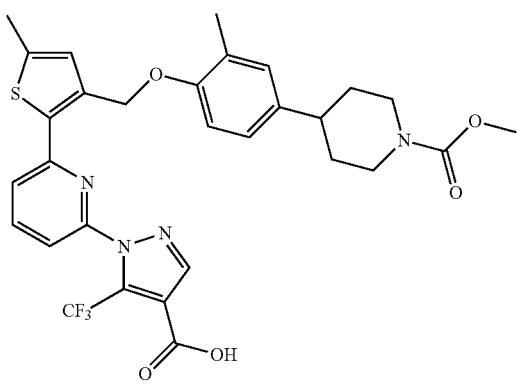

To a suspension of ethyl 1-(6-bromopyridin-2-yl)-5-(trifluoromethyl)-1H-pyrazole-4-carboxylate (440 mg, 1.21 mmol), bis(pinacolato)diboron (338 mg, 1.33 mmol), potassium acetate (356 mg, 3.63 mmol), 2-dicyclohexylphosphino-2',4',6'-triisopropylbiphenyl (CAS#564483-18-7) (81 mg, 0.17 mmol) in 1,4-dioxane (2.2 mL) was added Pd(OAc)$_2$ (30 mg, 0.13 mmol). The mixture was then stirred at 100° C. for ca. 1 h, and then cooled to room temperature. The reaction mixture was filtered through a plug of Celite®, and then concentrated. The resulting residue, methyl 4-(4-((2-bromo-5-methylthiophen-3-yl)methoxy)-3-methylphenyl)piperidine-1-carboxylate (Intermediate 3-3-1) (351 mg, 0.801 mmol), and 2M aq. Na$_2$CO$_3$ (0.8 mL, 1.60 mmol) in dioxane (7 mL) was added PdCl$_2$(dppf) CH$_2$Cl$_2$ adduct (20 mg, 0.02 mmol). The mixture was then stirred at 80° C. for 18 h, and then cooled to room temperature. The reaction mixture was diluted with EtOAc. The mixture was then washed successively with H$_2$O and brine, dried over MgSO4, filtered, and then concentrated. The resulting residue was semi-purified by silica gel flash column chromatography (0-100% EtOAc in hexane) and the resulting material was then dissolved in a mixture of THF/H2O (ca. 2 mL/2 mL). To the mixture was then added lithium hydroxide monohydrate (283 mg, 6.75 mmol). The mixture was then stirred at room temperature for 18 h, and then concentrated. The resulting residue was purified by RP-HPLC (HC-B) to afford the title compound. $^1$H NMR (400 MHz, CD$_3$OD) δ 7.97 (dd, J=7.80, 8.00 Hz, 1H), 7.93 (s, 1H), 7.68

(dd, J=0.61, 7.82 Hz, 1H), 7.52 (dd, J=0.61, 7.95 Hz, 1H), 6.98-7.01 (m, 1H), 6.91-6.97 (m, 2H), 6.78 (d, J=8.31 Hz, 1H), 5.25 (s, 2H), 3.02-3.11 (m, 4H), 2.49 (d, J=0.98 Hz, 3H), 2.35-2.48 (m, 3H), 2.16 (s, 3H), 1.71-1.78 (m, 4H). HRMS calcd. for $C_{30}H_{30}F_3N_4O_5S$ (M+H) 615.1889, found 615.1902.

Example 4

The following compounds were synthesized with a similar method as described above for Example 3 using the appropriate starting materials as delineated in the table below.

| Example | Structure/Chemical Name | Starting materials | NMR and HRMS |
|---|---|---|---|
| 4-1 | 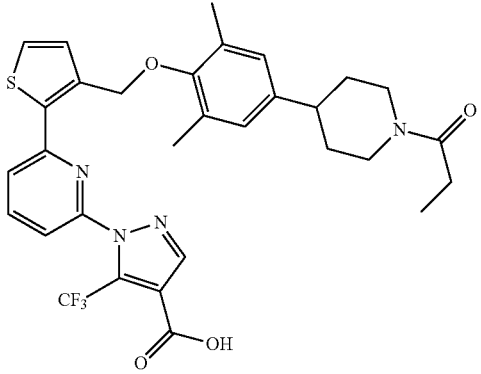 [SMILES: CCC(=O)N1CCC(c2cc(C)c(OCc3ccsc3-c3cccc(-n4ncc(C(=O)O)c4C(F)(F)F)n3)c(C)c2)CC1]<br>1-(6-(3-((2,6-dimethyl-4-(1-propionylpiperidin-4-yl)phenoxy)methyl)thiophen-2-yl(pyridin-2-yl)-5-(trifluoromethyl)-1H-pyrazole-4-carboxylic acid | Intermediate 1-1 and Intermediate 3-3-2 | $^1$H NMR (400 MHz, CD$_3$OD) δ 8.00-8.07 (m, 2H), 7.84 (dd, J = 0.73, 7.89 Hz, 1H), 7.58 (dd, J = 0.73, 7.89 Hz, 1H), 7.53 (d, J = 5.18 Hz, 1H), 7.29 (d, J = 5.18 Hz, 1H), 6.81 (s, 2H), 5.13 (s, 2H), 4.62-4.70 (m, 1H), 4.01-4.09 (m, 1H), 3.12-3.21 (m, 1H), 2.61-2.72 (m, 2H), 2.45 (q, J = 7.58 Hz, 2H), 2.10 (s, 6H), 1.76-1.89 (m, 2H), 1.44-1.64 (m, 2H), 1.14 (t, J = 7.58 Hz, 3H). HRMS calcd. for $C_{31}H_{32}F_3N_4O_4S$ (M + H) 613.2091, found 613.2127. |
| 4-2 | 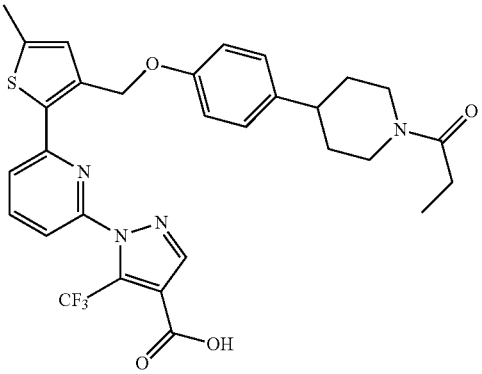 [SMILES: CCC(=O)N1CCC(c2ccc(OCc3cc(C)sc3-c3cccc(-n4ncc(C(=O)O)c4C(F)(F)F)n3)cc2)CC1]<br>1-(6-(5-Methyl-3-((4-(1-propionylpiperidin-4-yl)phenoxy)methyl)thiophen-2-yl)pyridin-2-yl)-5-(trifluoromethyl)-1H-pyrazole-4-carboxylic acid | Intermediate 1-1 and Intermediate 3-2 | $^1$H NMR (400 MHz, CD$_3$OD) δ 8.06 (s, 1H), 8.01 (dd, J = 7.80, 8.00 Hz, 1H), 7.71 (dd, J = 0.67, 7.89 Hz, 1H), 7.52 (dd, J = 0.61, 7.95 Hz, 1H), 7.07-7.14 (m, 2H), 6.94 (d, J = 0.98 Hz, 1H), 6.82-6.88 (m, 2H), 5.24 (s, 2H), 4.63-4.70 (m, 1H), 4.01-4.09 (m, 1H), 3.14-3.22 (m, 1H), 2.63-2.79 (m, 2H), 2.50 (d, J = 0.98 Hz, 3H), 2.45 (q, J = 7.50 Hz, 2H), 1.79-1.92 (m, 2H), 1.46-1.66 (m, 2H), 1.14 (t, J = 7.52 Hz, 3H). HRMS calcd. for $C_{30}H_{30}F_3N_4O_4S$ (M + H) 599.1940, found 599.1945 |
| 4-3 | 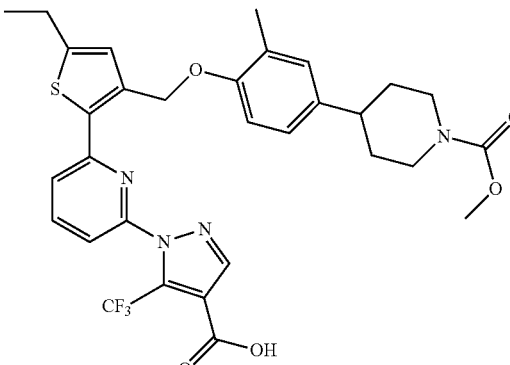<br>1-(6-(5-Ethyl-3-((4-(1-(methoxycarbonyl)piperidin-4-yl)-2-methylphenoxy)methyl)thiophen-2-yl)pyridin-2-yl)-5-(trifluoromethyl)-1H-pyrazole-4-carboxylic acid | Intermediate 1-1 and Intermediate 3-3-3 | $^1$H NMR (400 MHz, CD$_3$OD) δ 7.97 (t, J = 7.95 Hz, 1H), 7.91 (s, 1H), 7.68 (dd, J = 0.67, 7.89 Hz, 1H), 7.52 (dd, J = 0.61, 7.95 Hz, 1H), 6.98 (s, 2H), 6.92-6.97 (m, 1H), 6.79 (d, J = 8.44 Hz, 1H), 5.26 (s, 2H), 4.16-4.26 (m, 2H), 3.70 (s, 3H), 2.82-2.96 (m, 4H), 2.57-2.67 (m, 1H), 2.16 (s, 3H), 1.74-1.83 (m, 2H), 1.49-1.61 (m, 2H), 1.33 (t, J = 7.52 Hz, 3H). HRMS calcd. for $C_{31}H_{32}F_3N_4O_5S$ (M + H) 629.2046, found 629.2069. |

| Example | Structure/Chemical Name | Starting materials | NMR and HRMS |
|---|---|---|---|
| 4-4 | 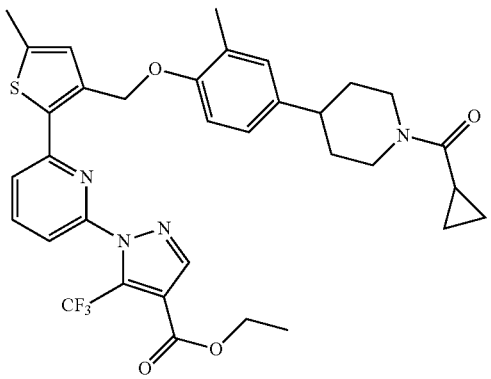<br>1-(6-(3-((4-(1-(Cyclopropanecarbonyl)piperidin-4-yl)-2-methylphenoxy)methyl)-4-methylthiophen-2-yl)pyridin-2-yl)-5-(trifluoromethyl)-1H-pyrazole-4-carboxylic acid | Intermediate 1-1 and Intermediate 3-6 | $^1$H NMR (400 MHz, CD$_3$OD) δ 8.08 (d, J = 0.8 Hz, 1H), 8.00 (t, J = 7.9 Hz, 1H), 7.74 (dd, J = 7.9, 0.8 Hz, 1H), 7.59 (dd, J = 8.0, 0.8 Hz, 1H), 7.22 (d, J = 1.1 Hz, 1H), 6.98 (d, J = 2.2 Hz, 1H), 6.95 (dd, J = 8.3, 2.3 Hz, 1H), 6.88 (d, J = 8.3 Hz, 1H), 5.19 (s, 2H), 4.64 (d, J = 13.1 Hz, 1H), 4.45 (d, J = 13.7 Hz, 1H), 3.27-3.20 (m, 1H), 2.74 (tt, J = 12.2, 3.7 Hz, 2H), 2.30 (d, J = 1.0 Hz, 3H), 2.07 (s, 3H), 2.00 (tt, J = 8.0, 4.8 Hz, 1H), 1.96-1.87 (m, 1H), 1.83 (d, J = 13.2 Hz, 1H), 1.71-1.45 (m, 2H), 0.94-0.86 (m, 2H), 0.85-0.78 (m, 2H). HRMS calcd for C$_{32}$H$_{32}$F$_3$N$_4$O$_4$S (M + H) 625.2018, found 625.2121. |

Example 5

Example 5-A. Ethyl 1-(6-(3-((4-(1-(cyclopropanecarbonyl)piperidin-4-yl)-2-methylphenoxy)methyl)-5-methylthiophen-2-yl)pyridin-2-yl)-5-(trifluoromethyl)-1H-pyrazole-4-carboxylate

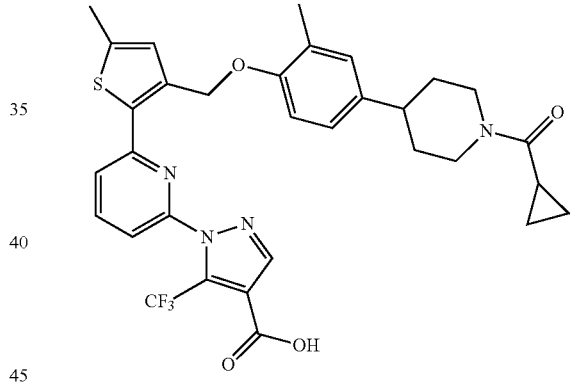

To a solution of Intermediate 4-1-D (30 mg, 0.073 mmol) and Intermediate 2-4 (30 mg, 0.116 mmol) in toluene (1 mL) was added 2-(tributylphosphoranylidene)acetonitrile (CAS#157141-27-0, 40 μL, 0.152 mmol). The mixture was then stirred at 80° C. for 4 h and then cooled to room temperature. The reaction mixture was purified by silica gel flash column chromatography (heptane/EtOAc=85/15 to 6/4) to afford the title compound. MS (ESI+) m/z 653.1 (M+H).

Example 5. 1-(6-(3-((4-(1-(Cyclopropanecarbonyl)piperidin-4-yl)-2-methylphenoxy)methyl)-5-methylthiophen-2-yl)pyridin-2-yl)-5-(trifluoromethyl)-1H-pyrazole-4-carboxylic acid To a solution of ethyl 1-(6-(3-((4-(1-(cyclopropanecarbonyl)piperidin-4-yl)-2-methylphenoxy)methyl)-5-methylthiophen-2-yl)pyridin-2-yl)-5-(trifluoromethyl)-1H-pyrazole-4-carboxylate (30 mg, 0.046 mmol) in THF/MeOH (1 mL/0.5 mL) was added LiOH in H$_2$O (500 μL, 0.5 mmol). The mixture was stirred at room temperature for 1.5 h, and then rendered acidic by 1/1 water sat. aq. KHSO$_4$. The mixture was then extracted with EtOAc. The organic phase was then washed successively with H$_2$O and brine, dried over Na$_2$SO$_4$, filtered, and then concentrated. The resulting residue was purified by RP-HPLC (HC-A) to afford the title compound. $^1$H-NMR (+5 uL TFA, 400 MHz, CD$_3$OD) δ 8.15 (s, 1H), 8.02 (t, J=7.9 Hz, 1H), 7.74 (dd, J=0.6, 7.9 Hz, 1H), 7.52 (dd, J=0.6, 7.9 Hz, 1H), 6.95-7.01 (m, 2H), 6.92 (dd, J=2.3, 8.4 Hz, 1H), 6.76 (d, J=8.4 Hz, 1H), 5.25 (s, 2H), 4.58-4.69 (m, 1H), 4.39-4.51 (m, 1H), 3.17-3.26 (m, 1H), 2.65-2.79 (m, 2H), 2.50 (d, J=1 Hz, 3H), 2.13 (s, 3H), 1.95-2.05 (m, 1H), 1.76-1.94 (m, 2H), 1.44-1.70 (m, 2H), 0.74-0.94 (m, 4H). HRMS calcd. for C$_{32}$H$_{32}$F$_3$N$_4$O$_4$S (M+H) 625.2096, found 625.2115.

Example 6

The following compounds were prepared by similar methods as described above for Example 5 using the appropriate starting materials delineated in the table below.

| | Structure/Chemical Name | Starting materials | MS (ESI+) m/z |
|---|---|---|---|
| 6-1 | 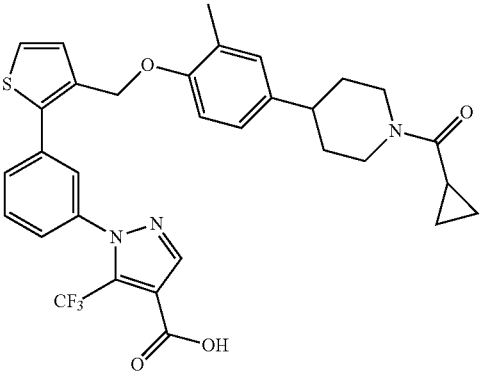 [SMILES: Cc1cc(C2CCN(C(=O)C3CC3)CC2)ccc1OCc1ccsc1-c1cccc(-n2ncc(C(=O)O)c2C(F)(F)F)c1]<br>1-(3-(3-((4-(1-(Cyclopropanecarbonyl)piperidin-4-yl)-2-methylphenoxy)methyl)thiophen-2-yl)phenyl)-5-(trifluoromethyl)-1H-pyrazole-4-carboxylic acid | Intermediate 2-4 and Intermediate 4-1-B | $^1$H NMR (400 MHz, CD$_3$OD) δ 8.08 (d, J = 0.7 Hz, 1H), 7.71 (ddd, J = 7.9, 1.7, 1.1 Hz, 1H), 7.63-7.58 (m, 2H), 7.48 (d, J = 5.2 Hz, 1H), 7.45 (ddd, J = 8.1, 2.2, 1.0 Hz, 1H), 7.26 (d, J = 5.2 Hz, 1H), 6.95-6.90 (m, 2H), 6.77 (d, J = 9.0 Hz, 1H), 4.99 (s, 2H), 4.63 (d, J = 13.0 Hz, 1H), 4.44 (d, J = 13.4 Hz, 1H), 3.28-3.19 (m, 1H), 2.71 (dtd, J = 15.8, 7.2, 3.4 Hz, 2H), 2.06 (s, 3H), 1.99 (tt, J = 8.0, 4.8 Hz, 1H), 1.90 (d, J = 13.4 Hz, 1H), 1.81 (d, J = 13.3 Hz, 1H), 1.69-1.44 (m, 2H), 0.93-0.77 (m, 4H), HRMS calcd. for C$_{32}$H$_{31}$F$_3$N$_3$O$_4$S (M + H) 610.1909, found 610.1923. |
| 6-2 | 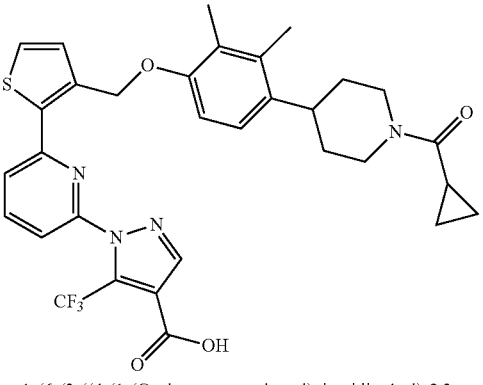<br>1-(6-(3-((4-(1-(Cyclopropanecarbonyl)piperidin-4-yl)-2,3-dimethylphenoxy)methyl)thiophen-2-yl)pyridin-2-yl)-5-(trifluoromethyl)-1H-pyrazole-4-carboxylic acid | Intermediate 2-8 and Intermediate 4-1-B | $^1$H NMR (400 MHz, CD$_3$OD) δ 8.01 (app. t, J = 7.96 Hz, 1H), 7.98 (s, 1H), 7.76 (dd, J = 0.67, 7.96 Hz, 1H), 7.57 (dd, J = 0.67, 7.96 Hz, 1H), 7.52 (d, J = 5.20 Hz, 1H), 7.25 (d, J = 5.20 Hz, 1H), 6.93 (d, J = 8.68 Hz, 1H), 6.74 (d, J = 8.68 Hz, 1H), 5.30 (s, 2H), 4.60-4.70 (m, 1H), 4.42-4.52 (m, 1H), 3.22-3.29 (m, 1H), 3.00-3.11 (m, 1H), 2.70-2.82 (m, 1H), 2.26 (s, 3H), 2.12 (s, 3H), 1.96- 2.04 (m, 1H), 1.82-1.91 (m, 1H), 1.72-1.82 (m, 1H), 1.43-1.71 (m, 2H), 0.76-0.94 (m, 4H). HRMS calcd. for C$_{32}$H$_{32}$F$_3$N$_4$O$_4$S (M + H) 625.2096, found 625.2123. |
| 6-3 | 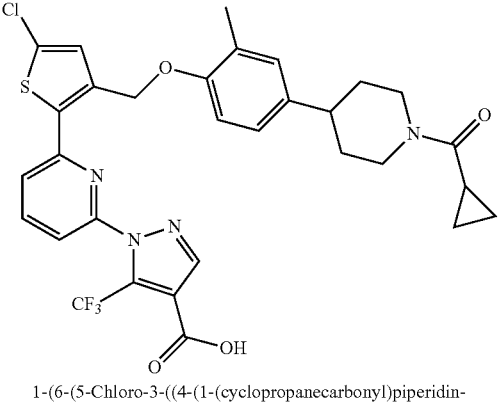<br>1-(6-(5-Chloro-3-((4-(1-(cyclopropanecarbonyl)piperidin-4-yl)-2-methylphenoxy)methyl)thiophen-2-yl)pyridin-2-yl)-5-(trifluoromethyl)-1H-pyrazole-4-carboxylic acid | Intermediate 2-4 and Intermediate 4-3 | $^1$H NMR (TFA salt, 400 MHz, CD$_3$OD) δ 8.17 (s, 1H), 8.07 (dd, J = 7.80, 8.00 Hz, 1H), 7.75-7.80 (m, 1H), 7.63 (d, J = 7.96 Hz, 1H), 7.15 (s, 1H), 7.00-7.04 (m, J = 2.00 Hz, 1H), 6.94-6.99 (m, 1H), 6.82 (d, J = 8.34 Hz, 1H), 5.25 (s, 2H), 4.60-4.69 (m, 1H), 4.39-4.50 (m, 1H), 3.20-3.29 (m, 1H), 2.67-2.79 (m, 2H), 2.14 (s, 3H), 1.96-2.03 (m, 1H), 1.87-1.95 (m, 1H), 1.78-1.87 (m, 1H), 1.46-1.70 (m, 2H), 0.75-0.93 (m, 4H). HRMS calcd. for C$_{31}$H$_{29}$ClF$_3$N$_4$O$_4$S (M + H) 645.1550, found 645.1581. |

| | Structure/Chemical Name | Starting materials | MS (ESI+) m/z |
|---|---|---|---|
| 6-4 | 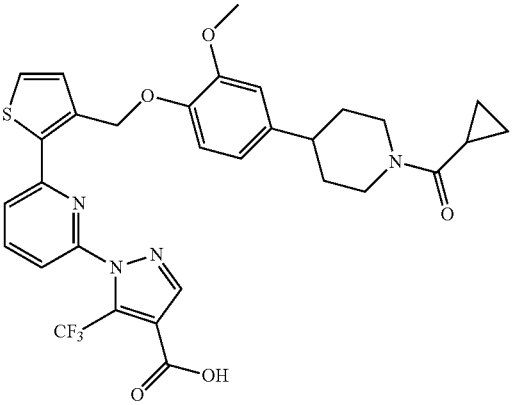 [SMILES: COc1cc(C2CCN(C(=O)C3CC3)CC2)ccc1OCc1ccsc1-c1cccc(-n2ncc(C(=O)O)c2C(F)(F)F)n1]<br>1-(6-(3-((4-(1-(Cyclopropanecarbonyl)piperidin-4-yl)-2-methoxyphenoxy)methyl)thiophen-2-yl)pyridin-2-yl)-5-(trifluoromethyl)-1H-pyrazole-4-carboxylic acid | Intermediate 2-5-3 and Intermediate 4-1-B | $^1$H NMR (400 MHz, DMSO-d$_6$) δ 8.12-8.24 (m, 2 H) 7.90 (d, J = 7.58 Hz, 1 H) 7.66-7.76 (m, 2 H) 7.28 (d, J = 5.14 Hz, 1 H) 6.95 (d, J = 8.31 Hz, 1 H) 6.88 (d, J = 1.96 Hz, 1 H) 6.72 (dd, J = 8.31, 1.96 Hz, 1 H) 5.25 (s, 2 H) 4.29-4.59 (m, 2 H) 3.75 (s, 3 H) 3.15 (t, J = 11.68 Hz, 1 H) 2.55-2.78 (m, 2 H) 1.93-2.05 (m, 1 H) 1.69-1.89 (m, 2 H) 1.36-1.63 (m, 2 H) 0.63-0.82 (m, 4 H). HRMS calcd. for C$_{31}$H$_{30}$F$_3$N$_4$O$_5$S (M + H) 627.1889, found 627.1896. |
| 6-5 | 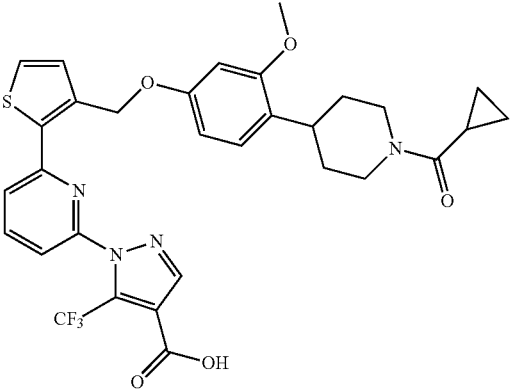 [SMILES: COc1cc(OCc2ccsc2-c2cccc(-n3ncc(C(=O)O)c3C(F)(F)F)n2)ccc1C1CCN(C(=O)C2CC2)CC1]<br>1-(6-(3-((4-(1-(Cyclopropanecarbonyl)piperidin-4-yl)-3-methoxyphenoxy)methyl)thiophen-2-yl)pyridin-2-yl)-5-(trifluoromethyl)-1H-pyrazole-4-carboxylic acid | Intermediate 2-5-4 and Intermediate 4-1-B | $^1$H NMR (400 MHz, DMSO-d$_6$ δ 8.13 (t, J = 7.89 Hz, 1 H) 7.87 (s, 1 H) 7.68-7.79 (m, 2 H) 7.65 (s, 1 H) 7.29 (d, J = 5.14 Hz, 1 H) 7.05 (d, J = 8.44 Hz, 1 H) 6.62 (s, 1 H) 6.55 (dd, J = 8.44, 2.32 Hz, 1 H) 5.26-5.35 (m, 2 H) 4.28-4.57 (m, 2 H) 3.67-3.77 (m, 3 H) 2.96-3.22 (m, 2H) 2.60 (t, J = 11.98 Hz, 1 H) 1.93-2.03 (m, 1 H) 1.29-1.83 (m, 4 H) 0.60-0.81 (m, 4 H). HRMS calcd. for C$_{31}$H$_{30}$F$_3$N$_4$O$_5$S (M + H) 627.1889, found 627.1890 |
| 6-6 | 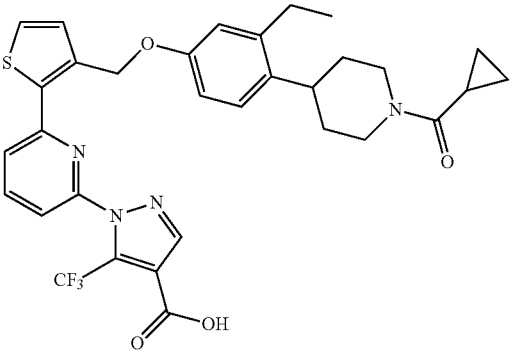 [SMILES: CCc1cc(OCc2ccsc2-c2cccc(-n3ncc(C(=O)O)c3C(F)(F)F)n2)ccc1C1CCN(C(=O)C2CC2)CC1]<br>1-(6-(3-((4-(1-(Cyclopropanecarbonyl)piperidin-4-yl)-3-ethylphenoxy)methyl)thiophen-2-yl)pyridin-2-yl)-5-(trifluoromethyl)-1H-pyrazole-4-carboxylic acid | Intermediate 2-5-5 and Intermediate 4-1-B | $^1$H NMR (400 MHz, DMSO-d$_6$) δ 8.12 (t, J = 7.95 Hz, 1 H) 7.84 (s, 1 H) 7.75 (d, J = 7.95 Hz, 1 H) 7.69 (s, 1 H) 7.64 (d, J = 7.95 Hz, 1 H) 7.27 (d, J = 5.14 Hz, 1 H) 7.08-7.14 (m, 1 H) 6.77-6.82 (m, 2 H) 5.29 (s, 2 H) 4.26-4.60 (m, 2 H) 3.20 (d, J = 12.10 Hz, 1 H) 2.85-3.02 (m, 1 H) 2.56-2.71 (m, 3 H) 2.00 (quin, J = 6.30 Hz, 1 H) 1.32-1.76 (m, 4 H) 1.01-1.19 (m, 3 H) 0.59-0.83 (m, 4 H). HRMS calcd. for C$_{32}$H$_{32}$F$_3$N$_4$O$_4$S (M + H) 625.2096, found 625.2106. |

| | Structure/Chemical Name | Starting materials | MS (ESI+) m/z |
|---|---|---|---|
| 6-7 | 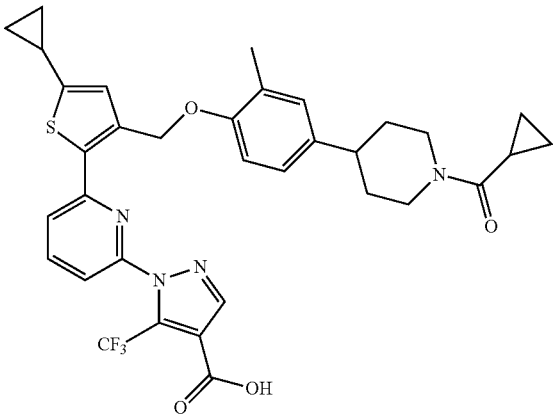 [SMILES: Cc1cc(C2CCN(C(=O)C3CC3)CC2)ccc1OCc1cc(C2CC2)sc1-c1cccc(-n2ncc(C(=O)O)c2C(F)(F)F)n1]<br>1-(6-(3-((4-(1-(Cyclopropanecarbonyl)piperidin-4-yl)-2-methylphenoxy)methyl)-5-cyclopropylthiophen-2-yl)pyridin-2-yl)-5-(trifluoromethyl)-1H-pyrazole-4-carboxylic acid | Intermediate 2-4 and Intermediate 4-4 | $^1$H NMR (TFA salt, 400 MHz, CD$_3$OD) δ 8.15 (s, 1H), 8.01 (dd, J = 7.80, 8.00 Hz, 1H), 7.73 (dd, J = 0.67, 8.01 Hz, 1H), 7.51 (dd, J = 0.61, 7.82 Hz, 1H), 6.97-7.00 (m, J = 2.00 Hz, 1H), 6.95 (s, 1H), 6.89-6.95 (m, 1H), 6.77 (d, J = 8.31 Hz, 1H), 5.24 (s, 2H), 4.57-4.68 (m, 1H), 4.41-4.50 (m, 1H) 3.19-3.27 (m, 1H), 2.67-2.78 (m, 2H) 2.09-2.18 (m, 4H), 1.96-2.03 (m, 1H) 1.88-1.95 (m, 1H), 1.78-1.87 (m, 1H) 1.46-1.69 (m, 2H), 1.03-1.10 (m, 2H) 0.74-0.94 (m, 6H). HRMS calcd. for C$_{34}$H$_{34}$F$_3$N$_4$O$_4$S (M + H) 651.2253, found 651.2275. |
| 6-8 | 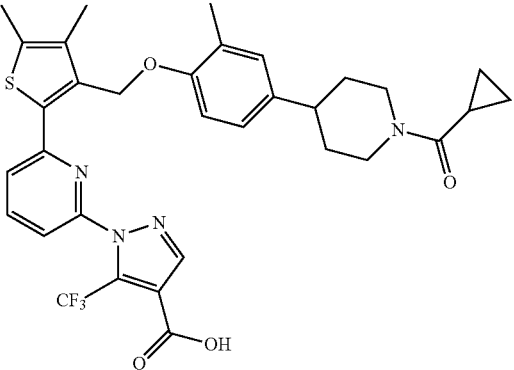 [SMILES: Cc1cc(C2CCN(C(=O)C3CC3)CC2)ccc1OCc1c(-c2cccc(-n3ncc(C(=O)O)c3C(F)(F)F)n2)sc(C)c1C]<br>1-(6-(3-((4-(1-(Cyclopropanecarbonyl)piperidin-4-yl)-2-methylphenoxy)methyl)-4,5-dimethylthiophen-2-yl)pyridin-2-yl)-5-(trifluoromethyl)-1H-pyrazole-4-carboxylic acid | Intermediate 2-4 and Intermediate 4-1 | $^1$H NMR (TFA salt, 400 MHz, CD$_3$OD) δ 8.12 (s, 1H), 7.98 (dd, J = 7.80, 8.00 Hz, 1H), 7.69 (dd, J = 0.63, 7.96 Hz, 1H), 7.51-7.56 (m, 1H), 6.96-7.00 (m, 1H), 6.91-6.95 (m, 1H), 6.83-6.88 (m, 1H), 5.16 (s, 2H), 4.59-4.68 (m, 1H), 4.39-4.51 (m, 1H), 3.20-3.27 (m, 1H), 2.68-2.80 (m, 2H), 2.43 (s, 3H), 2.18 (s, 3H), 2.07 (s, 3H), 1.97-2.04 (m, 1H), 1.88-1.96 (m, 1H), 1.79-1.87 (m, 1H), 1.43-1.72 (m, 2H), 0.75-0.96 (m, 4H). HRMS calcd. for C$_{33}$H$_{34}$F$_3$N$_4$O$_4$S (M + H) 639.2253, found 639.2264. |
| 6-9 | 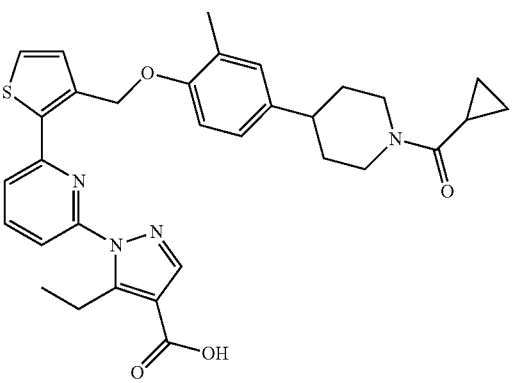 [SMILES: CCc1c(C(=O)O)cnn1-c1cccc(-c2sccc2COc2ccc(C3CCN(C(=O)C4CC4)CC3)cc2C)n1]<br>1-(6-(3-((4-(1-(Cyclopropanecarbonyl)piperidin-4-yl)-2-methylphenoxy)methyl)thiophen-2-yl)pyridin-2-yl)-5-ethyl-1H-pyrazole-4-carboxylic acid | Intermediate 2-4 and Intermediate 4-2-1 | $^1$H NMR (400 MHz, CD$_3$OD) δ 8.04-7.94 (m, 2H), 7.69 (ddd, J = 7.8, 2.4, 0.8 Hz, 2H), 7.54 (d, J = 5.2 Hz, 1H), 7.27 (d, J = 5.2 Hz, 1H), 7.03-6.96 (m, 2H), 6.89 (d, J = 8.3 Hz, 1H), 5.30 (s, 2H), 4.63 (d, J = 12.8 Hz. 1H), 4.45 (d, J = 13.4 Hz, 1H), 3.53 (q, J = 7.4 Hz, 2H), 2.74 (ddq, J = 12.2, 8.1, 3.9 Hz, 2H), 2.14 (s, 3H), 2.04-1.95 (m, 1H), 1.95-1.75 (m, 2H), 1.72-1.47 (m, 2H), 1.40-1.33 (m, 1H), 1.23 (t, J = 7.4 Hz, 3H), 0.96-0.75 (m, 4H). HRMS calcd. for C$_{32}$H$_{35}$N$_4$O$_4$S (M + H) 571.2379, found 571.2391. |

| | Structure/Chemical Name | Starting materials | MS (ESI+) m/z |
|---|---|---|---|
| 6-10 | 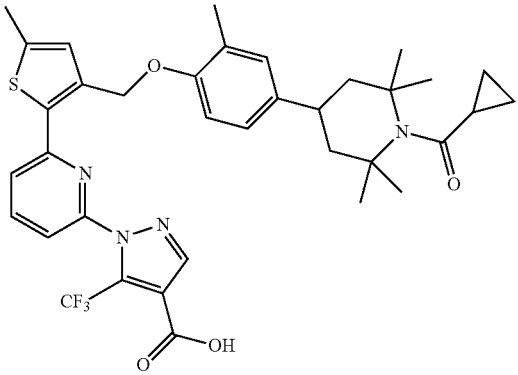 [SMILES: Cc1cc(COc2ccc(C3CC(C)(C)N(C(=O)C4CC4)C(C)(C)C3)cc2C)c(-c2cccc(-n3ncc(C(=O)O)c3C(F)(F)F)n2)s1]<br>1-(6-(3-((4-(1-(Cyclopropanecarbonyl)-2,2,6,6-tetramethylpiperidin-4-yl)-2-methylphenoxy)methyl)-5-methylthiophen-2-yl)pyridin-2-yl)-5-(trifluoromethyl)-1H-pyrazole-4-carboxylic acid | Intermediate 2-9 and Intermediate 4-1-D | $^1$H NMR (400 MHz, DMSO-d$_6$) δ 8.03-8.21 (m, 2 H) 7.77 (s, 1 H) 7.64 (d, J = 7.70 Hz, 1 H) 6.99-7.13 (m, 3 H) 6.90 (d, J = 8.56 Hz, 1 H) 5.26 (s, 2 H) 3.10 (t, J = 8.07 Hz, 1 H) 2.48 (d, J = 0.98 Hz, 3 H) 2.12 (s, 3 H) 1.83-2.03 (m, 5 H), 1.51 (s, 6 H), 1.48 (s, 6 H), 0.78-0.84 (m, 2 H) 0.68-0.75 (m, 2 H). HRMS calcd. for C$_{36}$H$_{40}$F$_3$N$_4$O$_4$S (M + H) 681.2717, found 681.2792. |
| 6-11 | 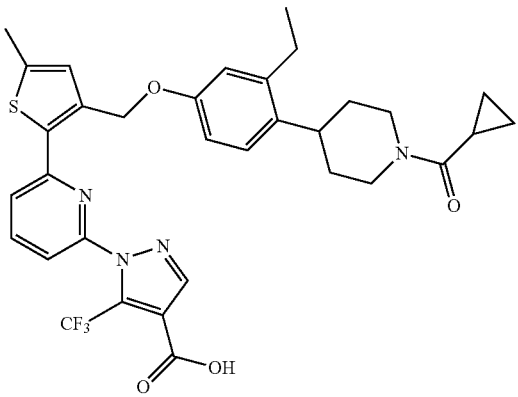 [SMILES: CCc1cc(OCc2cc(C)sc2-c2cccc(-n3ncc(C(=O)O)c3C(F)(F)F)n2)ccc1C1CCN(C(=O)C2CC2)CC1]<br>1-(6-(3-((4-(1-(Cyclopropanecarbonyl)piperidin-4-yl)-3-ethylphenoxy)methyl)-5-methylthiophen-2-yl)pyridin-2-yl)-5-(trifluoromethyl)-1H-pyrazole-4-carboxylic acid | Intermediate 2-5-5 and Intermediate 4-1-D | $^1$H NMR (400 MHz, DMSO-d$_6$) δ 8.03 (t, J = 7.96 Hz, 1 H) 7.84 (s, 1 H) 7.62 (d, J = 7.96 Hz, 1 H) 7.53 (d, J = 7.83 Hz, 1 H) 6.99-7.07 (m, 1 H) 6.92 (d, J = 1.01 Hz, 1 H) 6.67-6.73 (m, 2 H) 5.15 (s, 2 H) 4.23-4.51 (m, 2 H) 2.81-2.92 (m, 1 H) 2.54 (q, J = 7.45 Hz, 3 H) 2.40 (d, J = 1.01 Hz, 3H) 1.88-1.98 (m, 1 H) 1.27-1.69 (m, 5 H) 1.05 (t, J = 7.52 Hz, 3 H) 0.58-0.75 (m, 4 H). HRMS calcd. for C$_{33}$H$_{34}$F$_3$N$_4$O$_4$S (M + H) 639.2252, found 639.2289. |
| 6-12 | 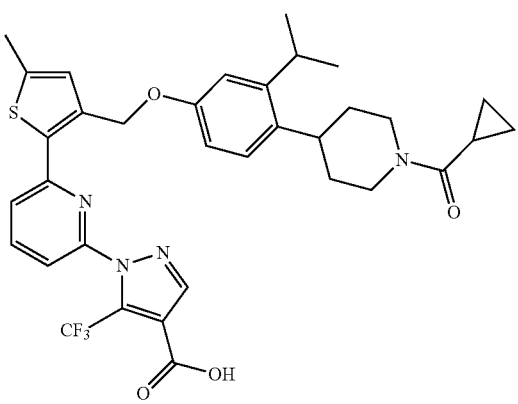 [SMILES: Cc1cc(COc2ccc(C3CCN(C(=O)C4CC4)CC3)c(C(C)C)c2)c(-c2cccc(-n3ncc(C(=O)O)c3C(F)(F)F)n2)s1]<br>1-(6-(3-((4-(1-(Cyclopropanecarbonyl)piperidin-4-yl)-3-isopropylphenoxy)methyl)-5-methylthiophen-2-yl)pyridin-2-yl)-5-(trifluoromethyl)-1H-pyrazole-4-carboxylic acid | Intermediate 2-10 and Intermediate 4-1-D | $^1$H NMR (400 MHz, DMSO-d$_6$) δ 8.09 (t, J = 7.95 Hz, 1 H) 7.84 (s, 1 H) 7.68 (d, J = 7.58 Hz, 1 H) 7.59 (d, J = 7.58 Hz, 1 H) 7.09 (d, J = 8.68 Hz, 1 H) 6.99 (d, J = 1.10 Hz, 1 H) 6.71-6.85 (m, 2 H) 5.23 (s, 2 H) 4.29-4.59 (m, 2 H) 3.21 (dq, J = 13.59, 6.76 Hz, 2 H) 2.94-3.07 (m, 1 H) 2.59-2.71 (m, 1 H) 2.47 (d, J = 0.86 Hz, 3 H) 1.93-2.04 (m, 1 H) 1.34-1.75 (m, 4 H) 1.06-1.17 (m, 6 H) 0.63-0.81 (m, 4 H). HRMS calcd. for C$_{34}$H$_{36}$F$_3$N$_4$O$_4$S (M + H) 653.2409, found 653.2437. |

| | Structure/Chemical Name | Starting materials | MS (ESI+) m/z |
|---|---|---|---|
| 6-13 | 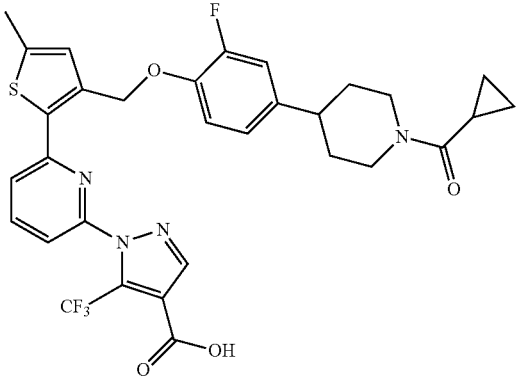 [SMILES: Cc1cc(COc2ccc(C3CCN(C(=O)C4CC4)CC3)cc2F)c(-c2cccc(-n3ncc(C(=O)O)c3C(F)(F)F)n2)s1]<br>1-(6-(3-((4-(1-(Cyclopropanecarbonyl)piperidin-4-yl)-2-fluorophenoxy)methyl)-5-methylthiophen-2-yl)pyridin-2-yl)-5-(trifluoromethyl)-1H-pyrazole-4-carboxylic acid | Intermediate 2-5-6 and Intermediate 4-1-D | $^1$H NMR (400 MHz, DMSO-$d_6$) δ 8.07 (t, J = 7.95 Hz, 1 H) 7.76 (s, 1 H) 7.68 (s, 1 H) 7.58 (d, J = 7.70 Hz, 1 H) 7.07-7.18 (m, 2 H) 6.94-7.02 (m, 2 H) 5.30 (s, 2 H) 4.29-4.57 (m, 2 H) 3.14 (t, J = 12.23 Hz, 1 H) 2.75 (tt, J = 12.00, 3.29 Hz, 1 H) 2.60 (t, J = 12.23 Hz, 1 H) 2.47 (d, J = 0.86 Hz, 3 H) 1.93-2.04 (m, 1 H) 1.70-1.88 (m, 2 H) 1.33-1.60 (m, 2 H) 0.63-0.80 (m, 4 H). HRMS calcd. for $C_{31}H_{29}F_4N_4O_4S$ (M + H) 629.1845, found 629.1881. |
| 6-14 | 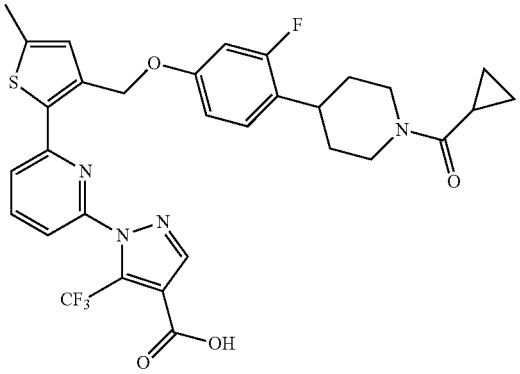 [SMILES: Cc1cc(COc2ccc(C3CCN(C(=O)C4CC4)CC3)c(F)c2)c(-c2cccc(-n3ncc(C(=O)O)c3C(F)(F)F)n2)s1]<br>1-(6-(3-((4-(1-(Cyclopropanecarbonyl)piperidin-4-yl)-3-fluorophenoxy)methyl)-5-methylthiophen-2-yl)pyridin-2-yl)-5-(trifluoromethyl)-1H-pyrazole-4-carboxylic acid | Intermediate 2-5-7 and Intermediate 4-1-D | $^1$H NMR (400 MHz, DMSO-$d_6$) δ 8.07 (t, J = 7.89 Hz, 1 H) 7.77 (s, 1 H) 7.64 (s, 1 H) 7.58 (d, J = 7.70 Hz, 1 H) 7.23 (t, J = 8.80 Hz, 1 H) 6.98 (d, J = 0.98 Hz, 1 H) 6.86 (dd, J = 12.53, 2.51 Hz, 1 H) 6.80 (dd, J = 8.56, 2.45 Hz, 1 H) 5.25 (s, 2 H) 4.29-4.58 (m, 2 H) 3.18 (t, J = 11.49 Hz, 1 H) 2.93-3.06 (m, 1 H) 2.58-2.69 (m, 1 H) 2.47 (d, J = 0.86 Hz, 3 H) 1.94-2.04 (m, 1 H) 1.38-1.84 (m, 4 H) 0.62-0.81 (m, 4 H). HRMS calcd. for $C_{31}H_{29}F_4N_4O_4S$ (M + H) 629.1845, found 629.1862. |
| 6-15 | 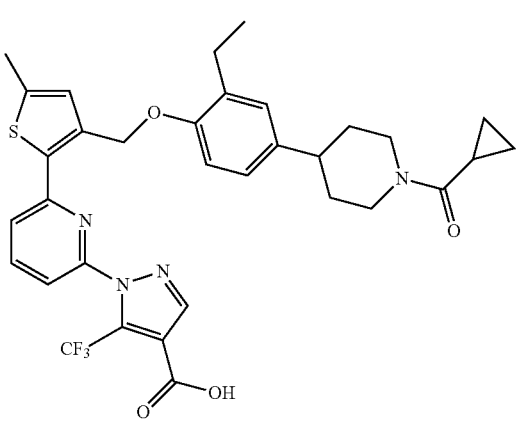 [SMILES: CCc1cc(C2CCN(C(=O)C3CC3)CC2)ccc1OCc1cc(C)sc1-c1cccc(-n2ncc(C(=O)O)c2C(F)(F)F)n1]<br>1-(6-(3-((4-(1-(Cyclopropanecarbonyl)piperidin-4-yl)-2-ethylphenoxy)methyl)-5-methylthiophen-2-yl)pyridin-2-yl)-5-(trifluoromethyl)-1H-pyrazole-4-carboxylic acid | Intermediate 2-5-8 and Intermediate 4-1-D | $^1$H NMR (400 MHz, CD$_3$OD) δ δ 8.15 (s, 1H), 8.02 (t, J = 7.9 Hz, 1H), 7.75 (dd, J = 8.0, 0.6 Hz, 1H), 7.53 (dd, J = 7.9, 0.6 Hz, 1H), 6.99 (d, J = 2.2 Hz, 1H), 6.98-6.90 (m, 2H), 6.79 (d, J = 8.4 Hz, 1H), 5.26 (s, 2H), 4.64 (d, J = 13.3 Hz, 1H), 4.45 (d, J = 13.3 Hz, 1H), 3.28-3.19 (m, 1H), 2.82-2.67 (m, 2H), 2.57 (q, J = 7.5 Hz, 2H), 2.51 (d, J = 1.0 Hz, 3H), 2.05-1.96 (m, 1H), 1.96-1.78 (m, 2H), 1.71-1.46 (m, 2H), 1.11 (t, J = 7.5 Hz, 3H), 0.96-0.76 (m, 4H). HRMS calcd. for $C_{33}H_{34}F_3N_4O_4S$ (M + H) 639.2247, found 639.2285. |

| | Structure/Chemical Name | Starting materials | MS (ESI+) m/z |
|---|---|---|---|
| 6-16 | 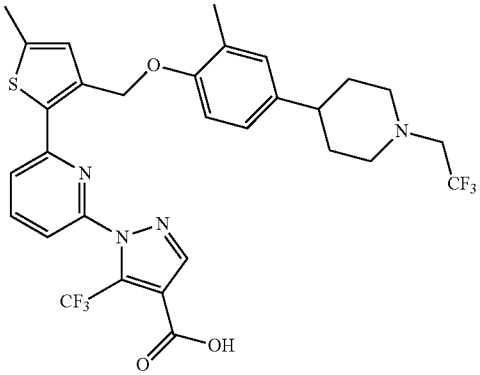 [SMILES: Cc1cc(COc2ccc(C3CCN(CC(F)(F)F)CC3)cc2C)c(-c2cccc(-n3ncc(C(=O)O)c3C(F)(F)F)n2)s1]<br>1-(6-(5-Methyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid | Intermediate 2-13 and Intermediate 4-1-D | $^1$H NMR (400 MHz, CD$_3$OD) δ 7.97 (dd, J = 7.80, 8.00 Hz, 1H), 7.93 (s, 1H), 7.68 (dd, J = 0.61, 7.82 Hz, 1H), 7.52 (dd, J = 0.61, 7.95 Hz, 1H), 6.98-7.01 (m, 1H), 6.91-6.97 (m, 2H), 6.78 (d, J = 8.31 Hz, 1H), 5.25 (s, 2H), 3.02-3.11 (m, 4H), 2.49 (d, J = 0.98 Hz, 3H), 2.35-2.48 (m, 3H), 2.16 (s, 3H), 1.71-1.78 (m, 4H). HRMS calcd. for C$_{30}$H$_{29}$F$_6$N$_4$O$_3$S (M +H) 639.1859, found 639.1899. |
| 6-17 | 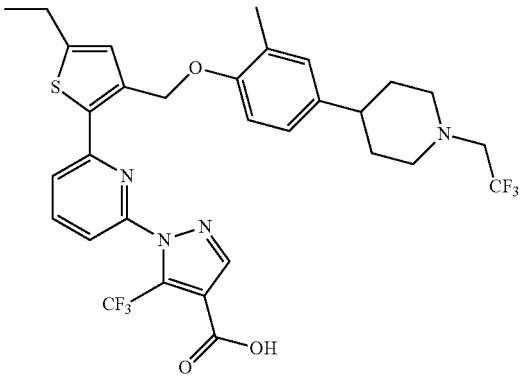 [SMILES: CCc1cc(COc2ccc(C3CCN(CC(F)(F)F)CC3)cc2C)c(-c2cccc(-n3ncc(C(=O)O)c3C(F)(F)F)n2)s1]<br>1-(6-(5-Ethyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid | Intermediate 2-13 and Intermediate 4-2-9 | $^1$H NMR (400 MHz, CD$_3$OD) δ 8.12 (s, 1H), 8.02 (t, J = 7.95 Hz, 1H), 7.75 (d, J = 7.46 Hz, 1H), 7.53 (dd, J = 0.61, 7.95 Hz, 1H), 6.97-7.02 (m, 2H), 6.93 (dd, J = 2.26, 8.38 Hz, 1H), 6.77 (d, J = 8.44 Hz, 1H), 5.25 (s, 2H), 3.03-3.11 (m, 4H), 2.88 (dq, J = 0.86, 7.54 Hz, 2H), 2.36-2.51 (m, 3H), 2.14 (s, 3H), 1.71-1.80 (m, 4H), 1.34 (t, J = 7.52 Hz, 3H). HRMS calcd. for C$_{31}$H$_{31}$F$_6$N$_4$O$_3$S (M + H) 653.2021, found 653.2040. |
| 6-18 | 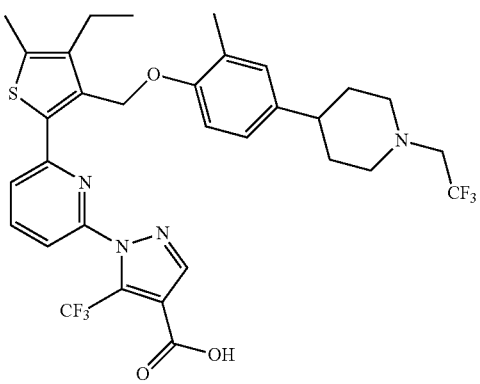 [SMILES: CCc1c(C)sc(-c2cccc(-n3ncc(C(=O)O)c3C(F)(F)F)n2)c1COc1ccc(C2CCN(CC(F)(F)F)CC2)cc1C]<br>1-(6-(4-Ethyl-5-methyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid | Intermediate 2-13 and Intermediate 4-2-10 | $^1$H NMR (400 MHz, CD$_3$OD) δ 7.98 (s, 1H), 7.92 (t, J = 7.95 Hz, 1H), 7.64 (d, J = 7.50 Hz, 1H), 7.53 (dd, J = 0.61, 7.95 Hz, 1H), 6.96-7.02 (m, 2H), 6.92 (br. d, J = 8.20 Hz, 1H), 5.09 (s, 2H), 3.04-3.13 (m, 4H), 2.65 (q, J = 7.53 Hz, 2H), 2.38-2.52 (m, 6H), 2.10 (s, 3H), 1.73-1.81 (m, 4H), 1.15 (t, J = 7.53 Hz, 3H). HRMS calcd. for C$_{32}$H$_{33}$F$_6$N$_4$O$_3$S (M + H) 667.2172, found 667.2217. |

| | Structure/Chemical Name | Starting materials | MS (ESI+) m/z |
|---|---|---|---|
| 6-19 | 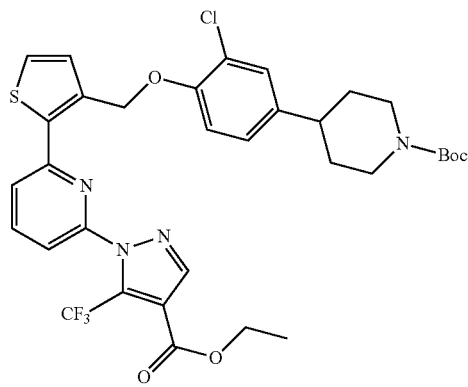 [SMILES: CCOC(=O)c1cnn(-c2cccc(-c3sccc3COc3ccc(C4CCN(C(=O)OC(C)(C)C)CC4)cc3Cl)n2)c1C(F)(F)F]

1-(6-(3-(((5-(1-(Cyclopropanecarbonyl)piperidin-4-yl)pyridin-2-yl)oxy)methyl)thiophen-2-yl)pyridin-2-yl)-5-(trifluoromethyl)-1H-pyrazole-4-carboxylic acid | Intermediate 2-5-9 and Intermediate 4-1-B | $^1$H NMR (400 MHz, DMSO-d$_6$) δ 8.10 (t, J = 7.89 Hz, 1 H) 8.05 (d, J = 2.45 Hz, 1 H) 7.75 (s, 2 H) 7.58-7.69 (m, 3 H) 7.23 (d, J = 5.14 Hz, 1 H) 6.83 (d, J = 8.56 Hz, 1 H) 5.55 (s, 2 H) 4.31-4.58 (m, 2 H) 3.07-3.22 (m, 1 H) 2.72-2.85 (m, 1 H) 2.60 (br. s., 1 H) 1.93-2.06 (m, 1 H) 1.69-1.89 (m, 2 H) 1.35-1.64 (m, 2 H) 0.64-0.81 (m, 4 H). HRMS; calcd. for C$_{29}$H$_{27}$F$_3$N$_5$O$_4$S (M + H) 598.1736, found 598.1748. |

Example 7

Example 7-A. tert-Butyl 4-(3-chloro-4-((2-(6-(4-(ethoxycarbonyl)-5-(trifluoromethyl)-1H-pyrazol-1-yl)pyridin-2-yl)thiophen-3-yl)methoxy)phenyl)piperidine-1-carboxylate

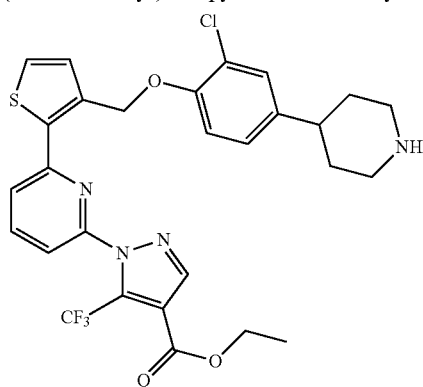

To a solution of Intermediate 2-11 (86 mg, 0.277 mmol) and Intermediate 4-1-B (100 mg, 0.252 mmol) in toluene (1.3 mL) was added 2-(tributylphosphoranylidene)acetonitrile (99 μl, 0.377 mmol). The mixture was then stirred at 100° C. for 2.5 h and then cooled to room temperature. The reaction was then quenched with H$_2$O. The mixture was then extracted three times with EtOAc. The combined organics were washed with brine, dried with Na$_2$SO$_4$, filtered and then concentrated. The resulting residue was purified by silica gel flash column (heptane/EtOAc=1/0 to 73/27) to afford the title compound. MS (ESI+) m/z 691.3 (M+H).

Example 7-B. Ethyl 1-(6-(3-((2-chloro-4-(piperidin-4-yl)phenoxy)methyl)thiophen-2-yl)pyridin-2-yl)-5-(trifluoromethyl)-1H-pyrazole-4-carboxylate

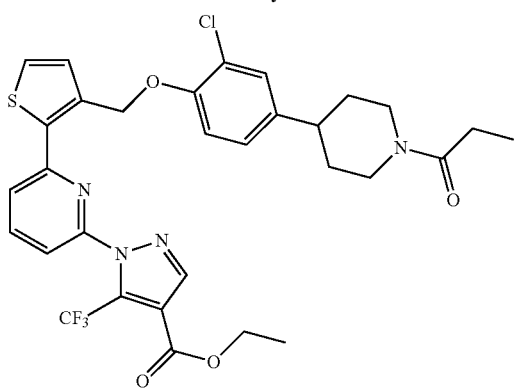

A mixture of tert-butyl 4-(3-chloro-4-((2-(6-(4-(ethoxycarbonyl)-5-(trifluoromethyl)-1H-pyrazol-1-yl)pyridin-2-yl)thiophen-3-yl)methoxy)phenyl)piperidine-1-carboxylate (140 mg, 0.203 mmol) and 4M HCl in 1,4-dioxane (1.01 mL) was stirred at room temperature for 4 h. The mixture was then concentrated to furnish the title compound as an HCl salt. MS (ESI+) m/z 591.2 (M+H).

Example 7-C. Ethyl 1-(6-(3-((2-chloro-4-(1-propionylpiperidin-4-yl)phenoxy)methyl)thiophen-2-yl)pyridin-2-yl)-5-(trifluoromethyl)-1H-pyrazole-4-carboxylate To a solution of ethyl 1-(6-(3-((2-chloro-4-(piperidin-4-yl)phenoxy)methyl)thiophen-2-yl)pyridin-2-yl)-5-(trifluoromethyl)-1H-pyrazole-4-carboxylate (60 mg, 0.096 mmol) in) in CH$_2$Cl$_2$ (1 mL) was added Et$_3$N (39.8 μL, 0.287 mmol and then propionyl chloride (9.18 μl, 0.105 mmol). The mixture was then stirred at room temperature for 16 h, and then concentrated. The resulting residue was purified by RP-HPLC (HC-C) to afford the title compound. MS (ESI+) m/z 647.3 (M+H).

Example 7. 1-(6-(3-((2-Chloro-4-(1-propionylpiperidin-4-yl)phenoxy)methyl)thiophen-2-yl)pyridin-2-yl)-5-(trifluoromethyl)-1H-pyrazole-4-carboxylic acid

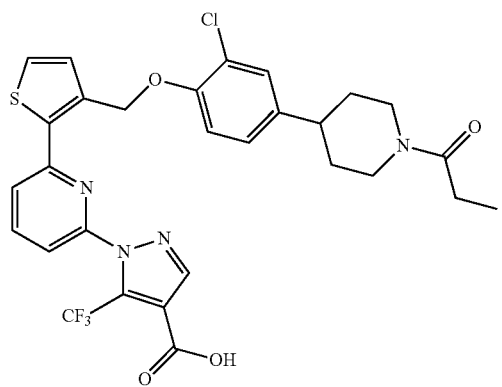 [SMILES: CCC(=O)N1CCC(c2ccc(OCc3ccsc3-c3cccc(-n4ncc(C(=O)O)c4C(F)(F)F)n3)c(Cl)c2)CC1]

To a solution of ethyl 1-(6-(3-((2-chloro-4-(1-propionylpiperidin-4-yl)phenoxy)methyl)thiophen-2-yl)pyridin-2-yl)-5-(trifluoromethyl)-1H-pyrazole-4-carboxylate (37 mg, 0.057 mmol) in THF (0.5 mL) and MeOH (0.5 mL) was added 1M aq. LiOH (286 μL, 0.286 mmol). The mixture was then stirred at 70° C. for 1 h, and then cooled to room temperature. The mixture was treated with 1M aq. HCl (300 μL), and then extracted three times with EtOAc. The combined organics were washed with brine, dried with Na$_2$SO$_4$, filtered and concentrated to afford the title compound without the need for further purification. $^1$H NMR (400 MHz, DMSO-d$_6$) δ 13.47 (s, 1H), 8.30 (s, 1H), 8.20 (t, J=7.9 Hz, 1H), 7.90 (dd, J=0.7, 7.9 Hz, 1H), 7.69-7.77 (m, 2H), 7.28-7.35 (m, 2H), 7.13 (d, J=1.2 Hz, 2H), 5.42 (s, 2H), 4.53 (d, J=13.0 Hz, 1H), 3.94 (d, J=13.3 Hz, 1H), 2.99-3.10 (m, 1H), 2.71 (ddd, J=3.6, 8.5, 12.1 Hz, 1H), 2.34 (q, J=7.4 Hz, 2H), 1.75 (t, J=11.9 Hz, 2H), 1.31-1.60 (m, 2H), 1.20-1.29 (m, 1H), 1.00 (t, J=7.4 Hz, 3H). HRMS calcd. for C$_{29}$H$_{27}$ClF$_3$N$_4$O$_4$S (M+H) 619.1434, found 619.1435.

Example 8. 1-(6-(3-((2-Chloro-4-(1-(cyclopropanecarbonyl)piperidin-4-yl)phenoxy)methyl)thiophen-2-yl)pyridin-2-yl)-5-(trifluoromethyl)-1H-pyrazole-4-carboxylic acid

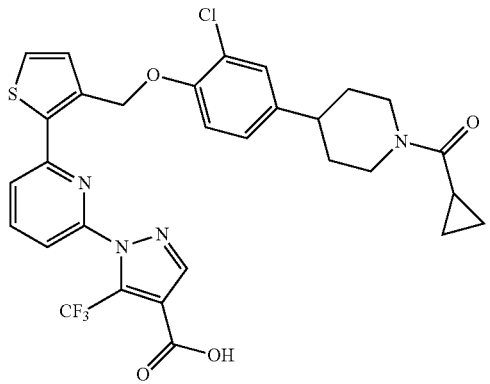 [SMILES: O=C(O)c1cnn(-c2cccc(-c3sccc3COc3ccc(C4CCN(C(=O)C5CC5)CC4)cc3Cl)n2)c1C(F)(F)F]

The title compound was prepared by a similar methods as described above for Example 7 employing cyclopropanecarbonyl chloride in place of propionyl chloride. $^1$H NMR (400 MHz, DMSO-d$_6$) δ 13.46 (s, 1H), 8.30 (s, 1H), 8.20 (t, J=7.9 Hz, 1H), 7.91 (dd, J=0.8, 8.0 Hz, 1H), 7.69-7.78 (m, 2H), 7.29-7.35 (m, 2H), 7.09-7.19 (m, 2H), 5.42 (s, 2H), 4.51 (d, J=12.9 Hz, 1H), 4.36 (d, J=13.2 Hz, 1H), 3.13 (s, 1H), 2.75 (tt, J=3.6, 12.0 Hz, 1H), 2.60 (s, 1H), 1.93-2.05 (m, 1H), 1.66-1.88 (m, 4H), 1.54 (d, J=13.7 Hz, 2H), 1.40 (d, J=13.6 Hz, 2H). HRMS calcd. for C$_{30}$H$_{27}$ClF$_3$N$_4$O$_4$S (M+H) 631.1388, found 631.1428.

Example 9

Example 9-A. Ethyl 1-(6-(3-((4-(1-(cyclopropanecarbonyl)piperidin-4-yl)-2-methylphenoxy)methyl)thiophen-2-yl)pyridin-2-yl)-5-methyl-1H-pyrazole-4-carboxylate

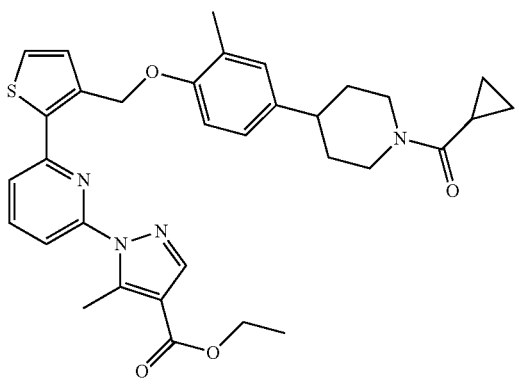 [SMILES: CCOC(=O)c1cnn(-c2cccc(-c3sccc3COc3ccc(C4CCN(C(=O)C5CC5)CC4)cc3C)n2)c1C]

To a solution of Intermediate 4-2-5 (136 mg, 0.396 mmol), Intermediate 2-4 (113 mg, 0.436 mmol), and PPh$_3$ (114 mg, 0.436 mmol) in THF (2 mL) at 0° C. was added DIAD (85 μl, 0.436 mmol). The mixture was then stirred at room temperature for 16 h, and then concentrated. The resulting residue was purified by silica gel flash column chromatography (heptane/EtOAc=1/0 to 1/1) to afford the title compound. MS (ESI+) m/z 585.5 (M+H).

Example 9. 1-(6-(3-((4-(1-(Cyclopropanecarbonyl)piperidin-4-yl)-2-methylphenoxy)methyl)thiophen-2-yl)pyridin-2-yl)-5-methyl-1H-pyrazole-4-carboxylic acid

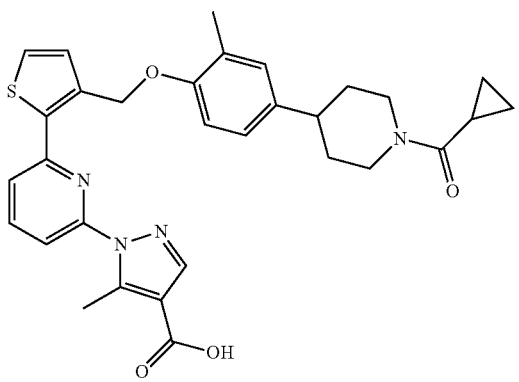 [SMILES: Cc1cc(C2CCN(C(=O)C3CC3)CC2)ccc1OCc1ccsc1-c1cccc(-n2ncc(C(=O)O)c2C)n1]

To a solution of ethyl 1-(6-(3-((4-(1-(cyclopropanecarbonyl)piperidin-4-yl)-2-methylphenoxy)methyl)thiophen-2-yl)pyridin-2-yl)-5-methyl-1H-pyrazole-4-carboxylate (65 mg, 0.111 mmol) in THF (1.1 mL)/MeOH (0.5 mL) was added 1M aq. LiOH (167 µL, 0.333 mmol). The mixture was then stirred at 50° C. for 18 h. The reaction was then quenched with 1M aq. HCl (0.3 mL). The reaction mixture was then diluted with EtOAc. The organic extracts were concentrated. The resulting residue was purified by RP-HPLC (HC-C) to afford the title compound. $^1$H NMR (400 MHz, CD$_3$OD) δ 8.02-7.96 (m, 2H), 7.70 (td, J=8.1, 0.7 Hz, 2H), 7.53 (d, J=5.2 Hz, 1H), 7.27 (d, J=5.2 Hz, 1H), 7.00 (d, J=2.2 Hz, 1H), 6.98 (dd, J=8.3, 2.4 Hz, 1H), 6.88 (d, J=8.3 Hz, 1H), 5.33 (s, 2H), 4.63 (d, J=12.9 Hz, 1H), 4.45 (d, J=13.4 Hz, 1H), 3.24-3.20 (m, 1H), 2.92 (s, 3H), 2.79-2.68 (m, 1H), 2.13 (s, 3H), 2.04-1.96 (m, 1H), 1.91 (d, J=13.0 Hz, 1H), 1.83 (d, J=13.3 Hz, 1H), 1.70-1.46 (m, 2H), 0.92-0.85 (m, 2H), 0.83 (dd, J=11.1, 8.0 Hz, 2H). HRMS calcd. for C$_{31}$H$_{33}$N$_4$O$_4$S (M+H) 557.2223, found 557.2239.

Example 10

The following compounds were prepared by similar methods as described above for Example 9 using the appropriate starting materials as delineated in the table below.

| Example | Structure/Chemical Name | Starting materials | NMR and HRMS |
|---|---|---|---|
| 10-1 | 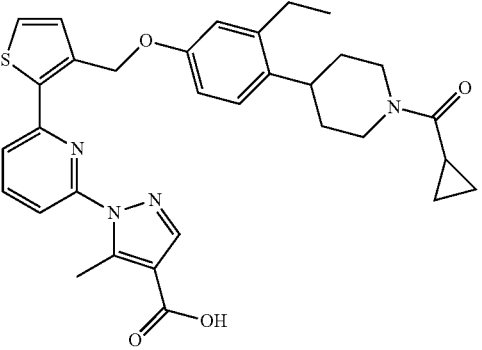 [SMILES: CCc1cc(OCc2ccsc2-c2cccc(-n3ncc(C(=O)O)c3C)n2)ccc1C1CCN(C(=O)C2CC2)CC1]<br>1-(6-(3-((4-(1-(Cyclopropanecarbonyl)piperidin-4-yl)-3-ethylphenoxy)methyl)thiophen-2-yl)pyridin-2-yl)-5-methyl-1H-pyrazole-4-carboxylic acid | Intermediate 2-5-5 and Intermediate 4-2-5 | $^1$H NMR (400 MHz, CD$_3$OD) δ 8.04-7.94 (m, 2H), 7.73-7.63 (m, 2H), 7.52 (d, J = 5.2 Hz, 1H), 7.26 (d, J = 5.2 Hz, 1H), 7.14-7.06 (m, 1H), 6.82-6.74 (m, 2H), 5.30 (s, 2H), 4.65 (d, J = 13.1 Hz, 1H), 4.46 (d, J = 13.5 Hz, 1H), 3.03 (tt, J = 12.1, 3.7 Hz, 1H), 2.92 (s, 3H), 2.81-2.70 (m, 1H), 2.66 (q, J = 7.5 Hz, 2H), 2.05-1.95 (m, 1H), 1.89-1.49 (m, 4H), 1.17 (t, J = 7.5 Hz, 3H), 0.95-0.75 (m, 4H). HRMS calcd. for C$_{32}$H$_{35}$N$_4$O$_4$S (M + H) 571.2379, found 571.2392. |
| 10-2 | 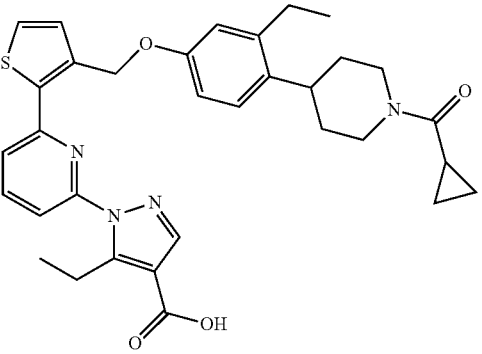 [SMILES: CCc1cc(OCc2ccsc2-c2cccc(-n3ncc(C(=O)O)c3CC)n2)ccc1C1CCN(C(=O)C2CC2)CC1]<br>1-(6-(3-((4-(1-(Cyclopropanecarbonyl)piperidin-4-yl)-3-ethylphenoxy)methyl)thiophen-2-yl)pyridin-2-yl)-5-ethyl-1H-pyrazole-4-carboxylic acid | Intermediate 2-5-5 and Intermediate 4-2-1 | $^1$H NMR (400 MHz, CD$_3$OD) δ 8.04-7.94 (m, 2H), 7.68 (ddd, J = 7.8, 4.9, 0.8 Hz, 2H), 7.52 (d, J = 5.2 Hz, 1H), 7.26 (d, J = 5.2 Hz, 1H), 7.13-7.06 (m, 1H), 6.82-6.75 (m, 2H), 5.27 (s, 2H), 4.65 (d, J = 13.0 Hz, 1H), 4.46 (d, J = 13.6 Hz, 1H), 3.54 (q, J = 7.3 Hz, 2H), 3.03 (tt, J = 12.0, 3.6 Hz, 1H), 2.81-2.62 (m, 3H), 2.06-1.94 (m, 1H), 1.86-1.52 (m, 4H), 1.13-1.26 (m, 6H), 0.96-0.76 (m, 4H). HRMS calcd. for C$_{33}$H$_{37}$N$_4$O$_4$S (M + H) 585.2536, found 585.2560. |
| 10-3 | 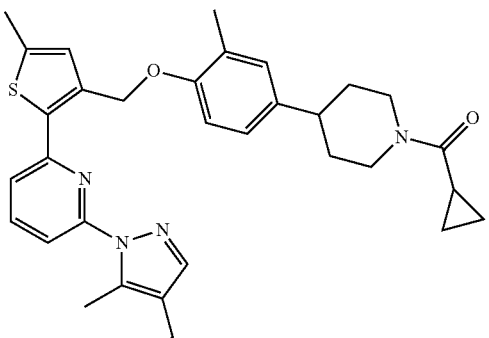<br>1-(6-(3-((4-(1-(Cyclopropanecarbonyl)piperidin-4-yl)-2-methylphenoxy)methyl)-5-methylthiophen-2-yl)pyridin-2-yl)-5-methyl-1H-pyrazole-4-carboxylic acid | Intermediate 2-4 and Intermediate 4-2-6 | $^1$H NMR (400 MHz, CD$_3$OD) δ 7.98 (s, 1H), 7.93 (t, J = 8.0 Hz, 1H), 7.63 (dd, J = 8.1, 0.7 Hz, 1H), 7.61 (s, 1H), 7.04-6.92 (m, 3H), 6.85 (d, J = 8.3 Hz, 1H), 5.24 (s, 2H), 4.63 (d, J = 13.4 Hz, 1H), 4.44 (d, J = 13.5 Hz, 1H), 2.91 (s, 3H), 2.73 (ddt, J = 12.4, 8.1, 4.0 Hz, 2H), 2.51 (d, J = 1.1 Hz, 3H), 2.15 (s, 3H), 2.05-1.94 (m, 1H), 1.96-1.76 (m, 2H), 1.71-1.45 (m, 2H), 0.95-0.76 (m, 4H). HRMS calcd. for C$_{32}$H$_{35}$N$_4$O$_4$S (M + H) 571.2379, found 571.2407. |

| Example | Structure/Chemical Name | Starting materials | NMR and HRMS |
|---|---|---|---|
| 10-4 | 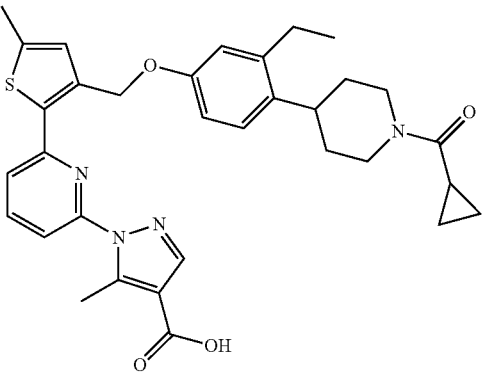 [SMILES: CCc1cc(OCc2cc(C)sc2-c2cccc(-n3ncc(C(=O)O)c3C)n2)ccc1C1CCN(C(=O)C2CC2)CC1]<br>1-(6-(3-((4-(1-(Cyclopropanecarbonyl)piperidin-4-yl)-3-ethylphenoxy)methyl)-5-methylthiophen-2-yl)pyridin-2-yl)-5-methyl-1H-pyrazole-4-carboxylic acid | Intermediate 2-5-5 and Intermediate 4-2-6 | $^1$H NMR (400 MHz, CD$_3$OD) δ 7.98 (s, 1H), 7.93 (t, J = 8.0 Hz, 1H), 7.63 (dd, J = 8.1, 0.7 Hz, 1H), 7.58 (dd, J = 7.8, 0.8 Hz, 1H), 7.11-7.05 (m, 1H), 6.94 (d, J = 1.2 Hz, 1H), 6.81-6.73 (m, 2H), 5.22 (s, 2H), 4.65 (d, J = 13.2 Hz, 1H), 4.46 (d, J = 13.6 Hz, 1H), 3.02 (tt, J = 11.9, 3.6 Hz, 1H), 2.91 (s, 3H), 2.81-2.61 (m, 3H), 2.50 (d, J = 1.1 Hz, 3H), 2.06-1.95 (m, 1H), 1.86-1.52 (m, 4H), 1.17 (t, J = 7.5 Hz, 3H), 0.95-0.75 (m, 4H). HRMS calcd. for C$_{33}$H$_{37}$N$_4$O$_4$S (M + H) 585.2536, found 585.2548. |
| 10-5 | 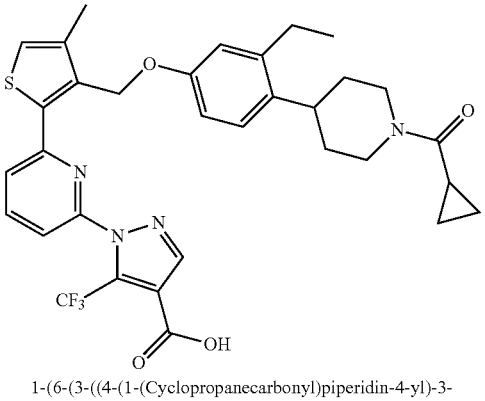<br>1-(6-(3-((4-(1-(Cyclopropanecarbonyl)piperidin-4-yl)-3-ethylphenoxy)methyl)-4-methylthiophen-2-yl)pyridin-2-yl)-5-(trifluoromethyl)-1H-pyrazole-4-carboxylic acid | Intermediate 2-5-5 and Intermediate 4-8 | $^1$H NMR (400 MHz, CD$_3$OD) δ 8.13 (d, J = 0.7 Hz, 1H), 8.04 (t, J = 7.9 Hz, 1H), 7.77 (dd, J = 7.9, 0.8 Hz, 1H), 7.60 (dd, J = 7.9, 0.8 Hz, 1H), 7.22 (q, J = 0.9 Hz, 1H), 7.09-7.05 (m, 1H), 6.78-6.73 (m, 2H), 5.20 (s, 2H), 4.66 (d, J = 13.1 Hz, 1H), 4.47 (d, J = 13.4 Hz, 1H), 3.26-3.22 (m, 1H), 3.03 (tt, J = 11.9, 3.6 Hz, 1H), 2.76 (t, J = 12.7 Hz, 1H), 2.66 (q, J = 7.5 Hz, 2H), 2.31 (d, J = 1.1 Hz, 3H), 2.05-1.97 (m, 1H), 1.91-1.49 (m, 4 H), 1.18 (t, J = 7.5 Hz, 3H), 0.96-0.75 (m, 4 H), HRMS calcd. for C$_{33}$H$_{34}$F$_3$N$_4$O$_4$S (M + H) 639.2175, found 639.2283. |
| 10-6 | 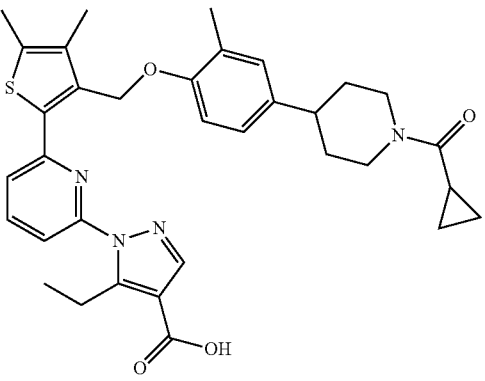 [SMILES: CCc1c(C(=O)O)cnn1-c1cccc(-c2sc(C)c(C)c2COc2ccc(C3CCN(C(=O)C4CC4)CC3)cc2C)n1]<br>1-(6-(3-((4-(1-(Cyclopropanecarbonyl)piperidin-4-yl)-2-methylphenoxy)methyl)-4,5-dimethylthiophen-2-yl)pyridin-2-yl)-5-ethyl-1H-pyrazole-4-carboxylic acid | Intermediate 2-4 and Intermediate 4-2-3 | $^1$H NMR (400 MHz, CD$_3$OD) δ 7.97 (s, 1H), 7.90 (t, J = 8.0 Hz, 1H), 7.65 (dd, J = 8.1, 0.8 Hz, 1H), 7.55 (dd, J = 7.8, 0.8 Hz, 1H), 7.05-6.95 (m, 2H), 6.91 (d, J = 8.3 Hz, 1H), 5.10 (s, 2H), 4.64 (d, J = 13.0 Hz, 1H), 4.45 (d, J = 13.5 Hz, 1H), 3.49 (q, J = 7.3 Hz, 2H), 3.24 (m, 1H), 2.74 (tq, J = 12.0, 3.6 Hz, 2H), 2.43 (d, J = 0.8 Hz, 3H), 2.18 (d, J = 0.8 Hz, 3H), 2.12 (s, 3H), 2.00 (tt, J = 7.9, 4.8 Hz, 1H), 1.98-1.78 (m, 2H), 1.71-1.46 (m, 2H), 1.21 (t, J = 7.3 Hz, 3H), 0.94-0.76 (m, 4H). HRMS calcd. for C$_{34}$H$_{39}$N$_4$O$_4$S (M + H) 599.2692, found 599.2708. |

-continued

| Example | Structure/Chemical Name | Starting materials | NMR and HRMS |
|---|---|---|---|
| 10-7 | 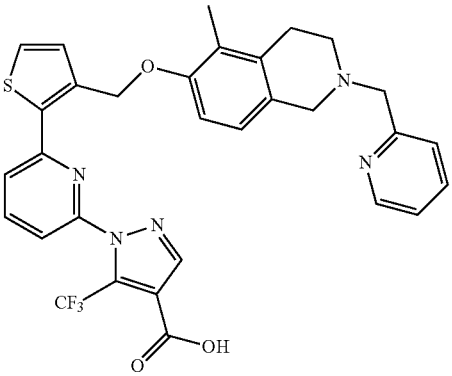 [SMILES: Cc1c(OCc2ccsc2-c2cccc(-n3ncc(C(=O)O)c3C(F)(F)F)n2)ccc2c1CCN(Cc1ccccn1)C2]<br>1-(6-(3-(((5-Methyl-2-(pyridin-2-ylmethyl)-1,2,3,4-tetrahydroisoquinolin-6-yl)oxy)methyl)thiophen-2-yl)pyridin-2-yl)-5-(trifluoromethyl)-1H-pyrazole-4-carboxylic acid | Intermediate 2-12 and Intermediate 4-1-B | $^1$H NMR (400 MHz, CD$_3$OD) δ 8.61-8.57 (m, 1H), 8.01 (t, J = 7.9 Hz, 1H), 7.93-7.84 (m, 2H), 7.78 (dd, J = 7.9, 0.8 Hz, 1H), 7.60 (dt, J = 7.9, 1.0 Hz, 1H), 7.56-7.50 (m, 2H), 7.40 (ddd, J = 7.6, 4.9, 1.2 Hz, 1H), 7.26 (d, J = 5.2 Hz, 1H), 6.79 (q, J = 8.5 Hz, 2H), 5.33 (s, 2H), 4.17 (s, 2H), 3.96 (s, 2H), 3.17 (t, J = 6.3 Hz, 2H), 2.88 (t, J = 6.2 Hz, 2H), 2.00 (s, 3H). HRMS calcd. for C$_{31}$H$_{27}$F$_3$N$_5$O$_3$S (M + H) 606.1781, found 606.1833. |
| 10-8 | 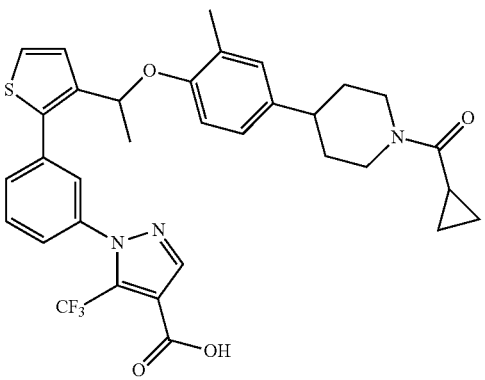 [SMILES: Cc1cc(C2CCN(C(=O)C3CC3)CC2)ccc1OC(C)c1ccsc1-c1cccc(-n2ncc(C(=O)O)c2C(F)(F)F)c1]<br>1-(3-(3-(1-(4-(1-(Cyclopropanecarbonyl)piperidin-4-yl)-2-methylphenoxy)ethyl)thiophen-2-yl)phenyl)-5-(trifluoromethyl)-1H-pyrazole-4-carboxylic acid | Intermediate 2-4, and Intermediate 4-15 | $^1$H NMR (400 MHz, CD3OD) δ 8.07 (s, 1H), 7.57-7.66 (m, 1H), 7.46-7.53 (m, 2H), 7.43 (d, J = 5.26 Hz, 1H), 7.21-7.30 (m, 2H), 6.87 (d, J = 2.08 Hz, 1H), 6.68 (dd, J = 2.26, 8.38 Hz, 1H), 6.29 (d, J = 8.44 Hz, 1H), 5.32 (q, J = 6.36 Hz, 1H), 4.59 (br. d, J = 12.60 Hz, 1H), 4.40 (br. d, J = 13.20 Hz, 1H), 3.14-3.25 (m, 1H), 2.55-2.76 (m, 2H), 2.09 (s, 3H), 1.92-2.03 (m, 1H), 1.65-1.86 (m, 5H), 1.34-1.60 (m, 2H), 0.74-0.94 (m, 4H). HRMS calcd. for C$_{33}$H$_{33}$F$_3$N$_3$O$_4$S (M + H) 624.2144, found 624.2145. |
| 10-9 | 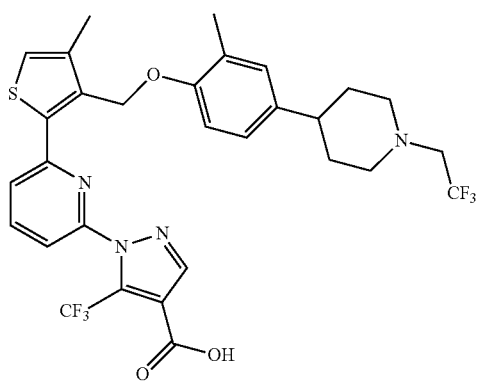 [SMILES: Cc1cc(C2CCN(CC(F)(F)F)CC2)ccc1OCc1c(C)csc1-c1cccc(-n2ncc(C(=O)O)c2C(F)(F)F)n1]<br>1-(6-(4-methyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid | Intermediate 2-13 and Intermediate 4-8 | $^1$H NMR (400 MHz, CD$_3$OD) δ 8.03 (s, 1H), 8.00 (t, J = 7.9 Hz, 1H), 7.73 (d, J = 7.8 Hz, 1H), 7.60 (d, J = 7.9 Hz, 1H), 7.22 (s, 1H), 7.00-6.94 (m, 2H), 6.88 (d, J = 8.3 Hz, 1H), 5.18 (s, 2H), 3.11-3.04 (m, 4H), 2.52-2.37 (m, 3H), 2.31 (s, 3H), 2.08 (s, 3H), 1.80-1.72 (m, 4H). HRMS calcd for C$_{30}$H$_{29}$F$_6$N$_4$O$_3$S (M + H) 639.1865, found 639.1907. |

Example 11

Example 11-A. tert-Butyl 4-(4-((2-(6-(4-(ethoxycarbonyl)-5-(trifluoromethyl)-1H-pyrazol-1-yl)pyridin-2-yl)thiophen-3-yl)methoxy)-3-methylphenyl)piperidine-1-carboxylate

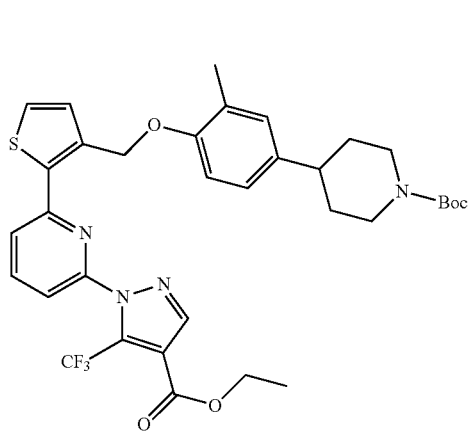 [SMILES: CCOC(=O)c1cnn(-c2cccc(-c3sccc3COc3ccc(C4CCN(C(=O)OC(C)(C)C)CC4)cc3C)n2)c1C(F)(F)F]

To a solution of Intermediate 4-1-B (1.61 g, 5.54 mmol), Intermediate 2-1 (2.0 g, 5.03 mmol), and PPh₃ (1.45 g, 5.54 mmol) in THF (20 mL) at 0° C. was added DIAD (1.08 mL, 5.54 mmol). The mixture was then stirred at room temperature for 16 h, and then concentrated. The resulting residue was purified by silica gel flash column chromatography (heptane/EtOAc=1/0 to 7/3) to afford the title compound. MS (ESI+) m/z 615.2 (M-tBu+2H).

Example 11-B. Ethyl 1-(6-(3-((2-methyl-4-(piperidin-4-yl)phenoxy)methyl)thiophen-2-yl)pyridin-2-yl)-5-(trifluoromethyl)-1H-pyrazole-4-carboxylate

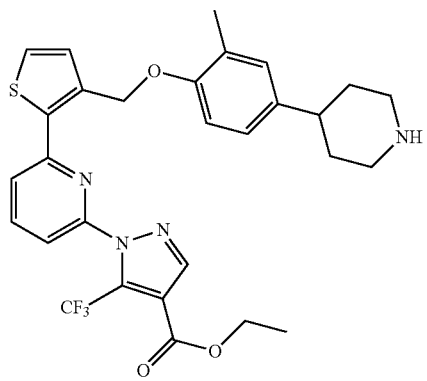 [SMILES: CCOC(=O)c1cnn(-c2cccc(-c3sccc3COc3ccc(C4CCNCC4)cc3C)n2)c1C(F)(F)F]

A mixture of tert-butyl 4-(4-((2-(6-(4-(ethoxycarbonyl)-5-(trifluoromethyl)-1H-pyrazol-1-yl)pyridin-2-yl)thiophen-3-yl)methoxy)-3-methylphenyl)piperidine-1-carboxylate (2.4 g, 3.58 mmol) and TFA (5.51 mL, 71.6 mmol) in CH₂Cl₂ (10 mL) was stirred for 2 h at room temperature. The mixture was diluted with CH₂Cl₂ and H₂O. The mixture was rendered basic (pH=8) by the addition of 30% aq. NH₄OH. The mixture was then separated. The organic phase was then dried over Na₂SO₄, filtered, and then concentrated to furnish the title compound. MS (ESI+) m/z 570.6 (M).

Example 11-C. Ethyl 1-(6-(3-((4-(1-(2-cyclopropylacetyl)piperidin-4-yl)-2-methylphenoxy)methyl)thiophen-2-yl)pyridin-2-yl)-5-(trifluoromethyl)-1H-pyrazole-4-carboxylate

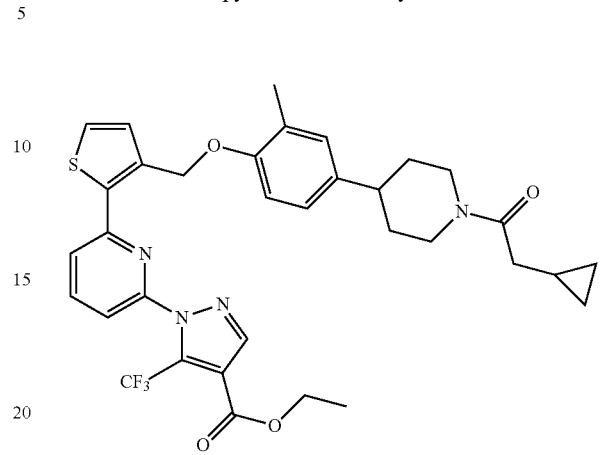

A solution of 2-cyclopropylacetic acid (CAS#5239-82-7, 17.54 mg, 0.175 mmol) and HATU (66.6 mg, 0.175 mmol) in DMF (2 mL) was stirred at room temperature for 0.5 h. To the solution was added then ethyl 1-(6-(3-((2-methyl-4-(piperidin-4-yl)phenoxy)methyl)thiophen-2-yl)pyridin-2-yl)-5-(trifluoromethyl)-1H-pyrazole-4-carboxylate (100 mg, 0.175 mmol), followed by DIPEA (61 µL, 0.350 mmol). The mixture was then stirred at room temperature for 16 h before being filtered. The filtrate was then purified by RP-HPLC (HC-B) to afford the title compound. MS (ESI+) m/z 653.2 (M+H).

Example 11. 1-(6-(3-((4-(1-(2-Cyclopropylacetyl)piperidin-4-yl)-2-methylphenoxy)methyl)thiophen-2-yl)pyridin-2-yl)-5-(trifluoromethyl)-1H-pyrazole-4-carboxylic acid

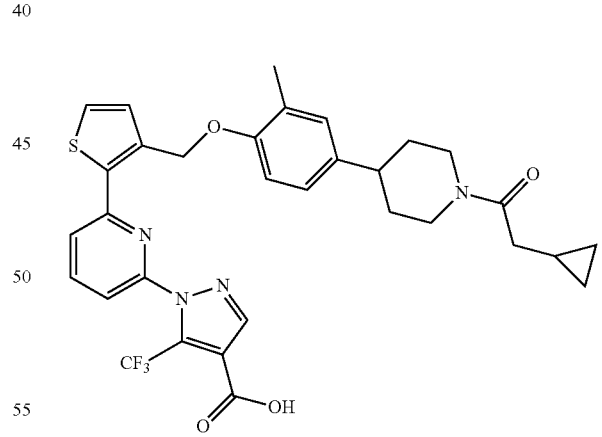

To a solution of ethyl 1-(6-(3-((4-(1-(2-cyclopropylacetyl)piperidin-4-yl)-2-methylphenoxy)methyl)thiophen-2-yl)pyridin-2-yl)-5-(trifluoromethyl)-1H-pyrazole-4-carboxylate (70 mg, 0.107 mmol) in acetonitrile (3 mL) was added 1M aq. LiOH (0.322 mL, 0.322 mmol). The mixture was stirred at 50° C. for 2 h. The reaction was then quenched with 1M aq. HCl (0.32 mL) The mixture was then filtered. The filtrate was then purified by RP-HPLC (HC-B) to afford the title compound. ¹H-NMR (400 MHz, CD₃OD) δ 8.06-7.97 (m, 2H), 7.78 (dd, J=7.8, 0.8 Hz, 1H), 7.58 (dd, J=8.0, 0.8 Hz, 1H), 7.52 (d, J=5.1 Hz, 1H), 7.26 (d, J=5.2 Hz, 1H), 6.99 (d, J=2.2 Hz, 1H), 6.94 (dd, J=8.3, 2.3 Hz, 1H), 6.80 (d, J=8.3 Hz, 1H), 5.33 (s, 2H), 4.67 (m, 1H), 4.06 (m, 1H), 3.24-3.14 (m, 1H), 2.76-2.63 (m, 2H), 2.36 (d, J=6.8 Hz, 2H), 2.14 (s, 3H), 1.93-1.79 (m, 2H), 1.56 (m, 2H), 1.08-0.96 (m, 1H), 0.60-0.50 (m, 2H), 0.21 (dt, J=6.0, 4.5 Hz, 2H). HRMS calcd. for $C_{32}H_{32}F_3N_4O_4S$ (M+H) 625.2096, found 625.2086.

Example 12

The following compounds were prepared by similar methods as described above for Example 11 using the appropriate starting materials delineated in the table below.

| Example | Structure/Chemical Name | Starting materials | NMR and HRMS |
|---|---|---|---|
| 12-1 | 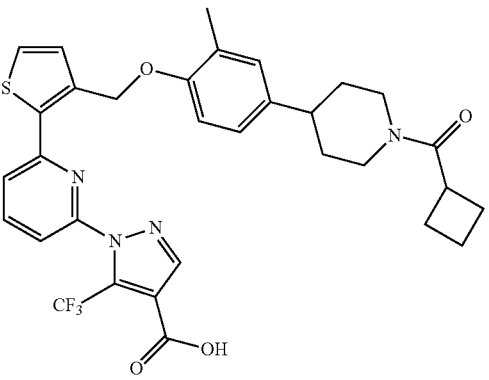 [SMILES: Cc1cc(C2CCN(C(=O)C3CCC3)CC2)ccc1OCc1ccsc1-c1cccc(-n2ncc(C(=O)O)c2C(F)(F)F)n1]<br>1-(6-(3-((4-(1-(Cyclobutanecarbonyl)piperidin-4-yl)-2-methylphenoxy)methyl)thiophen-2-yl)pyridin-2-yl)-5-(trifluoromethyl)-1H-pyrazole-4-carboxylic acid | Intermediate 2-1, Intermediate 4-1-B, and cyclobutane-carboxylic acid (CAS# 3721-95-7) | $^1$H NMR (400 MHz, CD$_3$OD) δ 8.02 (t, J = 7.9 Hz, 1H), 7.97 (d, J = 0.7 Hz, 1H), 7.77 (dd, J = 7.9, 0.8 Hz, 1H), 7.58 (dd, J = 8.0, 0.7 Hz, 1H), 7.52 (d, J = 5.2 Hz, 1H), 7.26 (d, J = 5.2 Hz, 1H), 7.00-6.91 (m, 2H), 6.80 (d, J = 8.4 Hz, 1H), 5.33 (s, 2H), 4.62 (ddt, J = 13.3, 4.4, 2.3 Hz, 1H), 3.90 (ddt, J = 13.6, 4.3, 2.4 Hz, 1H), 3.51-3.38 (m, 1H), 3.16-3.03 (m, 1H), 2.68 (td, J = 12.6, 3.0 Hz, 2H), 2.38-2.12 (m, 7H), 2.05-1.95 (m, 1H), 1.90-1.76 (m, 3H), 1.59-1.43 (m, 2H). HRMS calcd. for $C_{32}H_{32}F_3N_4O_4S$ (M + H) 625.2091, found 625.2182. |
| 12-2 | 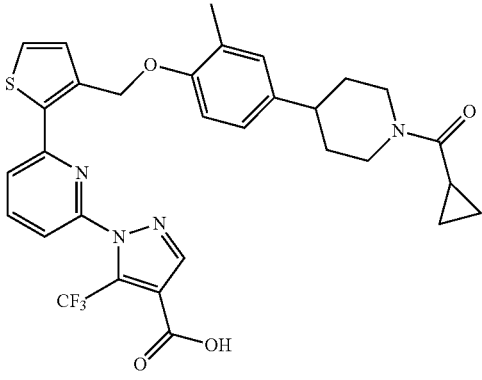<br>1-(6-(3-((4-(1-(Cyclopropanecarbonyl)piperidin-4-yl)-2-methylphenoxy)methyl)thiophen-2-yl)pyridin-2-yl)-5-(trifluoromethyl)-1H-pyrazole-4-carboxylic acid | Intermediate 2-1, Intermediate 4-1-B, and cyclopropane-carboxylic acid | $^1$H NMR (400 MHz, CD$_3$OD) δ 8.07-7.98 (m, 2H), 7.78 (dd, J = 7.9, 0.8 Hz, 1H), 7.58 (dd, J = 8.0, 0.7 Hz, 1H), 7.52 (d, J = 5.1 Hz, 1H), 7.26 (d, J = 5.2 Hz, 1H), 6.99 (d, J = 2.2 Hz, 1H), 6.95 (dd, J = 8.4, 2.3 Hz, 1H), 6.80 (d, J = 8.3 Hz, 1H), 5.32 (s, 2H), 4.63 (d, J = 12.9 Hz, 1H), 4.44 (d, J = 13.6 Hz, 1H), 3.28-3.18 (m, 1H), 2.73 (tt, J = 11.0, 3.3 Hz, 2H), 2.15 (s, 3H), 2.05-1.95 (m, 1H), 1.95-1.75 (m, 2H), 1.72-1.44 (m, 2H), 0.95-0.75 (m, 4H). HRMS calcd. for $C_{31}H_{30}F_3N_4O_4S$ (M + H) 611.1940, found 611.1934. |
| 12-3 | 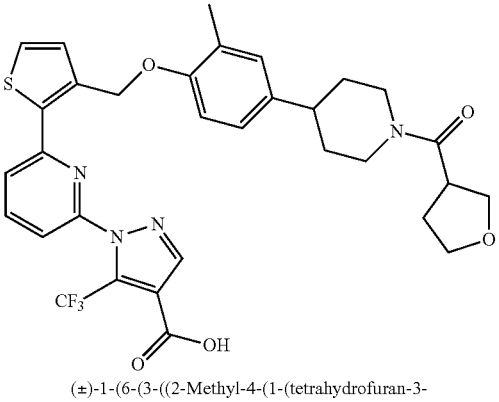<br>(±)-1-(6-(3-((2-Methyl-4-(1-(tetrahydrofuran-3-carbonyl)piperidin-4-yl)phenoxy)methyl)thiophen-2-yl)pyridin-2-yl)-5-(trifluoromethyl)-1H-pyrazole-4-carboxylic acid | Intermediate 2-1, Intermediate 4-1-B, and (±)-tetrahydrofuran-3-carboxylic acid (CAS# 89364-31-8) | $^1$H NMR (400 MHz, CD$_3$OD) δ 7.99-8.06 (m, 2H), 7.78 (dd, J = 0.7, 7.9 Hz, 1H), 7.58 (dd, J = 0.7, 8.0 Hz, 1H), 7.52 (d, J = 5.1 Hz, 1H), 7.26 (d, J = 5.1 Hz, 1H), 6.99 (d, J = 1.8 Hz, 1H), 6.91-6.97 (m, 1H), 6.80 (d, J = 8.4 Hz, 1H), 5.33 (s, 2H), 4.61-4.70 (m, 1H), 4.11-4.20 (m, 1H), 3.76-4.02 (m, 4H), 3.43-3.52 (m, 1H), 3.15-3.25 (m, 1H), 2.66-2.77 (m, 2H), 2.02-2.22 (m, 5H), 1.79-1.94 (m, 2H), 1.45-1.66 (m, 2H).<br>HRMS calcd. for $C_{32}H_{32}F_3N_4O_5S$ (M + H) 641.2040, found 641.2079. |

| Example | Structure/Chemical Name | Starting materials | NMR and HRMS |
|---|---|---|---|
| 12-4 | 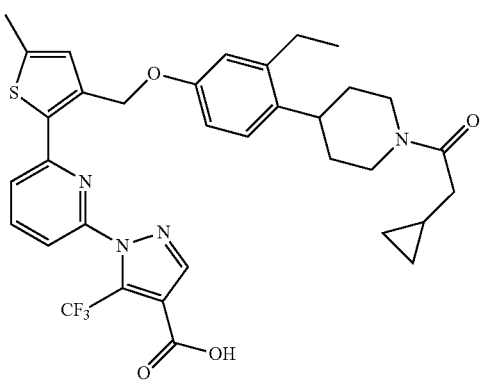 [SMILES: CCc1cc(OCc2cc(C)sc2-c2cccc(-n3ncc(C(=O)O)c3C(F)(F)F)n2)ccc1C1CCN(C(=O)CC2CC2)CC1]<br>1-(6-(3-((4-(1-(2-Cyclopropylacetyl)piperidin-4-yl)-3-ethylphenoxy)methyl)-5-methylthiophen-2-yl)pyridin-2-yl)-5-(trifluoromethyl)-1H-pyrazole-4-carboxylic acid | Intermediate 2-2, Intermediate 4-1-D, and cyclopropaneacetic acid (CAS# 5239-82-7) | $^1$H NMR (400 MHz, CD$_3$OD) δ 8.04-7.94 (m, 2H), 7.69 (dd, J = 7.9, 0.8 Hz, 1H), 7.52 (dd, J = 8.0, 0.7 Hz, 1H), 7.11-7.01 (m, 1H), 6.94 (q, J = 1.0 Hz, 1H), 6.72 (dt, J = 4.1, 2.2 Hz, 2H), 5.24 (s, 2H), 4.70 (ddd, J = 13.6, 4.5, 2.3 Hz, 1H), 4.13-4.03 (m, 1H), 3.27-3.15 (m, 1H), 2.99 (tt, J = 12.0, 3.6 Hz, 1H), 2.77-2.60 (m, 3H), 2.49 (d, J = 1.1 Hz, 3H), 2.37 (d, J = 6.9 Hz, 2H), 1.84-1.70 (m, 2H), 1.69-1.50 (m, 2H), 1.15 (t, J = 7.5 Hz, 3H), 1.09-0 96 (m, 1H), 0.59-0.51 (m, 2H), 0.23-0.18 (m, 2H). HRMS calcd. for C$_{34}$H$_{36}$F$_3$N$_4$O$_4$S (M + H) 653.2404, found 653.2471 |
| 12-5 | 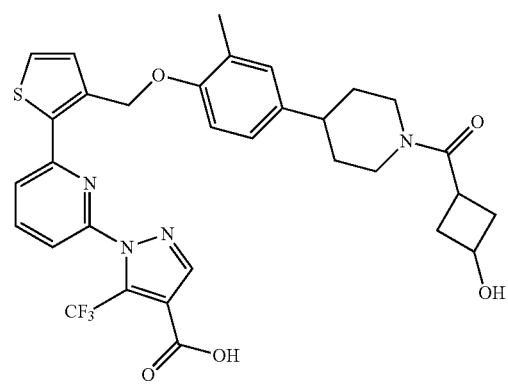 [SMILES: Cc1cc(C2CCN(C(=O)C3CC(O)C3)CC2)ccc1OCc1ccsc1-c1cccc(-n2ncc(C(=O)O)c2C(F)(F)F)n1]<br>1-(6-(3-((4-(1-(3-Hydroxycyclobutanecarbonyl)piperidin-4-yl)-2-methylphenoxy)methyl)thiophen-2-yl)pyridin-2-yl)-5-(trifluoromethyl)-1H-pyrazole-4-carboxylic acid | Intermediate 2-1, Intermediate 4-1-B, and 3-hydroxycyclobutane carboxylic acid (CAS# 194788-10-8) | $^1$H NMR (400 MHz, CD$_3$OD) δ 8.02 (t, J = 7.9 Hz, 1H), 7.96 (d, J = 0.8 Hz, 1H), 7.77 (dd, J = 7.9, 0.8 Hz, 1H), 7.58 (dd, J = 8.0, 0.7 Hz, 1H), 7.52 (d, J = 5.2 Hz, 1H), 7.26 (d, J = 5.2 Hz, 1H), 7.00-6.91 (m, 2H), 6.80 (d, J = 8.3 Hz, 1H), 5.33 (s, 2H), 4.61 (ddt, J = 13.2, 4.3, 2.2 Hz, 1H), 4.13 (tt, J = 8.2, 6.9 Hz, 1H), 4.02-3.93 (m, 1H), 2.88 (tt, J = 9.9, 7.7 Hz, 1H), 2.70 (td, J = 12.3, 11.6, 5.7 Hz, 2H), 2.57-2.43 (m, 2H), 2.18-2.05 (m, 5H), 1.84 (t, J = 12.8 Hz, 2H), 1.51 (qt, J = 12.8, 4.5 Hz, 2H), 1.36 (dd, J = 7.0, 5.4 Hz, 1H). HRMS calcd. for C$_{32}$H$_{32}$F$_3$N$_4$O$_5$S (M + H) 641.2040, found 641.2108 |
| 12-6 | 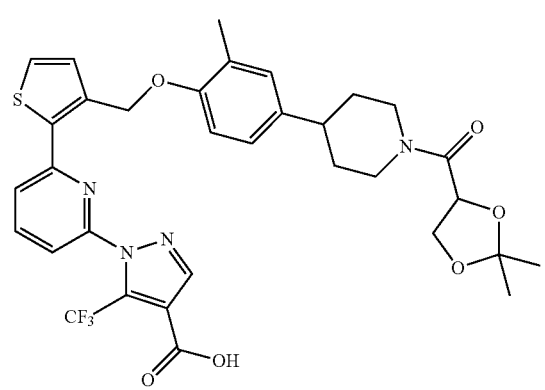 [SMILES: Cc1cc(C2CCN(C(=O)C3COC(C)(C)O3)CC2)ccc1OCc1ccsc1-c1cccc(-n2ncc(C(=O)O)c2C(F)(F)F)n1]<br>(±)-1-(6-(3-((4-(1-(2,2-Dimethyl-1,3-dioxolane-4-carbonyl)piperidin-4-yl)-2-methylphenoxy)methyl)thiophen-2-yl)pyridin-2-yl)-5-(trifluoromethyl)-1H-pyrazole-4-carboxylic acid | Intermediate 2-1, Intermediate 4-1-B, and (±)-3-2,2-dimethyl-1,3-dioxolane-4-carboxylic acid (CAS# 5736-06-1) | $^1$H NMR (400 MHz, CD$_3$OD) δ 8.08-7.97 (m, 2H), 7.79 (dd, J = 7.9, 0.8 Hz, 1H), 7.58 (d, J = 7.9 Hz, 1H), 7.52 (d, J = 5.2 Hz, 1H), 7.26 (d, J = 5.2 Hz, 1H), 7.01-6.91 (m, 2H), 6.84-6.77 (m, 1H), 5.33 (s, 2H), 4.97-4.88 (m, 1H), 4.61 (d, J = 12.7 Hz, 1H), 4.30-4.10 (m, 3H), 2.81-2.67 (m, 2H), 2.81-2.67 (m, 2H), 2.14 (s, 3H), 1.85 (d, J = 12.2 Hz, 2H), 1.73-1.45 (m, 2H), 1.45-1.34 (m, 6H). HRMS calcd. for C$_{33}$H$_{34}$F$_3$N$_4$O$_6$S (M + H) 671.2145, found 671.2194. |

| Example | Structure/Chemical Name | Starting materials | NMR and HRMS |
|---|---|---|---|
| 12-7 | 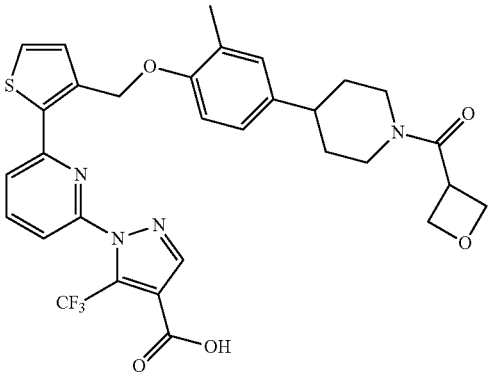 [SMILES: Cc1cc(C2CCN(C(=O)C3COC3)CC2)ccc1OCc1ccsc1-c1cccc(-n2ncc(C(=O)O)c2C(F)(F)F)n1]<br>1-(6-(3-((2-Methyl-4-(1-(oxetane-3-carbonyl)piperidin-4-yl)phenoxy)methyl)thiophen-2-yl)pyridin-2-yl)-5-(trifluoromethyl)-1H-pyrazole-4-carboxylic acid | Intermediate 2-1, Intermediate 4-1-B, and oxetane-3-carboxylic acid (CAS# 114012-41-8) | $^1$H NMR (400 MHz, CD$_3$OD) δ 8.07-7.97 (m, 2H), 7.78 (dd, J = 7.9, 0.8 Hz, 1H), 7.58 (dd, J = 8.0, 0.7 Hz, 1H), 7.52 (d, J = 5.1 Hz, 1H), 7.26 (d, J = 5.2 Hz, 1H), 6.98 (d, J = 2.2 Hz, 1H), 6.94 (dd, J = 8.4, 2.3 Hz, 1H), 6.79 (d, J = 8.3 Hz, 1H), 5.33 (s, 2H), 4.65 (ddt, J = 13.2, 4.5, 2.3 Hz, 1H), 4.22 (tt, J = 8.6, 7.0 Hz, 1H), 3.54 (ddt, J = 13.6, 4.3, 2.3 Hz, 1H), 3.16-3.06 (m, 1H), 2.79-2.63 (m, 2H), 2.14 (s, 3H), 1.88-1.78 (m, 2H), 1.60-1.45 (m, 2H), 1.37 (dd, J = 7.0, 2.2 Hz, 1H),. HRMS calcd. for C$_{31}$H$_{30}$F$_3$N$_4$O$_5$S (M + H) 627.1889, found 627.1909. |
| 12-8 | 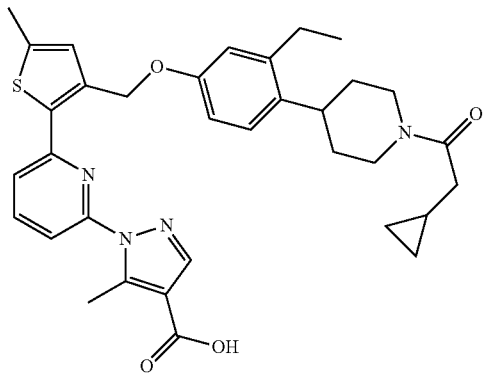 [SMILES: CCc1cc(OCc2cc(C)sc2-c2cccc(-n3ncc(C(=O)O)c3C)n2)ccc1C1CCN(C(=O)CC2CC2)CC1]<br>1-(6-(3-((4-(1-(2-Cyclopropylacetyl)piperidin-4-yl)-3-ethylphenoxy)methyl)-5-methylthiophen-2-yl)pyridin-2-yl)-5-methyl-1H-pyrazole-4-carboxylic acid | Intermediate 2-2, Intermediate 4-2-6, and cyclopropylacetic acid | $^1$H NMR (400 MHz, CD$_3$OD) δ 7.99 (s, 1H), 7.94 (t, J = 8.0 Hz, 1H), 7.64 (dd, J = 8.1, 0.7 Hz, 1H), 7.58 (dd, J = 7.8, 0.8 Hz, 1H), 7.11-7.04 (m, 1H), 6.94 (q, J = 1.0 Hz, 1H), 6.75 (h, J = 2.8 Hz, 2H), 5.22 (s, 2H), 4.70 (ddt, J = 13.2, 4.4, 2.3 Hz, 1H), 4.11-4.02 (m, 1H), 3.27-3.16 (m, 1H), 3.00 (tt, J = 12.0, 3.6 Hz, 1H), 2.90 (s, 3H), 2.76-2.60 (m, 3H), 2.50 (d, J = 1.1 Hz, 3H), 2.37 (d, J = 6.9 Hz, 2H), 1.84-1.70 (m, 2H), 1.71-1.50 (m, 2H), 1.16 (t, J = 7.5 Hz, 3H), 1.10-0.97 (m, 1H), 0.60-0.51 (m, 2H), 0.24-0.17 (m, 2H), HRMS calcd. for C$_{34}$H$_{39}$N$_4$O$_4$S (M + H) 599.2692, found 599.2715. |
| 12-9 | 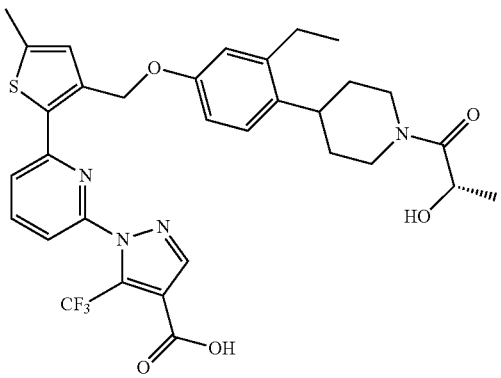 [SMILES: CCc1cc(OCc2cc(C)sc2-c2cccc(-n3ncc(C(=O)O)c3C(F)(F)F)n2)ccc1C1CCN(C(=O)[C@H](C)O)CC1]<br>(S)-1-(6-(3-((3-Ethyl-4-(1-(2-hydroxypropanoyl)piperidin-4-yl)phenoxy)methyl)-5-methylthiophen-2-yl)pyridin-2-yl)-5-(trifluoromethyl)-1H-pyrazole-4-carboxylic acid | Intermediate 2-2, Intermediate 4-1-D, and L-lactic acid (CAS# 79-33-4) | $^1$H NMR (400 MHz, DMSO-d$_6$) δ 8.11-8.18 (m, 2H), 7.74 (d, J = 7.58 Hz, 1H), 7.64 (d, J = 7.46 Hz, 1H), 7.05-7.11 (m, 1H), 7.00 (d, J = 1.10 Hz, 1H), 6.73-6.79 (m, 2H), 5.22 (s, 2H), 4.81 (br. s., 1H), 4.41-4.56 (m, 2H), 4.03-4.13 (m, 1H), 3.05-3.15 (m, 1H), 2.88-2.98 (m, 1H), 2.56-2.73 (m, 3H), 2.47 (d, J = 0.98 Hz, 3H), 1.62-1.70 (m, 2H), 1.37-1.62 (m, 2H), 1.16-1.25 (m, 3H), 1.11 (t, J = 7.46 Hz, 3H). HRMS calcd. for C$_{32}$H$_{34}$F$_3$N$_4$O$_5$S (M + H) 643.2202, found 643.2224. |

| Example | Structure/Chemical Name | Starting materials | NMR and HRMS |
|---|---|---|---|
| 12-10 | 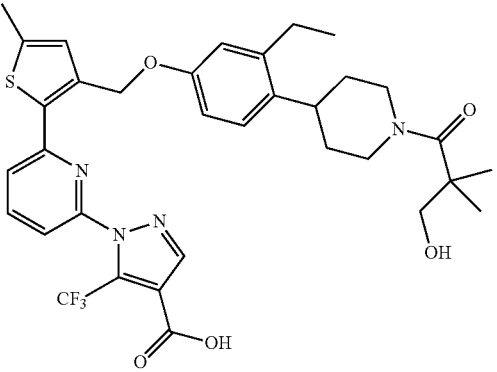 [SMILES: CCc1cc(OCc2cc(C)sc2-c2cccc(-n3ncc(C(=O)O)c3C(F)(F)F)n2)ccc1C1CCN(C(=O)C(C)(C)CO)CC1]<br>1-(6-(3-((3-Ethyl-4-(1-(3-hydroxy-2,2-dimethylpropanoyl) piperidin-4-yl)phenoxy)methyl)-5-methylthiophen-2-yl) pyridin-2-yl)-5-(trifluoromethyl)-1H-pyrazole-4-carboxylic acid | Intermediate 2-2, Intermediate 4-1-D, and 3-hydroxy-2,2-dimethylpropanoic acid (CAS# 4835-90-9) | 1H NMR (400 MHz, DMSO-$d_6$) δ 8.26 (s, 1H), 8.16 (t, J = 7.9 Hz, 1H), 7.77 (d, J = 7.5 Hz, 1H), 7.66 (d, J = 7.5 Hz, 1H), 7.08 (d, J = 8.6 Hz, 1H), 7.01 (d, J = 1.0 Hz, 1H), 6.75 (d, J = 7.8 Hz, 2H), 5.22 (s, 2H), 4.41 (d, J = 13.1 Hz, 2H), 3.43 (s, 2H), 2.98-2.78 (m, 3H), 2.60 (q, J = 7.5 Hz, 2H), 2.47 (d, J = 0.9 Hz, 3H), 1.65 (d, J = 11.0 Hz, 2H), 1.55-1.40 (m, 2H), 1.18 (s, 6H), 1.11 (t, J = 7.5 Hz, 3H). HRMS calcd. for $C_{34}H_{38}F_3N_4O_5S$ (M + H) 671.2515, found 671.2551. |
| 12-11 | 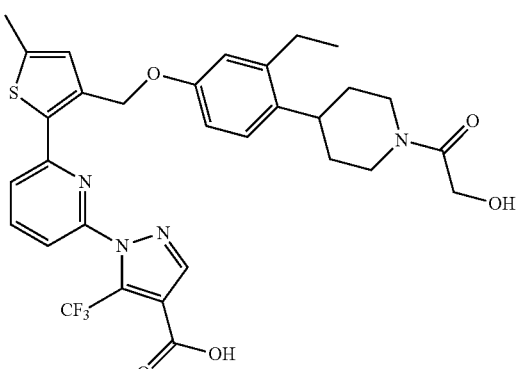<br>1-(6-(3-((3-Ethyl-4-(1-(2-hydroxyacetyl)piperidin-4-yl)phenoxy)methyl)-5-methylthiophen-2-yl)pyridin-2-yl)-5-(trifluoromethyl)-1H-pyrazole-4-carboxylic acid | Intermediate 2-2, Intermediate 4-1-D, and 2-hydroxyacetic acid (CAS# 79-14-1) | 1H NMR (400 MHz, DMSO-$d_6$) δ 13.48 (s, 1H), 8.14 (t, J = 7.9 Hz, 1H), 7.74 (d, J = 7.7 Hz, 1H), 7.64 (d, J = 7.9 Hz, 1H), 7.08 (d, J = 8.4 Hz, 1H), 7.00 (d, J = 1.0 Hz, 1H), 6.76 (d, J = 8.0 Hz, 2H), 6.54 (s, 1H), 5.22 (s, 2H), 4.56-4.37 (m, 2H), 4.18-4.02 (m, 2H), 3.75 (br d, J = 13.7 Hz, 1H), 3.06 (t, J = 11.1 Hz, 1H), 2.96-2.85 (m, 1H), 2.75-2.68 (m, 1H), 2.60 (q, J = 7.6 Hz, 2H), 2.47 (d, J = 0.9 Hz, 3H), 1.69-1.37 (m, 4H), 1.11 (t, J = 7.5 Hz, 3H). HRMS calcd. for $C_{31}H_{32}F_3N_4O_5S$ (M + H) 629.2046, found 629.2047. |

Example 13

Example 13-A. Ethyl 1-(6-(3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylate

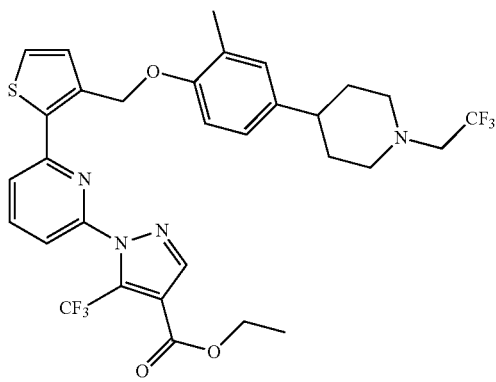 [SMILES: CCOC(=O)c1cnn(-c2cccc(-c3sccc3COc3ccc(C4CCN(CC(F)(F)F)CC4)cc3C)n2)c1C(F)(F)F]

To a solution of ethyl 1-(6-(3-((2-methyl-4-(piperidin-4-yl)phenoxy)methyl)thiophen-2-yl)pyridin-2-yl)-5-(trifluoromethyl)-1H-pyrazole-4-carboxylate (Example 11-B) (100 mg, 0.175 mmol) in THF (3 mL) was added 2,2,2-trifluoroethyl trifluoromethanesulfonate (CAS #6226-25-1, 81 mg, 0.350 mmol), followed by DIPEA (0.061 mL, 0.350 mmol).

The mixture was then stirred at room temperature for 16 h, and then diluted with EtOAc. The mixture was then washed successively with $H_2O$, brine, and dried over $MgSO_4$, filtered, and then concentrated. The resulting residue was purified by silica gel flash column chromatography (hexane/EtOAc=1/0 to 7/3) to afford the title compound. MS (ESI+) m/z 653.6 (M+H).

Example 13. 1-(6-(3-((2-Methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid

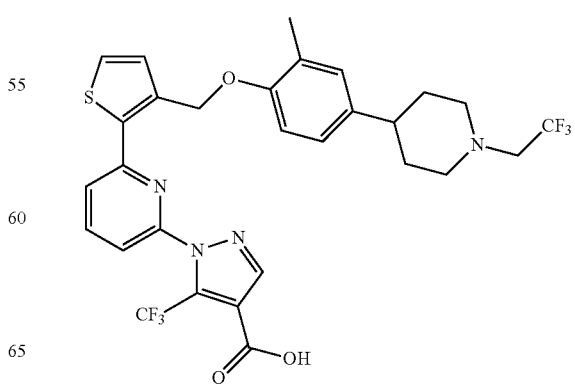

To a solution of ethyl 1-(6-(3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylate (90 mg, 0.138 mmol) in acetonitrile (3 mL) was added 1M aq. LiOH (0.414 mL, 0.414 mmol). The mixture was stirred at 50° C. for 2 h. The reaction was then quenched with 1M aq. HCl (0.47 mL). The resulting precipitate was collected by filtration. The collected solid was washed with H₂O, and then MeOH, and then dried in reducing pressure to afford the title compound. ¹H NMR (HCl salt, 400 MHz, CD₃OD) δ 8.16 (d, J=0.7 Hz, 1H), 8.07 (t, J=7.9 Hz, 1H), 7.85 (dd, J=7.9, 0.8 Hz, 1H), 7.59 (dd, J=7.9, 0.7 Hz, 1H), 7.54 (d, J=5.2 Hz, 1H), 7.27 (d, J=5.2 Hz, 1H), 7.03 (d, J=2.3 Hz, 1H), 6.97 (dd, J=8.4, 2.4 Hz, 1H), 6.82 (d, J=8.4 Hz, 1H), 5.37 (s, 2H), 4.28 (q, J=9.1 Hz, 2H), 3.80-3.71 (m, 2H), 3.42-3.33 (m, 2H), 2.81 (tt, J=12.0, 3.9 Hz, 1H), 2.18-1.94 (m, 7H). HRMS calcd. for $C_{29}H_{27}F_6N_4O_3S$ (M+H) 625.1708, found 625.1730.

Example 14

The following compounds were synthesized with a similar method described above for Example 13 using the appropriate starting materials as delineated in the table below.

| Example | Structure/Chemical Name | Starting materials | NMR and HRMS |
|---|---|---|---|
| 14-1 | 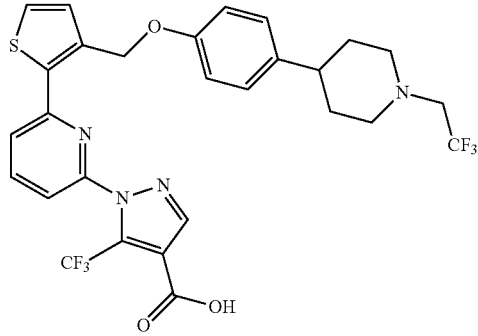 [SMILES: O=C(O)c1cnn(-c2cccc(-c3sccc3COc3ccc(C4CCN(CC(F)(F)F)CC4)cc3)n2)c1C(F)(F)F]<br>1-(6-(3-((4-(1-(2,2,2-Trifluoroethyl)piperidin-4-yl)phenoxy)methyl)thiophen-2-yl)pyridin-2-yl)-5-(trifluoromethyl)-1H-pyrazole-4-carboxylic acid | Example 1-B and 2,2,2-trifluoroethyl trifluoromethane sulfonate | ¹H NMR (400 MHz, CD₃OD) δ 8.16 (s, 1H), 8.07 (t, J = 7.95 Hz, 1H), 7.84 (dd, J = 0.61, 7.95 Hz, 1H), 7.59 (dd, J = 0.61, 7.95 Hz, 1H), 7.53 (d, J = 5.20 Hz, 1H), 7.26 (d, J = 5.20 Hz, 1H), 7.11-7.19 (m, 2H), 6.84-6.91 (m, 2H), 5.34 (s, 2H), 3.92 (br. s., 2H), 3.50-3.62 (m, 2H), 3.02-3.18 (m, 2H), 2.68-2.80 (m, 1H), 1.89-2.08 (m, 4H). HRMS calcd. for $C_{28}H_{25}F_6N_4O_3S$ (M + H) 611.1552, found 611.1534. |
| 14-2 | 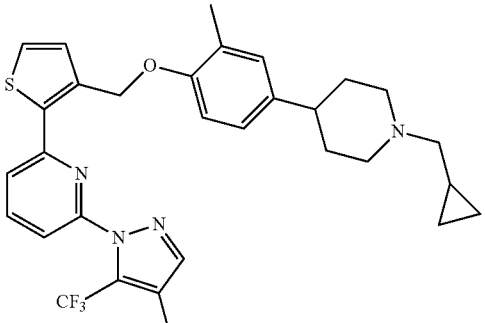<br>1-(6-(3-((4-(1-(Cyclopropylmethyl)piperidin-4-yl)-2-methylphenoxy)methyl)thiophen-2-yl)pyridin-2-yl)-5-(trifluoromethyl)-1H-pyrazole-4-carboxylic acid | Example 11-B and (bromomethyl)cyclopropane (CAS# 7051-34-5) | ¹H NMR (400 MHz, CD₃OD) δ 8.02 (t, J = 7.9 Hz, 1H), 7.94-7.88 (m, 1H), 7.77 (dd, J = 7.9, 0.8 Hz, 1H), 7.58-7.49 (m, 2H), 7.29 (d, J = 5.2 Hz, 1H), 6.96 (d, J = 9.2 Hz, 2H), 6.79 (d, J = 8.2 Hz, 1H), 5.37 (s, 2H), 3.67 (d, J = 12.2 Hz, 2H), 2.98 (d, J = 7.0 Hz, 4H), 2.72 (s, 1H), 2.13 (s, 3H), 2.04 (d, J = 14.3 Hz, 2H), 1.93 (t, J = 13.4 Hz, 2H), 1.20-1.07 (m, 1H), 0.81-0.73 (m, 2H), 0.48-0.37 (m, 2H). HRMS calcd. for $C_{31}H_{32}F_3N_4O_3S$ (M + H) 597.2147, found 597.2151. |

Example 15

Example 15-A. Ethyl 1-(6-(3-(((4-(1-(cyclopropanecarbonyl)piperidin-4-yl)-2-methylphenyl)amino)methyl)thiophen-2-yl)pyridin-2-yl)-5-methyl-1H-pyrazole-4-carboxylate

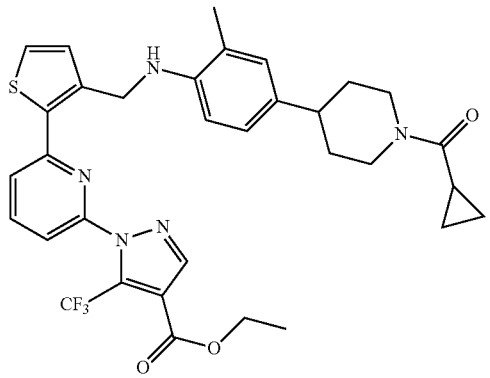 [SMILES: CCOC(=O)c1cnn(-c2cccc(-c3sccc3CNc3ccc(C4CCN(C(=O)C5CC5)CC4)cc3C)n2)c1C(F)(F)F]

A solution of Intermediate 4-2-4 (191 mg, 0.559 mmol) and Intermediate 2-14 (159 mg, 0.615 mmol) in AcOH (2.23 mL) was stirred for 1 h. To the mixture was then added NaB(OAc)$_3$H (166 mg, 0.783 mmol), and then the mixture was stirred at room temperature for 19 h. To the mixture was then added additional NaB(OAc)$_3$H (166 mg, 0.783 mmol). The mixture was then stirred at 50° C. for 2 h, and then poured into H$_2$O. The aqueous layer was then rendered basic by the addition of aqueous ammonium hydroxide (around pH 11), and then extracted with EtOAc. The organic layer was separated and concentrated. The resulting residue was purified by silica gel flash column chromatograph (heptane/EtOAc=1/0 to 0/1) to afford the title compound. MS (ESI+) m/z 584.3 (M+H).

Example 15. 1-(6-(3-(((4-(1-(Cyclopropanecarbonyl)piperidin-4-yl)-2-methylphenyl)amino)methyl)thiophen-2-yl)pyridin-2-yl)-5-methyl-1H-pyrazole-4-carboxylic acid

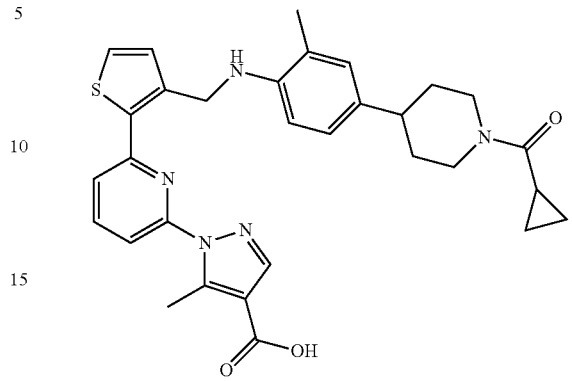

To a solution of ethyl 1-(6-(3-(((4-(1-(cyclopropanecarbonyl)piperidin-4-yl)-2-methylphenyl)amino)methyl)thiophen-2-yl)pyridin-2-yl)-5-methyl-1H-pyrazole-4-carboxylate (230 mg, 0.394 mmol) in MeOH (1.97 mL) and THF (1.97 mL) was added aq. LiOH (2M, 591 µl, 1.182 mmol). The mixture was then stirred at 50° C. for 3.5 h. The reaction mixture was then rendered acidic by the addition of 1M aq. HCl (1.2 mL), and then concentrated. The resulting residue was purified by RP-HPLC (HC-C) to afford the title compound. $^1$H NMR (400 MHz, CD$_3$OD) δ 8.04-7.98 (m, 2H), 7.71 (dd, J=7.8, 0.8 Hz, 1H), 7.66 (dd, J=8.0, 0.7 Hz, 1H), 7.44 (d, J=5.2 Hz, 1H), 7.16 (d, J=5.2 Hz, 1H), 6.88-6.81 (m, 2H), 6.50 (d, J=8.1 Hz, 1H), 4.61 (s, 3H), 4.42 (d, J=13.7 Hz, 1H), 3.20 (d, J=13.2 Hz, 1H), 2.87 (s, 3H), 2.76-2.60 (m, 2H), 2.03 (s, 3H), 2.02-1.94 (m, 1H), 1.84 (dd, J=35.3, 13.4 Hz, 2H), 1.68-1.42 (m, 2H), 0.92-0.76 (m, 4H). HRMS calcd. for C$_{31}$H$_{34}$N$_5$O$_3$S (M+H) 556.2304, found 556.2196.

Example 16

The following compounds were prepared with similar methods as described above for Example 15 using the appropriate starting materials as delineated in the table below.

| | Structure/Chemical Name | Starting materials | MS (ESI+) m/z |
|---|---|---|---|
| 16-1 | ![structure] 1-(6-(3-(((4-(1-(Cyclopropanecarbonyl)piperidin-4-yl)-2-methylphenyl)amino)methyl)thiophen-2-yl)pyridin-2-yl)-5-(trifluoromethyl)-1H-pyrazole-4-carboxylic acid | Intermediate 14 and Intermediate 4-1-A | $^1$H NMR (400 MHz, CD$_3$OD) δ 8.03 (t, J = 7.9 Hz, 1H), 7.99 (s, 1H), 7.79 (dd, J = 7.9, 0.8 Hz, 1H), 7.42 (d, J = 5.2 Hz, 1H), 7.55 (dd, J = 7.9, 0.8 Hz, 1H), 7.13 (d, J = 5.2 Hz, 1H), 6.87-6.79 (m, 2H), 6.47 (d, J = 8.2 Hz, 1H), 4.59 (m, 3H), 4.48-4.36 (m, 1H), 3.21 (t, J = 12.9 Hz, 1H), 2.77-2.58 (m, 2H), 2.02 (s, 3H), 2.01-1.93 (m, 1H), 1.91-1.83 (m, 1H), 1.83-1.74 (m, 1H), 1.65-1.41 (m, 2H), 0.94-0.76 (m, 4H). HRMS calcd. for C$_{31}$H$_{31}$F$_3$N$_5$O$_3$S (M + H) 610.2100, found 610.2115. |

| Structure/Chemical Name | Starting materials | MS (ESI+) m/z |
|---|---|---|
| 16-2 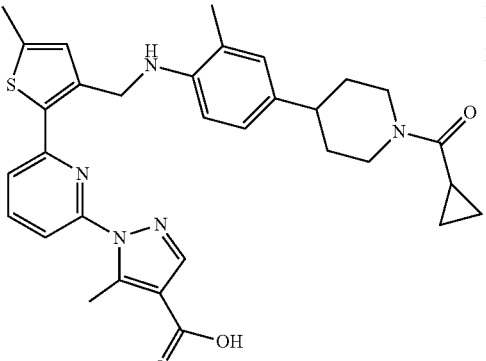<br>1-(6-(3-(((4-(1-(Cyclopropanecarbonyl)piperidin-4-yl)-2-methylphenyl)amino)methyl)-5-methylthiophen-2-yl)pyridin-2-yl)-5-methyl-1H-pyrazole-4-carboxylic acid | Intermediate 2-14 and Intermediate 4-10 | 1H NMR (400 MHz, CD$_3$OD) δ 7.99 (s, 1H), 7.96 (t, J = 8.0 Hz, 1H), 7.61 (ddd, J = 8.8, 8.0, 0.7 Hz, 2H), 6.87-6.81 (m, 3H), 6.49 (d, J = 8.0 Hz, 1H), 4.60 (d, J = 13.1 Hz, 1H), 4.51 (s, 2H), 4.41 (d, J = 13.6 Hz, 1H), 3.27-3.16 (m, 1H), 2.84 (s, 3H), 2.75-2.59 (m, 2H), 2.45 (d, J = 1.1 Hz, 3H), 2.01 (s, 3H), 2.00-1.94 (m, 1H), 1.92-1.84 (m, 1H), 1.79 (d, J = 13.3 Hz, 1H), 1.67-1.41 (m, 2H), 0.92-0.84 (m, 2H), 0.80 (dd, J = 8.2, 2.7 Hz, 2H). HRMS calcd. for C$_{32}$H$_{36}$N$_5$O$_3$S (M + H) 570.2461, found 570.2532. |
| 16-3 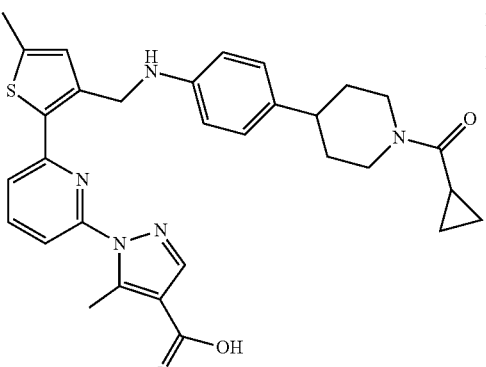<br>1-(6-(3-(((4-(1-(Cyclopropanecarbonyl)piperidin-4-yl)phenyl)amino)methyl)-5-methylthiophen-2-yl)pyridin-2-yl)-5-methyl-1H-pyrazole-4-carboxylic acid | Intermediate 2-15 and Intermediate 4-10 | $^1$H NMR (400 MHz, CD3OD) δ 8.00 (s, 1H), 7.96 (t, J = 7.95 Hz, 1H), 7.63 (dd, J = 2.57, 7.95 Hz, 1H), 6.97 (d, J = 8.56 Hz, 2H), 6.87 (d, J = 1.10 Hz, 1H), 6.55-6.60 (m, 2H), 4.62 (d, J = 12.59 Hz, 1H), 4.38-4.47 (m, 3H), 3.18-3.24 (m, 1H), 2.89 (s, 3H), 2.62-2.77 (m, 2H), 2.46 (d, J = 0.98 Hz, 3H), 1.95-2.02 (m, 1H), 1.90 (d, J = 13.69 Hz, 1H), 1.81 (d, J = 11.49 Hz, 1H), 1.44-1.67 (m, 2H), 0.75-0.92 (m, 4H). HRMS calcd. for C$_{31}$H$_{34}$N$_5$O$_3$S (M + H) 556.2382, found 556.2390. |

Example 17

Example 17-A. Ethyl 1-(6-(3-((4-(1-(cyclopropanecarbonyl)piperidin-4-yl)-2-methylphenoxy)methyl)-4-ethyl-5-methylthiophen-2-yl)pyridin-2-yl)-5-(trifluoromethyl)-1H-pyrazole-4-carboxylate

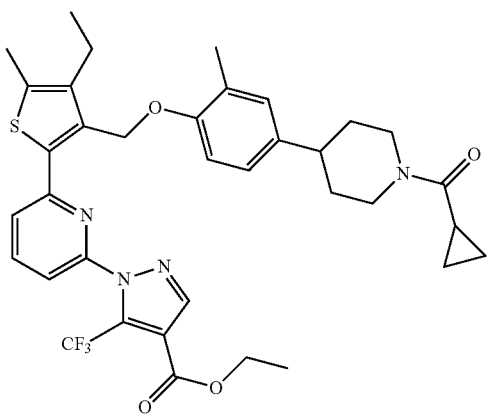 [SMILES: CCOC(=O)c1cnn(-c2cccc(-c3sc(C)c(CC)c3COc3ccc(C4CCN(C(=O)C5CC5)CC4)cc3C)n2)c1C(F)(F)F]

To a solution of Intermediate 4-2-10 (150 mg, 0.341 mmol) and CBr$_4$ (150 mg, 0.452 mmol) in CH$_2$Cl$_2$ (1 mL) at room temperature was added PPh$_3$ (150 mg, 0.572 mmol). The mixture was then stirred at room temperature for 0.5 h. To the mixture were then added Intermediate 2-4 (120 mg, 0.463 mmol) and K$_2$CO$_3$ (200 mg, 1.447 mmol), followed by DMF (2 mL). The mixture was then stirred at room temperature for 1.5 h, and diluted with EtOAc. The mixture was washed successively with 1/1 water:satd. KHSO$_4$, H$_2$O, and brine, dried over Na$_2$SO$_4$, filtered, and then concentrated. The resulting residue was purified by basic alumina gel flash column chromatography (heptane/EtOAc=1/0 to 2/3) to afford the title compound. MS (ESI+) m/z 681.3 (M+H).

Example 17. 1-(6-(3-((4-(1-(Cyclopropanecarbonyl)piperidin-4-yl)-2-methylphenoxy)methyl)-4-ethyl-5-methylthiophen-2-yl)pyridin-2-yl)-5-(trifluoromethyl)-1H-pyrazole-4-carboxylic acid

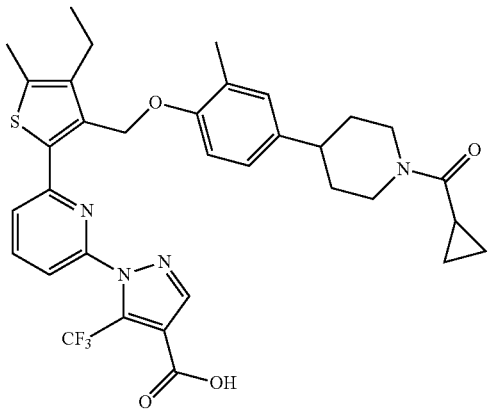 [SMILES: CCc1c(C)sc(-c2cccc(-n3ncc(C(=O)O)c3C(F)(F)F)n2)c1COc1ccc(C2CCN(C(=O)C3CC3)CC2)cc1C]

To a solution of ethyl 1-(6-(3-((4-(1-(cyclopropanecarbonyl)piperidin-4-yl)-2-methylphenoxy)methyl)-4-ethyl-5-methylthiophen-2-yl)pyridin-2-yl)-5-(trifluoromethyl)-1H-pyrazole-4-carboxylate (100 mg, 0.147 mmol) in THF/MeOH (1 mL/0.5 mL) was added LiOH in H$_2$O (1M, 0.147 mL, 0.147 mmol). The mixture was then stirred at room temperature for 16 h, and then rendered acidic by 1/1 water:satd. KHSO$_4$. The mixture was then extracted with EtOAc. The organic phase was then washed successively with H$_2$O and brine, dried over Na$_2$SO$_4$, filtered, and then concentrated. The resulting residue was purified by RP-HPLC (HC-C) to afford the title compound. $^1$H NMR (400 MHz, CD$_3$OD) δ 8.09 (s, 1H), 7.96 (dd, J=7.80, 8.00 Hz, 1H), 7.69 (dd, J=0.67, 7.89 Hz, 1H), 7.53 (dd, J=0.67, 7.89 Hz, 1H), 6.94-7.00 (m, 2H), 6.89-6.93 (m, 1H), 5.12 (s, 2H), 4.59-4.69 (m, 1H), 4.40-4.51 (m, 1H), 3.21-3.27 (m, 1H), 2.70-2.80 (m, 2H), 2.61-2.70 (m, 2H), 2.46 (s, 3H), 2.07 (s, 3H), 1.97-2.05 (m, 1H), 1.89-1.97 (m, 1H), 1.80-1.89 (m, 1H), 1.47-1.71 (m, 2H), 1.15 (t, J=7.52 Hz, 3H), 0.77-0.95 (m, 4H). HRMS calcd. for. C$_{34}$H$_{36}$F$_3$N$_4$O$_4$S (M+H) 653.2404, found 665.2424.

Example 18

The following compounds were synthesized with a similar method described above for Example 17 using the appropriate starting materials as delineated in the table below.

| Example | Structure/ Chemical Name | Starting materials | NMR and HRMS |
|---|---|---|---|
| 18-1 | 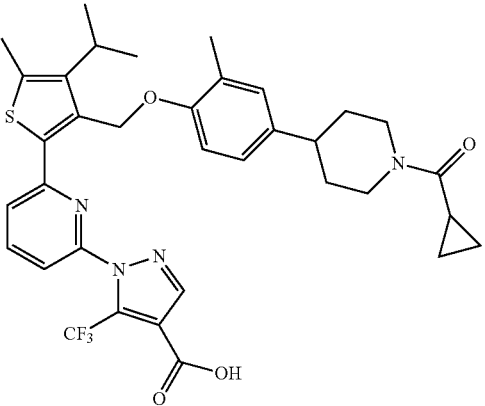 [SMILES: Cc1cc(C2CCN(C(=O)C3CC3)CC2)ccc1OCc1c(-c2cccc(-n3ncc(C(=O)O)c3C(F)(F)F)n2)sc(C)c1C(C)C]<br>1-(6-(3-((4-(1-(Cyclopropanecarbonyl)piperidin-4-yl)-2-methylphenoxy)methyl)-4-isopropyl-5-methylthiophen-2-yl)pyridin-2-yl)-5-(trifluoromethyl)-1H-pyrazole-4-carboxylic acid | Intermediate 2-4 and Intermediate 4-12 | $^1$H NMR (400 MHz, CD$_3$OD) δ 7.85-7.94 (m, 2H), 7.52-7.62 (m, 2H), 6.96-7.04 (m, 2H), 6.91 (d, J = 8.20 Hz, 1H), 5.09 (s, 2H), 4.64 (br. d, J = 12.50 Hz, 1H), 4.46 (br. d, J = 12.50 Hz, 1H), 3.17-3.28 (m, 2H), 2.69-2.81 (m, 2H), 2.52 (s, 3H), 2.14 (s, 3H), 1.97-2.05 (m, 1H), 1.90-1.96 (m, 1H), 1.79-1.89 (m, 1H), 1.48-1.74 (m, 2H), 1.34 (d, J = 7.21 Hz, 6H), 0.75-0.96 (m, 4H). HRMS calcd. for C$_{35}$H$_{38}$F$_3$N$_4$O$_4$S (M + H) 667.2560, found 667.2574. |
| 18-2 | 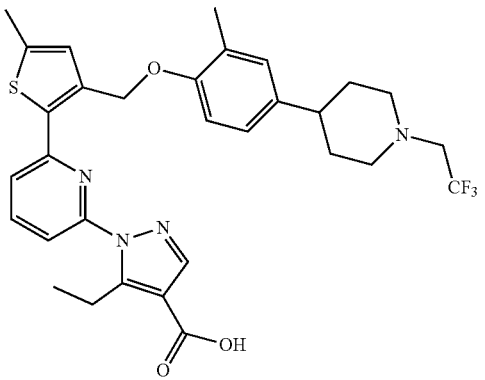 [SMILES: CCc1c(C(=O)O)cnn1-c1cccc(-c2sc(C)cc2COc2ccc(C3CCN(CC(F)(F)F)CC3)cc2C)n1]<br>5-Ethyl-1-(6-(5-methyl-3-((2-methyl-4-(1-(2,2,2-trifluoroethyl)piperidin-4-yl)phenoxy)methyl)thiophen-2-yl)pyridin-2-yl)-1H-pyrazole-4-carboxylic acid | Intermediate 2-13 and Intermediate 4-2-2 | $^1$H NMR (400 MHz, CD$_3$OD) δ 7.96-7.88 (m, 2H), 7.59 (ddd, J = 7.8, 5.9, 0.7 Hz, 2H), 7.03-6.92 (m, 3H), 6.86 (d, J = 8.3 Hz, 1H), 5.21 (s, 2H), 3.57 (q, J = 7.4 Hz, 2H), 3.10-3.02 (m, 4H), 2.51 (d, J = 1.1 Hz, 3H), 2.44 (dt, J = 13.8, 8.2 Hz, 3H), 2.16 (s, 3H), 1.75 (td, J = 9.2, 3.6 Hz, 4H), 1.19 (t, J = 7.4 Hz, 3H). HRMS calcd. for C$_{31}$H$_{34}$F$_3$N$_4$O$_3$S (M + H) 599.2304, found 599.2318. |

| Example | Structure/ Chemical Name | Starting materials | NMR and HRMS |
|---|---|---|---|
| 18-3 | 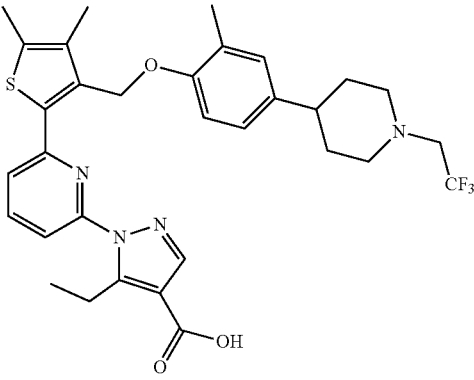 [SMILES: CCc1c(C(=O)O)cnn1-c1cccc(-c2sc(C)c(C)c2COc2ccc(C3CCN(CC(F)(F)F)CC3)cc2C)n1]<br>1-(6-(4,5-Dimethyl-3-((2-methyl-4-(1-(2,2,2-trifluoroethyl)piperidin-4-yl)phenoxy)methyl)thiophen-2-yl)pyridin-2-yl)-5-ethyl-1H-pyrazole-4-carboxylic acid | Intermediate 2-13 and Intermediate 4-2-3 | $^1$H NMR (400 MHz, CD$_3$OD) δ 7.98 (s, 1H), 7.91 (t, J = 8.0 Hz, 1H), 7.66 (dd, J = 8.1, 0.8 Hz, 1H), 7.57 (dd, J = 7.8, 0.8 Hz, 1H), 7.03-6.96 (m, 2H), 6.91 (d, J = 8.3 Hz, 1H), 5.10 (s, 2H), 3.54-3.43 (m, 2H), 3.11-3.02 (m, 4H), 2.53-2.37 (m, 6H), 2.18 (d, J = 0.8 Hz, 3H), 2.12 (s, 3H), 1.76 (tt, J = 5.8, 3.0 Hz, 4H), 1.27-1.18 (m, 3H). HRMS calcd. for C$_{32}$H$_{36}$F$_3$N$_4$O$_3$S (M + H) 613.2460, found 613.2481. |
| 18-4 | 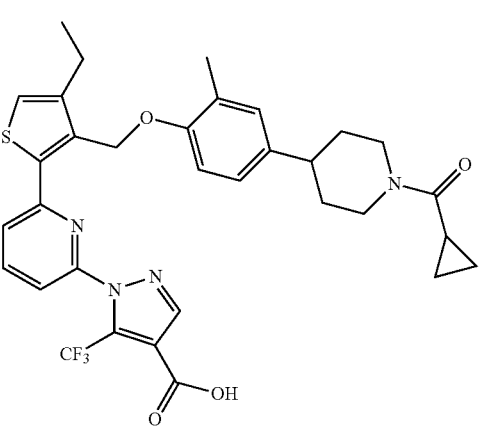 [SMILES: CCc1csc(-c2cccc(-n3ncc(C(=O)O)c3C(F)(F)F)n2)c1COc1ccc(C2CCN(C(=O)C3CC3)CC2)cc1C]<br>1-(6-(3-((4-(1-(Cyclopropanecarbonyl)piperidin-4-yl)-2-methylphenoxy)methyl)-4-ethylthiophen-2-yl)pyridin-2-yl)-5-(trifluoromethyl)-1H-pyrazole-4-carboxylic acid | Intermediate 2-4 and Intermediate 4-9 | 1H NMR (400 MHz, CD$_3$OD) δ 7.94-8.01 (m, 2H), 7.71 (dd, J = 0.67, 7.89 Hz, 1H), 7.59 (dd, J = 0.61, 7.95 Hz, 1H), 7.26 (s, 1H), 6.95-7.01 (m, 2H), 6.90 (d, J = 8.20 Hz, 1H), 5.16 (s, 2H), 4.59-4.68 (m, 1H), 4.40-4.50 (m, 1H), 3.20-3.27 (m, 1H), 2.66-2.80 (m, 4H), 2.08 (s, 3H), 1.97-2.05 (m,? 1H), 1.89-1.96 (m, 1H), 1.79-1.88 (m, 1H), 1.47-1.72 (m, 2H), 1.28 (t, J = 7.52 Hz, 3H), 0.76-0.95 (m, 4H). HRMS; calcd. for C$_{33}$H$_{34}$F$_3$N$_4$O$_4$S (M + H) 639.2253, found 639.2253 |

-continued

| Example | Structure/ Chemical Name | Starting materials | NMR and HRMS |
|---|---|---|---|
| 18-5 | 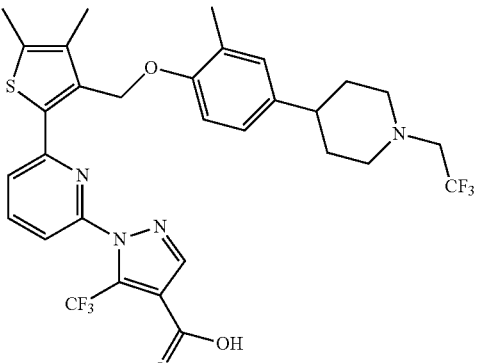<br>1-(6-(4,5-Dimethyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid | Intermediate 2-13 and Intermediate 4-1 | 1H NMR (HCl salt, 400 MHz, CD$_3$OD) δ 8.12 (s, 1H), 7.98 (t, J = 7.95 Hz, 1H), 7.69 (dd, J = 0.61, 7.95 Hz, 1H), 7.54 (dd, J = 0.61, 7.95 Hz,? 1H), 6.91-6.99 (m, 2H), 6.86 (d, J = 8.30 Hz, 1H), 5.15 (s, 2H), 3.04-3.12 (m, 4H), 2.37-2.52 (m, 6H), 2.18 (s, 3H), 2.08 (s, 3H), 1.71-1.80 (m, 4H). HRMS; calcd. for C$_{31}$H$_{31}$F$_6$N$_4$O$_3$S (M + H) 653.2021, found 653.2004 |
| 18-6 | 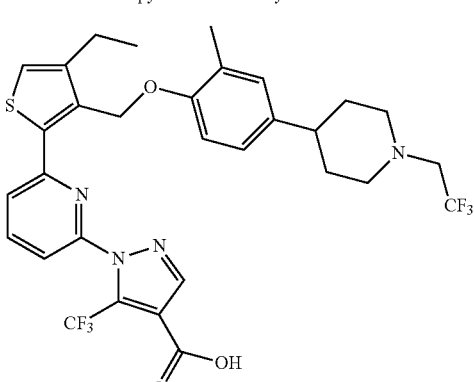<br>1-(6-(4-Ethyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid | Intermediate 2-13 and Intermediate 4-9 | 1H NMR (400 MHz, CD$_3$OD) δ 8.04 (s, 1H), 7.99 (dd, J = 7.80, 8.00 Hz, 1H), 7.73 (dd, J = 0.67, 7.89 Hz, 1H), 7.59 (dd, J = 0.61, 7.95 Hz, 1H), 7.27 (s, 1H), 6.94-7.02 (m, 2H), 6.86-6.93 (m, 1H), 5.16 (s, 2H), 4.57 (br. s., 1H), 3.03-3.13 (m, 4H), 2.71 (dq, J = 0.79, 7.52 Hz, 2H), 2.37-2.53 (m, 3H), 2.08 (s, 3H), 1.73-1.80 (m, 3H), 1.29 (t, J = 7.46 Hz, 3H). HRMS; calcd. for C$_{31}$H$_{31}$F$_6$N$_4$O$_3$S (M + H) 653.2021, found 653.2030. |

Example 19

Example 19-A. Ethyl 1-(6-(3-(((4-(1-(cyclopropanecarbonyl)piperidin-4-yl)-2-methylphenyl)amino)methyl)-4-methylthiophen-2-yl)pyridin-2-yl)-5-(trifluoromethyl)-1H-pyrazole-4-carboxylate

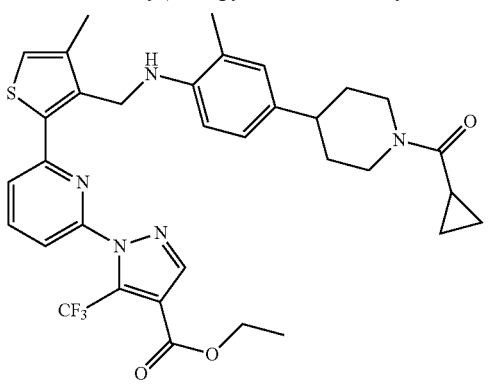

To a solution of Intermediate 4-8 (0.1 g, 0.243 mmol) and CBr$_4$ (0.1 g, 0.304 mmol) in CH$_2$Cl$_2$ (2.4 mL) at room temperature was added PPh$_3$ (0.083 g, 0.316 mmol). The mixture was then stirred at room temperature for ca. 20 min. To the mixture were then added Intermediate 2-14 (0.094 g, 0.365 mmol) and K$_2$CO$_3$ (0.10 g, 0.729 mmol), followed by DMF (2.4 mL). The mixture was then stirred at room temperature for 1 h, and diluted with EtOAc. The mixture was washed successively with 1/1 water and brine, then brine. The organic layer was then dried over Na$_2$SO$_4$, filtered, and concentrated. The resulting residue was purified by silica gel flash column chromatography (heptane/EtOAc=1/0 to 0/1) to afford the title compound. MS (ESI+) m/z 652.4 (M+H).

153

Example 19. 1-(6-(3-(((4-(1-(Cyclopropanecarbonyl)piperidin-4-yl)-2-methylphenyl)amino)methyl)-4-methylthiophen-2-yl)pyridin-2-yl)-5-(trifluoromethyl)-1H-pyrazole-4-carboxylic acid

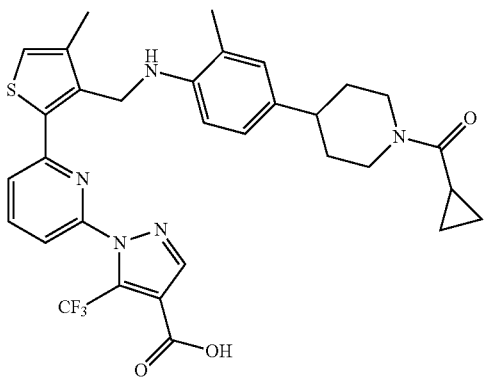 [SMILES: Cc1cc(C2CCN(C(=O)C3CC3)CC2)ccc1NCc1c(C)csc1-c1cccc(-n2ncc(C(=O)O)c2C(F)(F)F)n1]

To a solution of ethyl 1-(6-(3-(((4-(1-(cyclopropanecarbonyl)piperidin-4-yl)-2-methylphenyl)amino)methyl)-4-methylthiophen-2-yl)pyridin-2-yl)-5-(trifluoromethyl)-1H-

154 pyrazole-4-carboxylate (138 mg, 0.212 mmol) in MeOH (2.1 mL) and THF (2.1 mL) was added 1M aq. LiOH (1.1 mL, 1.1 mmol). The mixture was then stirred at room temperature for 2 h, and rendered neutral by the addition of 1M aq. HCl. The reaction mixture was then extracted with EtOAc. The organic layer was then concentrated. The resulting residue was purified by RP-HPLC (HC-C) to afford the title compound. $^1$H NMR (400 MHz, CD$_3$OD) δ 8.23 (d, J=0.8 Hz, 1H), 8.16 (t, J=7.9 Hz, 1H), 7.94 (dd, J=7.9, 0.8 Hz, 1H), 7.63 (d, J=7.9 Hz, 1H), 7.36 (d, J=1.2 Hz, 1H), 7.11 (s, 1H), 7.00 (dd, J=8.2, 2.1 Hz, 1H), 6.79 (d, J=8.2 Hz, 1H), 4.82 (s, 2H), 4.65 (d, J=13.2 Hz, 1H), 4.47 (d, J=13.6 Hz, 1H), 3.26-3.21 (m, 1H), 2.86-2.69 (m, 2H), 2.21 (d, J=1.1 Hz, 3H), 2.14 (s, 3H), 2.05-1.96 (m, 1H), 1.91 (d, J=13.4 Hz, 1H), 1.83 (d, J=13.0 Hz, 1H), 1.57 (dd, J=46.4, 13.2 Hz, 2H), 0.89 (p, J=6.5 Hz, 2H), 0.83 (dd, J=7.8, 2.2 Hz, 2H). HRMS calcd. for C$_{32}$H$_{33}$F$_3$N$_5$O$_3$S (M+H) 624.2178, found 624.2279.

Example 20

The following compounds were synthesized with a similar method described above for Example 19 using the appropriate starting materials as delineated in the table below.

| Example | Structure/ Chemical Name | Starting materials | NMR and HRMS |
|---|---|---|---|
| 20-1 | 1-(6-(3-(((4-(1-(Cyclopropanecarbonyl)piperidin-4-yl)phenyl)amino)methyl)-4-methylthiophen-2-yl)pyridin-2-yl)-5-(trifluoromethyl)-1H-pyrazole-4-carboxylic acid | Intermediate 2-15 and Intermediate 8 | $^1$H NMR (400 MHz, CD$_3$OD) δ 8.22-8.16 (m, 2H), 8.00 (dd, J = 8.0, 0.8 Hz, 1H), 7.63 (dd, J = 7.9, 0.7 Hz, 1H), 7.39 (d, J = 1.2 Hz, 1H), 7.26-7.22? (m, 2H), 7.01-6.97 (m, 2H), 4.79 (s, 2H), 4.66 (d, J = 13.0 Hz, 1H), 4.48 (d, J = 13.3 Hz, 1H), 3.26-3.22 (m, 1H), 2.87 (tt, J = 12.2, 8.6, 3.7 Hz, 1H), 2.76 (t, J = 12.7 Hz, 1H), 2.29 (d, J = 1.0 Hz, 3H), 2.05-1.97 (m, 1H), 1.93 (d, J = 12.2 Hz, 1H), 1.86 (d, J = 13.2 Hz, 1H), 1.73-1.47 (m, 2H), 0.95-0.87 (m, 2H), 0.87-0.79 (m, 2H). HRMS calcd. for C$_{31}$H$_{31}$F$_3$N$_5$O$_3$S (M + H) 610.2021, found 610.2106. |

| Example | Structure/ Chemical Name | Starting materials | NMR and HRMS |
|---|---|---|---|
| 20-2 | 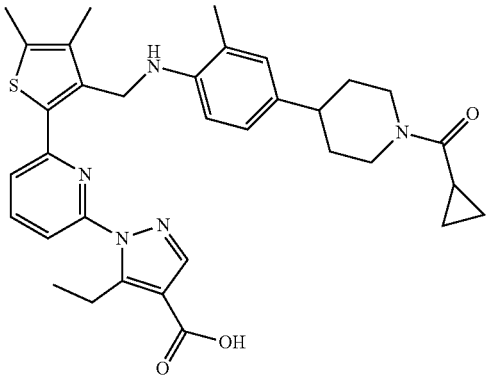 [SMILES: CCc1c(C(=O)O)cnn1-c1cccc(-c2sc(C)c(C)c2CNc2ccc(C3CCN(C(=O)C4CC4)CC3)cc2C)n1]<br>1-(6-(3-(((4-(1-(Cyclopropanecarbonyl)piperidin-4-yl)-2-methylphenyl)amino)methyl)-4,5-dimethylthiophen-2-yl)pyridin-2-yl)-5-ethyl-1H-pyrazole-4-carboxylic acid | Intermediate 2-14 and Intermediate 4-2-3 | $^1$H NMR (400 MHz, CD$_3$OD) δ 7.95 (s, 1H), 7.91 (t, J = 7.9 Hz, 1H), 7.66 (dd, J = 7.8, 0.8 Hz, 1H), 7.58 (dd, J = 8.0, 0.8 Hz, 1H), 6.93 (dd, J = 8.2, 2.2 Hz, 1H), 6.88 (d, J = 2.1 Hz, 1H), 6.65 (d, J = 8.2 Hz, 1H), 4.63 (d, J = 13.0 Hz, 1H), 4.44 (d, J = 13.5 Hz, 1H), 4.31 (s, 2H), 3.39 (q, J = 7.4 Hz, 2H), 3.28-3.19 (m, 1H), 2.80-2.63 (m, 2H), 2.42 (d, J = 0.8 Hz, 3H), 2.18 (d, J = 0.8 Hz, 3H), 2.05-1.95 (m, 4H), 1.87 (dd, J = 34.8, 13.2 Hz, 2H), 1.70-1.44 (m, 2H), 1.16 (t, J = 7.4 Hz, 3H), 0.95-0.76 (m, 4H). HRMS calcd. or C$_{34}$H$_{40}$N$_5$O$_3$S (M + H) 598.2852, found 598.2870. |
| 20-3 | 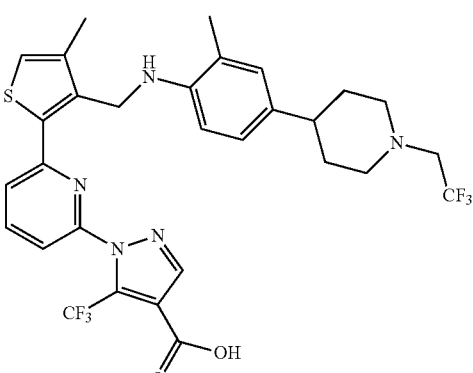<br>1-(6-(4-Methyl-3-(((2-methyl-4-(1-(2,2,2-trifluoroethyl)piperidin-4-yl)phenyl)amino)methyl)thiophen-2-yl)pyridin-2-yl)-5-(trifluoromethyl)-1H-pyrazole-4-carboxylic acid | Intermediate 2-25 and Intermediate 4-8 | $^1$H NMR (400 MHz, CD$_3$OD) δ 8.04-7.97 (m, 2H), 7.82 (dd, J = 8.0, 0.8 Hz, 1H), 7.53 (dd, J = 7.9, 0.8 Hz, 1H), 7.21 (d, J = 1.2 Hz, 1H), 6.92 (dd, J = 8.2, 2.2 Hz, 1H), 6.85 (d, J = 2.1 Hz, 1H), 6.65 (d, J = 8.2 Hz, 1H), 4.36 (s, 2H), 3.10-3.03 (m, 4H), 2.53-2.42 (m, 2H), 2.36 (q, J = 7.6 Hz, 1H), 2.31 (d, J = 1.0 Hz, 3H), 1.94 (s, 3H), 1.80-1.70 (m, 4H). HRMS calcd for C$_{30}$H$_{30}$F$_6$N$_5$O$_2$S (M + H) 638.2024, found 638.2032. |

Example 21

Example 21-A. Ethyl 1-(6-(5-methyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylate

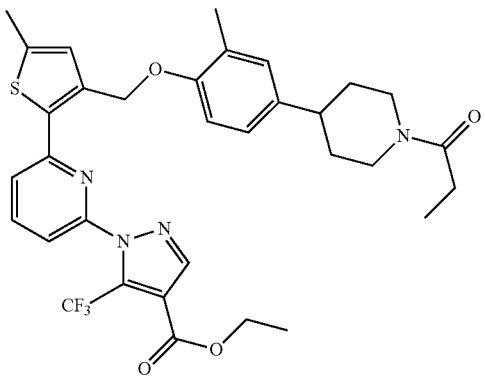 [SMILES: CCOC(=O)c1cnn(-c2cccc(-c3sc(C)cc3COc3ccc(C4CCN(C(=O)CC)CC4)cc3C)n2)c1C(F)(F)F]

To a solution of Intermediate 4-1-D (365 mg, 0.89 mmol) in $CH_2Cl_2$ (7.3 mL) was added DIPEA (464 µL, 2.66 mmol), followed by MsCl (124 µL, 1.60 mmol) dropwise. The mixture was then stirred at room temperature for 18 h, and then diluted with $CH_2Cl_2$. The organic layer was washed with $H_2O$. The aqueous layer was then extracted three times with $CH_2Cl_2$. The combined organics were then washed with brine, dried over $MgSO_4$, filtered, and then concentrated. The resulting residue was dissolved in DMF (5 mL). To the mixture was added Intermediate 2-6 (109 mg, 0.442 mmol), followed by potassium carbonate (204 mg, 1.476 mmol). The mixture was stirred at 50° C. for 18 h, and then diluted with EtOAc. The organic layer was washed with $H_2O$ and then twice with brine, dried over $MgSO_4$, filtered, and then concentrated. The resulting residue was purified by silica gel flash column chromatography (hexane/EtOAc=10/1 to 1/1) afford the title compound. MS (ESI+) m/z 641.1 (M+H).

Example 21. 1-(6-(5-Methyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylic acid

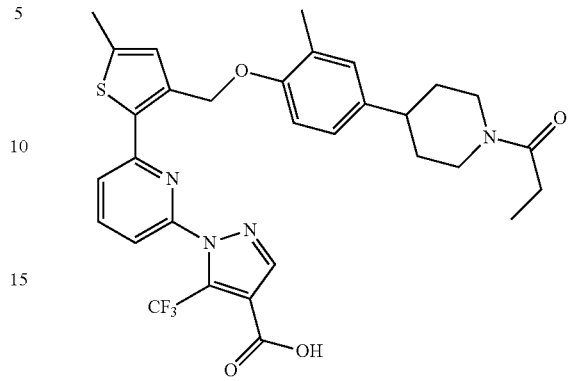

To a solution of ethyl 1-(6-(5-methyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylate (204 mg, 0.318 mmol) in $THF/H_2O$ (6/1.5 mL) was added lithium hydroxide monohydrate (134 mg, 3.184 mmol). The mixture was then stirred at room temperature for 72 h, and then partially concentrated. The resulting residue purified by RP-HPLC (HC-C) to afford the title compound. $^1H$ NMR (400 MHz, $CD_3OD$) δ 7.96 (t, J=7.95 Hz, 1H), 7.91 (s, 1H), 7.67 (d, J=7.82 Hz, 1H), 7.51 (d, J=7.82 Hz, 1H), 6.92-7.00 (m, 3H), 6.78 (d, J=8.31 Hz, 1H), 5.25 (s, 2H), 4.62-4.69 (m, 1H), 4.01-4.09 (m, 1H), 3.11-3.21 (m, 1H), 2.63-2.75 (m, 2H), 2.49 (d, J=0.98 Hz, 3H), 2.44 (q, J=7.58 Hz, 2H), 2.16 (s, 3H), 1.78-1.91 (m, 2H), 1.45-1.66 (m, 2H), 1.13 (t, J=7.46 Hz, 3H). HRMS calcd. for $C_{31}H_{32}F_3N_4O_4S$ (M+H) 613.2096, found 613.2126.

Example 22

The following compounds were synthesized with a similar method described above using the appropriate starting materials.

| Example | Structure/ Chemical Name | Starting materials | NMR and HRMS |
| --- | --- | --- | --- |
| 22-1 | ![structure]<br>1-(6-(3-((4-(1-(Cyclopropanecarbonyl)piperidin-4-yl)-2-methylphenoxy)methyl)-5-ethylthiophen-2-yl)pyridin-2-yl)-5-(trifluoromethyl)-1H-pyrazole-4-carboxylic acid | Intermediate 2-4 and Intermediate 4-2-9 | $^1H$ NMR (400 MHz, $CD_3OD$) δ 7.97 (t, J = 8.0 Hz, 1H), 7.91 (s, 1H), 7.68 (dd, J = 0.7, 7.9 Hz, 1H), 7.52 (dd, J = 0.7, 8.0 Hz, 1H), 6.93-7.01 (m, 3H), 6.80 (d, J = 8.4 Hz, 1H), 5.27 (s, 2H), 4.58-4.68 (m, 1H), 4.40-4.49 (m, 1H), 3.19-3.26 (m, 1H), 2.87 (dq, J = 0.9, 7.6 Hz, 2H), 2.67-2.79 (m, 2H), 2.17 (s, 3H), 1.96-2.04 (m, 1H), 1.87-1.95 (m, 1H), 1.77-1.86 (m, 1H), 1.46-1.70 (m, 2H), 1.33 (t, J = 7.6 Hz, 3H), 0.77-0.93 (m, 4H). HRMS cal. for $C_{33}H_{34}F_3N_4O_4S$ (M + H) 639.2253, found 639.2275. |

Example 23

Example 23-A. Ethyl 1-(6-(3-(((1,2,3,4-tetrahydroisoquinolin-6-yl)oxy)methyl)thiophen-2-yl)pyridin-2-yl)-5-(trifluoromethyl)-1H-pyrazole-4-carboxylate

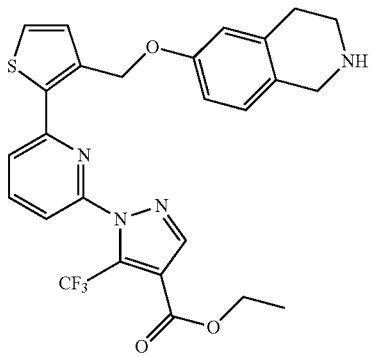 [SMILES: CCOC(=O)c1cnn(-c2cccc(-c3sccc3COc3ccc4c(c3)CCNC4)n2)c1C(F)(F)F]

Reaction of Intermediate 1-1 with Intermediate 3-8, in a fashion analogous for the preparation of Example 1-A, and the Boc group of the resulting coupling product was removed analogous to the transformation outlined for Intermediate Example 1-B to furnish ethyl 1-(6-(3-(((1,2,3,4-tetrahydroisoquinolin-6-yl)oxy)methyl)thiophen-2-yl)pyridin-2-yl)-5-(trifluoromethyl)-1H-pyrazole-4-carboxylate.

Example 23-B. Ethyl 1-(6-(3-(((2-(pyridin-2-ylmethyl)-1,2,3,4-tetrahydroisoquinolin-6-yl)oxy)methyl)thiophen-2-yl)pyridin-2-yl)-5-(trifluoromethyl)-1H-pyrazole-4-carboxylate

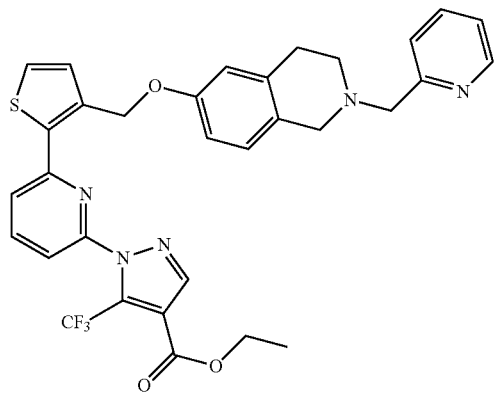 [SMILES: CCOC(=O)c1cnn(-c2cccc(-c3sccc3COc3ccc4c(c3)CCN(Cc3ccccn3)C4)n2)c1C(F)(F)F]

A mixture of ethyl 1-(6-{3-[(1,2,3,4-tetrahydroisoquinolin-6-yloxy)methyl]thiophen-2-yl}pyridin-2-yl)-5-(trifluoromethyl)pyrazole-4-carboxylate (Example 23-A) (200 mg, 0.378 mmol) and 2-pyridinecarboxaldehyde (CAS#1121-60-4, 40 mL, 3.23 mmol) in MeOH (4 mL) and AcOH (50 uL) was stirred for 1 h at room temperature. To the mixture was then added NaBH$_3$CN (33 mg, 0.530 mmol). The mixture was then stirred at 50° C. for 16 h. The reaction was then quenched with sat. aq. NaHCO$_3$. The mixture was then extracted with EtOAc. The organic layer was then washed successively with H$_2$O and brine, dried over MgSO$_4$, filtered, and then concentrated. The resulting residue was purified by silica gel flash column chromatography (hexane/EtOAc=1/0 to 0/1) to afford the title compound. MS (ESI+) m/z 620.6 (M+H).

Example 23. 1-(6-(3-(((2-(Pyridin-2-ylmethyl)-1,2,3,4-tetrahydroisoquinolin-6-yl)oxy)methyl)thiophen-2-yl)pyridin-2-yl)-5-(trifluoromethyl)-1H-pyrazole-4-carboxylic acid

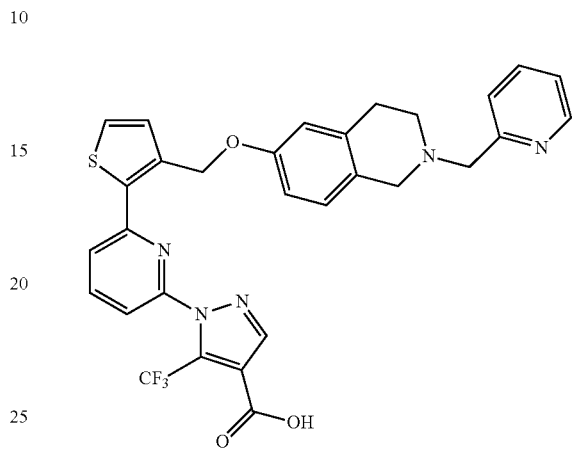

The title compound was synthesized in a similar manner as described in Example 7 using ethyl 1-(6-(3-(((2-(pyridin-2-ylmethyl)-1,2,3,4-tetrahydroisoquinolin-6-yl)oxy)methyl)thiophen-2-yl)pyridin-2-yl)-5-(trifluoromethyl)-1H-pyrazole-4-carboxylate. $^1$H NMR (400 MHz, CD$_3$OD) δ 8.60-8.67 (m, 1H), 7.99-8.06 (m, 1H), 7.86-7.94 (m, 2H), 7.81 (dd, J=0.61, 7.82 Hz, 1H), 7.60 (d, J=7.95 Hz, 1H), 7.50-7.55 (m, 2H), 7.39-7.46 (m, 1H), 7.27 (d, J=5.14 Hz, 1H), 6.94 (d, J=8.31 Hz, 1H), 6.67-6.75 (m, 2H), 5.35 (s, 2H), 4.36 (s, 2H), 4.15 (s, 2H), 3.32-3.35 (m, 2H), 3.03 (t, J=6.24 Hz, 2H). HRMS calcd. for C$_{30}$H$_{23}$F$_3$N$_5$O$_3$S (M−H) 590.1474, found 590.1462.

Example 24. 1-(6-(3-(((4-(1-(Cyclopropanecarbonyl)piperidin-4-yl)-3-ethylphenyl)amino)methyl)-5-methylthiophen-2-yl)pyridin-2-yl)-5-(trifluoromethyl)-1H-pyrazole-4-carboxylic acid

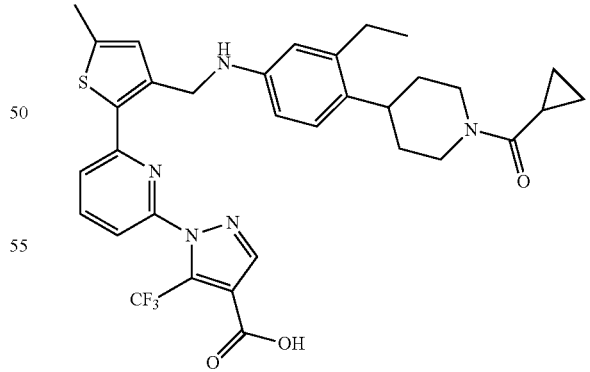

Reaction of Intermediate 4-1-D with Intermediate 2-16 in a fashion analogous to the preparation of Example 19-A, followed by deprotection of the Boc group in a manner analogous to the transformation outlined in Example 1-B, followed by reaction with cyclopropanecarboxylic acid in a similar manner for the procedure as described for Example 11-C, and lastly saponification as described in Example 9 furnished 1-(6-(3-(((4-(1-(cyclopropanecarbonyl)piperidin-4-yl)-3-ethylphenyl)amino)methyl)-5-methylthiophen-2-yl)pyridin-2-yl)-5-(trifluoromethyl)-1H-pyrazole-4-carboxylic acid. $^1$H NMR (400 MHz, DMSO-$d_6$) δ 13.45 (br. s., 1H) 8.29 (s, 1H) 8.15 (t, J=7.89 Hz, 1H) 7.79 (d, J=7.58 Hz, 1H) 7.64 (d, J=7.46 Hz, 1H), 6.76-6.96 (m, 2H) 6.21-6.43 (m, 2H) 5.92 (br. s., 1H) 4.19-4.58 (m, 4H) 3.15 (br. s., 1H) 2.75-2.88 (m, 1H) 2.54-2.66 (m, 1H) 2.44-2.48, (m, 2H) 2.42 (d, J=0.98 Hz, 3H) 1.91-2.03 (m, 1H) 1.27-1.72 (m, 4H) 1.05 (t, J=7.52 Hz, 3H) 0.61-0.81 (m, 4H). HRMS calcd. for $C_{33}H_{35}F_3N_5O_3S$ (M+H) 638.2413, found 638.2427.

Example 25

Example 25-A. tert-Butyl 4-(4-(2-(2-(6-(4-(ethoxycarbonyl)-5-(trifluoromethyl)-1H-pyrazol-1-yl)pyridin-2-yl)-5-methylthiophen-3-yl)vinyl)-3-methylphenyl)piperidine-1-carboxylate

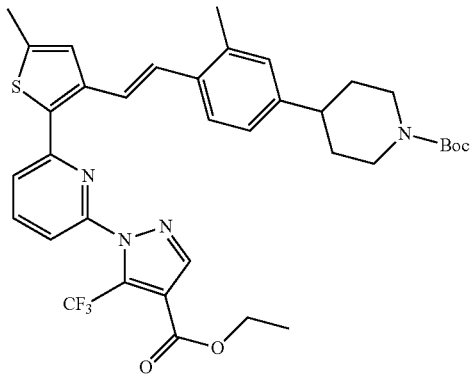 [SMILES: CCOC(=O)c1cnn(-c2cccc(-c3sc(C)cc3/C=C/c3ccc(C4CCN(C(=O)OC(C)(C)C)CC4)cc3C)n2)c1C(F)(F)F]

To a solution of Intermediate 2-17 (503 mg, 1.19 mmol) and Intermediate 4-13 (403 mg, 0.99 mmol) in DMF (7.5 mL) was added PdCl$_2$(dppf) CH$_2$Cl$_2$ adduct (162 mg, 0.20 mmol), followed by tri(2-furyl)phosphine (CAS #, 5518-52-5, 57 mg, 0.25 mmol) and diisopropylamine (0.3 mL, 2.18 mmol). The mixture was then stirred at 110° C. for 1 h under microwave irradiation. The reaction mixture was then diluted in H$_2$O, and then extracted with EtOAc. The organic layer was then dried over MgSO4, filtered and then concentrated. The resulting residue was purified by silica gel flash column chromatography (heptane/EtOAc=8/2) to afford the title compound. MS (ESI+) m/z 681.4 (M+H).

Example 25-B. tert-Butyl 4-(4-(2-(2-(6-(4-(ethoxycarbonyl)-5-(trifluoromethyl)-1H-pyrazol-1-yl)pyridin-2-yl)-5-methylthiophen-3-yl)ethyl)-3-methylphenyl)piperidine-1-carboxylate

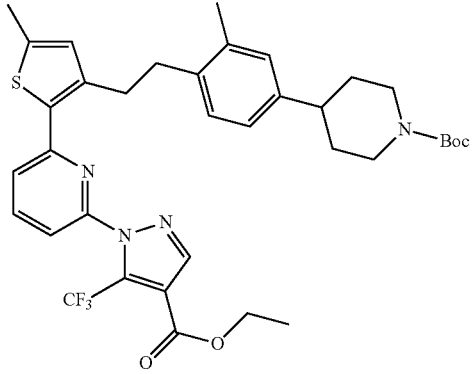 [SMILES: CCOC(=O)c1cnn(-c2cccc(-c3sc(C)cc3CCc3ccc(C4CCN(C(=O)OC(C)(C)C)CC4)cc3C)n2)c1C(F)(F)F]

To a mixture of tert-butyl 4-(4-(2-(2-(6-(4-(ethoxycarbonyl)-5-(trifluoromethyl)-1H-pyrazol-1-yl)pyridin-2-yl)-5-methylthiophen-3-yl)vinyl)-3-methylphenyl)piperidine-1-carboxylate (184 mg, 0.27 mmol) and palladium hydroxide on carbon (20 weight %, 14 mg, 0.03 mmol) in MeOH (4 mL) was added ammonium formate (85 mg, 1.35 mmol). The mixture was then stirred at 70° C. for 16 h. The reaction was then diluted with water. The mixture was then extracted with EtOAc, dried over MgSO$_4$, filtered and concentrated. The resulting residue was purified by silica gel flash column chromatography (15% EtOAc in heptane) to furnish the title compound. MS (ESI+) m/z 627.3 (M-tBu+2H).

Example 25. 1-(6-(3-(4-(1-(Cyclopropanecarbonyl)piperidin-4-yl)-2-methylphenethyl)-5-methylthiophen-2-yl)pyridin-2-yl)-5-(trifluoromethyl)-1H-pyrazole-4-carboxylic acid

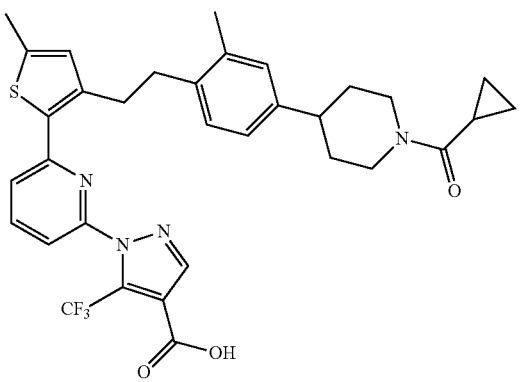 [SMILES: Cc1cc(CCc2ccc(C3CCN(C(=O)C4CC4)CC3)cc2C)c(-c2cccc(-n3ncc(C(=O)O)c3C(F)(F)F)n2)s1]

Reaction of tert-Butyl 4-(4-(2-(2-(6-(4-(ethoxycarbonyl)-5-(trifluoromethyl)-1H-pyrazol-1-yl)pyridin-2-yl)-5-methylthiophen-3-yl)ethyl)-3-methylphenyl)piperidine-1-carboxylate (Example 25-B) in a fashion analogous to Example 5. $^1$H NMR (400 MHz, CD$_3$OD) δ 8.13 (s, 1H), 7.93 (t, J=7.9 Hz, 1H), 7.51 (dd, J=7.9, 0.8 Hz, 1H), 7.44 (dd, J=7.9, 0.7 Hz, 1H), 6.88 (d, J=1.8 Hz, 1H), 6.82 (dd, J=7.8, 1.9 Hz, 1H), 6.75 (d, J=7.8 Hz, 1H), 6.69 (q, J=1.0 Hz, 1H), 4.62 (d, J=13.2 Hz, 1H), 4.44 (d, J=13.4 Hz, 1H), 3.22 (d, J=14.5 Hz, 1H), 3.06-3.16 (m, 2H), 2.77-2.87 (m, 2H), 2.64-2.77 (m, 2H), 2.47 (d, J=1.1 Hz, 3H), 2.11 (s, 3H), 1.96-2.02 (m, 1H), 1.88 (d, J=13.3 Hz, 1H), 1.79 (d, J=13.3 Hz, 1H), 1.44-1.68 (m, 2H), 0.74-0.97 (m, 4H). HRMS calcd. For $C_{33}H_{34}F_3N_4O_3S$ (M+H) 623.2304, found 623.2332.

Example 26. 1-(6-(3-(4-(1-(Cyclopropanecarbonyl)piperidin-4-yl)-2-methylphenethyl)thiophen-2-yl)pyridin-2-yl)-5-(trifluoromethyl)-1H-pyrazole-4-carboxylic acid

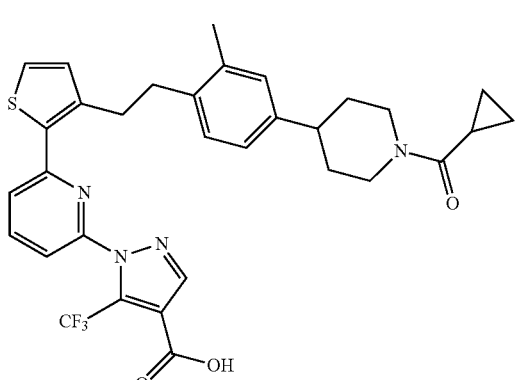

Reaction of Intermediate 4-14 with Intermediate 2-18-2, in a fashion analogous to Example 25-A and Example 25-B, followed by a saponification as outlined for the preparation of Example 1 furnished, after purification by SFC (stationary phase; PrincetonSFC 2-Ethylpyridine 5 μm, 21×150 mm: Mobile phase gradient Methanol/CO$_2$) in place of crystallization, the title compound, 1-(6-(3-(4-(1-(cyclopropanecarbonyl)piperidin-4-yl)-2-methylphenethyl)thiophen-2-yl)pyridin-2-yl)-5-(trifluoromethyl)-1H-pyrazole-4-carboxylic acid. $^1$H NMR (400 MHz, CD$_3$OD) δ 8.16 (s, 1H), 7.98 (t, J=7.9 Hz, 1H), 7.59 (dd, J=7.9, 0.6 Hz, 1H), 7.51 (dd, J=7.9, 0.6 Hz, 1H), 7.44 (d, J=5.1 Hz, 1H), 7.00 (d, J=5.1 Hz, 1H), 6.85-6.90 (m, 1H), 6.81 (dd, J=7.9, 1.7 Hz, 1H), 6.74 (d, J=7.8 Hz, 1H), 4.63 (d, J=12.8 Hz, 1H), 4.44 (d, J=14.2 Hz, 1H), 3.16-3.23 (m, 3H), 2.79-2.91 (m, 2H), 2.60-2.79 (m, 3H), 2.10 (s, 3H), 1.95-2.05 (m, 1H), 1.74-1.93 (m, 2H), 1.42-1.69 (m, 2H), 0.73-0.97 (m, 4H). HRMS calcd. For C$_{32}$H$_{32}$F$_3$N$_4$O$_3$S (M+H) 609.2147 found 609.2171.

Example 27

Example 27-A. Ethyl 1-(6-(3-(4-bromostyryl)thiophen-2-yl)pyridin-2-yl)-5-(trifluoromethyl)-1H-pyrazole-4-carboxylate

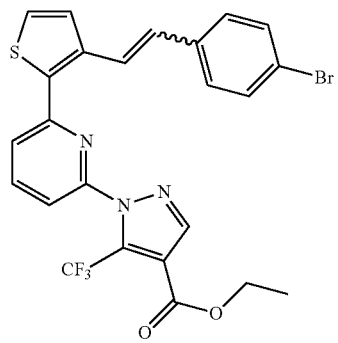 [SMILES: CCOC(=O)c1cnn(-c2cccc(-c3sccc3C=Cc3ccc(Br)cc3)n2)c1C(F)(F)F]

At room temperature, LHMDS (1 M in THF, 1.8 mL, 1.8 mmol) was added to a suspension of (4-bromobenzyl)triphenylphosphonium bromide (CAS#51044-13-4, 0.972 g, 1.90 mmol) in THF (4 mL). The mixture was then stirred at this temperature for 0.5 h. To the mixture was then added a solution of Intermediate 4-1-A (0.5 g, 1.27 mmol) in THF (1 mL). The mixture was then stirred for 3 h at room temperature. The reaction was then quenched with satd. aq. NH$_4$Cl. The mixture was then extracted with CH$_2$Cl$_2$. The organic layer was dried over Na$_2$SO$_4$, filtered and then concentrated. The resulting residue was purified by silica gel flash column chromatography (heptane/EtAOc=1/0 to 0/1)) to furnish the title compound. MS (ESI+) m/z 548.06 (M+H).

Example 27-B. tert-Butyl 4-(4-(2-(2-(6-(4-(ethoxycarbonyl)-5-(trifluoromethyl)-1H-pyrazol-1-yl)pyridin-2-yl)thiophen-3-vinyl)phenyl)-5,6-dihydropyridine-1(2H)-carboxylate

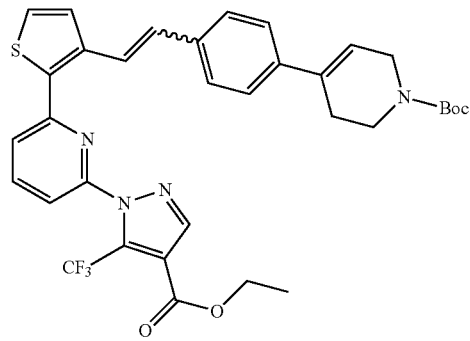 [SMILES: CCOC(=O)c1cnn(-c2cccc(-c3sccc3C=Cc3ccc(C4=CCN(C(=O)OC(C)(C)C)CC4)cc3)n2)c1C(F)(F)F]

The title compound was synthesized in a similar manner to the preparation of Intermediate 2-1-A starting with ethyl 1-(6-(3-(4-bromostyryl)thiophen-2-yl)pyridin-2-yl)-5-(trifluoromethyl)-1H-pyrazole-4-carboxylate using tert-butyl 4-(4,4,5,5-tetramethyl-1,3,2-dioxaborolan-2-yl)-5,6-dihydropyridine-1(2H)-carboxylate. MS (ESI+) m/z 651.3 (M+H).

Example 27. 1-(6-(3-(4-(1-(Cyclopropanecarbonyl)piperidin-4-yl)phenethyl)thiophen-2-yl)pyridin-2-yl)-5-(trifluoromethyl)-1H-pyrazole-4-carboxylic acid

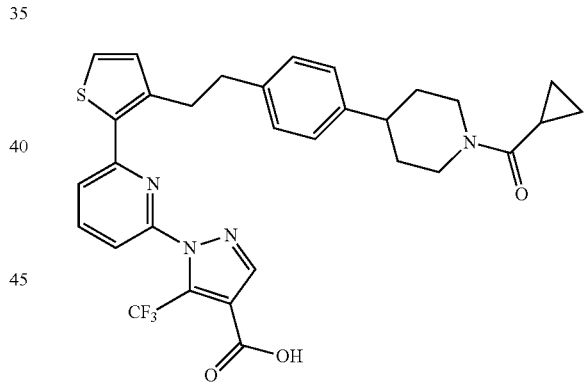

Hydrogenation of Example 27-B, tert-Butyl 4-(4-(2-(2-(6-(4-(ethoxycarbonyl)-5-(trifluoromethyl)-1H-pyrazol-1-yl)pyridin-2-yl)thiophen-3-yl)vinyl)phenyl)-5,6-dihydropyridine-1(2H)-carboxylate, in a fashion analogous to the preparation of Example 25-B, and subsequent treatment with TFA followed by cyclopropylcarbonyl chloride in manner analogous to the transformation outlined for the preparations of Example 1-B and Example 1-C, followed lastly by saponification as described for the procedure to prepare Example 1 furnished, after purification by SFC (stationary phase; PrincetonSFC 2-Ethylpyridine 5 μm, 21×150 mm: Mobile phase gradient Methanol/CO$_2$) in place of crystallization, the title compound, 146434441-(cyclopropanecarbonyl)piperidin-4-yl)phenethyl)thiophen-2-yl)pyridin-2-yl)-5-(trifluoromethyl)-1H-pyrazole-4-carboxylic acid. $^1$H NMR (400 MHz, CD$_3$OD) δ 8.16 (s, 1H), 7.98 (t, J=7.9 Hz, 1H), 7.59 (dd, J=8.0, 0.8 Hz, 1H), 7.51 (dd, J=7.9, 0.8 Hz, 1H), 7.44 (d, J=5.1 Hz, 1H), 7.00 (d, J=5.1 Hz, 1H), 6.88 (d, J=1.9 Hz, 1H), 6.85-6.66 (m, 2H), 4.63 (d, J=12.7 Hz, 1H), 4.44 (d, J=13.5 Hz, 1H), 3.25-3.16 (m, 2H), 2.84 (dd, J=8.7, 6.7 Hz, 2H), 2.79-2.61 (m, 3H), 2.10 (s, 3H), 2.06-1.94 (m, 1H), 1.88 (d, J=13.1 Hz, 1H), 1.80 (d, J=13.0 Hz, 1H), 1.69-1.41 (m, 2H), 0.95-0.71 (m, 4H). HRMS calcd. for $C_{31}H_{30}F_3N_4O_3S$ (M+H) 595.1991, found 595.2010.

Example 28. 1-(6-(3-(((4-(1-(Cyclopropanecarbonyl)piperidin-4-yl)phenyl)amino)methyl)thiophen-2-yl)pyridin-2-yl)-5-(trifluoromethyl)-1H-pyrazole-4-carboxylic acid

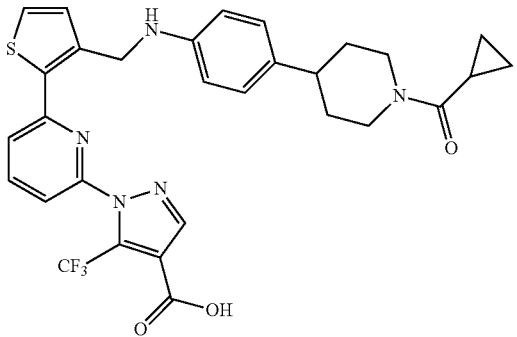 [SMILES: O=C(O)c1cnn(-c2cccc(-c3sccc3CNc3ccc(C4CCN(C(=O)C5CC5)CC4)cc3)n2)c1C(F)(F)F]

Reaction of Intermediate 4-1-A with tert-butyl 4-(4-aminophenyl)piperidine-1-carboxylate (CAS#170011-57-1), in a fashion analogous Example 15-A, afforded a Boc protected amine which was deprotected analogous to the transformation outlined in Example 1-B, the subsequent amine was then be reacted with cyclopropanecarboxylic acid in a similar manner to the procedure as described in Example 11-C. The resulting product was saponified as described in Example 11. $^1$H NMR (400 MHz, $CD_3OD$) δ 8.01 (t, J=7.9 Hz, 1H), 7.93 (d, J=0.8 Hz, 1H), 7.78 (dd, J=7.9, 0.8 Hz, 1H), 7.55 (dd, J=8.0, 0.7 Hz, 1H), 7.43 (d, J=5.1 Hz, 1H), 7.16 (d, J=5.2 Hz, 1H), 7.01-6.92 (m, 2H), 6.61-6.52 (m, 2H), 4.61 (d, J=13.0 Hz, 1H), 4.50 (s, 2H), 4.42 (d, J=13.6 Hz, 1H), 3.27-3.17 (m, 1H), 2.78-2.61 (m, 2H), 1.99 (tt, J=8.0, 4.8 Hz, 1H), 1.95-1.75 (m, 2H), 1.68-1.42 (m, 2H), 0.94-0.74 (m, 4H). HRMS calcd. for $C_{30}H_{29}F_3N_5O_3S$ (M+H) 596.1943, found 596.1943.

Example 29

Example 29-A. Ethyl 1-(6-(3-((2-methyl-4-(1-(oxetan-3-yl)piperidin-4-yl)phenoxy)methyl)thiophen-2-yl)pyridin-2-yl)-5-(trifluoromethyl)-1H-pyrazole-4-carboxylate

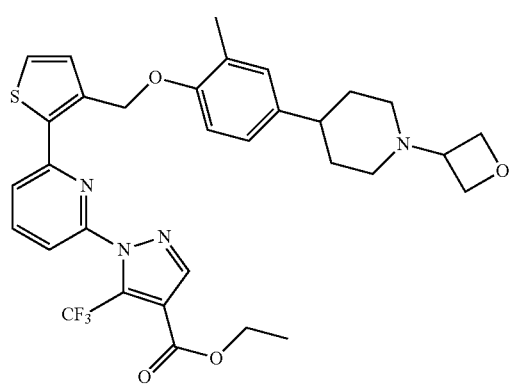 [SMILES: CCOC(=O)c1cnn(-c2cccc(-c3sccc3COc3ccc(C4CCN(C5COC5)CC4)cc3C)n2)c1C(F)(F)F]

A solution of ethyl 1-(6-(3-((2-methyl-4-(piperidin-4-yl)phenoxy)methyl)thiophen-2-yl)pyridin-2-yl)-5-(trifluoromethyl)-1H-pyrazole-4-carboxylate (Example 11-B) (100 mg, 0.175 mmol) and oxetan-3-one (CAS#6704-31-0) (15.2 mg, 0.210 mmol) in acetic acid (2 mL) was stirred at room temperature for 1 h. To the mixture in the acetic acid solution was then added NaB(OAc)$_3$H (111 mg, 0.526 mmol), and then the whole mixture was stirred for 1 h. To the mixture was then added another portion of NaB(OAc)$_3$H (111 mg, 0.526 mmol). The mixture was continued to stir for another 16 h. The reaction mixture was then poured into H2O, and then mixture was neutralized with aq. ammonium hydroxide (ca. 28%). The mixture was then extracted with EtOAc. The organic layer was concentrated. The resulting residue was purified by silica gel flash column chromatography (0-30% EtOAc/heptane) to afford the title compound. MS (ESI+) m/z 627.3 (M+H).

Example 29. 1-(6-(3-((2-Methyl-4-(1-(oxetan-3-yl)piperidin-4-yl)phenoxy)methyl)thiophen-2-yl)pyridin-2-yl)-5-(trifluoromethyl)-1H-pyrazole-4-carboxylic acid

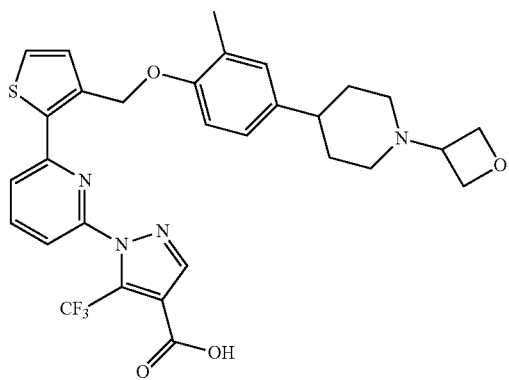 [SMILES: Cc1cc(C2CCN(C3COC3)CC2)ccc1OCc1ccsc1-c1cccc(-n2ncc(C(=O)O)c2C(F)(F)F)n1]

A mixture of ethyl 1-(6-(3-((2-methyl-4-(1-(oxetan-3-yl)piperidin-4-yl)phenoxy)methyl)thiophen-2-yl)pyridin-2-yl)-5-(trifluoromethyl)-1H-pyrazole-4-carboxylate (50 mg, 0.080 mmol) and aq. LiOH (1 M, 0.319 mL, 0.319 mmol) in $CH_3CN$ (2 mL) was stirred at 50° C. for 2 h. The reaction mixture was treated with 1M aq. HCl (ca. 0.32 mL), and then filtered. The filtrate was directly purified by RP-HPLC (HC-C) to afford the title compound. $^1$H NMR (400 MHz, $CD_3OD$) δ 8.01 (t, J=7.9 Hz, 1H), 7.96-7.91 (m, 1H), 7.76 (dd, J=7.9, 0.8 Hz, 1H), 7.58 (dd, J=8.0, 0.7 Hz, 1H), 7.51 (d, J=5.2 Hz, 1H), 7.26 (d, J=5.2 Hz, 1H), 7.00 (d, J=2.2 Hz, 1H), 6.96 (dd, J=8.3, 2.4 Hz, 1H), 6.81 (d, J=8.4 Hz, 1H), 5.33 (s, 2H), 4.71 (t, J=6.8 Hz, 2H), 4.67-4.60 (m, 2H), 3.64-3.52 (m, 1H), 2.93 (d, J=11.0 Hz, 2H), 2.48 (ddt, J=11.8, 8.1, 4.1 Hz, 1H), 2.16 (s, 3H), 2.09-1.97 (m, 2H), 1.88-1.68 (m, 4H). HRMS calcd. for $C_{30}H_{30}F_3N_4O_4S$ (M+H) 599.1940, found 599.1971.

Example 30

Example 30-A. Ethyl 1-(6-(3-((4-bromo-3-formylphenoxy)methyl)-5-methylthiophen-2-yl)pyridin-2-yl)-5-(trifluoromethyl)-1H-pyrazole-4-carboxylate

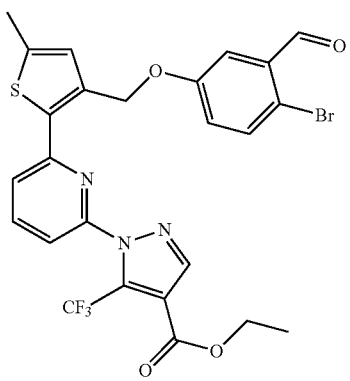 [SMILES: CCOC(=O)c1cnn(-c2cccc(-c3sc(C)cc3COc3ccc(Br)c(C=O)c3)n2)c1C(F)(F)F]

The title compound was synthesized as described for the preparation of Example 17-A but using with ethyl 1-(6-(3-(hydroxymethyl)-5-methylthiophen-2-yl)pyridin-2-yl)-5-(trifluoromethyl)-1H-pyrazole-4-carboxylate (Intermediate 4-1-D) instead of Intermediate 4-2-10 and 2-bromo-5-hydroxybenzaldehyde (CAS#2973-80-0) in the place of Intermediate 2-4. MS (ESI+) m/z 594.08 (M+H).

Example 30-B. Ethyl 1-(6-(3-((4-bromo-3-(hydroxymethyl)phenoxy)methyl)-5-methylthiophen-2-yl)pyridin-2-yl)-5-(trifluoromethyl)-1H-pyrazole-4-carboxylate

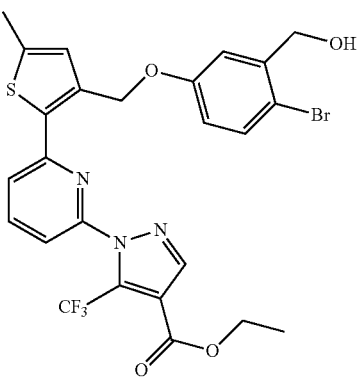 [SMILES: CCOC(=O)c1cnn(-c2cccc(-c3sc(C)cc3COc3ccc(Br)c(CO)c3)n2)c1C(F)(F)F]

To a solution of ethyl 1-(6-(3-((4-bromo-3-formylphenoxy)methyl)-5-methylthiophen-2-yl)pyridin-2-yl)-5-(trifluoromethyl)-1H-pyrazole-4-carboxylate (0.346 g, 0.419 mmol) in MeOH (2.80 mL) and THF (1.4 mL) at 0° C. was added NaBH$_4$ (0.032 g, 0.839 mmol). The mixture was then stirred for 1 h, and then diluted with H$_2$O and EtOAc. The organic layer was then separated, and dried over Na$_2$SO$_4$, filtered, and then concentrated. The resulting residue was purified by silica gel flash column chromatography (heptane/EtOAc=1/0 to 0/1) to afford the title compound. MS (ESI+) m/z 596.1 (M+H).

Example 30-C. tert-Butyl 4-(4-((2-(6-(4-(ethoxycarbonyl)-5-(trifluoromethyl)-1H-pyrazol-1-yl)pyridin-2-yl)-5-methylthiophen-3-yl)methoxy)-2-(hydroxymethyl)phenyl)-5,6-dihydropyridine-1(2H)-carboxylate

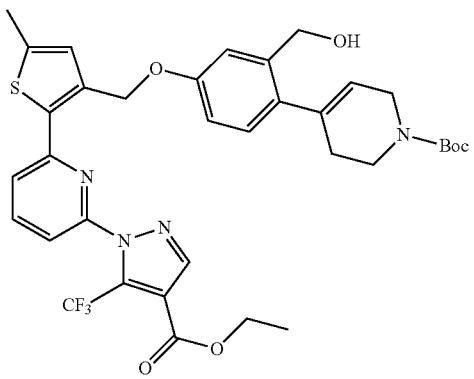 [SMILES: CCOC(=O)c1cnn(-c2cccc(-c3sc(C)cc3COc3ccc(C4=CCN(C(=O)OC(C)(C)C)CC4)c(CO)c3)n2)c1C(F)(F)F]

The title compound was synthesized in a similar manner to the preparation of Intermediate 2-1-A starting with ethyl 1-(6-(3-((4-bromo-3-(hydroxymethyl)phenoxy)methyl)-5-methylthiophen-2-yl)pyridin-2-yl)-5-(trifluoromethyl)-1H-pyrazole-4-carboxylate using 2-(3,6-dihydro-2H-pyran-4-yl)-4,4,5,5-tetramethyl-1,3,2-dioxaborolane. MS (ESI+) m/z 699.5 (M+H).

Example 30-D. tert-Butyl 4-(4-((2-(6-(4-(ethoxycarbonyl)-5-(trifluoromethyl)-1H-pyrazol-1-yl)pyridin-2-yl)-5-methylthiophen-3-yl)methoxy)-2-(hydroxymethyl)phenyl)piperidine-1-carboxylate

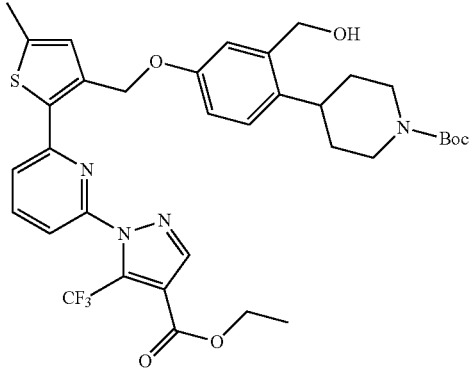 [SMILES: CCOC(=O)c1cnn(-c2cccc(-c3sc(C)cc3COc3ccc(C4CCN(C(=O)OC(C)(C)C)CC4)c(CO)c3)n2)c1C(F)(F)F]

A mixture of ethyl 1-(6-(3-((4-bromo-3-(hydroxymethyl)phenoxy)methyl)-5-methylthiophen-2-yl)pyridin-2-yl)-5-(trifluoromethyl)-1H-pyrazole-4-carboxylate (0.18 g, 0.258 mmol) and 10% Pd/C (82 mg) in EtOH (5.15 mL) was stirred at 78° C. for 1.5 h under H$_2$ atmosphere. The reaction mixture was then cooled to room temperature, and then filtered through a plug of Celite®. The filtrate was then concentrated to furnish the title compound. MS (ESI+) m/z 701.4 (M+H).

Example 30-E. Ethyl 1-(6-(3-((3-(hydroxymethyl)-4-(piperidin-4-yl)phenoxy)methyl)-5-methylthiophen-2-yl)pyridin-2-yl)-5-(trifluoromethyl)-1H-pyrazole-4-carboxylate

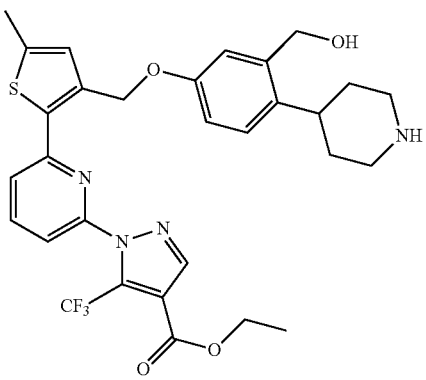 [SMILES: CCOC(=O)c1cnn(-c2cccc(-c3sc(C)cc3COc3ccc(C4CCNCC4)c(CO)c3)n2)c1C(F)(F)F]

To a solution of tert-butyl 4-(4-((2-(6-(4-(ethoxycarbonyl)-5-(trifluoromethyl)-1H-pyrazol-1-yl)pyridin-2-yl)-5-methylthiophen-3-yl)methoxy)-2-(hydroxymethyl)phenyl)piperidine-1-carboxylate (100 mg, 0.143 mmol) in CH$_2$Cl$_2$ (1 mL) was added 4M HCl in 1,4-dioxane (0.178 mL, 0.714 mmol). The mixture was then stirred at room temperature for 2 h, and then concentrated to furnish the title compound as an HCl salt. MS (ESI+) m/z 601.3 (M+H).

Example 30. 1-(6-(3-((4-(1-(Cyclopropanecarbonyl)piperidin-4-yl)-3-(hydroxymethyl)phenoxy)methyl)-5-methylthiophen-2-yl)pyridin-2-yl)-5-(trifluoromethyl)-1H-pyrazole-4-carboxylic acid

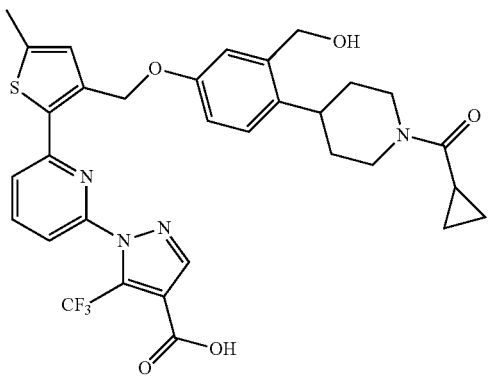 [SMILES: Cc1cc(COc2ccc(C3CCN(C(=O)C4CC4)CC3)c(CO)c2)c(-c2cccc(-n3ncc(C(=O)O)c3C(F)(F)F)n2)s1]

Ethyl 1-(6-(3-((3-(hydroxymethyl)-4-(piperidin-4-yl)phenoxy)methyl)-5-methylthiophen-2-yl)pyridin-2-yl)-5-(trifluoromethyl)-1H-pyrazole-4-carboxylate was reacted with cyclopropylcarbonyl chloride analogous to the transformation outlined in Example 1-C. The resulting product was saponified as described in Example 11 to furnish the title compound. $^1$H NMR (400 MHz, DMSO-d$_6$) δ 8.23 (s, 1H) 8.15 (t, J=7.95 Hz, 1H) 7.76 (d, J=7.70 Hz, 1H) 7.66 (d, J=7.70 Hz, 1H) 7.13 (d, J=8.56 Hz, 1H) 6.96-7.03 (m, 2H) 6.82 (dd, J=8.56, 2.81 Hz, 1H) 5.23 (s, 2H) 4.28-4.60 (m, 4H) 3.17 (d, J=11.86 Hz, 1H) 2.89-3.02 (m, 1H) 2.55-2.65 (m, 1H) 2.47 (d, J=0.98 Hz, 3H) 1.93-2.05 (m, 1H) 1.31-1.82 (m, 4H) 0.63-0.81 (m, 4H). HRMS calcd. for C$_{32}$H$_{32}$F$_3$N$_4$O$_5$S (M+H) 641.2046, found 641.2057.

Example 31

Example 31-A. Ethyl 1-(6-(3-methoxythiophen-2-yl)pyridin-2-yl)-5-(trifluoromethyl)-1H-pyrazole-4-carboxylate

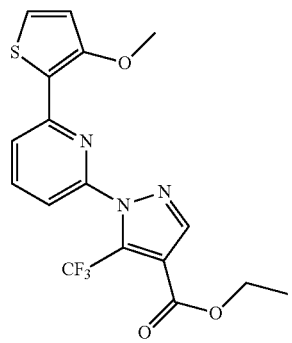 [SMILES: CCOC(=O)c1cnn(-c2cccc(-c3sccc3OC)n2)c1C(F)(F)F]

The title compound was synthesized in a similar manner as described in Example 1-A using Intermediate 1-1 and 2-bromo-3-methoxythiophene (CAS#174756-14-0). MS (ESI+) m/z 398.0 (M+H).

Example 31-B. 1-(6-(3-Hydroxythiophen-2-yl)pyridin-2-yl)-5-(trifluoromethyl)-1H-pyrazole-4-carboxylic acid

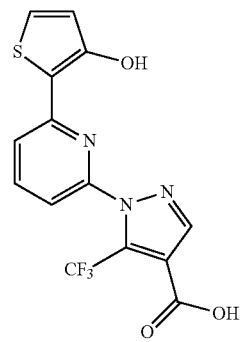 [SMILES: O=C(O)c1cnn(-c2cccc(-c3sccc3O)n2)c1C(F)(F)F]

A mixture of ethyl 1-(6-(3-methoxythiophen-2-yl)pyridin-2-yl)-5-(trifluoromethyl)-1H-pyrazole-4-carboxylate (567 mg, 1.43 mmol) and 48% aq. HBr (3 mL, 5 mmol) was stirred under reflux conditions for 64 h. The reaction mixture was then concentrated directly to furnish the title compound. MS (ESI+) m/z 356.0 (M+H).

Example 31-C. Methyl 1-(6-(3-hydroxythiophen-2-yl)pyridin-2-yl)-5-(trifluoromethyl)-1H-pyrazole-4-carboxylate

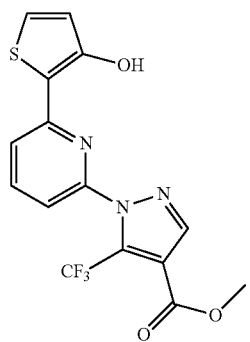 [SMILES: COC(=O)c1cnn(-c2cccc(-c3sccc3O)n2)c1C(F)(F)F]

A mixture of 1-(6-(3-hydroxythiophen-2-yl)pyridin-2-yl)-5-(trifluoromethyl)-1H-pyrazole-4-carboxylic acid (283 mg, 0.80 mmol) and 4M HCl in 1,4-dioxane (14 mL) in MeOH (14 mL) was stirred for 16 h at room temperature, and then at 40° C. for 24 h. The reaction mixture was then rendered basic by the addition of sat. aq. NaHCO$_3$. The mixture was then extracted three times with CH$_2$Cl$_2$. The combined organic extracts were concentrated. The resulting residue was purified by silica gel flash column chromatography (hexane/EtOAc=9/1 to 8/1) to afford the title compound. MS (ESI+) m/z 370.0 (M+H).

Example 31-D. tert-Butyl 4-(4-(((2-(6-(4-(methoxycarbonyl)-5-(trifluoromethyl)-1H-pyrazol-1-yl)pyridin-2-yl)thiophen-3-yl)oxy)methyl)phenyl)piperidine-1-carboxylate

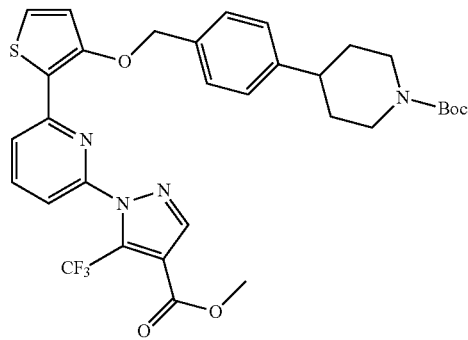 [SMILES: COC(=O)c1cnn(-c2cccc(-c3sccc3OCc3ccc(C4CCN(C(=O)OC(C)(C)C)CC4)cc3)n2)c1C(F)(F)F]

To a solution of tert-butyl 4-(4-(hydroxymethyl)phenyl)piperidine-1-carboxylate (CAS#864359-18-2, 300 mg, 1.03 mmol) in CH$_2$Cl$_2$ (6 mL) at 0° C. was added triethylamine (431 mL, 3.09 mmol), followed by MsCl (119 μL, 1.54 mmol). The mixture was then stirred at 0° C. for 0.5 h, and then stirred at room temperature for 3.5 h, and then diluted with CH$_2$Cl$_2$. The mixture was then washed with H$_2$O, dried over MgSO$_4$, filtered and then concentrated. The resulting residue was dissolved in DMF (10 mL). To the solution was added methyl 146-(3-hydroxythiophen-2-yl)pyridin-2-yl)-5-(trifluoromethyl)-1H-pyrazole-4-carboxylate (338 mg, 0.9 mmol) and K$_2$CO$_3$ (253 mg, 1.83 mmol). The mixture was then stirred at 50° C. for 3 days, and then cooled to room temperature. The mixture was then diluted with H$_2$O. The mixture was then extracted three times with EtOAc. The combined organic extracts were dried over Na$_2$SO$_4$, filtered, and then concentrated. The resulting residue was purified by silica gel flash column chromatography (hexane/EtOAc=9/1 to 3/1) to afford the title compound. MS (ESI+) m/z 643.1 (M+H).

Example 31. 1-(6-(3-((4-(1-Propionylpiperidin-4-yl)benzyl)oxy)thiophen-2-yl)pyridin-2-yl)-5-(trifluoromethyl)-1H-pyrazole-4-carboxylic acid

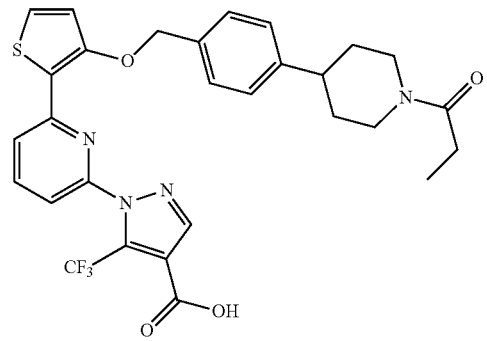 [SMILES: CCC(=O)N1CCC(c2ccc(COc3ccsc3-c3cccc(-n4ncc(C(=O)O)c4C(F)(F)F)n3)cc2)CC1]

The Boc group of tert-Butyl 4-(4-(((2-(6-(4-(methoxycarbonyl)-5-(trifluoromethyl)-1H-pyrazol-1-yl)pyridin-2-yl)thiophen-3-yl)oxy)methyl)phenyl)piperidine-1-carboxylate was removed analogous to the transformation outlined in Example 1-B, and the subsequent amine was then reacted with cyclopropanecarbonyl chloride in a similar manner to the procedure as described in Example 1-C. The resulting product was saponified as described in Example 7 to furnish the title compound. $^1$H NMR (400 MHz, DMSO-d$_6$) δ 13.45 (br. s., 1H), 8.26 (br. s, 1H), 8.19 (dd, J=0.73, 7.95 Hz, 1H), 8.09 (t, J=7.95 Hz, 1H), 7.64 (d, J=5.50 Hz, 1H), 7.54 (dd, J=0.73, 7.82 Hz, 1H), 7.42-7.48 (m, 2H), 7.27-7.33 (m, 2H), 7.23 (d, J=5.62 Hz, 1H), 5.32 (s, 2H), 4.49-4.61 (m, 1H), 3.89-4.02 (m, 1H), 3.01-3.14 (m, 1H), 2.72-2.85 (m, 1H), 2.54-2.64 (m, 1H), 2.29-2.39 (m, 2H), 1.72-1.86 (m, 2H), 1.36-1.63 (m, 2H), 1.00 (t, J=7.46 Hz, 3H). HRMS calcd. for C$_{29}$H$_{28}$F$_3$N$_4$O$_4$S (M+H) 585.1783, found 585.1796.

Example 32

Example 32-A. tert-Butyl 4-(4-((2-(6-(4-(ethoxycarbonyl)-5-(trifluoromethyl)-1H-pyrazol-1-yl)pyridin-2-yl)-5-methylthiophen-3-yl)methoxy)-3-(trifluoromethyl)phenyl)piperidine-1-carboxylate

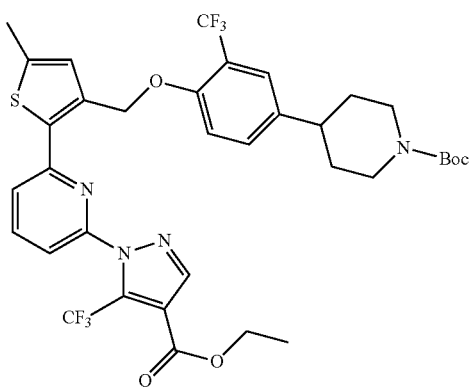 [SMILES: CCOC(=O)c1cnn(-c2cccc(-c3sc(C)cc3COc3ccc(C4CCN(C(=O)OC(C)(C)C)CC4)cc3C(F)(F)F)n2)c1C(F)(F)F]

To a solution of Intermediate 2-3-1 (126 mg, 0.365 mmol) and Intermediate 4-1-D (100 mg, 0.243 mmol) in toluene (2.5 mL) was added 2-(tributylphoranylidene)acetonitrile (0.1 mL, 0.381 mmol). The mixture was then stirred at 70° C. for 18.5 h and then cooled to room temperature. The reaction mixture was directly purified by silica gel flash column (heptane/EtOAc=1/0 to 0/1) to afford the title compound. MS (ESI+) m/z 739.1 (M+H).

Example 32-B. Ethyl 1-(6-(3-((4-(1-(cyclopropanecarbonyl)piperidin-4-yl)-2-(trifluoromethyl)phenoxy)methyl)-5-methylthiophen-2-yl)pyridin-2-yl)-5-(trifluoromethyl)-1H-pyrazole-4-carboxylate

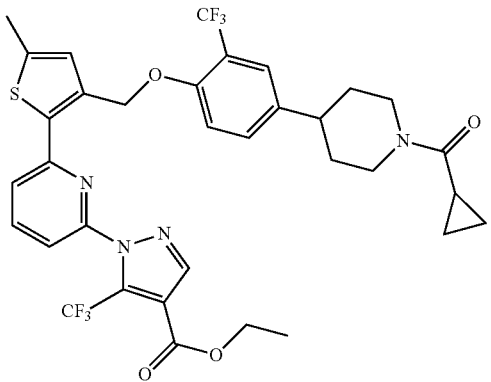 [SMILES: CCOC(=O)c1cnn(-c2cccc(-c3sc(C)cc3COc3ccc(C4CCN(C(=O)C5CC5)CC4)cc3C(F)(F)F)n2)c1C(F)(F)F]

A mixture of tert-butyl 4-(4-((2-(6-(4-(ethoxycarbonyl)-5-(trifluoromethyl)-1H-pyrazol-1-yl)pyridin-2-yl)-5-methylthiophen-3-yl)methoxy)-3-(trifluoromethyl)phenyl)piperidine-1-carboxylate (180.7 mg, 0.245 mmol) and TFA (0.34 mL, 4.40 mmol) in $CH_2Cl_2$ (3 mL) was stirred at room temperature for 3 h. To the mixture was then added DIPEA (1.025 ml, 5.87 mmol), followed by cyclopropanecarbonyl chloride (0.022 mL, 0.245 mmol). The mixture was then stirred at room temperature for 20 h. The reaction mixture was then diluted with $H_2O$, and then extracted with EtOAc. The organic layer was then dried over $Na_2SO_4$, filtered, and then concentrated. The resulting residue was purified by RP-HPLC (HC-A) to afford the title compound. MS (ESI+) m/z 707.1 (M+H).

Example 32. 1-(6-(3-((4-(1-(Cyclopropanecarbonyl)piperidin-4-yl)-2-(trifluoromethyl)phenoxy)methyl)-5-methylthiophen-2-yl)pyridin-2-yl)-5-(trifluoromethyl)-1H-pyrazole-4-carboxylic acid

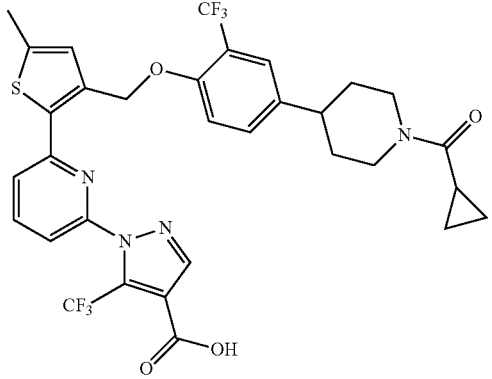 [SMILES: Cc1cc(COc2ccc(C3CCN(C(=O)C4CC4)CC3)cc2C(F)(F)F)c(-c2cccc(-n3ncc(C(=O)O)c3C(F)(F)F)n2)s1]

To a solution of ethyl 1-(6-(3-((4-(1-(cyclopropanecarbonyl)piperidin-4-yl)-2-(trifluoromethyl)phenoxy)methyl)-5-methylthiophen-2-yl)pyridin-2-yl)-5-(trifluoromethyl)-1H-pyrazole-4-carboxylate (33 mg, 0.047 mmol) in THF/MeOH/$H_2O$ (1 mL/1 mL/1 mL) was added LiOH (20.13 mg, 0.841 mmol). The mixture was then stirred at room temperature for 20 h, and then diluted with $H_2O$. The mixture was then rendered acidic by the addition of 1M aq. HCl until pH=2. The mixture was then extracted with EtOAc. The organic layer was then dried with $MgSO_4$, filtered and concentrated to afford the title compound. $^1H$ NMR (400 MHz, $CD_3OD$) δ 8.15 (s, 1H), 8.04 (t, J=7.9 Hz, 1H), 7.76 (d, J=8.1 Hz, 1H), 7.53 (d, J=7.5 Hz, 1H), 7.43 (d, J=2.2 Hz, 1H), 7.35 (d, J=8.9 Hz, 1H), 7.01 (d, J=8.7 Hz, 1H), 6.98 (d, J=1.3 Hz, 1H), 5.40 (s, 2H), 4.60-4.71 (m, 1H), 4.41-4.53 (m, 1H), 2.80-2.93 (m, 1H), 2.74 (t, J=13.0 Hz, 1H), 2.51 (d, J=0.8 Hz, 3H), 1.79-2.06 (m, 3H), 1.45-1.73 (m, 2H), 0.75-0.97 (m, 4H). HRMS calcd. for $C_{32}H_{29}F_6N_4O_4S$ (M+H) 679.1814, found 679.1848.

Example 33

The following compounds were synthesized by a similar method as described above for Example 32 using the appropriate starting materials as delineated in the table below.

| Example | Structure/Chemical Name | Starting materials | NMR and HRMS |
| --- | --- | --- | --- |
| 33-1 | 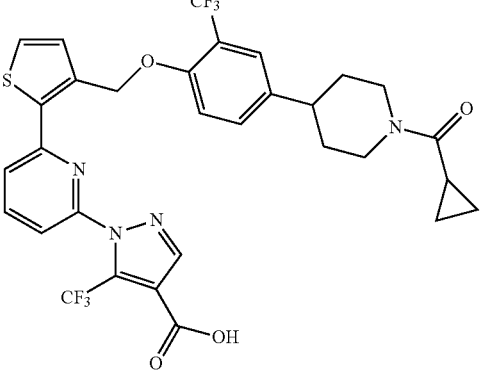<br>1-(6-(3-((4-(1-(Cyclopropanecarbonyl)piperidin-4-yl)-2-(trifluoromethyl)phenoxy)methyl)thiophen-2-yl)pyridin-2-yl)-5-(trifluoromethyl)-1H-pyrazole-4-carboxylic acid | Intermediate 2-3-1, Intermediate 4-1-B, and cyclopropane-carbonyl chloride | $^1H$ NMR (400 MHz, $CD_3OD$) δ 8.05 (t, J = 7.9 Hz, 1H), 7.98 (s, 1H), 7.80 (d, J = 7.8 Hz, 1H), 7.58 (dd, J = 7.9, 0.7 Hz, 1H), 7.53 (d, J = 5.2 Hz, 1H), 7.44 (d, J = 2.2 Hz, 1H), 7.39 (d, J = 8.2 Hz, 1H), 7.29 (d, J = 5.3 Hz, 1H), 7.05 (d, J = 8.6 Hz, 1H), 5.49 (s, 2H), 4.46 (d, J = 13.4 Hz, 3H), 2.85 (t, J = 12.3 Hz, 1H), 2.74 (s, 1H), 1.80-2.05 (m, 3H), 1.47-1.72 (m, 2H), 0.76-0.95 (m, 4H). HRMS calcd. for $C_{31}H_{27}F_6N_4O_4S$ (M + H) 665.1652, found 665.1694. |

-continued

| Example | Structure/Chemical Name | Starting materials | NMR and HRMS |
|---|---|---|---|
| 33-2 | 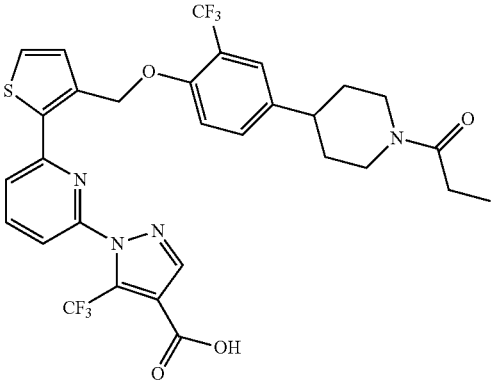 [SMILES: CCC(=O)N1CCC(c2ccc(OCc3ccsc3-c3cccc(-n4ncc(C(=O)O)c4C(F)(F)F)n3)c(C(F)(F)F)c2)CC1]<br>(6-(3-((4-(1-Propionylpiperidin-4-yl)-2-(trifluoromethyl)phenoxy)methyl)thiophen-2-yl)pyridin-2-yl)-5-(trifluoromethyl)-1H-pyrazole-4-carboxylic acid | Intermediate 2-3-1, Intermediate 4-1-B, and propionyl chloride | $^1$H NMR (400 MHz, CD$_3$OD) δ 8.16 (dd, J = 8.6, 0.7 Hz, 1H), 8.09 (t, J = 7.9 Hz, 1H), 7.86 (dd, J = 7.9, 0.7 Hz, 1H), 7.59 (dd, J = 7.9, 0.7 Hz, 1H), 7.55 (d, J = 5.2 Hz, 1H), 7.43 (d, J = 2.3 Hz, 1H), 7.34 (dd, J = 8.6, 2.3 Hz, 1H), 7.30 (d, J = 5.2 Hz, 1H), 7.03 (d, J = 8.6 Hz, 1H), 5.47 (s, 2H), 4.64-4.73 (m, 1H), 4.02-4.12 (m, 1H), 3.15-3.24 (m, 1H), 2.76-2.88 (m, 1H), 2.65-2.75 (m, 1H), 2.45 (q, J = 7.5 Hz, 2H), 1.81-1.95 (m, 2H), 1.46-1.67 (m, 2H), 1.14 (t, J = 7.5 Hz, 3H). HRMS calcd. for C$_{30}$H$_{27}$F$_6$N$_4$O$_4$S (M + H) 653.1657, found 653.1683. |

Example 34

Example 34-A. tert-Butyl 4-(4-((4-cyclopropyl-2-(6-(4-(ethoxycarbonyl)-5-(trifluoromethyl)-1H-pyrazol-1-yl)pyridin-2-yl)-5-methylthiophen-3-yl)methoxy)-3-methylphenyl)piperidine-1-carboxylate

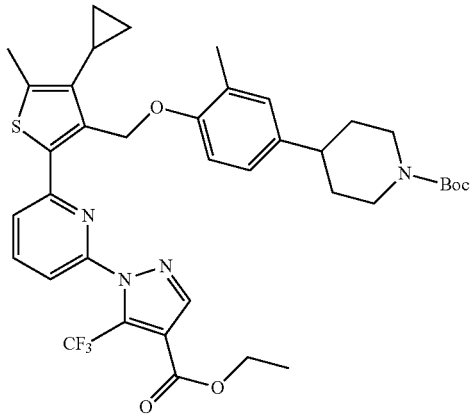 [SMILES: CCOC(=O)c1cnn(-c2cccc(-c3sc(C)c(C4CC4)c3COc3ccc(C4CCN(C(=O)OC(C)(C)C)CC4)cc3C)n2)c1C(F)(F)F]

To a solution of Intermediate 4-5 (80 mg, 0.177 mmol) and Intermediate 2-1 (70 mg, 0.240 mmol) in toluene (1.5 mL) was added 2-(tributylphosphoranylidene)acetonitrile (100 μL, 0.381 mmol). The mixture was then stirred at 80° C. for 4 h, and cooled to room temperature. The mixture was directly purified by silica gel flash column chromatograph (heptane/EtOAc=76/24) to afford the title compound. MS (ESI+) m/z 725.2 (M+H).

Example 34-B. Ethyl 1-(6-(4-cyclopropyl-5-methyl-3-((2-methyl-4-(piperidin-4-yl)phenoxy)methyl)thiophen-2-yl)pyridin-2-yl)-5-(trifluoromethyl)-1H-pyrazole-4-carboxylate

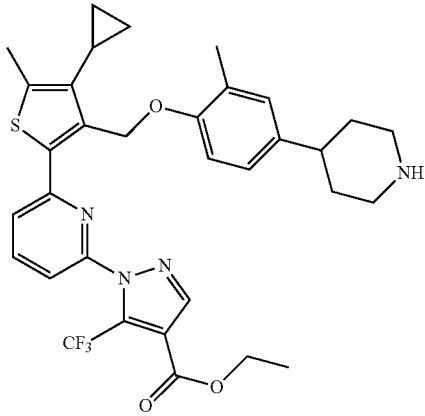 [SMILES: CCOC(=O)c1cnn(-c2cccc(-c3sc(C)c(C4CC4)c3COc3ccc(C4CCNCC4)cc3C)n2)c1C(F)(F)F]

A solution of tert-butyl 4-(4-((4-cyclopropyl-2-(6-(4-(ethoxycarbonyl)-5-(trifluoromethyl)-1H-pyrazol-1-yl)pyridin-2-yl)-5-methylthiophen-3-yl)methoxy)-3-methylphenyl)piperidine-1-carboxylate (160 mg, 0.221 mmol) in TFA/CH$_2$Cl$_2$ (2 mL/6 mL) was stirred at room temperature for 2 h, and then diluted with EtOAc. The mixture was rendered basic by the addition of 5% aq. NaHCO$_3$. The mixture was then stirred at room temperature for 1 h. The mixture was then washed successively with H$_2$O and brine. The organic layer was separated, dried over Na$_2$SO$_4$, filtered, and then concentrated to furnish the title compound. MS (ESI+) m/z 625.1 (M+H).

177

Example 34-C. Ethyl 1-(6-(3-((4-(1-(cyclopropanecarbonyl)piperidin-4-yl)-2-methylphenoxy)methyl)-4-cyclopropyl-5-methylthiophen-2-yl)pyridin-2-yl)-5-(trifluoromethyl)-1H-pyrazole-4-carboxylate

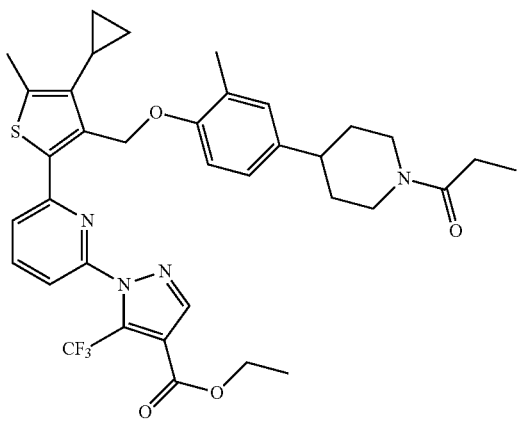 [SMILES: CCOC(=O)c1cnn(-c2cccc(-c3sc(C)c(C4CC4)c3COc3ccc(C4CCN(C(=O)CC)CC4)cc3C)n2)c1C(F)(F)F]

To a suspension of ethyl 1-(6-(4-cyclopropyl-5-methyl-3-((2-methyl-4-(piperidin-4-yl)phenoxy)methyl)thiophen-2-yl)pyridin-2-yl)-5-(trifluoromethyl)-1H-pyrazole-4-carboxylate (100 mg, 0.160 mmol) in $CH_2Cl_2$/5% aq. $NaHCO_3$ (2 mL/2 mL) was added propionyl anhydride (20.52 μL, 0.160 mmol). The mixture was then stirred at room temperature for 3 h. The reaction was then quenched with N,N-dimethylethylenediamine. The mixture was then stirred at room temperature for 0.5 h. The mixture was then extracted with $CH_2Cl_2$. The organic phase was then washed successively with 1/1 water:satd. aq. $KHSO_4$, 5% aq. $NaHCO_3$, and brine. The organic layer was dried over $Na_2SO_4$, filtered, and then concentrated to furnish the title compound. MS (ESI+) m/z 681.2 (M+H).

178

Example 34. 1-(6-(3-((4-(1-(Cyclopropanecarbonyl)piperidin-4-yl)-2-methylphenoxy)methyl)-4-cyclopropyl-5-methylthiophen-2-yl)pyridin-2-yl)-5-(trifluoromethyl)-1H-pyrazole-4-carboxylic acid

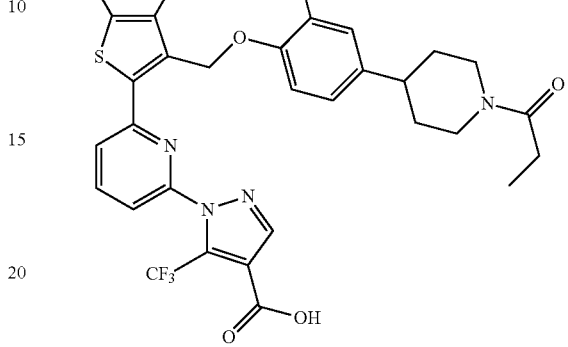

A mixture of ethyl 1-(6-(3-((4-(1-(cyclopropanecarbonyl)piperidin-4-yl)-2-methylphenoxy)methyl)-4-cyclopropyl-5-methylthiophen-2-yl)pyridin-2-yl)-5-(trifluoromethyl)-1H-pyrazole-4-carboxylate (109 mg, 0.160 mmol) and LiOH in $H_2O$ (300 μL, 0.300 mmol) in DMSO/THF (1 mL/0.5 mL) was stirred at 50° C. for 1.5 h, and then cooled to room temperature. The reaction mixture was then diluted with $CH_2Cl_2$. The mixture was then washed successively with 1/1 water:satd. aq. $KHSO_4$, $H_2O$, and brine. The organic layer was then dried over $Na_2SO_4$, filtered, and then concentrated. The resulting residue was purified by RP-HPLC (HC-A) to afford the title compound. $^1$H NMR (TFA salt, 400 MHz, $CD_3OD$) δ 8.10 (s, 1H), 7.95 (dd, J=7.80, 8.00 Hz, 1H), 7.72 (dd, J=0.69, 7.89 Hz, 1H), 7.52 (dd, J=0.63, 7.96 Hz, 1H), 6.96-7.01 (m, 2H), 6.90-6.95 (m, 1H), 5.26 (s, 2H), 4.64-4.72 (m, 1H), 4.02-4.12 (m, 1H), 3.15-3.24 (m, 1H), 2.66-2.77 (m, 2H), 2.53 (d, J=1.01 Hz, 3H), 2.46 (q, J=7.54 Hz, 2H), 2.06 (s, 3H), 1.84-1.95 (m, 2H), 1.48-1.72 (m, 3H), 1.15 (t, J=7.52 Hz, 3H), 0.83-0.93 (m, 2H), 0.60-0.66 (m, 2H). HRMS calcd. for $C_{34}H_{36}F_3N_4O_4S$ (M+H) 653.2409, found 653.2442.

Example 35

The following compounds were prepared by similar methods as described above for Example 34 with the propionyl anhydride replaced with the appropriate anhydride, carbamic chloride or acid chloride reagent as delineated in the table below.

| | Structure/Chemical Name | Starting materials | MS (ESI+) m/z |
|---|---|---|---|
| 35-1 | 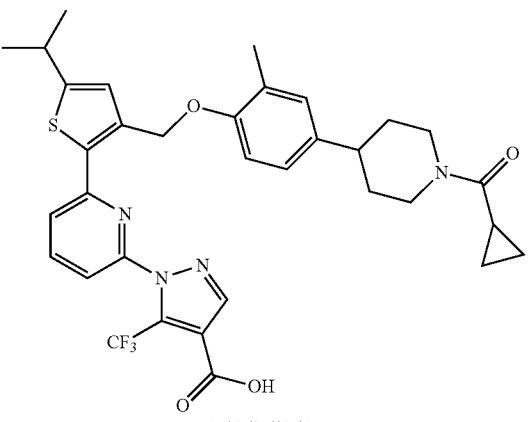<br>1-(6-(3-((4-(1-(Cyclopropanecarbonyl)piperidin-4-yl)-2-methylphenoxy)methyl)-5-isopropylthiophen-2-yl)pyridin-2-yl)-5-(trifluoromethyl)-1H-pyrazole-4-carboxylic acid | Intermediate 2-1, Intermediate 4-6, and cyclopropane-carbonyl chloride | $^1$H NMR (TFA salt, 400 MHz, CD$_3$OD) δ 8.15 (s, 1H), 8.02 (t, J = 8.0 Hz, 1H), 7.76 (dd, J = 0.6, 8.0 Hz, 1H), 7.52 (dd, J = 0.6, 8.0 Hz, 1H), 7.02 (d, J = 0.9 Hz, 1H), 6.98 (d, J = 2.0 Hz, 1H), 6.92 (dd, J = 2.0, 8.3 Hz, 1H), 6.77 (d, J = 8.3 Hz, 1H), 5.25 (s, 2H), 4.58-4.68 (m, 1H), 4.40-4.51 (m, 1H), 3.15-3.28 (m, 2H), 2.67-2.78 (m, 2H), 2.12 (s, 3H), 1.96-2.04 (m, 1H), 1.87-1.94 (m, 1H), 1.77-1.86 (m, 1H), 1.45-1.69 (m, 2H), 1.35 (d, J = 6.9 Hz, 6H), 0.72-0.96 (m, 4H). HRMS calcd. for C$_{34}$H$_{36}$F$_3$N$_4$O$_4$S (M + H) 653.2409, found 653.2436. |
| 35-2 | 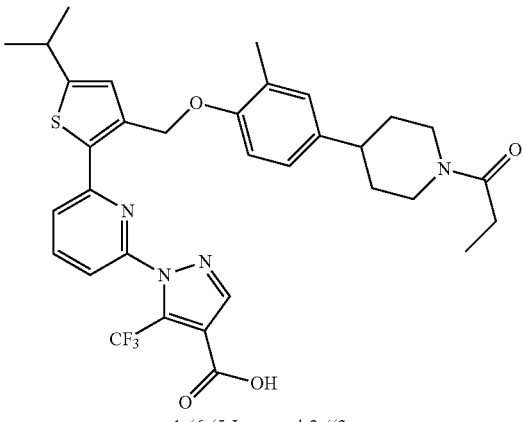<br>1-(6-(5-Isopropyl-3-((2-methyl-4-(1-propionylpiperidin-4-yl)phenoxy)methyl)thiophen-2-yl)pyridin-2-yl)-5-(trifluoromethyl)-1H-pyrazole-4-carboxylic acid | Intermediate 2-1, Intermediate 4-6, and propionic anhydride | $^1$H NMR (TFA salt, 400 MHz, DMSO-d$_6$) δ 13.45 (br. s., 1H), 8.29 (s, 1H), 8.15 (dd, J = 7.96, 7.83 Hz, 1H), 7.80 (d, J = 7.96 Hz, 1H), 7.66 (d, J = 7.83 Hz, 1H), 7.08 (d, J = 0.88 Hz, 1H), 7.00-7.04? (m, 1H), 6.94-7.00 (m, 1H), 6.85-6.93 (m, 1H), 5.24 (s, 2H), 4.48-4.58 (m, 1H), 3.90-3.98 (m, 1H), 3.12-3.24 (m, 1H), 3.00-3.11 (m, 1H), 2.54-2.70 (m, 2H), 2.34 (q, J = 7.39 Hz, 2H), 2.07 (s, 3H), 1.67-1.80 (m, 2H), 1.44-1.58 (m, 1H), 1.32-1.44 (m, 1H), 1.30 (d, J = 6.82 Hz, 6H), 1.00 (t, J = 7.39 Hz, 3H). HRMS calcd. for C$_{33}$H$_{36}$F$_3$N$_4$O$_4$S (M + H) 641.2409, found 641.24051 |

| | Structure/Chemical Name | Starting materials | MS (ESI+) m/z |
|---|---|---|---|
| 35-3 | 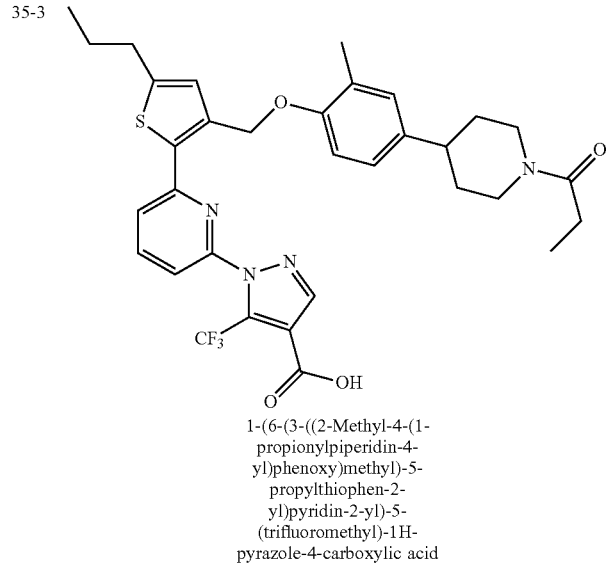<br>1-(6-(3-((2-Methyl-4-(1-propionylpiperidin-4-yl)phenoxy)methyl)-5-propylthiophen-2-yl)pyridin-2-yl)-5-(trifluoromethyl)-1H-pyrazole-4-carboxylic acid | Intermediate 2-1, Intermediate 4-7, and propionic anhydride | $^1$H NMR (TFA salt, 400 MHz, CD$_3$OD) δ 8.15 (s, 1H), 8.02 (dd, J = 7.80, 8.00 Hz, 1H), 7.76 (dd, J = 0.73, 7.95 Hz, 1H), 7.53 (dd, J = 0.67, 7.89 Hz, 1H),? 6.95-6.99 (m, 2H), 6.89-6.93 (m, 1H), 6.73-6.79 (m, 1H), 5.26 (s, 2H), 4.62-4.70 (m, 1H), 4.00-4.10 (m, 1H), 3.14-3.22 (m, 1H), 2.82 (t, J = 7.15 Hz, 2H), 2.63-2.74 (m, 2H), 2.45 (q, J = 7.50 Hz, 2H), 2.13 (s, 3H), 1.79-1.91 (m, 2H), 1.68-1.78 (m, 2H), 1.44-1.66 (m, 2H), 1.14 (t, J = 7.46 Hz, 3H), 1.00 (t, J = 7.34 Hz, 3H). HRMS calcd. for C$_{33}$H$_{36}$F$_3$N$_4$O$_4$S (M + H) 641.2409, found 641.2431. |
| 35-4 | 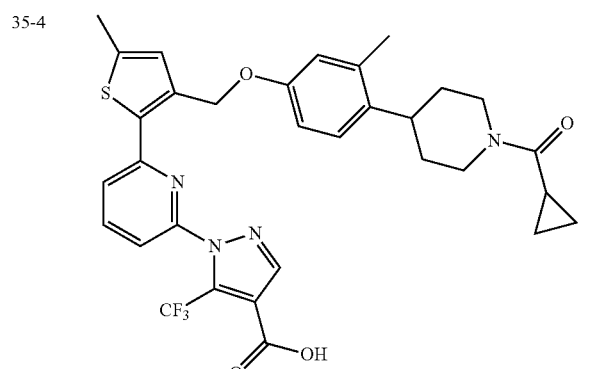<br>1-(6-(3-((4-(1-(Cyclopropanecarbonyl)piperidin-4-yl)-3-methylphenoxy)methyl)-5-methylthiophen-2-yl)pyridin-2-yl)-5-(trifluoromethyl)-1H-pyrazole-4-carboxylic acid | Intermediate 2-3-2, Intermediate 4-1-D, and cyclopropanecarbonyl chloride | $^1$H NMR (400 MHz, DMSO-d$_6$) δ 8.07 (t, J = 7.95 Hz, 1 H) 7.75 (s, 1 H) 7.64 (d, J = 7.46 Hz, 1 H) 7.57 (d, J = 7.46 Hz, 1 H) 7.08 (d, J = 8.44 Hz, 1 H) 6.97 (d, J = 0.98 Hz, 1 H) 6.72-6.84 (m, 2 H) 5.20 (s, 2 H) 4.28-4.59 (m, 2 H) 3.18 (t, J = 12.29 Hz, 1 H) 2.84-2.97 (m, 1 H) 2.57-2.70 (m, 1 H) 2.47 (d, J = 0.86 Hz, 3 H) 2.28 (s, 3 H) 1.94-2.05 (m, 1 H) 1.61-1.80 (m, 2 H) 1.32-1.59 (m, 2 H) 0.63-0.80 (m, 4 H). HRMS calcd. for C$_{32}$H$_{32}$F$_3$N$_4$O$_4$S (M + H) 625.2096, found 625.2137. |

| | Structure/Chemical Name | Starting materials | MS (ESI+) m/z |
|---|---|---|---|
| 35-5 | 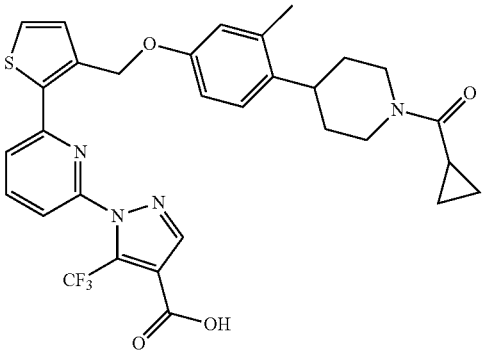 [SMILES: Cc1cc(OCc2ccsc2-c2cccc(-n3ncc(C(=O)O)c3C(F)(F)F)n2)ccc1C1CCN(C(=O)C2CC2)CC1]<br>1-(6-(3-((4-(1-(Cyclopropanecarbonyl)piperidin-4-yl)-3-methylphenoxy)methyl)thiophen-2-yl)pyridin-2-yl)-5-(trifluoromethyl)-1H-pyrazole-4-carboxylic acid | Intermediate 2-3-2, Intermediate 4-1-B, and cyclopropanecarbonyl chloride | $^1$H NMR (400 MHz, DMSO-d$_6$) δ 8.10 (t, J = 7.95 Hz, 1 H) 7.66-7.76 (m, 3 H) 7.62 (d, J = 8.07 Hz, 1 H) 7.26 (d, J = 5.14 Hz, 1 H) 7.09 (d, J = 8.31 Hz, 1 H) 6.74-6.85 (m, 2 H) 5.27 (s, 2 H) 4.30-4.59 (m, 2 H) 3.18 (br. s., 1 H) 2.85-2.96 (m, 1 H) 2.58-2.66 (m, 1 H) 2.29 (s, 3 H) 1.95-2.05 (m, 1 H) 1.61-1.81 (m, 2 H) 1.31-1.59 (m, 2 H) 0.60-0.82 (m, 4 H). HRMS calcd. for C$_{31}$H$_{30}$F$_3$N$_4$O$_4$S (M + H) 611.1939, found 611.1978. |
| 35-6 ♦ | 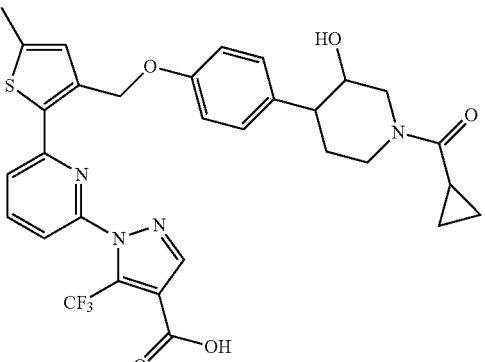<br>(+)-trans-1-(6-(3-((4-((3,4)-1-(cyclopropanecarbonyl)-3-hydroxypiperidin-4-yl)phenoxy)methyl)-5-methylthiophen-2-yl)pyridin-2-yl)-5-(trifluoromethyl)-1H-pyrazole-4-carboxylic acid | (3R,4R)-tert-butyl 3-hydroxy-4-(4-hydroxyphenyl)piperidine-1-carboxylate (which can be prepared as described in Bioorg Med. Chem Lett, 2005, 13, 59 or as described in WO2005061457) and Intermediate 4-1-D, and cyclopropanecarbonyl chloride | $^1$H NMR (120° C., 600 MHz, DMSO-d$_6$) δ 8.17 (s, 1H), 8.09 (t, J = 7.89 Hz, 1H), 7.75 (d, J = 7.43 Hz, 1H), 7.57 (d, J = 7.89 Hz, 1H), 7.09-7.15 (m, 2H), 6.97 (d, J = 0.92 Hz, 1H), 6.81-6.88 (m, 2H), 5.24 (s, 2H), 4.38-4.46 (m, 1H), 4.24-4.31 (m, 1H), 3.44-3.50 (m, 1H), 2.80-2.90 (m, 1H), 2.61-2.70 (m, 1H), 2.50-2.56 (m, 1H), 1.86-1.92 (m, 1H), 1.73-1.78 (m, 1H), 1.48-1.57 (m, 1H), 0.73-0.79 (m, 2H), 0.66-0.72 (m, 2H). HRMS calcd. for C$_{31}$H$_{30}$F$_3$N$_{14}$O$_5$S (M + H) 627.1889, found 627.1914. |
| 35-7 | 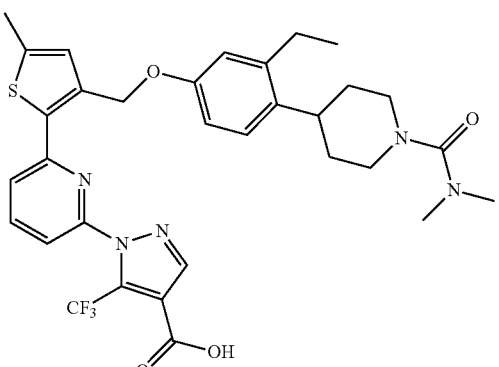<br>1-(6-(3-((4-(1-(Dimethylcarbamoyl)piperidin-4-yl)-3-ethylphenoxy)methyl)-5-methylthiophen-2-yl)pyridin-2-yl)-5-(trifluoromethyl)-1H-pyrazole-4-carboxylic acid | Intermediate 2-2, Intermediate 4-1-D, and dimethylcarbamic chloride? (CAS# 79-44-7) | $^1$H NMR (400 MHz, CD$_3$OD) δ 8.07-7.94 (m, 2H), 7.70 (dd, J = 8.0, 0.8 Hz, 1H), 7.53 (dd, J = 7.9, 0.8 Hz, 1H), 7.09 (dt, J = 9.0, 1.4 Hz, 1H), 6.95 (q, J = 1.0 Hz, 1H), 6.78-6.66 (m, 2H), 5.24 (s, 2H), 3.85-3.72 (m, 2H), 2.83-2.95 (m, 9H), 2.63 (q, J = 7.6 Hz, 2H), 2.49 (d, J = 1.1 Hz, 3H), 1.75-1.63 (m, 4H), 1.15 (t, J = 7.5 Hz, 3H). HRMS calcd. for C$_{32}$H$_{35}$F$_3$N$_5$O$_4$S (M + H) 642.2356, found 642.2413 |

| | Structure/Chemical Name | Starting materials | MS (ESI+) m/z |
|---|---|---|---|
| 35-8 | 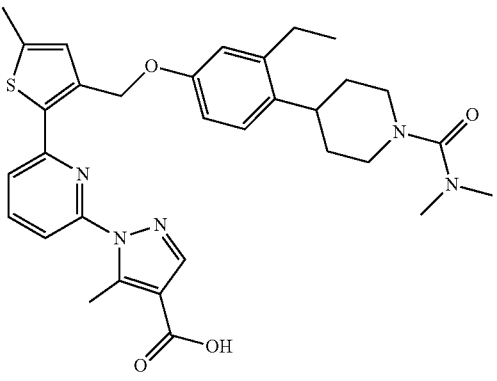<br>1-(6-(3-((4-(1-(Dimethylcarbamoyl)piperidin-4-yl)-3-ethylphenoxy)methyl)-5-methylthiophen-2-yl)pyridin-2-yl)-5-methyl-1H-pyrazole-4-carboxylic acid | Intermediate 2-2, Intermediate 4-2-6, and dimethylcarbamic chloride | $^1$H NMR (400 MHz, CD$_3$OD) δ 7.98 (s, 1H), 7.94 (dd, J = 7.8, 8.0 Hz, 1H), 7.64 (dd, J = 0.6, 8.0 Hz, 1H), 7.59 (dd, J = 0.6, 7.8 Hz, 1H), 7.09-7.14 (m, 1H), 6.95 (d, J = 1.0 Hz, 1H), 6.74-6.79 (m, 2H), 5.22 (s, 2H), 3.75-3.82 (m, 2H), 2.84-2.96 (m, 12H), 2.64 (q, J = 7.6 Hz, 2H), 2.50 (d, J = 1.0 Hz, 3H), 1.65-1.74 (m, 4H), 1.16 (t, J = 7.6 Hz, 3H). HRMS calcd. for C$_{32}$H$_{38}$N$_5$O$_4$S (M + H) 588.2645, found 588.2657. |
| 35-9 | 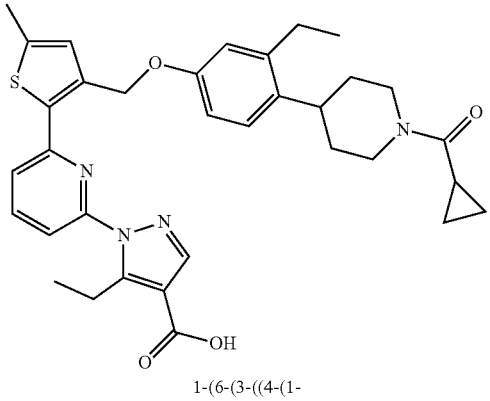<br>1-(6-(3-((4-(1-(Cyclopropanecarbonyl)piperidin-4-yl)-3-ethylphenoxy)methyl)-5-methylthiophen-2-yl)pyridin-2-yl)-5-ethyl-1H-pyrazole-4-carboxylic acid | Intermediate 2-2, Intermediate 4-2-2, and cyclopropanecarbonyl chloride | $^1$H NMR (400 MHz, CD$_3$OD) δ 7.90-7.98 (m, 2H), 7.57-7.64 (m, 2H), 7.06-7.11 (m, 1H), 6.94 (d, J = 0.98 Hz, 1H), 6.73-6.79 (m, 2H), 5.19 (s, 2H), 4.65 (br. d, J = 13.00 Hz, 1H), 4.46 (br. d, J = 13.00 Hz, 1H), 3.53 (q, J = 7.34 Hz, 2H), 3.22-3.28 (m, 1H), 2.98-3.08 (m, 1H), 2.70-2.80 (m, 1H), 2.66 (q, J = 7.50 Hz, 2H), 2.50 (d, J = 0.98 Hz, 3H), 1.96-2.05 (m, 1H), 1.50-1.86 (m, 4H), 1.13-1.24 (m, 6H), 0.77-0.95 (m, 4H). HRMS; calcd. for C$_{34}$H$_{39}$N$_4$O$_4$S (M + H) 599.2692, found 599.2666. |

| | Structure/Chemical Name | Starting materials | MS (ESI+) m/z |
|---|---|---|---|
| 35-10 | 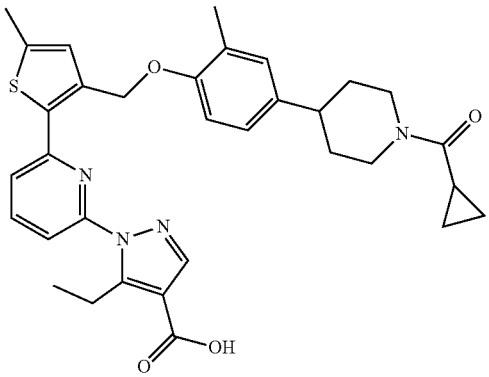 [SMILES: CCc1c(C(=O)O)cnn1-c1cccc(-c2sc(C)cc2COc2ccc(C3CCN(C(=O)C4CC4)CC3)cc2C)n1]<br>1-(6-(3-((4-(1-(Cyclopropanecarbonyl)piperidin-4-yl)-2-methylphenoxy)methyl)-5-methylthiophen-2-yl)pyridin-2-yl)-5-ethyl-1H-pyrazole-4-carboxylic acid | Intermediate 2-1, Intermediate 4-2-2, and cyclopropanecarbonyl chloride | $^1$H NMR (400 MHz, CD$_3$OD) δ 7.89-7.96 (m, 2H), 7.55-7.63 (m, 2H), 6.93-7.03 (m, 3H), 6.86 (d, J = 8.31 Hz, 1H), 5.22 (s, 2H), 4.58-4.68 (m, 1H), 4.39-4.49 (m, 1H), 3.57 (q, J = 7.38 Hz, 2H), 3.19-3.27 (m, 1H), 2.67-2.79 (m, 2H), 2.51 (d, J = 0.86 Hz, 3H), 2.16 (s, 3H), 1.96-2.04 (m, 1H), 1.78-1.95 (m, 2H), 1.46-1.70 (m, 2H), 1.18 (t, J = 7.38 Hz, 3H), 0.75-0.95 (m, 4H). HRMS; calcd. for C$_{33}$H$_{37}$N$_4$O$_4$S (M + H) 585.2536, found 585.2513. |
| 35-11 | 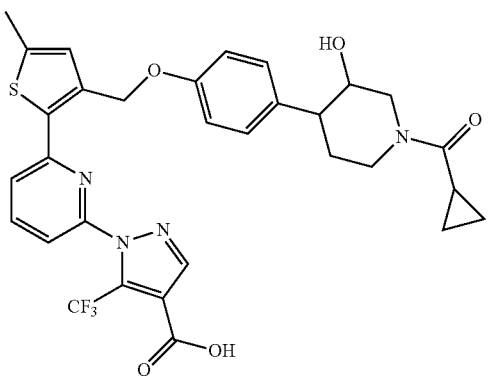 [SMILES: Cc1cc(COc2ccc(C3CCN(C(=O)C4CC4)CC3O)cc2)c(-c2cccc(-n3ncc(C(=O)O)c3C(F)(F)F)n2)s1]<br>(±)-trans-1-(6-(3-((4-(1-(Cyclopropanecarbonyl)-3-hydroxypiperidin-4-yl)phenoxy)methyl)-5-methylthiophen-2-yl)pyridin-2-yl)-5-(trifluoromethyl)-1H-pyrazole-4-carboxylic acid | trans-4-(4-hydroxyphenyl)piperidin-3-ol (CAS# 188866-44-6) as described in Bioorg. Med. Chem. Lett. 9 (1999) 1397-1402, Intermediate 4-1-D, and cyclopropanecarbonyl chloride | $^1$H NMR (120° C., 600 MHz, DMSO-d$_6$) δ 8.17 (s, 1H), 8.09 (t, J = 7.9 Hz, 1H), 7.75 (d, J = 7.4 Hz, 1H), 7.57 (d, J = 7.9 Hz, 1H), 7.09-7.15 (m, 2H), 6.97 (d, J = 0.9 Hz, 1H), 6.81-6.88 (m, 2H), 5.24 (s, 2H), 4.38-4.46 (m, 1H), 4.24-4.31 (m, 1H), 3.44-3.50 (m, 1H), 2.80-2.90 (m, 1H), 2.61-2.70 (m, 1H), 2.50-2.56 (m, 1H), 1.86-1.92 (m, 1H), 1.73-1.78 (m, 1H), 1.48-1.57 (m, 1H), 0.73-0.79 (m, 2H), 0.66-0.72 (m,? 2H). (3H was obstructed under the solvent (DMSO-d$_6$) peak). HRMS; calcd. for C$_{31}$H$_{30}$F$_3$N$_4$O$_5$S (M + H) 627.1889, found 627.1951. |

| | Structure/Chemical Name | Starting materials | MS (ESI+) m/z |
|---|---|---|---|
| 35-12 | 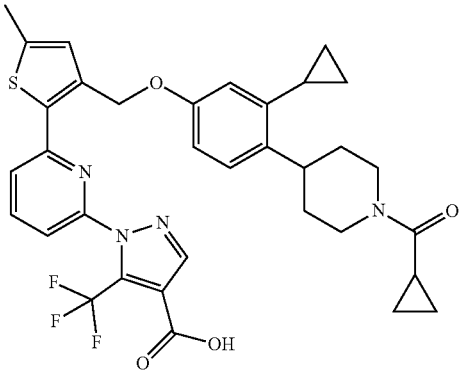 [SMILES: Cc1cc(COc2ccc(C3CCN(C(=O)C4CC4)CC3)c(C3CC3)c2)c(-c2cccc(-n3ncc(C(=O)O)c3C(F)(F)F)n2)s1]<br>1-(6-(3-((4-(1-(Cyclopropanecarbonyl)piperidin-4-yl)-3-cyclopropylphenoxy)methyl)-5-methylthiophen-2-yl)pyridin-2-yl)-5-(trifluoromethyl)-1H-pyrazole-4-carboxylic acid | Intermediate 2-20, Intermediate 4-1-D, and cyclopropane-carbonyl chloride | $^1$H NMR (400 MHz, CD$_3$OD) δ 7.96-8.04 (m, 2 H) 7.69 (dd, J = 7.95, 0.61 Hz, 1 H) 7.53 (dd, J = 7.95, 0.61 Hz, 1 H) 7.05 (d, J = 8.56 Hz, 1 H) 6.92 (d, J = 0.98 Hz, 1 H) 6.71 (dd, J = 8.56, 2.81 Hz, 1 H) 6.54 (d, J = 2.69 Hz, 1 H) 5.23 (s, 2 H) 4.41-4.71 (m, 3 H) 3.37-3.46 (m, 1 H) 2.76 (t, J = 12.35 Hz, 1 H) 2.49 (d, J = 0.98 Hz, 3? H) 1.94-2.05 (m, 2 H) 1.76-1.94 (m, 2 H) 1.48-1.73 (m, 2 H) 0.86-0.95 (m, 4 H) 0.76-0.85 (m, 2 H) 0.48-0.56 (m, 2 H). HRMS calcd. for C$_{34}$H$_{34}$N$_4$O$_4$F$_3$S (M + H) 651.2259, found 651.2253. |
| 35-13 | 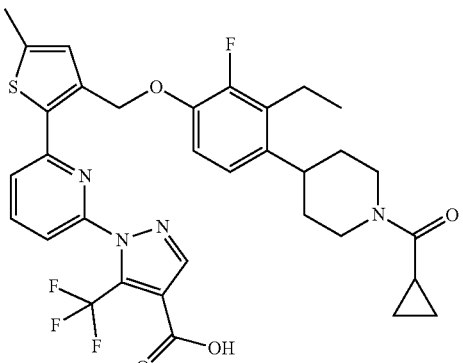<br>1-(6-(3-((4-(1-(Cyclopropanecarbonyl)piperidin-4-yl)-3-ethyl-2-fluorophenoxy)methyl)-5-methylthiophen-2-yl)pyridin-2-yl)-5-(trifluoromethyl)-1H-pyrazole-4-carboxylic acid | Intermediate 2-22, Intermediate 4-1-D, and cyclopropane-carbonyl chloride | 1H NMR (400 MHz, DMSO-d$_6$) δ 8.09 (t, J = 7.95 Hz, 1 H) 7.88 (br. s., 1 H) 7.71 (s, 1 H) 7.60 (d, J = 7.82 Hz, 1 H) 6.91-7.04 (m, 3 H) 5.27 (s, 2 H) 4.22-4.65 (m, 2 H) 3.13-3.22 (m, 1 H) 2.85-3.00 (m, 1 H) 2.61-2.75 (m, 3 H) 2.47 (d, J = 0.86 Hz, 3 H) 1.93-2.05 (m, 1 H)? 1.34-1.79 (m, 4 H) 1.12 (d, J = 14.92 Hz, 3 H) 0.56-0.86 (m, 4 H). HRMS; calcd. for C$_{33}$H$_{33}$N$_4$O$_4$F$_4$S. (M + H) 657.2137, found 657.2159. |

| | Structure/Chemical Name | Starting materials | MS (ESI+) m/z |
|---|---|---|---|
| 35-14 | 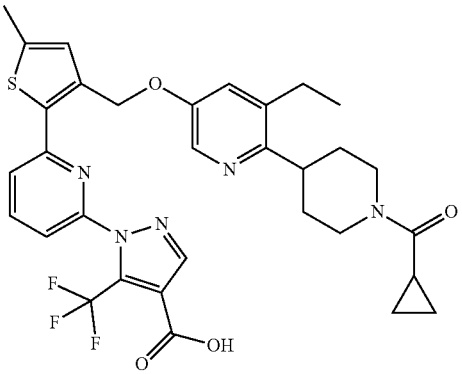 [SMILES: CCc1cc(OCc2cc(C)sc2-c2cccc(-n3ncc(C(=O)O)c3C(F)(F)F)n2)cnc1C1CCN(C(=O)C2CC2)CC1]  1-(6-(3-(((6-(1-(Cyclopropanecarbonyl)piperidin-4-yl)-5-ethylpyridin-3-yl)oxy)methyl)-5-methylthiophen-2-yl)pyridin-2-yl)-5-(trifluoromethyl)-1H-pyrazole-4-carboxylic acid | Intermediate 2-24, Intermediate 4-1-D, and cyclopropanecarbonyl chloride | 1H NMR (400 MHz, DMSO-$d_6$) δ 8.06-8.17 (m, 2 H) 7.94 (s, 1 H) 7.71 (d, J = 7.96 Hz, 1 H) 7.61 (d, J = 7.58 Hz, 1 H) 7.18 (d, J = 2.91 Hz, 1 H) 7.01 (d, J = 1.01 Hz, 1 H) 5.31 (s, 2 H) 4.26-4.55 (m, 2 H) 3.04-3.15 (m, 2 H) 2.59-2.71 (m, 3 H) 2.47 (d, J = 0.88 Hz, 3 H) 1.93-2.04 (m, 1 H) 1.53-1.82 (m, 4 H) 1.13 (t, J = 7.52 Hz, 3 H) 0.65-0.78 (m, 4 H). HRMS; calcd. for $C_{32}H_{33}N_5O_4F_3S$ (M + H) 640.2193, found 640.2205. |
| 35-15 | 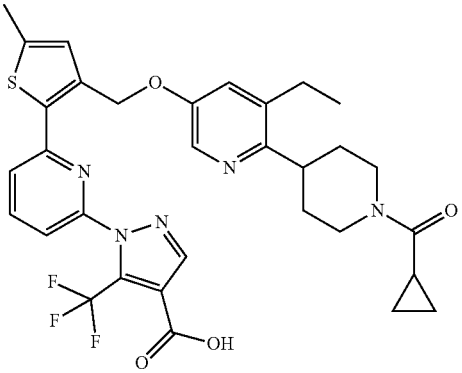  1-(6-(3-((4-(1-(Cyclopropanecarbonyl)piperidin-4-yl)-3-propylphenoxy)methyl)-5-methylthiophen-2-yl)pyridin-2-yl)-5-(trifluoromethyl)-1H-pyrazole-4-carboxylic acid | Intermediate 2-21, Intermediate 4-1-D, and cyclopropanecarbonyl chloride | 1H NMR (400 MHz, DMSO-$d_6$) δ 13.46 (br. s., 1 H) 8.27 (br. s., 1 H) 8.16 (t, J = 7.95 Hz, 1 H) 7.78 (s, 1 H) 7.66 (d, J = 7.82 Hz, 1 H) 7.10 (s, 1H) 7.00 (d, J = 0.98 Hz, 1 H) 6.66-6.80 (m, 2 H) 5.22 (s, 2 H) 4.27-4.58 (m, 2 H) 3.29 (s, 3 H) 3.20 (d, J = 18.58 Hz, 1 H) 2.91 (t, J = 11.98 Hz, 1 H) 2.47 (d, J = 0.86 Hz, 3 H) 1.93-2.04 (m, 1 H) 1.33-1.75 (m, 6 H) 0.85-0.95 (m, 3 H) 0.59-0.81 (m, 4 H). HRMS calcd. for $C_{34}H_{36}F_3N_4O_4S$ (M + H) 653.? 2409, found 653. 2418 |

♦ Absolute stereochemistry has not been assigned with complete confidence. The compound is trans and is the (+) optical rotation enantiomer. However, the absolute stereochemical assignment of 3R,4R listed in provisional application USSN62/020,182 has not been confirmed.

Example 36

Example 36-A. Ethyl 1-(3-(3-(1-((4-(1-(cyclopropanecarbonyl)piperidin-4-yl)-2-methylphenyl)amino)ethyl)thiophen-2-yl)phenyl)-5-(trifluoromethyl)-1H-pyrazole-4-carboxylate

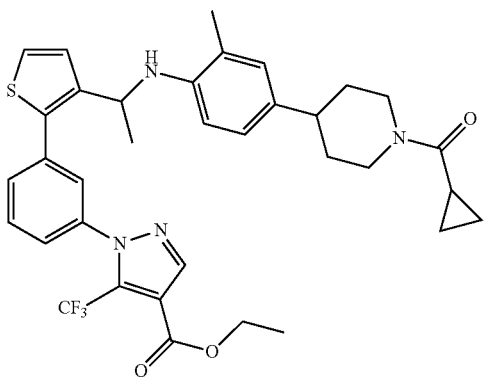 [SMILES: CCOC(=O)c1cnn(-c2cccc(-c3sccc3C(C)Nc3ccc(C4CCN(C(=O)C5CC5)CC4)cc3C)c2)c1C(F)(F)F]

A round-bottomed flask equipped with a Dean-Stark apparatus, was charged with Intermediate 2-14 (190 mg, 0.735 mmol), Intermediate 4-16 (300 mg, 0.735 mmol), TsOH (7 mg, 0.037 mmol) and toluene (20 mL). The mixture was then refluxed for 18 h with separation of water, and then concentrated. The resulting residue was dissolved in EtOH (20 mL). To the solution at 0° C. was added sodium borohydride (41.7 mg, 1.10 mmol), and then the mixture was stirred at 0° C. for 3 h. The reaction was then quenched with water and satd. aq. NH$_4$Cl. The mixture was then extract with CH$_2$Cl$_2$. The organic layer was concentrated with Celite®. The resulting residue was purified by silica gel flash column chromatography (0-40% EtOAc in heptane) to afford the title compound. MS (ESI+) m/z 651.4 (M+H).

Example 36. 1-(3-(3-(1-((4-(1-(Cyclopropanecarbonyl)piperidin-4-yl)-2-methylphenyl)amino)ethyl)thiophen-2-yl)phenyl)-5-(trifluoromethyl)-1H-pyrazole-4-carboxylic acid

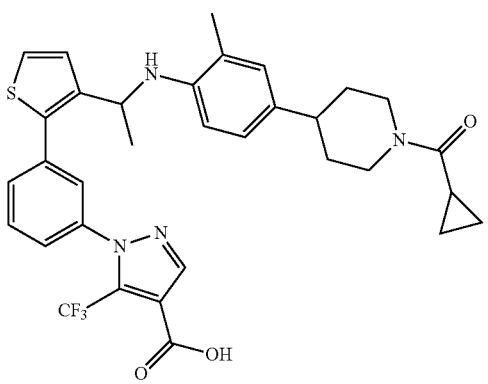 [SMILES: Cc1cc(C2CCN(C(=O)C3CC3)CC2)ccc1NC(C)c1ccsc1-c1cccc(-n2ncc(C(=O)O)c2C(F)(F)F)c1]

To a solution of ethyl 1-(3-(3-(1-((4-(1-(cyclopropanecarbonyl)piperidin-4-yl)-2-methylphenyl)amino)ethyl)thiophen-2-yl)phenyl)-5-(trifluoromethyl)-1H-pyrazole-4-carboxylate (100 mg, 0 154 mmol) in acetonitrile (4 mL) was added LiOH (1 M in H$_2$O, 0 92 mL, 0.92 mmol). The mixture was then stirred at 50° C. for 2 h, and then cooled to room temperature. The reaction mixture was added 1M aq. HCl (0 94 mL), and then filtered. The filtrate was purified by RP-HPLC (HC-B) to afford the title compound. $^1$H NMR (400 MHz, CD$_3$OD) δ 7.97 (s, 1H), 7.60-7.66 (m, 1H), 7.54-7.59 (m, 1H), 7.49-7.54 (m, 1H), 7.39-7.44 (m, 1H), 7.34 (d, J=5.26 Hz, 1H), 7.19 (d, J=5.38 Hz, 1H), 6.78 (br. d, J=1.80 Hz, 1H), 6.62 (dd, J=2.14, 8.25 Hz, 1H), 6.05 (d, J=8.31 Hz, 1H), 4.49-4.69 (m, 2H), 4.32-4.45 (m, 1H), 3.14-3.24 (m, 1H), 2.62-2.74 (m, 1H), 2.52-2.62 (m, 1H), 2.06 (s, 3H), 1.94-2.02 (m, 1H), 1.67-1.85 (m, 2H), 1.61 (d, J=6.72 Hz, 3H), 1.35-1.58 (m, 2H), 0.72-0.93 (m, 4H). HRMS; calcd for C$_{33}$H$_{34}$F$_3$N$_4$O$_3$S 623.2298, found 623.2151.

Example 37. 1-(6-(3-(((4-(1-(Cyclopropanecarbonyl)piperidin-4-yl)-3-ethylphenyl)amino)methyl)-5-methylthiophen-2-yl)pyridin-2-yl)-5-ethyl-1H-pyrazole-4-carboxylic acid

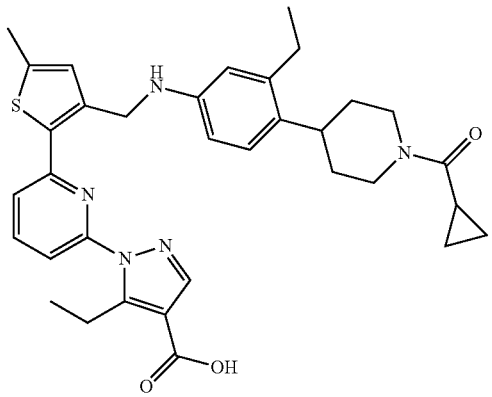 [SMILES: CCc1cc(NCc2cc(C)sc2-c2cccc(-n3ncc(C(=O)O)c3CC)n2)ccc1C1CCN(C(=O)C2CC2)CC1]

Reaction of Intermediate 4-2-2 with Intermediate 2-16, in a fashion analogous Example 19-A, and subsequent Boc removal, in a manner similar to the procedure described for Example 1-B, and reaction with cyclopropanecarboxylic acid in a similar manner to the procedure as described in Example 11-C, followed lastly by saponification in a manner similar to the procedure as described for the preparation for Example 19 furnished the title compound. $^1$H NMR (400 MHz, CD$_3$OD) δ 7.92-7.99 (m, 2H) 7.58-7.63 (m, 2H) 6.93 (d, J=8.1 Hz, 1H) 6.88 (d, J=1.1 Hz, 1H) 6.44-6.50 (m, 2H) 4.65 (d, J=12.6 Hz, 1H) 4.40-4.49 (m, 3H) 3.55 (q, J=7.5 Hz, 2H) 3.42 (dt, J=3.3, 1.7 Hz, 1H) 2.90-3.03 (m, 1H) 2.74 (t, J=12.3 Hz, 1H) 2.54-2.64 (m, 2H) 2.48 (d, J=1.0 Hz, 3H) 1.93-2.07 (m, 1H) 1.47-1.86 (m, 4H) 1.20 (t, J=7.4 Hz, 3H) 1.14 (t, J=7.6 Hz, 3H) 0.72-0.97 (m, 4H). HRMS calcd. for C$_{34}$H$_{40}$N$_5$O$_3$S (M+H) 598.2827, found 598.2852.

Example 38. 1-(6-(3-(((4-(1-(Cyclopropanecarbonyl)piperidin-4-yl)-3-ethylphenyl)amino)methyl)-4-(trifluoromethyl)thiophen-2-yl)pyridin-2-yl)-5-ethyl-1H-pyrazole-4-carboxylic acid

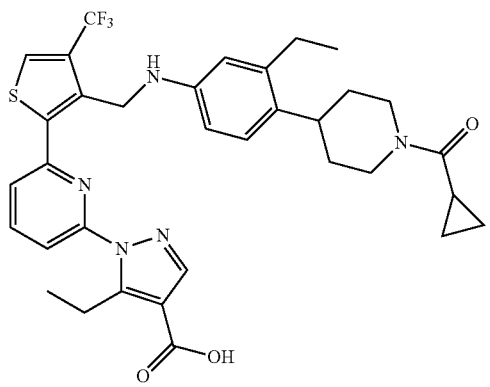 [SMILES: CCc1cc(NCc2c(C(F)(F)F)csc2-c2cccc(-n3ncc(C(=O)O)c3CC)n2)ccc1C1CCN(C(=O)C2CC2)CC1]

The title compound was synthesized starting from Intermediate 4-17 and Intermediate 2-16, in accordance with the preparation of Example 19-A, followed by subsequent Boc removal, in a manner similar to the procedure described for Example 1-B, followed by reaction with cyclopropanecarboxylic acid in a similar manner to the procedure as described in Example 11-C, followed lastly by saponification in a manner similar to the procedure as described for the preparation for Example 19, to furnish the title compound. $^1$H NMR (400 MHz, CD$_3$OD) δ 8.13 (s, 1H), 7.97-8.03 (m, 2H), 7.88-7.92 (m, 1H), 7.79 (d, J=8.1 Hz, 1H), 6.96 (d, J=8.3 Hz, 1H), 6.45-6.50 (m, 2H), 4.61-4.69 (m, 1H), 4.56 (br. s, 1H), 4.37-4.50 (m, 3H), 3.46-3.54 (m, 2H), 3.20-3.27 (m, 1H), 2.93-3.03 (m, 1H), 2.69-2.79 (m, 1H), 2.62 (q, J=7.5 Hz, 2H), 1.97-2.05 (m, 1H), 1.49-1.85 (m, 4H), 1.25 (t, J=7.3 Hz, 3H), 1.17 (t, J=7.5 Hz, 3H), 0.77-0.94 (m, 4H). HRMS; calcd. for C$_{34}$H$_{37}$F$_3$N$_5$O$_3$S (M+H) 652.2569, found 652.2537.

Example 39

Example 39-A. tert-Butyl 4-(6-((2-(6-(4-(ethoxycarbonyl)-5-(trifluoromethyl)-1H-pyrazol-1-yl)pyridin-2-yl)-5-methylthiophen-3-yl)methoxy)-2-ethylpyridin-3-yl)piperidine-1-carboxylate

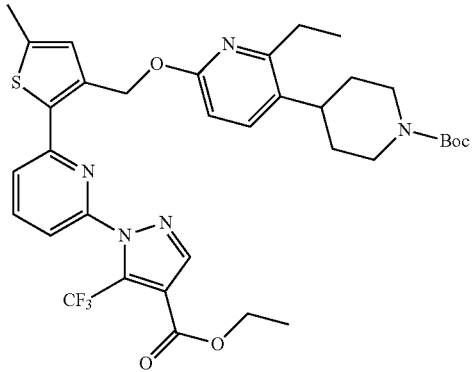 [SMILES: CCOC(=O)c1cnn(-c2cccc(-c3sc(C)cc3COc3ccc(C4CCN(C(=O)OC(C)(C)C)CC4)c(CC)n3)n2)c1C(F)(F)F]

To a solution of Intermediate 4-1-D (81 mg, 0.19 mmol) in CH$_2$Cl$_2$ (0.5 mL) at room temperature was added triphenylphosphine (77 mg, 0.29 mmol), followed by CBr$_4$ (65 mg, 0.20 mmol). The mixture was then stirred at room temperature for 0.5 h. To the solution were then added Intermediate 2-23 (30 mg, 0.098 mmol) and silver carbonate (53 mg, 0.192 mmol) in Toluene (0.5 mL), and then the mixture was stirred at 75° C. for 2 h. The reaction mixture was cooled to room temperature, and then diluted with EtOAc. The mixture was then washed with H$_2$O, dried over dried over Na$_2$SO$_4$, filtered, and then concentrated with silica gel. The resulting residue was purified by silica gel flash column chromatography (0-50% EtOAc in heptane) to afford the title compound. MS (ESI+) m/z 700.5 (M+H).

Example 39. 1-(6-(3-(((5-(1-(Cyclopropanecarbonyl)piperidin-4-yl)-6-ethylpyridin-2-yl)oxy)methyl)-5-methylthiophen-2-yl)pyridin-2-yl)-5-(trifluoromethyl)-1H-pyrazole-4-carboxylic acid

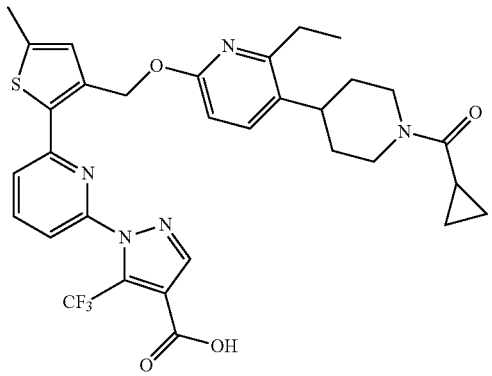 [SMILES: CCc1nc(OCc2cc(C)sc2-c2cccc(-n3ncc(C(=O)O)c3C(F)(F)F)n2)ccc1C1CCN(C(=O)C2CC2)CC1]

The title compound was synthesized starting from tert-butyl 4-(6-((2-(6-(4-(ethoxycarbonyl)-5-(trifluoromethyl)-1H-pyrazol-1-yl)pyridin-2-yl)-5-methylthiophen-3-yl)methoxy)-2-ethylpyridin-3-yl)piperidine-1-carboxylate by the method outlined in Example 37. 1H NMR (400 MHz, DMSO-d$_6$) δ 8.07-8.20 (m, 2H) 7.80 (d, J=7.7 Hz, 1H) 7.64 (d, J=7.6 Hz, 1H) 7.54 (d, J=8.6 Hz, 1H) 6.99 (d, J=1.1 Hz, 1H) 6.61 (d, J=8.4 Hz, 1H) 5.52 (s, 2H) 4.31-4.57 (m, 2H) 3.20 (br. s., 1H) 2.90-3.01 (m, 1H) 2.62-2.73 (m, 3H) 2.45 (d, J=1.0 Hz, 3H) 1.93-2.05 (m, 1H) 1.34-1.77 (m, 4H) 1.08 (t, J=7.5 Hz, 3H) 0.65-0.82 (m, 4H). HRMS calcd. for C$_{32}$H$_{33}$N$_5$O$_4$F$_3$S (M+H) 640.2195, found 640.2205.

Example 40. 1-(6-(5-Isopropyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid

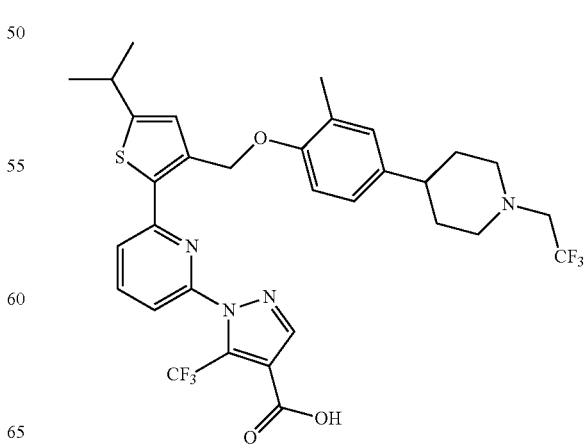

Reaction of ethyl 1-(6-(3-(hydroxymethyl)-5-isopropylthiophen-2-yl)pyridin-2-yl)-5-(trifluoromethyl)-1H-pyrazole-4-carboxylate (Intermediate 4-6) with tert-butyl 4-(4-hydroxy-3-methylphenyl)piperidine-1-carboxylate (Intermediate 2-1) in a manner similar to the procedure described for Example 7-A followed by treatment with TFA, in a fashion analogous to procedure described for the synthesis of Example 1-B, and then alkylation with 2,2,2-trifluoroethyl trifluoromethanesulfonate followed by saponification, as outlined for the synthesis of Example 13, afforded 1-(6-(5-isopropyl-3-((2-methyl-4-(1-(2,2,2-trifluoroethyl)piperidin-4-yl)phenoxy)methyl)thiophen-2-yl)pyridin-2-yl)-5-(trifluoromethyl)-1H-pyrazole-4-carboxylic acid. $^1$H NMR (TFA salt, 400 MHz, CD$_3$OD) δ 8.15 (s, 1H), 8.01 (dd, J=7.8, 8.0 Hz, 1H), 7.75 (dd, J=0.6, 8.0 Hz, 1H), 7.50-7.54 (m, 1H), 7.01 (d, J=0.8 Hz, 1H), 6.99 (d, J=1.9 Hz, 1H), 6.91-6.95 (m, 1H), 6.77 (d, J=8.3 Hz, 1H), 5.25 (s, 2H), 3.48 (q, J=9.6 Hz, 2H), 3.26-3.30 (m, 2H), 3.14-3.23 (m, 1H), 2.71-2.81 (m, 2H), 2.48-2.59 (m, 1H), 2.13 (s, 3H), 1.76-1.91 (m, 4H), 1.36 (d, J=6.8 Hz, 6H). HRMS; calcd. for C$_{32}$H$_{33}$F$_6$N$_4$O$_3$S (M+H) 667.2178, found 667.2214.

Example 41. 1-(6-(3-((2-Methyl-4-(1-(2,2,2-trifluoroethyl)piperidin-4-yl)phenoxy)methyl)-5-propylthiophen-2-yl)pyridin-2-yl)-5-(trifluoromethyl)-1H-pyrazole-4-carboxylic acid

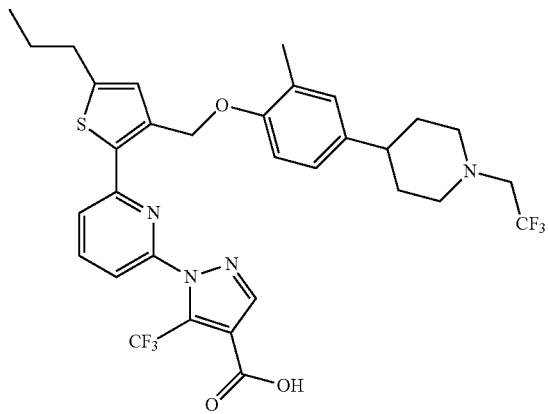 [SMILES: CCCc1cc(COc2ccc(C3CCN(CC(F)(F)F)CC3)cc2C)c(-c2cccc(-n3ncc(C(=O)O)c3C(F)(F)F)n2)s1]

Reaction of ethyl 1-(6-(3-(hydroxymethyl)-5-propylthiophen-2-yl)pyridin-2-yl)-5-(trifluoromethyl)-1H-pyrazole-4-carboxylate (Intermediate 4-7) with tert-butyl 4-(4-hydroxy-3-methylphenyl)piperidine-1-carboxylate (Intermediate 2-1) in a manner similar to the procedure described for Example 7-A followed by treatment with TFA, in a fashion analogous to procedure described for the synthesis of Example 1-B, and then alkylation with 2,2,2-trifluoroethyl trifluoromethanesulfonate followed by saponification, as outlined for the synthesis of Example 13, afforded 1-(6-(3-((2-methyl-4-(1-(2,2,2-trifluoroethyl)piperidin-4-yl)phenoxy)methyl)-5-propylthiophen-2-yl)pyridin-2-yl)-5-(trifluoromethyl)-1H-pyrazole-4-carboxylic acid. $^1$H NMR (TFA salt, 400 MHz, CD$_3$OD) δ 8.15 (s, 1H), 8.00-8.05 (m, 1H), 7.76 (dd, J=0.6, 8.0 Hz, 1H), 7.53 (dd, J=0.6, 7.8 Hz, 1H), 7.00 (d, J=2.2 Hz, 1H), 6.98 (s, 1H), 6.94 (dd, J=2.2, 8.3 Hz, 1H), 6.78 (d, J=8.44 Hz, 1H), 5.28 (s, 2H), 3.67-3.83 (m, 2H), 3.38-3.51 (m, 2H), 2.92-3.05 (m, 2H), 2.82 (t, J=7.21 Hz, 2H), 2.58-2.70 (m, 1H), 2.14 (s, 3H), 1.82-2.01 (m, 4H), 1.69-1.79 (m, 2H), 1.00 (t, J=7.4 Hz, 3H). HRMS; calcd. for C$_{32}$H$_{33}$F$_6$N$_4$O$_3$S (M+H) 667.2178, found 667.2205.

Example 42. (±)-1-(6-(3-((2-Methyl-4-(1-(pyrrolidine-3-carbonyl)piperidin-4-yl)phenoxy)methyl)thiophen-2-yl)pyridin-2-yl)-5-(trifluoromethyl)-1H-pyrazole-4-carboxylic acid

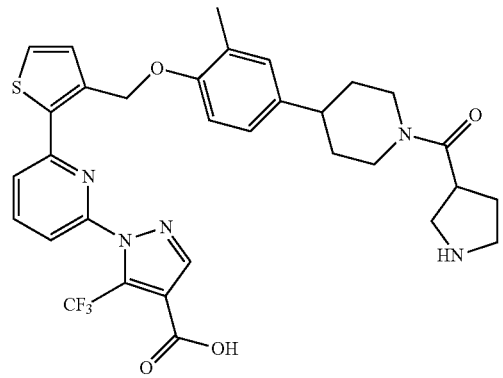 [SMILES: Cc1cc(C2CCN(C(=O)C3CCNC3)CC2)ccc1OCc1ccsc1-c1cccc(-n2ncc(C(=O)O)c2C(F)(F)F)n1]

The title compound was synthesized starting from ethyl 1-(6-(3-((2-methyl-4-(piperidin-4-yl)phenoxy)methyl)thiophen-2-yl)pyridin-2-yl)-5-(trifluoromethyl)-1H-pyrazole-4-carboxylate (Example 11-B). Reaction of ethyl 1-(6-(3-((2-methyl-4-(piperidin-4-yl)phenoxy)methyl)thiophen-2-yl)pyridin-2-yl)-5-(trifluoromethyl)-1H-pyrazole-4-carboxylate with (±)-1-(tert-butoxycarbonyl)pyrrolidine-3-carboxylic acid (CAS#59378-75-5), in a fashion analogous to the procedure described for Example 11-C, and then treatment with TFA in a manner similar to the preparation of Example 11-B, followed by saponification analogously to the preparation of Example 11 to afford (±)-1-(6-(3-((2-methyl-4-(1-(pyrrolidine-3-carbonyl)piperidin-4-yl)phenoxy)methyl)thiophen-2-yl)pyridin-2-yl)-5-(trifluoromethyl)-1H-pyrazole-4-carboxylic acid. $^1$H NMR (400 MHz, CD$_3$OD) δ 8.01 (t, J=7.9 Hz, 1H), 7.92 (d, J=0.8 Hz, 1H), 7.75 (dd, J=7.9, 0.8 Hz, 1H), 7.6-7.54 (m, 1H), 7.51 (d, J=5.2 Hz, 1H), 7.26 (dd, J=5.2, 1.0 Hz, 1H), 7.03-6.90 (m, 2H), 6.79 (dd, J=8.4, 1.0 Hz, 1H), 5.34 (s, 2H), 4.64 (d, J=13.2 Hz, 1H), 4.15 (d, J=13.5 Hz, 1H), 3.50-2.98 (m, 6H), 2.78-2.63 (m, 2H), 2.22-2.08 (m, 4H), 2.06-1.92 (m, 1H), 1.92-1.77 (m, 2H), 1.61-1.49 (m, 2H). HRMS calcd. for C$_{32}$H$_{33}$F$_3$N$_5$O$_4$S (M+H) 640.2205, found 640.2235.

Example 43. 1-(6-(3-((4-(1-(Azetidine-3-carbonyl)piperidin-4-yl)-2-methylphenoxy)methyl)thiophen-2-yl)pyridin-2-yl)-5-(trifluoromethyl)-1H-pyrazole-4-carboxylic acid

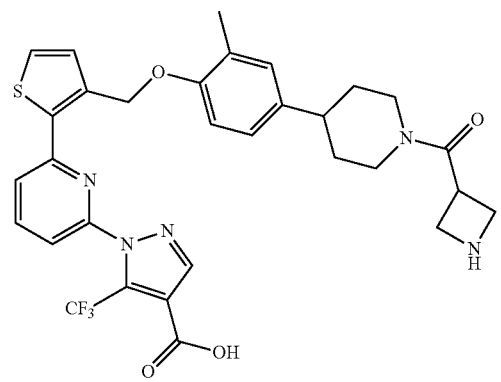 [SMILES: Cc1cc(C2CCN(C(=O)C3CNC3)CC2)ccc1OCc1ccsc1-c1cccc(-n2ncc(C(=O)O)c2C(F)(F)F)n1]

The title compound was synthesized analogously to the synthesis of Example 42, but using 1-(tert-butoxycarbonyl) azetidine-3-carboxylic acid (CAS#142253-55-2) in the place of (±)-1-(tert-butoxycarbonyl)pyrrolidine-3-carboxylic acid. $^1$H NMR (400 MHz, CD$_3$OD) δ 8.01 (t, J=7.9 Hz, 1H), 7.92 (d, J=0.8 Hz, 1H), 7.75 (dd, J=7.8, 0.8 Hz, 1H), 7.57 (dd, J=8.0, 0.7 Hz, 1H), 7.51 (d, J=5.2 Hz, 1H), 7.26 (d, J=5.2 Hz, 1H), 7.01-6.89 (m, 2H), 6.78 (d, J=8.4 Hz, 1H), 5.34 (s, 2H), 4.67-4.56 (m, 1H), 4.10-4.00 (m, 2H), 4.01-3.85 (m, 3H), 3.67 (d, J=13.6 Hz, 1H), 3.19-3.06 (m, 1H), 2.78-2.62 (m, 2H), 2.14 (s, 3H), 1.83 (d, J=13.1 Hz, 2H), 1.56-1.48 (m, 2H). HRMS calcd. for C$_{31}$H$_{31}$F$_3$N$_5$O$_4$S (M+H) 626.2043, found 626.2105.

Example 44

Example 44-A. (±)-Ethyl 1-(6-(3-((4-(1-(2,2-dimethyl-1,3-dioxolane-4-carbonyl)piperidin-4-yl)-3-ethylphenoxy)methyl)-5-methylthiophen-2-yl)pyridin-2-yl)-5-(trifluoromethyl)-1H-pyrazole-4-carboxylate

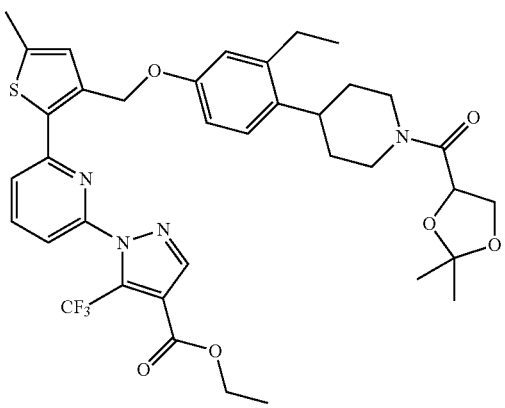 [SMILES: CCOC(=O)c1cnn(-c2cccc(-c3sc(C)cc3COc3ccc(C4CCN(C(=O)C5COC(C)(C)O5)CC4)c(CC)c3)n2)c1C(F)(F)F]

The title compound was synthesized as outlined in the synthesis of Example 11-A, 11-B, and 11-C. but using ethyl 5-ethyl-1-(6-(3-(hydroxymethyl)-5-methylthiophen-2-yl)pyridin-2-yl)-1H-pyrazole-4-carboxylate (Intermediate 4-2-2) instead of Intermediate 4-1-B, tert-butyl 4-(2-ethyl-4-hydroxyphenyl)piperidine-1-carboxylate (Intermediate 2-2) instead of Intermediate 2-1, and (±)-2,2-dimethyl-1,3-dioxolane-4-carboxylic acid (CAS#5736-06-1) instead of 2-cyclopropylacetic acid. MS (ESI+) m/z 727.5 (M+H).

Example 44-B. (±)-Ethyl 1-(6-(3-((4-(1-(2,3-dihydroxypropanoyl)piperidin-4-yl)-3-ethylphenoxy)methyl)-5-methylthiophen-2-yl)pyridin-2-yl)-5-(trifluoromethyl)-1H-pyrazole-4-carboxylate

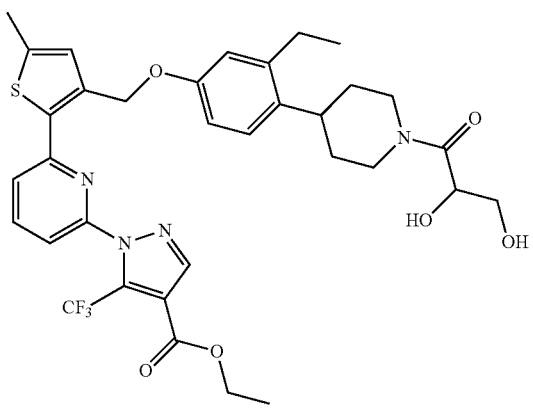 [SMILES: CCOC(=O)c1cnn(-c2cccc(-c3sc(C)cc3COc3ccc(C4CCN(C(=O)C(O)CO)CC4)c(CC)c3)n2)c1C(F)(F)F]

A mixture of Example 44-A (100 mg, 0.138 mmol) and 1M HCl in MeOH (0.4 mL) in MeOH (4 mL) was stirred at room temperature for 2 h. The mixture was then concentrated to directly furnish the title compound. MS (ESI+) m/z 687.3 (M+H).

Example 44. (±)-1-(6-(3-((4-(1-(2,3-Ddihydroxypropanoyl)piperidin-4-yl)-3-ethylphenoxy)methyl)-5-methylthiophen-2-yl)pyridin-2-yl)-5-(trifluoromethyl)-1H-pyrazole-4-carboxylic acid

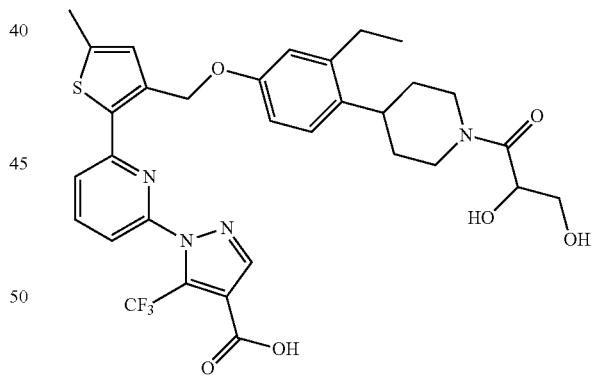

The title compound was synthesized by a saponification of Example 44-B by a similar method as described for Example 11. $^1$H NMR (400 MHz, CD$_3$OD) δ 8.05-7.95 (m, 2H), 7.70 (dd, J=8.0, 0.8 Hz, 1H), 7.52 (dd, J=8.0, 0.7 Hz, 1H), 7.07 (dd, J=9.3, 3.6 Hz, 1H), 6.95 (d, J=1.2 Hz, 1H), 6.72 (h, J=2.9 Hz, 2H), 5.24 (s, 2H), 4.67 (d, J=12.7 Hz, 1H), 4.55 (q, J=5.1 Hz, 1H), 4.20 (d, J=13.6 Hz, 1H), 3.76-3.63 (m, 2H), 3.26-3.15 (m, 1H), 3.01 (t, J=12.4 Hz, 1H), 2.78 (t, J=12.7 Hz, 1H), 2.64 (q, J=7.5 Hz, 2H), 2.49 (d, J=1.1 Hz, 3H), 1.83-1.55 (m, 4H), 1.15 (t, J=7.5 Hz, 3H). HRMS calcd. for C$_{32}$H$_{34}$F$_3$N$_4$O$_6$S (M+H) 659.2145, found 659.2200.

Example 45

Example 45-A. tert-Butyl 4-(4-(2-(2-(6-(4-(ethoxycarbonyl)-5-ethyl-1H-pyrazol-1-yl)pyridin-2-yl)-5-methylthiophen-3-yl)vinyl)-3-methylphenyl)piperidine-1-carboxylate

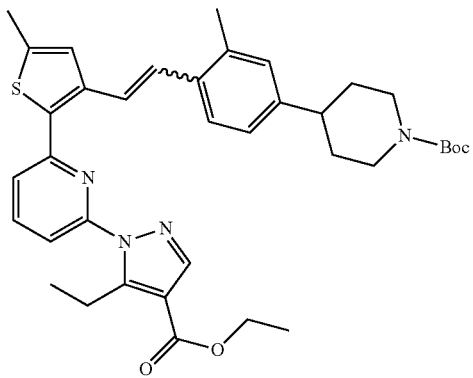 [SMILES: CCOC(=O)c1cnn(-c2cccc(-c3sc(C)cc3C=Cc3ccc(C4CCN(C(=O)OC(C)(C)C)CC4)cc3C)n2)c1CC]

To a suspension of (4-(1-(tert-butoxycarbonyl)piperidin-4-yl)-2-methylbenzyl)triphenylphosphonium bromide (Intermediate 2-26) (1.5 g, 2.38 mmol) in THF (22 mL) at room temperature was added LHMDS (3.3 mL, 3.3 mmol). The resulting solution was stirred for 0.5 h. To the solution was then added a solution of ethyl 5-ethyl-1-(6-(3-formyl-5-methylthiophen-2-yl)pyridin-2-yl)-1H-pyrazole-4-carboxylate (Intermediate 4-2-11) (600 mg, 1.62 mmol) in THF (5 mL). The mixture was then stirred for 3 h at room temperature. The reaction was then quenched with satd. aq. NH$_4$Cl. The mixture was then extracted twice with CH$_2$Cl$_2$. The combined organic layers were dried over sodium sulfate, filtered and then concentrated. The resulting residue was purified by silica gel flash column chromatography (0-100% EtOAc in heptane) to afford the title product. MS (ESI+) m/z 641.4 (M+H).

Example 45. 1-(6-(3-(4-(1-(Cyclopropanecarbonyl)piperidin-4-yl)-2-methylphenethyl)-5-methylthiophen-2-yl)pyridin-2-yl)-5-ethyl-1H-pyrazole-4-carboxylic acid

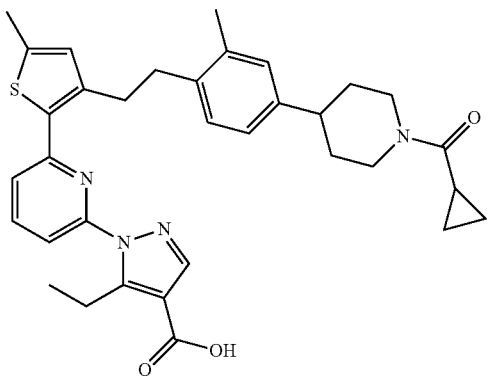 [SMILES: CCc1c(C(=O)O)cnn1-c1cccc(-c2sc(C)cc2CCc2ccc(C3CCN(C(=O)C4CC4)CC3)cc2C)n1]

The title compound was synthesized starting from Example 45-A. Hydrogenation of Example 45-A, similarly to the preparation of Example 25-B, and then subsequent treatment with TFA, in a fashion analogous Example 1-B, afforded an amine which was then reacted with cyclopropylcarbonyl chloride analogous to the transformation outlined in Example 1-C. The resulting product was saponified as described in Example 7 to furnish the title compound. $^1$H-NMR (400 MHz, CD$_3$OD) δ 8.00 (s, 1H), 7.87 (t, J=8.0 Hz, 1H), 7.56 (dd, J=8.0, 0.7 Hz, 1H), 7.38 (d, J=7.9 Hz, 1H), 6.91-6.63 (m, 4H), 4.66-4.56 (m, 1H), 4.47-4.35 (m, 1H), 3.21 (s, 1H), 3.16-3.06 (m, 3H), 2.92-2.82 (m, 2H), 2.77-2.57 (m, 2H), 2.47 (d, J=1.0 Hz, 3H), 2.14 (s, 3H), 2.04-1.92 (m, 1H), 1.88-1.68 (m, 2H), 1.65-1.40 (m, 2H), 1.25-1.14 (m, 4H), 0.96-0.74 (m, 4H). HRMS calcd. for C$_{34}$H$_{39}$N$_4$O$_3$S (M+H) 583.2743, found 583.2758.

Example 46. 1-(6-(3-(4-(1-(tert-Butoxycarbonyl)piperidin-4-yl)-2-methylphenethyl)-5-methylthiophen-2-yl)pyridin-2-yl)-5-(trifluoromethyl)-1H-pyrazole-4-carboxylic acid

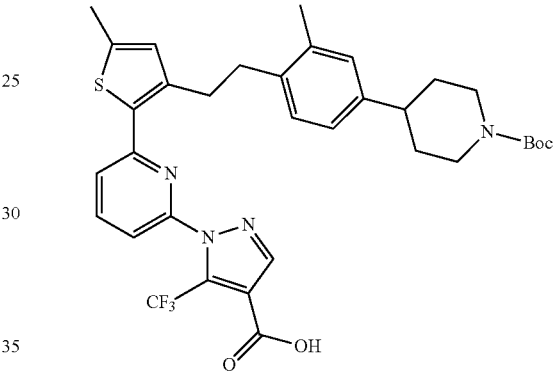

The title compound was synthesized by saponification of tert-butyl 4-(4-(2-(2-(6-(4-(ethoxycarbonyl)-5-(trifluoromethyl)-1H-pyrazol-1-yl)pyridin-2-yl)-5-methylthiophen-3-yl)ethyl)-3-methylphenyl)piperidine-1-carboxylate (Example 25-B) via method analogous to the preparation of Example 7. $^1$H-NMR (400 MHz, CD$_3$OD) δ 8.00 (s, 1H), 7.87 (t, J=8.0 Hz, 1H), 7.56 (dd, J=8.0, 0.7 Hz, 1H), 7.38 (d, J=7.9 Hz, 1H), 6.91-6.63 (m, 4H), 4.66-4.56 (m, 1H), 4.47-4.35 (m, 1H), 3.21 (s, 1H), 3.16-3.06 (m, 3H), 2.92-2.82 (m, 2H), 2.77-2.57 (m, 2H), 2.47 (d, J=1.0 Hz, 3H), 2.14 (s, 3H), 2.04-1.92 (m, 1H), 1.88-1.68 (m, 2H), 1.65-1.40 (m, 2H), 1.25-1.14 (m, 4H), 0.96-0.74 (m, 4H). HRMS calcd. for C$_{34}$H$_{39}$N$_4$O$_3$S (M+H) 583.2743, found 583.2758.

Biological Example-1. CHO Cellular Assay

Chinese hamster ovary (CHO) cells overexpressing soluble guanylate cyclase were generated to test the effect of sGC activators in a cellular context. Human cDNAs for GUCYA3 (RefSeq: NM_000856.3) and GUCYB3 (RefSeq: NM_000857.1) were amplified by PCR from a HUVEC (Human Umbilical Vein Endothelial Cells) cDNA library and cloned into mammalian expression vectors. CHO K1 cells (ATCC CCL-61) were transfected using Lipofectamine 2000 following manufacturer's instructions and stably expressing clones were identified by antibiotic selection. CHO GUCY clone 8E10 was used for subsequent experiments.

Cells were seeded at a density of 3000 cells/well in white 384-well proxyplates (Perkin Elmer) and incubated overnight, then the medium was removed and cells were washed with assay buffer (HBSS, 0.1% BSA, 1 mM IBMX, 20 uM ODQ). sGC activators were serially diluted in DMSO, then diluted in assay buffer prior to adding to cells (10 ul/well, final DMSO concentration 0.5%). Cells were incubated with compounds for 1 h room temperature, then assayed for cGMP production using Cisbio cGMP HTRF kit (62GM2PEC) according to manufacturer's instructions.

The EC50s are calculated based on the amount of cGMP interpolated from the standard curve, using a 4-parameter sigmoidal dose-response.

Compounds of invention are active on sGC activation. Data on Table 1 collected using the assay of Biological Example 1. The minimum $EC_{50}$ quantification limit of the assay is 0.5 nM, therefore any compound listed as having an $EC_{50}$ value of ≤0.0005 µM has an actual $EC_{50}$ of ≤0.5 nM.

TABLE 1

| Example number | $EC_{50}$ (µM) | Example number | $EC_{50}$ (µM) |
| --- | --- | --- | --- |
| Example 1 | 0.024 | Example 12-3 | 0.0069 |
| Example 2-1 | 0.0028 | Example 12-4 | 0.0005 |
| Example 2-2 | 0.032 | Example 12-5 | 0.046 |
| Example 2-3 | 0.0028 | Example 12-6 | 0.048 |
| Example 2-4 | 0.0005 | Example 12-7 | 0.0075 |
| Example 2-5 | 0.0055 | Example 12-8 | 0.001 |
| Example 3 | 0.0014 | Example 12-8 | 0.0044 |
| Example 4-1 | 0.002 | Example 13 | 0.001 |
| Example 4-2 | 0.003 | Example 14-1 | 0.012 |
| Example 4-3 | 0.0055 | Example 14-2 | 0.43 |
| Example 4-4 | 0.0005 | Example 15 | 0.0005 |
| Example 5 | 0.0005 | Example 16-1 | 0.0088 |
| Example 6-1 | 0.001 | Example 16-2 | 0.001 |
| Example 6-2 | 0.033 | Example 16-3 | 0.0005 |
| Example 6-3 | 0.0005 | Example 17 | 0.001 |
| Example 6-4 | 0.002 | Example 18-1 | 0.007 |
| Example 6-5 | 0.001 | Example 18-2 | 0.002 |
| Example 6-6 | 0.0005 | Example 18-3 | 0.002 |
| Example 6-7 | 0.0014 | Example 19 | 0.001 |
| Example 6-8 | 0.0005 | Example 20-1 | 0.012 |
| Example 6-9 | 0.0005 | Example 20-2 | 0.0005 |
| Example 6-10 | 0.001 | Example 21 | 0.0005 |
| Example 6-11 | 0.0005 | Example 22-1 | 0.002 |
| Example 6-12 | 0.001 | Example 23 | 0.038 |
| Example 6-13 | 0.001 | Example 24 | 0.006 |
| Example 6-14 | 0.003 | Example 25 | 0.0005 |
| Example 6-15 | 0.0095 | Example 26 | 0.0005 |
| Example 6-16 | 0.0063 | Example 27 | 0.0005 |
| Example 6-17 | 0.014 | Example 28 | 0.0045 |
| Example 6-18 | 0.0024 | Example 29 | 0.067 |
| Example 7 | 0.0005 | Example 30 | 0.061 |
| Example 8 | 0.0005 | Example 31 | 0.013 |
| Example 9 | 0.0005 | Example 32 | 0.0005 |
| Example 10-1 | 0.0005 | Example 33-1 | 0.023 |
| Example 10-2 | 0.0005 | Example 33-2 | 0.015 |
| Example 10-3 | 0.0005 | Example 34 | 0.002 |
| Example 10-4 | 0.0005 | Example 35-1 | 0.096 |
| Example 10-5 | 0.0005 | Example 35-2 | 0.678 |
| Example 10-6 | 0.0005 | Example 35-3 | 0.195 |
| Example 10-7 | 0.037 | Example 35-4 | 0.002 |
| Example 10-8 | 0.015 | Example 35-5 | 0.003 |
| Example 11 | 0.002 | Example 35-6 | 0.091 |
| Example 12-1 | 0.0005 | Example 35-7 | 0.0005 |
| Example 12-2 | 0.0045 | Example 35-8 | 0.0005 |
| Example 6-19 | 0.002 | Example 36 | 0.015 |
| Example 10-9 | 0.057 | Example 35-14 | 0.015 |
| Example 12-10 | 0.033 | Example 35-15 | 0.0014 |
| Example 12-11 | 0.036 | Example 37 | 0.0005 |
| Example 18-4 | 0.0059 | Example 38 | 0.0005 |
| Example 18-5 | 0.0035 | Example 39 | 0.001 |
| Example 18-6 | 0.018 | Example 40 | 0.37 |
| Example 20-3 | 0.039 | Example 41 | 0.428 |
| Example 35-9 | 0.0005 | Example 42 | 0.62 |
| Example 35-10 | 0.0005 | Example 43 | 0.887 |
| Example 35-11 | 0.16 | Example 44 | 0.13 |
| Example 35-12 | 0.001 | Example 45 | 0.0005 |
| Example 35-13 | 0.001 | Example 46 | 0.003 |

What is claimed is:

1. A compound according to Formula (I)

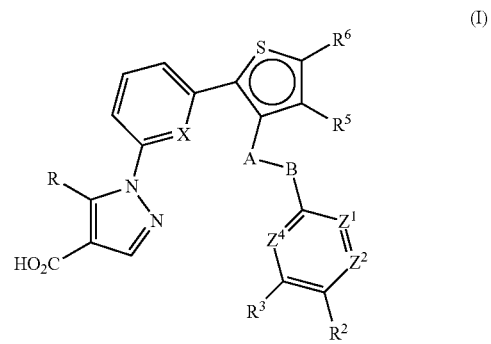

Or a pharmaceutically acceptable salt thereof, wherein
X is N or CH;
$Z^1$ is N or $CR^1$;
$Z^2$ is N or CH;
$Z^4$ is N or $CR^4$,
A is $CHR^A$ or O, wherein $R^A$ is hydrogen or $C_1$-$C_4$alkyl;
B is $CHR^A$, O or N(H); wherein one or both of A and B is $CHR^A$;
R is hydrogen, $C_1$-$C_4$alkyl, monofluoromethyl, difluoromethyl or trifluoromethyl;
$R^1$ is hydrogen, halogen or $C_1$-$C_4$alkyl;
$R^2$ is piperidinyl which is N-substituted with $C_1$-$C_4$alkyl, $C_3$-$C_6$cycloalkyl, halo$C_1$-$C_4$alkyl, C(O)$C_1$-$C_4$alkyl, C(O)NH($C_1$-$C_4$alkyl), C(O)N($C_1$-$C_4$alkyl)$_2$, S(O)$_2$$C_1$-$C_4$alkyl, C(O)$C_3$-$C_6$cycloalkyl, heterocycle, C(O)heterocycle, C(O)halo$C_1$-$C_4$alkyl, C(O)$C_1$-$C_4$alkoxy, C(O)$C_1$-$C_4$alkenoxy, heteroaryl or CO(O)$_2$benzyl, wherein each cycloalkyl is optionally substituted by hydroxy and each alkyl or alkoxy is optionally substituted by hydroxyl, $C_1$-$C_4$alkoxy, $C_3$-$C_6$cycloalkyl or heterocycle, wherein each heterocycle has 4, 5 or 6 ring atoms and 1 or 2 ring oxygen atoms and which heterocycle is optionally substituted with 1 or 2 $C_1$-$C_4$alkyl or hydroxy substituents and wherein each heteroaryl has 5 or 6 ring atoms, 1, 2 or 3 ring heteroatoms independently selected from N, O and S and is optionally substituted with 1 or 2 $C_1$-$C_4$alkyl substituents, and wherein the piperidinyl is optionally further substituted by hydroxy or by 1-4 independently selected $C_1$-$C_4$alkyl groups;
$R^3$ is hydrogen, halogen, $C_1$-$C_4$alkyl, $C_3$-$C_6$cycloalkyl, hydroxymethyl or $C_1$-$C_4$alkoxy, $R^2$ and $R^3$, taken in combination, form a 5 or 6 member fused saturated azacyclic ring optionally substituted with benzyl or 5 or 6 member heteroarylmethyl, which heteroaryl has 1 or 2 ring heteroatoms independently selected from N, O and S;
$R^4$ is hydrogen, halogen, $C_1$-$C_4$alkyl, hydroxylmethyl, halo$C_1$-$C_4$alkyl or $C_1$-$C_4$alkoxy;
$R^5$ is hydrogen, $C_1$-$C_4$alkyl, trifluoromethyl, halogen or $C_3$-$C_6$cycloalkyl; and $R^6$ is hydrogen, $C_1$-$C_4$alkyl, halogen or $C_3$-$C_6$cycloalkyl.

2. The compound of claim 1, wherein $Z^1$ is N, $Z^2$ is CH and $Z^4$ is $CR^4$.

3. The compound of claim 1, wherein $Z^1$ is $CR^1$, $Z^2$ is CH and $Z^4$ is N.

4. The compound of claim 1, wherein $Z^1$ is $CR^1$, $Z^2$ is N and $Z^4$ is $CR^4$.

5. A compound according to Formula (Ia)

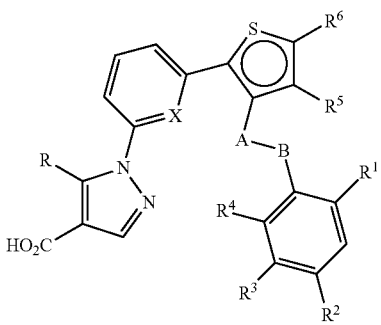

(Ia)

Or a pharmaceutically acceptable salt thereof, wherein
X is N or CH;
A is $CHR^A$ or O, wherein $R^A$ is hydrogen or $C_1$-$C_4$alkyl;
B is $CHR^A$, O or N(H); wherein one or both of A and B is $CHR^A$; or
R is $C_1$-$C_4$alkyl or trifluoromethyl;
$R^1$ and $R^4$ are each independently selected from hydrogen, halogen or $C_1$-$C_4$alkyl; or
$R^4$ is halo$C_1$-$C_4$alkyl or $C_1$-$C_4$alkoxy;
$R^2$ is piperidinyl which is N-substituted with $C_1$-$C_4$alkyl, $C_3$-$C_5$cycloalkyl-$C_1$-$C_4$alkyl, halo$C_1$-$C_4$alkyl, $C(O)C_1$-$C_4$alkyl, which alkyl is optionally substituted with hydroxyl or amino, $C(O)C_1$-$C_4$alkyl, $C(O)C_3$-$C_6$cycloalkyl, which cycloalkyl is optionally substituted by hydroxy, $C(O)CH_2$—$C_3$-$C_6$cycloalkyl $C(O)$halo$C_1$-$C_4$alkyl, $C(O)$heterocycle, $C(O)NH(C_1$-$C_4$alkyl), $C(O)N(C_1$-$C_4$alkyl)$_2$, $C(O)C_1$-$C_4$alkoxy, wherein the piperidinyl is optionally further substituted by hydroxy or by 1-4 independently selected $C_1$-$C_4$alkyl groups and wherein the heterocycle is a 4 to 6 member saturated ring having 1 or 2 ring oxygen atoms and substituted with 0, 1, or 2 $C_1$-$C_4$alkyl groups;
$R^3$ is hydrogen, halogen, $C_1$-$C_4$alkyl, hydroxymethyl or $C_1$-$C_4$alkoxy; or
$R^2$ and $R^3$, taken in combination form a 6 member fused saturated azacyclic ring optionally substituted with benzyl or 5, 6, 9 or 10 member heteroarylmethyl, which heteroaryl has 1 or 2 rings and 1 or 2 ring heteroatoms independently selected from N, O and S;
$R^5$ is hydrogen, $C_1$-$C_4$alkyl, halogen or $C_3$-$C_6$cycloalkyl, and
$R^6$ is hydrogen, $C_1$-$C_4$alkyl, halogen or $C_3$-$C_6$cycloalkyl.

6. The compound of claim 5, wherein $R^2$ is N-substituted piperidin-4-yl wherein the N-substituent is C(O)cyclopropyl, $C(O)C_1$-$C_4$alkyl, halo$C_1$-$C_4$alkyl, or $C(O)C_1$-$C_4$alkoxy.

7. The compound of claim 5, wherein $R^2$ is N-substituted piperidin-4-yl wherein the N-substituent is 2,2,2-trifluoroethyl, C(O)cyclopropyl or $C(O)C_1$-$C_4$alkyl.

8. The compound of claim 5, wherein $R^1$ is methyl and $R^3$ and $R^4$ are hydrogen.

9. The compound of claim 5, wherein $R^1$ and $R^4$ are hydrogen and $R^3$ is ethyl.

10. The compound of claim 5, wherein $R^1$ and $R^4$ are hydrogen and $R^3$ is methoxy.

11. The compound of claim 5, wherein $R^1$ and $R^3$ are hydrogen and $R^4$ is methoxy.

12. The compound of claim 5, wherein R is trifluoromethyl, methyl or ethyl.

13. The compound of claim 5, wherein R is methyl or ethyl.

14. The compound of claim 5, wherein R is trifluoromethyl.

15. The compound of claim 5, wherein $R^5$ is hydrogen, $C_1$-$C_4$alkyl, cyclopropyl or trifluoromethyl and $R^6$ is hydrogen, $C_1$-$C_4$alkyl, cyclopropyl or chloro.

16. The compound of claim 5, wherein
A is $CH_2$;
B is O or N(H);
R is methyl or ethyl;
$R^1$ is methyl;
$R^2$ is N-substituted piperidin-4-yl wherein the N-substituent is C(O)cyclopropyl, 2,2,2-trifluoroethyl or $C(O)C_1$-$C_4$alkyl;
$R^3$ is hydrogen, methyl, ethyl or methoxy;
$R^4$ is hydrogen;
$R^5$ is hydrogen, methyl, ethyl or trifluoromethyl; and $R^6$ is hydrogen, methyl, cyclopropyl or chloro, wherein at least one of $R^5$ or $R^6$ is not hydrogen.

17. A pharmaceutical composition comprising a compound of claim 5, or a salt thereof, and a pharmaceutically acceptable excipient.

18. An ophthalmic pharmaceutical composition useful in the treatment of glaucoma and control of intraocular pressure comprising: an effective amount of a compound of claim 5, or a pharmaceutically acceptable salt thereof.

19. A method of treating glaucoma and controlling intraocular pressure comprising: applying a therapeutically effective amount of a pharmaceutical composition comprising a compound of claim 5, or a pharmaceutically acceptable salt thereof to an affected eye of a patient.

* * * * *